United States Patent [19]

Barth et al.

[11] Patent Number: 5,380,746

[45] Date of Patent: Jan. 10, 1995

[54] BIS-(1H-INDOL-3-YL)-MALEINIMIDE DERIVATIVES, PROCESSES FOR THE PREPARATION THEREOF AND PHARMACEUTICAL COMPOSITIONS CONTAINING THEM

[75] Inventors: Hubert Barth, Emmendingen; Johannes Hartenstein, Stegen-Wittental; Claus Rudolph, Vörstetten; Christoph Schächtele, Freiburg; Hans-Jürgen Betche, Vörstetten; Reinhard Reck, Sexau; Hartmut Osswald, Tübingen, all of Germany

[73] Assignee: Goedecke Aktiengesellschaft, Berlin, Germany

[21] Appl. No.: 28,528

[22] Filed: Mar. 9, 1993

Related U.S. Application Data

[63] Continuation of Ser. No. 715,064, Jun. 11, 1991, abandoned, which is a continuation-in-part of Ser. No. 515,795, Apr. 27, 1990, abandoned.

[30] Foreign Application Priority Data

May 5, 1989 [DE] Germany ................. 3914764
Dec. 27, 1989 [DE] Germany ................. 3942991

[51] Int. Cl.⁶ ............... C07D 401/14; C07D 403/14; C07D 413/14; A61K 31/40; A61K 31/445; A61K 31/535

[52] U.S. Cl. ............................ 514/414; 514/422; 514/235.2; 514/340; 514/43; 548/455; 548/430; 546/198; 544/142; 544/143; 536/28.6

[58] Field of Search ............. 548/455, 430; 514/422, 514/235.2, 340, 43, 414; 546/198; 544/142, 143; 536/23

[56] References Cited

U.S. PATENT DOCUMENTS 4,912,107 3/1990 Kleinschroth et al. .......... 514/232.5

OTHER PUBLICATIONS

*Tetrahedron Letters*, 28(38):4441–4444 (1987), J. Bergman et al., "Coupling of Indoleacetic Acid Trianion . . .".

*Febs Lett.*, 259(1): 61–63 (1989), P. D. Davis et al., "Potent Selective Inhibitors of Protein Kinase-C".

*Primary Examiner*—David B. Springer
*Attorney, Agent, or Firm*—Elizabeth M. Anderson

[57] ABSTRACT

The present invention provides bis-(1H-indol-3-yl)maleinimide derivatives and the pharmacologically acceptable salts thereof, processes for the preparation of these compounds, and pharmaceutical compositions containing them for the treatment of heart and blood vessel diseases, such as thromboses, arteriosclerosis, hypertension, of inflammatory processes, allergies, cancer, and certain degenerative damages of the central nervous system, as well as of diseases of the immune system and viral diseases.

28 Claims, No Drawings

BIS-(1H-INDOL-3-YL)-MALEINIMIDE DERIVATIVES, PROCESSES FOR THE PREPARATION THEREOF AND PHARMACEUTICAL COMPOSITIONS CONTAINING THEM

This application is a continuation of U.S. Ser. No. 07/715,064, filed Jun. 11, 1991, which is a continuation-in-part of U.S. Ser. No. 07/515,795, filed Apr. 27, 1990, both abandoned.

BACKGROUND OF THE INVENTION

Protein kinase C plays an outstanding part in the regulation of cellular processes which are closely connected with the physiological control of contractile, secretory and proliferative processes (see Y. Nishizuka, Nature, 308, 593-698/1984). The physiological activation of protein kinase C takes place via "a second messenger" resulting by a receptor-initiated breakdown of membrane-bound phosphatidylinositols.

The present invention is concerned with new bis-(1H-indol-3-yl)-maleinimide derivatives which are potent inhibitors of protein kinase C.

SUMMARY OF THE INVENTION

The present invention is new bis-(1H-indol-3-yl)maleinimides of formula

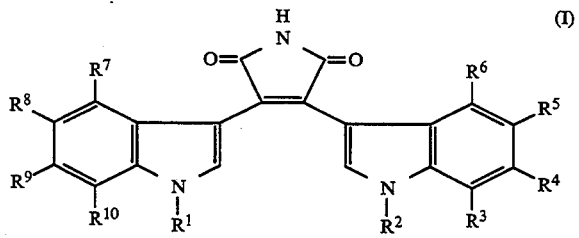

or a pharmaceutically acceptable salt thereof wherein $R^1$ to $R^{10}$ are as defined below.

Preferred compounds of the instant invention are those wherein $R^1$ and $R^2$ are each independently hydrogen, straight or branched alkyl of from one to four carbon atoms, aminoalkyl of from one to four carbon atoms which alkyl is unsubstituted or substituted by alkoxy of from one to four carbon atoms or by hydroxy and which nitrogen is unsubstituted, mono- or disubstituted by alkyl of from one to four carbon atoms or in which the substituents, together with the nitrogen to which they are attached, form a heterocyclic ring containing from three to six carbon atoms wherein the alkyl chain is unsubstituted or substituted by an alkyl of from one to four carbon atoms;

$R^3$, $R^6$, $R^7$, and $R^{10}$ are each hydrogen and $R^4$, $R^5$, $R^8$, and $R^9$ are each independently hydrogen, halogen, alkyl of from one to four carbon atoms, alkoxy of from one to four carbon atoms, benzyloxy, hydroxy, aminoalkoxy of from one to four carbon atoms, the alkyl portion of which is unsubstituted or substituted by alkoxy of from one to four carbon atoms and the nitrogen portion of which is unsubstituted, mono- or disubstituted by alkyl of from one to four carbon atoms or two substituents of $R^4$, $R^5$, $R^8$, and $R^9$ together with the nitrogen to which they are attached form a heterocyclic ring containing from three to six carbon atoms, wherein the alkyl chain is unsubstituted or substituted by an alkyl of from one to four carbon atoms or two substituents from $R^4$, $R^5$, $R^8$, and $R^9$ together form methylenedioxy.

More preferred compounds of the instant invention are those wherein $R^1$ and $R^2$ are each independently hydrogen, straight or branched alkyl of from one to four carbon atoms, aminoalkyl of from one to four carbon atoms, the alkyl portion of which can be unsubstituted or substituted by alkoxy of from one to four carbon atoms and the nitrogen of which can be unsubstituted, mono- or disubstituted by alkyl of from one to four carbon atoms;

$R^3$, $R^6$, $R^7$, and $R^{10}$ are each hydrogen;

$R^4$, $R^5$, $R^8$, and $R^9$ are each independently hydrogen, alkyl of from one to four carbon atoms, alkoxy of from one to four carbon atoms, halogen, amino, nitro, dimethylamino, trifluoromethyl, benzyloxy, hydroxy, aminoalkoxy of from one to four carbon atoms, which alkyl portion is unsubstituted or substituted by alkoxy of from one to four carbon atoms and which nitrogen portion is unsubstituted or mono- or disubstituted by alkyl of from one to four carbon atoms or two adjacent substituents of $R^4$, $R^5$, $R^8$, and $R^9$ are together methylenedioxy.

Still more preferred compounds of the instant invention are those of Formula I wherein: $R^1$ and $R^2$ are each independently hydrogen, methyl, ethyl, n-propyl, isopropyl, n-butyl, benzyl, acetyl, methoxycarbonylmethyl, 2-methoxyethyl, 2-aminoethyl, 3-aminopropyl, 1-amino-2-propyl, 2-dimethylaminoethyl, 3-dimethylamino-1-propyl, 3-dimethlyamino-2-propyl, 2-diethylaminoethyl, 2-(N-benzyl-N-methylamino)-ethyl, 3-(N-benzyl-N-methylamino)-propyl, 3-dimethylamino-2-hydroxy-1-propyl, 2-piperidinoethyl, 3-piperidinopropyl, 2-pyrrolidinyoethyl, 3-pyrrolidinopropyl, 2-morpholinoethyl, 3-morpholinopropyl, pyrrolidin-2-ylmethyl, N-methylpyrrolidin-2-yl-methyl, glucosyl, rhamnosyl, ribosyl, deoxyribosyl, aminoglycosyl, 3-hydroxypropyl, 2-carboxyethyl, 2-dimethylaminoethylcarbonyl, dimethylaminomethylcarbonyl, 2-hydroxyethoxymethyl, (2-hydroxy-1-hydroxymethyl)ethoxymethyl or (3-hydroxy-1-hydroxymethyl)propoxymethyl radicals and $R^5$ and $R^8$ are each independently hydrogen, chlorine, bromine, fluorine, trifluoromethyl, methyl, ethyl, hydroxyl, benzyloxy, methoxy, amino, dimethylamino, 2-aminoethoxy, 3-aminopropoxy, 1-amino-2-propoxy, 2-dimethylaminoethoxy, 3-dimethylamino-1-propoxy, 3-dimethylamino-2-propoxy, 2-diethylaminoethoxy, 2-[N-benzyl-N-methylamino]ethoxy, 3-[N-benzyl-N-methylamino]-propoxy, 3-dimethylamino-2-hydroxy-1-propoxy, 2-piperidinoethoxy, 3-piperidinopropoxy, 2-pyrrolidinoethoxy, 3-pyrrolidinopropoxy, 2-morpholinoethoxy, 3-morpholinopropoxy, 2-piperazinoethyl, 3-piperazinopropyl, pyrrolidin-2-ylmethoxy or N-methylpyrrolidin-2-ylmethoxy or $R^4$ and $R^5$ together and $R^8$ and $R^9$ together are each independently methylenedioxy.

Yet more preferred compounds of the instant invention are selected from the group consisting of:
2-(1H-indol-3-yl)-3-(1-methyl-1H-indol-3-yl)-maleinimide,
2-(1H-indol-3-yl)-3-[1-(3-dimethylaminopropyl)-1H-indol-3-yl]-maleinimide,
2-(5-hydroxy-1H-indol-3-yl)-3-(1H-indol-3-yl)-maleinimide,
2-(5-benzyloxy-1H-indol-3-yl)-3-(1H-indol-3-yl)-maleinimide,
2,3-bis-(5-methoxy-1H-indol-3-yl)-maleinimide, 2-(1H-indol-3-yl)-3-(5,6-methylenedioxy-1H-indol-3-yl)-maleinimide,
2-(1H-indol-3-yl)-3-(5,6-dimethoxy-1H-indol-3-yl)-maleinimide, and
2,3-bis-(5,6-methylenedioxy-1H-indol-3-yl)-maleinimide.

Other more preferred compounds are those selected from the list consisting of:
2,3-bis(1-methyl-1H-indol-3-yl)maleinimide,
2-[1-(3-diethylaminopropyl)-6-methoxy-1H-indol-3-yl]-3-(5-methoxy-1H-indol-3-yl)-maleinimide,
2-[1-(3-diethylaminopropyl)-5-methoxy-1H-indol-3-yl]-3-(5,6-dimethoxy-1-methyl-1H-indol-3-yl)maleinimide,
2-[1-(3-diethylaminopropyl)-5-methoxy-1H-indol-3-yl]-3-(6-methoxy-1H-indol-3-yl)maleinimide,
2-[1-(3-diethylaminopropyl)-6-methoxy-1H-indol-3-yl]-3-(5-methoxy-1H-indol-3-yl)maleinimide,
2-(5-benzyloxy-1H-indol-3-yl)-3-[1-(3-dimethylaminopropyl)-1H-indol-3-yl]maleinimide,
2-[5-benzyloxy-1-(3-dimethylaminopropyl)-1H-indol-3-yl]-3-(1H-indol-3-yl)maleinimide,
2-(5-methoxy-1H-indol-3-yl)-3-[5-methoxy-1-(3-dimethylaminopropyl)-1H-indol-3-yl]maleinimide,
(±)-2-(1H-indol-3-yl)-3-[1-(3-dimethylamino-2-methoxypropyl)-1H-indol-3-yl]maleinimide,
2-(1H-indol-3-yl)-3-[5-(3-dimethylaminopropyloxy)-1H-indol-3-yl]maleinimide,
2-(5-fluoro-1H-indol-3-yl)-3-[5-fluoro-1-(3-dimethylaminopropyl)-1H-indol-3-yl]maleinimide,
2-(5-benzyloxy-1H-indol-3-yl)-3-[5-benzyloxy-1-(3-dimethylaminopropyl-1H-indol-3-yl]maleinimide,
2-[5-benzyloxy-1-(3-dimethylaminopropyl)-1H-indol-indol-3-yl]-3-(1-methyl-1H-indol-3-yl)maleinimide,
2-(5-chloro-1H-indol-3-yl)-3-[5-chloro-1-(3-dimethylaminopropyl)-1H-indol-3-yl]maleinimide,
2-(5-methyl-1H-indol-3-yl)-3-[5-methyl-1-(3-dimethylaminopropyl)-1H-indol-3-yl]maleinimide,
2-(5-bromo-1H-indol-3-yl)-3-[5-bromo-1-(3-dimethylaminopropyl)-1H-indol-3-yl]maleinimide,
2-(1H-indol-3-yl)-3-[1-(2-dimethylaminoethyl)-1H-indol-3-yl]maleinimide,
2-(1H-indol-3-yl)-3-[1-(3-(1-piperidino)propyl)-1H-indol-3-yl]maleinimide,
2-(1H-indol-3-yl)-3-[1-(3-(4-morpholino)propyl)-1H-indol-3-yl]maleinimide,
2-[1-(3-diethylaminopropyl)-1H-indol-3-yl]-3-(1H-indol-3-yl)maleinimide,
2-(5-methoxy-1H-indol-3-yl)-3-[1-(3-dimethylaminopropyl)-1H-indol-3-yl]maleinimide,
2-(1H-indol-3-yl)-3-[5-methoxy-1-(3-dimethylaminopropyl)-1H-indol-3-yl]maleinimide,
2-(5-methoxy-1H-indol-3-yl)-3-[1-(3-(4-morpholino)propyl)-1H-indol-3-yl]maleinimide,
2-(1H-indol-3-yl)-3-[5-methoxy-1-(3-(4-morpholino)propyl)-1H-indol-3-yl]maleinimide,
2-(5-fluoro-1H-indol-3-yl)-3-[1-(3-dimethylaminopropyl)-1H-indol-3-yl]maleinimide,
2-(1H-indol-3-yl)-3-[5-methoxy-1-(3-(1-piperidino)propyl)-1H-indol-3-yl]maleinimide,
2-(5-methoxy-1H-indol-3-yl)-3-[1-(3-(1-piperidino)propyl)-1H-indol-3-yl]maleinimide,
2-[1-(3-diethylaminopropyl)-5-methoxy-1H-indol-3-yl[-3-(1H-indol-3-yl) maleinimide,
2-[1-(3-diethylaminopropyl)-1H-indol-3-yl)-3-(5-methoxy-1H-indol-3-yl)maleinimide,
2-[5-fluoro-1-(3-dimethylaminopropyl)-1H-indol-3-yl)maleinimide, and
2-(5-fluoro-1H-indol-3-yl)-3-[1-(3-dimethylaminopropyl)-1H-indol-3-yl]maleinimide.
2-(1H-indol-3-yl)-3-(5-methoxy-1H-indol-3-yl)maleinimide,
2,3-bis-(5-fluoro-1H-indol-3-yl)maleinimide,
2,3-bis-(5-benzyloxy-1H-indol-3-yl)maleinimide,
2,3-bis-(5-chloro-1H-indol-3-yl)maleinimide,
2,3-bis-(5-methyl-1H-indol-3-yl)maleinimide,
2,3-bis-(5-bromo-1H-indol-3-yl)maleinimide,
(±)-2-[1-(3-diethylamino-2-hydroxypropyl)-1H-indol-3-yl]-3-(1H-indol-3-yl)maleinimide,
(+)-2-[1-(3-diethylamino-2-hydroxypropyl)-1H-indol-3-yl]-3-(1H-indol-3-yl)maleinimide,
(−)-2-[1-(3-diethylamino-2-hydroxypropyl)-1H-indol-3-yl]-3-(1H-indol-3-yl)maleinimide,
(±)-2-[1-(2,3-dihydroxypropyl)-1H-indol-3-yl]-3-(1H-indol-3-yl)maleinimide,
(+)-2-[1-(2,3-dihydroxypropyl)-1H-indol-3-yl]-3-(1H-indol-3-yl)maleinimide,
(−)-2-[1-(2,3-dihydroxypropyl)-1H-indol-3-yl]-3-(1H-indol-3-yl)maleinimide,
(±)-2-[1-(3-ethoxy-2-hydroxypropyl)-1H-indol-3-yl]-3-(1H-indol-3-yl)maleinimide,
(+)-2-[1-(3-ethoxy-2-hydroxypropyl)-1H-indol-3-yl]-3-(1H-indol-3-yl)maleinimide,
(−)-2-[1-(3-ethoxy-2-hydroxypropyl)-1H-indol-3-yl]-3-(1H-indol-3-yl)maleinimide,
(±)-2-[1-(2-hydroxy-3-(1-piperidino)-propyl)-1H-indol-3-yl]-3-(1H-indol-3-yl)maleinimide,
(+)-2-[1-(2-hydroxy-3-(1-piperidino)-propyl)-1H-indol-3-yl]-3-(1H-indol-3-yl)maleinimide,
(−)-2-[1-(2-hydroxy-3-(1-piperidino)-propyl)-1H-indol-3-yl]-3-(1H-indol-3-yl)maleinimide,
(±)-2-[1-(3-diethylamino-2-hydroxypropyl)-5-methoxy-1H-indol-3-yl]-3-(1H-indol-3-yl)maleinimide,
(+)-2-[1-(3-diethylamino-2-hydroxypropyl)-5-methoxy-1H-indol-3-yl]-3-(1H-indol-3-yl)maleinimide,
(−)-2-[1-(3-diethylamino-2-hydroxypropyl)-5-methoxy-1H-indol-3-yl]-3-(1H-indol-3-yl)maleinimide,
(±)-2-[1-(3-diethylamino-2-hydroxypropyl)-1H-indol-3-yl]-3-(5-methoxy-1H-indol-3-yl)maleinimide,
(+)-2-[1-(3-diethylamino-2-hydroxypropyl)-1H-indol-3-yl]-3-(5-methoxy-1H-indol-3-yl)maleinimide,
(−)-2-[1-(3-diethylamino-2-hydroxypropyl)-1H-indol-3-yl]-3-(5-methoxy-1H-indol-3-yl)maleinimide.

The present invention is also concerned with the use of compounds of formula I, including compounds in which $R^1$ to $R^{10}$ are hydrogen atoms or in which $R^4$ or $R^4$ and $R^9$ are hydroxyl groups and the other groups of $R^1$ to $R^{10}$ are hydrogen atoms, for the preparation of pharmaceutical compositions for the prevention or treatment of diseases in which the inhibition of protein kinase C is of importance.

The present invention also provides pharmaceutical compositions which, in addition to conventional adjuvant and additive materials, contain at least one compound of formula I, including compounds in which $R^1$ to $R^{10}$ are hydrogen atoms or in which $R^4$ or $R^4$ and $R^9$ are hydroxyl groups and the other groups of $R^1$ to $R^{10}$ are hydrogen atoms.

The present invention also concerns a method of using the above pharmaceutical compositions for treating diseases of the heart or blood vessels.

The present invention also concerns a method of using the above pharmaceutical composition for treat-

DETAILED DESCRIPTION

The present invention is concerned with new bis-(1H-indol-3-yl)maleinimide derivatives of

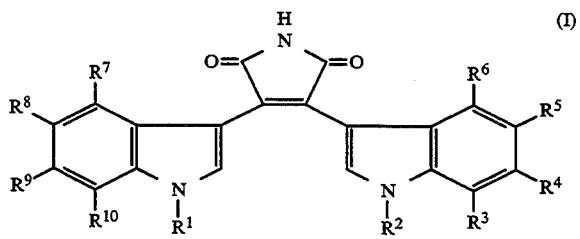 (I)

or a pharmaceutically acceptable salt thereof wherein $R^1$ and $R^2$ are each independently hydrogen, a straight or branched alkyl of from one to eighteen carbon atoms, unsubstituted or substituted benzyl wherein the substituent is alkyl of from one to three carbon atoms, alkoxy of from one to four carbon atoms, halogen, aminoalkyl of from one to twelve carbon atoms which is unsubstituted, mono- or disubstituted on the nitrogen by benzyl or alkyl of from one to four carbon atoms or wherein the substituents, together with the nitrogen to which they are attached form a heterocyclic ring containing from three to six carbon atoms and wherein the alkyl portion of the aminoalkyl is unsubstituted or substituted by alkyl of from one to four carbon atoms, hydroxy, or alkoxy of from one to four carbon atoms, amidinothioalkyl of from one to twelve carbon atoms, nitroguanidinoalkyl of from one to twelve carbon atoms, isothiocyanatoalkyl of from one to six carbon atoms, epoxyalkyl of from one to six carbon atoms, alkoxycarbonylalkyl of from one to six carbon atoms, or $CH_2$—CO—$NR^{11}R^{12}$ wherein $R^{11}$ and $R^{12}$ are each independently hydrogen, alkyl of from one to six carbon atoms, benzyl, haloalkyl of from one to six carbon atoms, hydroxy alkyl of from one to six carbon atoms wherein $R^{11}$ or $R^{12}$ can each be unsubstituted or substituted by halogen, alkoxy alkyl, by one to three hydroxy groups, or $R^{11}$ and $R^{12}$ are each independently acyl of from one to four carbon atoms or glycoside;

$R^3$, $R^4$, $R^5$, $R^6$, $R^7$, $R^8$, $R^9$, and $R^{10}$ are each independently hydrogen, halogen, alkyl of from one to four carbon atoms, alkoxy of from one to four carbon atoms, acyloxy of from one to four carbon atoms, nitro, amino which is unsubstituted or mono- or disubstituted by benzyl, alkyl of from one to four carbon atoms, benzyloxy, hydroxy, aminoalkoxy of from one to twelve carbon atoms and which nitrogen can be unsubstituted or mono- or disubstituted by benzyl or by alkyl of from one to four carbon atoms or the substituents together with the nitrogen to which they are attached form a heterocyclic ring containing from three to six carbon atoms or the alkyl is unsubstituted or substituted by alkyl of from one to four carbon atoms, hydroxy, alkoxy of from one to four carbon atoms, trifluoromethyl or two neighboring substituents form methylene, with the proviso that not all of $R^1$ to $R^{10}$ are hydrogen or when $R^4$ or $R^4$ and $R^9$ are hydroxy, the others of $R^1$ to $R^{10}$ are not hydrogen.

$R^{10}$ can also be cyanoalkyl.

The preparation of the compounds of formula I is analogous to the processes described in the literature (Tetrahedron, 44, 2887/1988; Tetrahedron Lett., 1985, 4015; European Patent Number 0 269 025) has counterparts U.S. Pat. Nos. 4,785,085 and 4,808,613 or with the use of appropriate variations of these processes.

The process according to the present invention is characterized in that either (A) a dibromomaleinimide of the formula II,

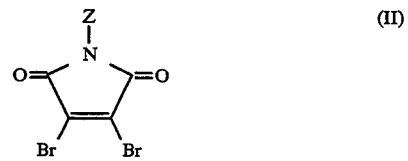 (II)

in which Z is an appropriate protective group which can be split off, is reacted in known manner with an indole Grignard reagent of the formula (A)

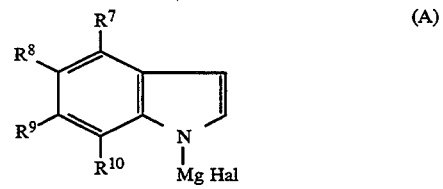 (A)

in which $R^7$, $R^8$, $R^9$, and $R^{10}$ have the above-given meanings except that they are not hydroxyl groups or acyloxy radicals, and the product obtained of the formula III,

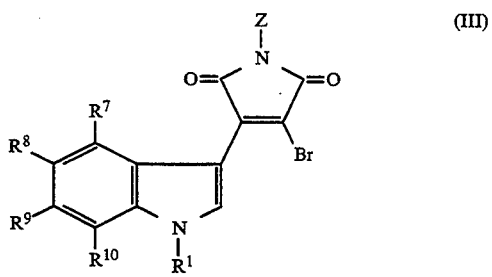 (III)

in which $R^1$ is a hydrogen atom, is optionally alkylated in known manner on the indole nitrogen atom with an alkylation agent of the formula $R^1$-X, in which $R^1$ has the same meaning as above with the exception of hydrogen and also does not contain a functional group which would disturb the following reactions and X is a group which is easily removed, such as a chlorine or bromine atom, to give a compound of formula III in which $R^1$ is other than a hydrogen atom and subsequently the product of formula III is reacted with an indole Grignard reagent of the formula (B),

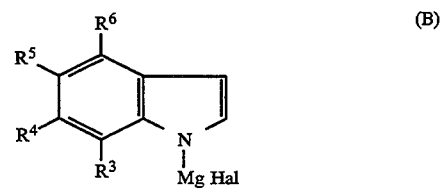 (B)

in which $R^3$, $R^4$, $R^5$, and $R^6$ have the above-given meanings except that they are not hydroxyl groups or acyloxy radicals, and optionally subsequently alkylates with an alkylation agent of the general formula $R^2$-X in which X has the above-given meaning and $R^2$ has the above-given meaning with the exception of hydrogen, to give a compound of the formula IV,

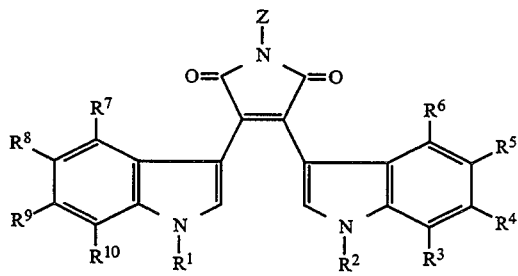
(IV)

whereafter the substituted imide group is converted into an unsubstituted imide group of formula I; or (B) a compound of the formula V,

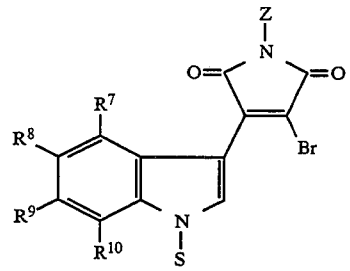
(V)

in which S and z are appropriate protective groups which can be split off, is reacted with an indole Grignard reagent of the formula (B),

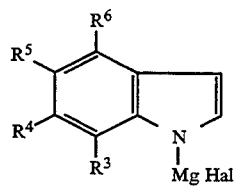
(B)

in which $R^3$, $R^4$, $R^5$, and $R^6$ have the above-given meanings except that they are not hydroxyl groups or acyloxy radicals, and subsequently optionally alkylates with an alkylation agent of the formula $R^2$-X in which X has the above-given meaning and $R^2$ has the above-given meaning with the exception of hydrogen, to give a compound of the formula VI,

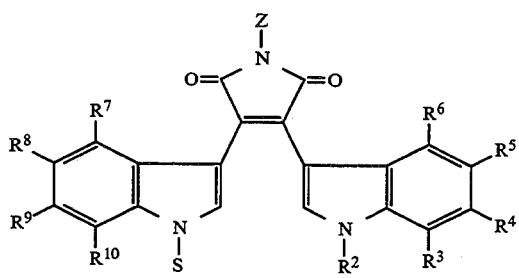
(VI)

whereafter the protected indole group is converted into a free indole group and the substituted imide group is converted into an unsubstituted imide group of formula I in which $R^1$ is a hydrogen atom and $R^2$ to $R^{10}$ have the above-given meanings; or (C) a dibromomaleinimide of the formula II,

(II)

in which Z is an appropriate protective group which can be split off, is reacted with an excess of an indole Grignard reagent of the formula (A),

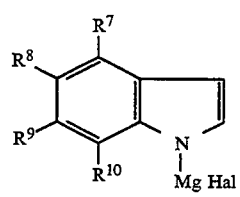
(A)

in which $R^7$, $R^8$, $R^9$, and $R^{10}$ have the above-given meanings with the exception of hydroxyl groups or acyloxy radicals, and the compound obtained of the formula VII

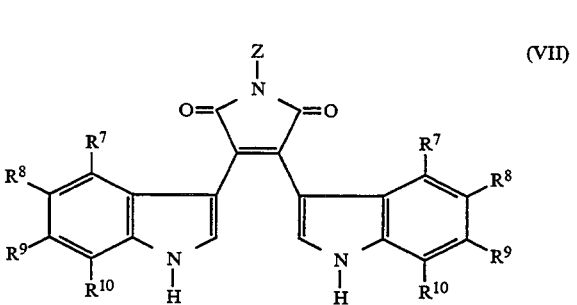
(VII)

is optionally alkylated on the indole nitrogen atom with an alkylation agent of the general formula $R^1$-X, in which $R^1$ has the above-given meaning with the exception of hydrogen and X is a group which can easily be removed, for example, a chlorine or bromine atom, to give a compound of the formula VIII

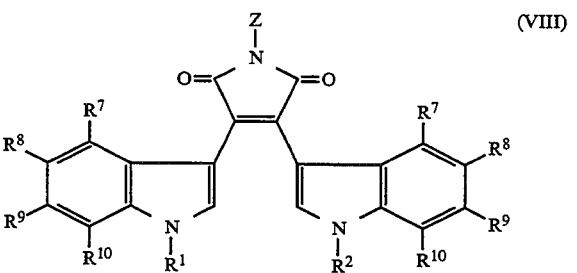
(VIII)

in which $R^1$ is other than a hydrogen atom and $R^2$ is a hydrogen atom and $R^7$ to $R^{10}$ have the above-given meanings with the exception of hydroxyl groups and acyloxy radicals, whereafter the substituted imide group is converted into an unsubstituted imide group of formula I.

Compounds of formula VIII, in which $R^1$ is other than a hydrogen atom and $R^2$ is a hydrogen atom, can be reacted with an alkylation agent of the formula $R^2$-X, in which, with the exception of being a hydrogen atom, $R^2$ has the above-given meaning and is different from $R^1$ and X is a group which can easily be removed, for example, a chlorine or bromine atom, to give a compound of formula VIII, in which $R^1$ is different from $R^2$ and both radicals are other than hydrogen.

After conversion of the substituted imide group in VII or VIII into a free imide group, there are obtained compounds of formula I in which $R^1$ to $R^{10}$ have the above-given meanings and $R^3$ is the same as $R^{10}$, $R^4$ is the same as $R^9$, $R^5$ is the same as $R^8$, and $R^6$ is the same as $R^7$.

Symmetrically substituted bis-indolylmaleinimides of formula I, in which $R^1$ and $R^2$ are hydrogen atoms and $R^3$ is the same as $R^{10}$, $R^4$ is the same as $R^9$, $R^5$ is the same as $R^8$, and $R^6$ is the same $R^7$ and have the above-given meanings but are not hydroxyl groups or acyloxy radicals, can also be obtained by reacting dibromomaleinimide with an excess of indole Grignard reagent of formula A.

The conversion of the substituted imides into the free imides described in processes A to C can be carried out analogously to the processes described in the literature. If, for example, Z is a methyl radical, then, by reaction with a solution of potassium hydroxide in water/methanol and subsequent acidification, there is first prepared the corresponding cyclic anhydride and this is converted by heating with ammonium acetate or ethanolic ammonia solution into the free imide (Tetrahedron, 44, 2887/1988). If, for example, Z is a benzyloxymethyl radical, then the conversion into the free imide is carried out by hydrogenation in the presence of palladium/charcoal (Tetrahedron Lett., 26, 4015/1985).

As protective group S in process B, there is especially preferred the tert.-butoxycarbonyl (BOC) radical, the p-toluenesulphonic acid (tosyl) radical, and the trimethylsilylethoxymethyl (SEM) radical. The BOC and tosyl radicals are split off in the case of the conversion of the substituted imide into the free imide and the SEM radical can easily be split off with tetra-n-butylammonium fluoride (J. Org. Chem., 49, 205/1984).

For carrying out the alkylations according to processes A to C with compounds of the general formulae $R^1$-X or $R^2$-X, especially preferred bases include the hydrides, carbonate, amides, hydroxide, oxides, and alkoxides of the alkali metals and alkaline earth metals and organo-lithium compounds. As solvents, it is especially preferred to use dipolar aprotic solvents, for example, acetone, dimethyl sulphoxide, dimethylformamide or tetrahydrofuran. The glycosidation takes place with the use of appropriate O-acylated glycosyl halides.

Compounds of formula I, in which $R^1$ and/or $R^2$ are alkoxycarbonylalkyl radicals, can be prepared according to processes A to C, starting from N-benzyloxymethyldibromomaleinimide with the use of appropriate alkoxycarbonylalkyl halides. In this case, the alkylation takes place after carrying out the reactions with the indole Grignard reagent. By reaction on the alkoxycarbonyl radicals with appropriate amines, there can be prepared here from the corresponding amides by known methods.

Compounds of the formula I, in which $R^1$ and/or $R^2$ are haloalkyl radicals, are prepared from compounds of formula I, in which $R^1$ and/or $R^2$ are hydrogen atoms, by acylation with the use of an appropriate acyl halide or anhydride in an appropriate solvent, for example, pyridine.

Compounds of formula I, in which $R^1$ and/or $R^2$ are epoxyalkyl radicals, are prepared from compounds of formula I, in which $R^1$ and/or $R^2$ are both hydrogen atoms and $R^3$ to $R^{10}$ have the above-given meanings but are not hydroxyl groups, by reaction with an appropriate haloepoxyalkane. If the reaction of haloepoxyalkanes takes place with compounds of formula VI or VII and if Z is a methyl radical, then the epoxide ring is opened in the case of the conversion of the substituted imide into the free imide with the formation of vicinal diols, compounds being obtained of formula I, in which $R^1$ and/or $R^2$ are dihydroxyalkyl radicals. The epoxide ring can also be opened with amines before splitting off the protective group Z. After conversion of the substituted imide group into the free imide group, there are obtained compounds of formula I, in which $R^1$ and/or $R^2$ are aminohydroxyalkyl radicals.

Compounds of formula I, in which one or up to four of the symbols $R^3$ to $R^{10}$ are hydroxyl groups, can be prepared in known manner by the ether splitting of compounds of formula I, in which on or more of the symbols $R^3$ to $R^{10}$ are $C_1$-$C_4$-alkoxy radicals.

Compounds of formula I, in which one or up to four of the symbols $R^3$ to $R^{10}$ are unsubstituted or substituted aminoalkoxy or acyloxy radicals, can be prepared in known manner by the aminoalkylation or acylation of compounds of formula I, in which one or up to four of the symbols $R^3$ to $R^{10}$ are hydroxyl groups.

Compounds of formula I may also be obtained by the processes described in EP-A-0 328 026.

Compounds of formula I which have a chiral center can be used in the form of stereoisomeric mixtures or in the form of enantiomers. The enantiomers can be obtained by the processes usually employed for the optical separation of stereoisomers.

Compounds of formula I may be obtained as regioisomeric mixtures which may be separated into the single compounds by the usually known processes.

Thus, other aspects of the present invention are the enantiomers of the stereoisomeric mixtures and the single compounds of the regioisomeric mixture.

Basic compounds of formula I which contain a basic center on at least one of the substituents $R^1$ to $R^{10}$ are, for the purpose of purification and for galenical reasons, preferably converted into crystalline, pharmacologically acceptable salts. The salts are obtained in the usual way by neutralizing the bases with appropriate inorganic or organic acids. As acids, there can be used, for example, hydrochloric acid, sulphuric acid, phosphoric acid, hydrobromic acid, acetic acid, tartaric acid, lactic acid, citric acid, malic acid, salicylic acid, ascorbic acid, malonic acid, fumaric acid, oxalic acid or succinic acid. As a rule, the acid addition salts are obtained in known manner by mixing the free base or a solution thereof with an appropriate acid or a solution thereof in an organic solvent, for example, a lower alcohol, such as methanol, ethanol or propan-2-ol, or a lower ketone, such as acetone or butan-2-one, or an ether, such as diethyl ether, diisopropyl ether, tetrahydrofuran or dioxan.

The compounds of the present invention are potent inhibitors of protein kinase C. Surprisingly, they show a selective action, because much higher concentrations of the compounds of the present invention have to be used for inhibiting other kinases, for example, the A-kinase, the G-kinase, or the MLC-kinase. This takes place especially for compounds of formula I in which one indole group is unsubstituted on the indole nitrogen atom and the other indole group is appropriately substituted on the indole nitrogen atom and in the benzene moiety. Thus, for example, the compound of Example 1 shows, in the enzyme assay of protein kinase C, a 50% inhibition at a concentration of 0.14 μmol/L, whereas the IC values of the inhibition of the A-kinase, G-kinase, and MLC-kinase are 77 μmol/L, 15 μmol/L, and 4.5 μmol/L, respectively.

Protein kinase C plays an important key role for the intracellular signal transduction and is closely connected with the regulation of contractile, secretory, and proliferative processes. On the basis of these properties, the compounds according to the present invention can be used for the treatment of heart and blood vessel diseases such as thromboses, arteriosclerosis and hypertension, of inflammatory processes, allergies, cancer and certain degenerative damages of the central nervous system, as well as of diseases of the immune system and viral diseases. In the particularly appropriate formulation, the compounds can be administered enterally or parenterally in doses of 1 to 500 mg/kg and preferably of 1 to 50 mg/kg. With respect to the good to excellent selectivity against PKC compared to other kinases, the compounds of the present invention have much fewer side effects in the treatment of the above-mentioned diseases.

The compounds of formula I, according to the present invention, can be administered orally or parenterally in liquid or solid form. As injection solution, it is especially preferred to use water which contains the additives usual in the case of injection solutions, such as stabilizing agents, solubilizing agents, and/or buffers. Such additives include, for example, tartrate and citrate buffers, ethanol, complex formers (such as ethylenediaminetetracetic acid and the nontoxic salts thereof), as well as high molecular weight polymers (such as liquid polyethylene oxide) for viscosity regulation. Solid carrier materials include, for example, starch, lactose, mannitol, methylcellulose, talc, highly dispersed silicic acids, high molecular weight fatty acids (such as stearic acid), gelatine, agar-agar, calcium phosphate, magnesium stearate, animal and vegetable fats, and solid high molecular weight polymers (such as polyethylene glycol). Compositions suitable for oral administration can, if desired, additionally contain flavoring and/or sweetening agents.

The following Examples are given for the purpose of illustrating the present invention.

EXAMPLE 1

2-(1H-Indol-3-yl)-3-(1-methyl-1H-indol-3-yl)maleinimide 0.3 g (0.87 mmol) 2-(1H-indol-3-yl)-3-(1-methyl-1H-indol-3-yl)-maleic acid anhydride and 15 g ammonium acetate are heated to 140° C. for 30 minutes. After cooling, the reaction mixture is stirred with a large amount of water, the red precipitate is filtered off with suction, well washed with water and dried in a vacuum at 0.1 Torr and 120° C. There is obtained 0.25 g (83% of theory) of red product; m.p. 210° C. (decomp.); RF=0.40 (toluene/ethanol 10:2 v/v).

The 2-(1H-indol-3-yl)-3-(1-methyl-1H-indol-3-yl)maleic acid anhydride used as starting material is prepared as follows: 0.5 g (1.4 mmole) 2-(1H-indol-3-yl)-3-(1-methyl-1H-indol-3-yl)-N-methylmaleinimide and a solution of 10 g potassium hydroxide in 100 ml methanol/water (1:1 v/v) is heated under reflux for 1 hour. After cooling, the red reaction mixture is acidified with semiconcentrated hydrochloric acid and extracted with chloroform. After drying over anhydrous sodium sulphate, the extraction agent is removed by rotary evaporation and the residue is triturated with a little toluene. The red product is filtered off with suction and dried in a vacuum at 0.1 Torr and 70° C. There is obtained 0.38 g (79% of theory) of red crystals; m.p. 234° C. (decomp.); RF=0.60 (toluene/ethanol 10:1 v/v).

The 2-(1H-indol-3-yl)-3-(1-methyl-1H-indol-3-yl)-N-methylmaleinimide used as starting material is prepared as follows: A solution of 9.1 mmol ethyl magnesium bromide in 10 ml tetrahydrofuran is mixed with a solution of 1.1 g (9.1 mmol) indole in 10 ml tetrahydrofuran. The reaction mixture is stirred for 1 hour at ambient temperature, mixed with a solution of 1.2 g (3.7 mmol) 2-bromo-3-(1-methyl-1H-indol-3-yl)-N-methylmaleinimide in 10 ml, tetrahydrofuran and heated under reflux for 4 hours. The reaction mixture is allowed to cool, decomposed with a saturated solution of ammonium chloride and extracted with ethyl acetate, After drying over anhydrous sodium sulphate, the ethyl ester is removed by rotary evaporation and the residue is flash chromatographed on silica gel (Merck type 7734), using a mixture of toluene and ethanol (10+0.5 v/v) as elution agent. The unreacted starting material is first eluted and then the desired product. The product-containing fractions are combined, the elution agent is stripped off and the residue is triturated with a little toluene/petroleum ether. After suction filtration and drying in a vacuum at 0.1Torr and 70° C., there is obtained 0.6 g of red crystals (45% of theory); m.p. 205° C.; RF=0.32 (toluene+ethanol 10+2 v/v).

The 2-bromo-3-(1-methyl-1H-indol-3-yl)-N-methylmaleinimide used as starting material is prepared as follows: 1.4 g (5 mmol) 2-bromo-3-(1H-indol-3-yl)maleinimide is dissolved in 20 ml dimethylformamide and carefully mixed under an atmosphere of nitrogen with 0.3 sodium hydride (80% suspension in paraffin oil). The reaction mixture is further stirred for 1 hour at ambient temperature, mixed with a solution of 1.6 g (11.2 mmol) methyl iodide in 5 ml dimethylformamide and heated to 60° C. for 6 hours. After cooling, the solvent is distilled off under water-pump vacuum and the residue is triturated with water. The orange-coloured precipitate is filtered off with suction and crystallised from a little methanol. There are obtained 1.3 g (81% of theory) of orange-coloured crystals; m.p. 167° C.; RF=0.48 (hexane/ethyl acetate 1:1 v/v).

The 2-bromo-3-(1H-indol-3-yl)-maleinimide used as starting material is prepared as follows: A solution of 49.3 mmol ethyl magnesium bromide in 30 ml tetrahydrofuran is mixed with a solution of 5.8 g (49.5 mmol) indole in 50 ml toluene. The reaction mixture is stirred for 1 hour at ambient temperature, a solution of 2.5 g (9.8 mmol) dibromomaleinimide in 20 ml tetrahydrofuran/50 ml toluene is then slowly added dropwise thereto and heated under reflux for 30 hours. After cooling, the reaction mixture is decomposed with a saturated aqueous solution of ammonium chloride, the products are extracted with ethyl acetate and the organic phase is subsequently dried over anhydrous sodium sulphate. After evaporation, the red residue obtained is triturated with a little dichloromethane, filtered off with suction and dried in a vacuum at 0.1 Torr and 70° C. There are obtained 2.2 g (75% of theory) of orange-coloured product; m.p. 196° C.; RF=0.35 (hexane/ethyl acetate 1:1 v/v).

EXAMPLE 2

2-(1H-Indol-3-yl)-3-[1-(3-dimethylaminopropyl)-1H-indol-3-yl]-maleinimide 0.20 g (0,44 mmol) 2-(1H-indol-3-yl)-3-[1-(3-dimethylaminopropyl)-1H-indol-3-yl]-maleic acid anhydride hydrochloride and 10 g ammonium acetate are heated to 140° C. for 30 minutes. After cooling, the reaction mixture is mixed with water and extracted with ethyl acetate. The organic phase is well washed out with an aqueous solution of sodium bicarbonate and thereafter with water and dried over anhydrous sodium sulphate. The ethyl acetate is removed by rotary evaporation, the red residue obtained is stirred with a little water and the precipitated red product is filtered off with suction. After drying in a vacuum at 0.1 Torr and 140° C., there is obtained 0.156 g (91% of theory) of red product; m.p. about 280° C. (decomp.); RF=0.16 (chloroform/methanol 10:2 v.v).

The 2-(1H-indol-3-yl)-3-[1-(3-dimethylaminopropyl)-1H-indol-3-yl]-maleic acid anhydride used as starting material is prepared as follows: 0.5 g (0.95 mmol) 2-(1-tert.-butoxycarbonyl-1H-indol-3-yl)-3-[1-(3-dimethylaminopropyl)-1H-indol-3-yl)-N-methylmaleinimide and 50 ml of a 10% solution of potassium hydroxide in methanol/water (1:1 v/v) are heated under reflux for 30 minutes. After cooling, the reaction mixture is carefully acidified with concentrated hydrochloric acid and extracted with chloroform. The organic phase is washed out with water and evaporated to dryness. The red residue is triturated with a little methanol/toluene, filtered off with suction and dried at 80° C. There are obtained 0.34 g (79.5% of theory) of a dark red product; m.p. 232°–234° C. (decomp.).

The 2-(1-tert. -butoxycarbonyl-1H-indol-3-yl)-3-[1-(3-dimethylaminopropyl)-1H-indol-3-yl]-N-methylmaleinimide used as starting material is prepared as follows: A mixture of 0.9 g (2.03 mmol) 2-(1-tert.-butoxycarbonyl-1H-indol-3-yl)-3-(1H-indol-3-yl)-N-methylmaleinimide (Tetrahedron, 44, 2887/1988), 0,3 g potassium carbonate and 0.3 g (2.4 mmol) 3-dimethylaminopropyl chloride in 10 ml acetone is stirred for 12 hours at ambient temperature and for 8 hours under reflux. After cooling, the reaction mixture is poured into water and extracted with ethyl acetate. The red extract is evaporated and the residue flash chromatographed on silica gel (Merck Type 7734) using, as elution agent, a mixture of toluene/ethanol (10+1.5 v/v). The desired product is obtained in the form of a red oil and used as such in the above reaction. Yield 0.8 g (74% of theory); RF=0,20 (toluene/ethanol 1:2 v/v).

EXAMPLE 3

2-(5-Hydroxy-1H-indol-3-yl)-3-(1H-indol-3-yl)maleinimide 0.15 g (0.34 mmol) 2-(5-benzyloxy-1H-indol-3-yl)-3-(1H-indol-3-yl)-maleinimide and 4.0 g (34 mmol) pyridinium hydrochloride are heated under an atmosphere of nitrogen for 1 hour at 150° C. After cooling, the reaction mixture is diluted with ice water and extracted with ethyl acetate. The organic phase is washed out with water and evaporated to dryness. The solid residue is triturated with a little water, filtered off with suction and dried in a vacuum at 0.1 Torr and 80° C. There are obtained 85 mg (73% of theory) of dark red product; m.p. 200°–205° C.; RF=0.29 (toluene/ethanol 10:2 v/v).

EXAMPLE 4

2-(5-Benzyloxy-1H-indol-3-yl)-3-(1H-indol-3-yl)maleinimide 0.7 g (1.6 mmol) 2-(5-benzyloxy-1H-indol-3-yl)-3-(1H-indol-3-yl)-maleic acid anhydride and 9.5 g ammonium acetate are heated to 140° C. for 30 minutes. After cooling, the reaction mixture is stirred with water, the precipitate obtained is filtered off with suction, well washed out with water and dried in a vacuum at 0.1 Torr and 80° C. There is obtained 0.54 g (78% of theory) of orange-coloured product; m.p. 308°–312° C.; RF=0.29 (hexane/ethyl acetate 1:1 v/v).

The 2-(5-benzyloxy-1H-indol-3-yl)-3-(1H-indol-3-yl)maleic acid anhydride used as starting material is prepared as follows: A solution of 1.0 g (1.83 mmol) 2-(5-benzyloxy-1H-indol-3-yl)-3-(1-tert.-butoxycarbonyl-1H-indol-3-yl)-N-methylmaleinimide in 100 ml 10% potassium hydroxide solution (methanol/water 1:1 v/v) is heated under reflux for 1 hour. After cooling, the reaction mixture is carefully acidified with semi-concentrated hydrochloric acid, a red precipitate thereby being obtained. The precipitate is filtered off with suction, well washed out with water and dried in the air. There is obtained 0,7 g (87% of theory) of orange-coloured product; m.p. 236° C.; RF=0.43 (hexane/ethyl acetate 1:1 v/v).

The 2-(5-benzyloxy-1H-indol-3-yl)-3-(1-tert.-butoxycarbonyl-1H-indol-3-yl)-N-methylmaleinimide used as starting material is prepared as follows: A solution of 20 mmol ethyl magnesium bromide in 30 ml tetrahydrofuran is mixed with a solution of 4.46 g (20 mmol) 5-benzoxyindole in 20 ml tetrahydrofuran. The reaction mixture is maintained at 50° C. for 1 hour and then, within the course of 1 hour, a solution of 3.0 g (7.4 mmol) 2-bromo-3-[1-tert.-butoxycarbonyl-1H-indol-3-yl]-N-methylmaleinimide (Tetrahedron, 44, 2887/1988) in 40 ml tetrahydrofuran added dropwise thereto. The reaction mixture is heated under reflux for 2 hours, allowed to cool and then decomposed with a saturated aqueous solution of ammonium chloride. The reaction product is extracted with ethyl acetate, the organic phase is dried over anhydrous sodium sulphate and evaporated to dryness. The residue is flash chromatographed on silica gel (Merck Type 7734) using dichloromethane as elution agent. After elution of unreacted starting material, the desired product is obtained by evaporation of the appropriate fractions and stirring the red residue with a little toluene. There are obtained 1.3 g (32% of theory) of red crystals; m.p. 123° C.

EXAMPLE 5

2,3-Bis-(5-methoxy-1H-indol-3-yl)-maleinimide

A solution of 22 mmol ethyl magnesium bromide in 30 ml tetrahydrofuran is mixed at ambient temperature with a solution of 2.8 g (19 mmol) 5-methoxyindole in 50 ml toluene and stirred for 1 hour at ambient temperature. Under an atmosphere of nitrogen, there is then added dropwise thereto a solution of 1.5 g (5.8 mmol) dibromomaleinimide in 20 ml tetrahydrofuran/50 ml toluene and heated under reflux for 20 hours. After cooling, the reaction mixture is decomposed with a saturated aqueous solution of ammonium chloride, the products are extracted with ethyl acetate and the organic phase is dried over anhydrous sodium sulphate. After evaporation, the red residue obtained is triturated with a little methanol and the precipitated red product is filtered off with suction and dried in a vacuum at 0.1 Torr and 100° C. There is obtained 0.9 g (36% of theory) of red crystals; m.p. 336° C. (decomp.); RF=0.30 (toluene/ethanol 10:2 v.v).

EXAMPLE 6

2-(1H-Indol-3-yl)-3-(5,5-methylenedioxy-1H-indol-3-yl)-maleinimide 0.8 g (2.1 mmol) 2-(1H-indol-3-yl)-3-(5,6-methylenedioxy-1H-indol-3-yl)-maleic acid anhydride, together with 20 g ammonium acetate, are heated for 1 hour to 140° C. (melt). After cooling, the reaction mixture is mixed with water and the red-brown precipitate obtained is filtered off with suction. For purification, it is chromatographed on silica gel with dichloromethane/ethyl acetate (3:1 v/v) as elution agent. There is obtained 0.40 g (45% of theory) 2-(1H-indol-3-yl)-3-(5,6-methylenedioxy-1H-indol-3-yl)maleinimide in the form of red crystals; m.p. 150° C. (decomp.); RF=0.4 (methylene chloride/ethyl acetate 3:1 v/v).

The 2-(1H-indol-3-yl)-3-(5,6-methylenedioxy-1H-indol-3-yl)-maleic acid anhydride used as starting material is prepared as follows: 4.0 g (10.4 mmol) 2-(1H-indol-3-yl)-3-(5,6-methylenedioxy-1H-indol-3-yl)-N-methylmaleinimide, together with a solution of 160 g potassium hydroxide in 1600 ml water, are heated under reflux for 30 minutes. The initially red suspension thereby passes over into a brown solution. It is allowed to cool, acidified with concentrated hydrochloric acid and the red precipitate obtained is filtered off with suction. There are obtained 3.40 g (88% of theory) 2-(1H-indol-3-yl)-3-(5,6-methylenedioxy-1H-indol-3-yl)-maleic acid anhydride in the form of bright red crystals; m.p. 200° C. (decomp.) after recrystallisation from methanol; RF=0.70 (dichloromethane/ethyl acetate 3:1 v/v).

The 2-(1H-indol-3-yl)-3-(5,6-methylenedioxy-1H-indol-3-yl)-N-methylmaleinimide used as starting material is prepared as follows: 8.06 g (50 mmol) 5,6-methylenedioxy-indole are dissolved in 400 ml toluene and mixed at 60° C. with 25 ml of a 2M solution of ethyl magnesium bromide in tetrahydrofuran (Aldrich). After 1 hour at 60° C., a solution of 8.1 g (20 mmol) 2-bromo-3-(1-tert.-butyloxycarbonyl-1H-indol-3-yl)-N-methylmaleinimide in 100 ml toluene is added dropwise thereto, followed by heating under reflux for 3 hours. After cooling to ambient temperature, hydrolysis is carried out by the addition of 100 ml saturated aqueous ammonium chloride solution. The organic phase is separated off, the aqueous phase is shaken out with ethyl acetate, the residues are dissolved in ethyl acetate, the combined organic phases are dried and evaporated and the residue is chromatographed on 600 g silica gel with dichloromethane/ethyl acetate (3:1 v/v) as elution agent. There are obtained 3.75 g 5,6-methylenedioxyindole; m.p. 104°-106° C., 0.55 g 2-bromo-3-(1H-indol-3-yl)-N-methylmaleinimide and 7.27 g (94% of theory) 2-(1H-indol-3-yl)-3-(5,6-methylenedioxy-1H-indol-3-yl)-N-methylmaleinimide in the form of red crystals; m.p. 140° C. (decomp.); RF=0.6 dichloromethane/ethyl acetate 3:1 v/v).

EXAMPLE 7

2-(1H-Indol-3-yl)-3-(5,6-dimethoxy-1H-indol-3-yl)maleinimide 3.0 g (7.72 mmol) 2-(1H-indol-3-yl)-3-(5,6-dimethoxy-1H-indol-3-yl)-maleic acid anhydride, together with 75 g ammonium acetate, are heated to 140° C. for 1 hour. After cooling, the reaction mixture is mixed with 1.5 l of water and the dark red precipitate is filtered off with suction. There is obtained a crude yield of 2.61 g. For purification, 1.75 g thereof is chromatographed on silica gel with dichloromethane/ethyl acetate (8:1 v/v) as elution agent. There are obtained 1.20 g 2-(1H-indol-3-yl)-3-(5,6-dimethoxy-1H-indol-3-yl)-maleinimide×0.5 ethyl acetate in the form of dark red crystals; m.p. 120° C. (decomp.); RF=0.32 (dichloromethane/ethyl acetate 3:1 v/v). Yield 54% of theory.

The 2-(1H-indol-3-yl)-3-(5,6-dimethoxy-1H-indol-3-yl)maleic acid anhydride used as starting material is prepared as follows: 10 g (25 mmol) 2-(1H-indol-3-yl)-3-(5,6-dimethoxy-1H-indol-3-yl)-N-methylmaleinimide are heated under reflux for 30 minutes in 4000 ml 10% aqueous potassium hydroxide solution. The initially red suspension thereby passes over into a brown solution. After cooling, acidification is carried out with concentrated hydrochloric acid and the red precipitate obtained is filtered off with suction. The precipitate is heated in methanol and filtered. There are obtained 8.46 g 2-(1H-indol-3-yl)-3-(5,6-dimethoxy-1H-indol-3-yl)-maleic acid anhydride (87.6% of theory) in the form of dark red crystals; m.p. about 320 ° C. (decomp.); RF=0.50 (dichloromethane/ethyl acetate 3:1 v/v).

The 2-(1H-indol-3-yl)-3-(5,6-dimethoxy-1H-indol-3-yl)-N-methylmaleinimide used as starting material is prepared as follows: 22.15 g (0.125 mol) 5,6-dimethoxyindole are dissolved in 1000 ml toluene and mixed at 40° C. with 62.5 ml of a 2M solution of ethyl magnesium bromide in tetrahydrofuran (Aldrich). After 1 hour at 60° C., there is added dropwise a solution of 20.26 g (0.05 mol) 2-bromo-3-(1-tert.-butyloxycarbonyl-1H-indol-3-yl)-N-methylmaleinimide in 250 ml toluene, followed by heating under reflux for 3 hours. After cooling, hydrolysis is carried out by the addition of a saturated aqueous solution of ammonium chloride. The red precipitate formed is filtered off and chromatographed on silica gel with dichloromethane/ethyl acetate (10:1 v/v) as elution agent. There are obtained 6.51 g 2-(1H-indol-3-yl)-3-(5,6-dimethoxy-1H-indol-3-yl)-N-methylmaleinimide (32% of theory) in the form of red crystals; m.p. 258° C.; RF=0.44 (dichloromethane/ethyl acetate 3:1 v/v); and 7.17 g (about 35% of theory) of red crystals of the same but slightly contaminated compound; m.p. 250°-254° C.

EXAMPLE 8

2,3-Bis-(5,6-methylenedioxy-1H-indol-3-yl)maleinimide 6.44 g (40 mmol) 5,6-methylenedioxyindole are dissolved in 300 ml anhydrous toluene and mixed dropwise at 60° C. with 20 ml of a 2M solution of ethyl magnesium bromide in tetrahydrofuran (Aldrich). After completion of the addition, there is added dropwise thereto a solution of 1.7 g (6.67 mmol) dibromomaleinimide in 50 ml toluene, with the addition of the minimum amount of tetrahydrofuran required for solution, and then heated under reflux for 18 hours. After cooling, the reaction mixture is mixed with a saturated aqueous solution of ammonium chloride, the organic phase is separated off and the aqueous phase is extracted three times with toluene and once with ethyl acetate. The combined organic phases are dried, rotary evaporated and chromatographed in silica gel (elution agent: dichloromethane/ethyl acetate 30:1 v/v). There is obtained 1.27 g (56% of theory) 2-bromo-3-(5,6-methylenedioxy-1H-indol-3-yl)maleinimide; m.p. about 185° C. (decomp.); RF=0.50 (dichloromethane/ethyl acetate 3:1 v/v); and 0.63 g (22.5% of theory) 2,3-bis-(5,6-methylenedioxy-1H-indol-3-yl)-maleinimide in the form of red crystals; m.p, about 270° C. (decomp.), after recrystallisation from propanol; RF=0.36 (dichloromethane/ethyl acetate 3:1 v/v).

EXAMPLE 9

2,3-Bis-(1H-indol-3-yl)-maleinimide was obtained in the manner described in the literature (Tetrahedron, 44, 2887/1988).

EXAMPLE 10

2-(6-Hydroxy-1H-indol-3-yl)-3-(1H-indol-3-yl)maleinimide was obtained in the manner described in the literature (Tetrahedron, 44, 2887/1988).

In an analogous manner to Examples 1 to 10 and to the other processes as disclosed there are obtained:

11.) 2-(5-benzyloxy-1H-indol-3-yl)-3-[1-(3-dimethylaminopropyl)-1H-indol-3-yl]maleinimide, 188°-189° C.;

12.) 2-[5-benzyloxy-1-(3-dimethylaminopropyl)-1H-indol-3-yl]-3-(1H-indol-3-yl)maleinimide, 240°-241° C.;

13.) 2-(5-methoxy-1H-indol-3-yl)-3-[5-methoxy-1-(3-dimethylaminopropyl)-1H-indol-3-yl]maleinimide, 250°-251° C.;

14.) (±)-2-(1H-indol-3-yl)-3-[1-(3-dimethylamino-2-methoxypropyl)-1H-indol-3-yl]maleinimide, 218° C., decomp.;

15.) 2-(1H-indol-3-yl)-3-[5-(3-dimethylaminopropyloxy)-1H-indol-3-yl]maleinimide, 235° C.;

16.) 2,3-bis-(5-fluoro-1H-indol-3-yl)maleinimide, 320° C., decomp.;

17.) 2-(5-fluoro-1H-indol-3-yl)-3-[5-fluoro-1-(3-dimethylaminopropyl)-1H-indol-3-yl]maleinimide, 283°-285° C.;

18.) 2,3-bis-(5-benzyloxy-1H-indol-3-yl)maleinimide, 130° C., Zers.;

19.) 2-(5-benzyloxy-1H-indol-3-yl)-3-[5-benzyloxy-1-(3-dimethylaminopropyl-1H-indol-3-yl]maleinimide, 277° C., Zers.;

20.) 2-(5-benzyloxy-1-methyl-1H-indol-3-yl)-3-(1-methyl-1H-indol-3-yl)maleinimide;

21.) 2-[5-benzyloxy-1-(3-dimethylaminopropyl)-1H-indol-3-yl]-3-(1-methyl-1H-indol-3-yl)maleinimide, 181°-182° C.;

22.) 2,3-bis-(5-chloro-1H-indol-3-yl)maleinimide, 279°-281° C., decomp.;

23.) 2-(5-chloro-1H-indol-3-yl)-3-[5-chloro-1-(3-dimethylaminopropyl)-1H-indol-3-yl]maleinimide, 255°-257° C., decomp.;

24.) 2,3-bis-(5-methyl-1H-indol-3-yl)maleinimide, 180° C., decomp.;

25.) 2-(5-methyl-1H-indol-3-yl)-3-[5-methyl-1-(3-dimethylaminopropyl)-1H-indol-3-yl]maleinimide, 215° C.;

26.) 2,3-bis-(5-brom-1H-indol-3-yl)maleinimide, 351° C.;

27.) 2-(5-bromo-1H-indol-3-yl)-3-[5-bromo-1-(3-dimethylaminopropyl)-1H-indol-3-yl]maleinimide, 257°-258° C.;

28.) 2-(1H-indol-3-yl)-3-[1-(3-dimethylaminoethyl)-1H-indol-3-yl]-maleinimide, pale red crystals, 246°-248° C., decomp., prepared by process C;

29.) 2-(1H-indol-3-yl)-3-[1-(3-(1-piperidino)propyl)-1H-indol-3-yl]-maleinimide, pale orange crystals, 204° C., prepared by process C;

30.) 2-(1H-indol-3-yl)-3-[1-(3-(4-morpholino)propyl)-1H-indol-3-yl]-maleinimide, pale orange crystals, 285°-287° C., decomp., prepared by process C;

31.) 2-[1-(3-diethylaminopropyl)-1H-indol-3-yl]-3-(1H-indol-3-yl)-maleinimide, pale orange crystals, 241°-242° C., decomp., prepared by process C;

32.) (±)-2-[1-(3-diethyl amino-2-hydroxypropyl)-1H-indol-3-yl]-3-(1H-indol-3-yl)-maleinimide, dark red crystals, 158° C., prepared by process C by use of 1,1-diethyl-3-hydroxyazetidiniumchloride as alkylating agent;

33.) 2-(5-methoxy-1H-indol-3-yl)-3-[1-(3-dimethylaminopropyl)-1H-indol-3-yl]-maleinimide, pale orange crystals, 224°-225° C., prepared by process C by use of the SEM protecting group;

34.) 2-(1H-indol-3-yl)-3-[5-methoxy-1-(3-dimethylaminopropyl)-1H-indol-3-yl]-maleinimide, pale red crystals, 234°-236° C., prepared by process B by use of the SEM protecting group;

35.) (±)-2-[1-(2,3-dihydroxypropyl)-1H-indol-3-yl]-3-(1H-indol-3-yl)-maleinimide, dark red crystals, 135° C., prepared by process B by use of the BOC protecting group and epibromohydrin as alkylating agent;

36.) 2-(5-methoxy-1H-indol-3-yl)-3-[1-(3-(4-morpholino)propyl)-1H-indol-3-yl]-maleinimide and 37.) 2-(1H-indol-3-yl)-3-[5-methoxy-1-(3-(4-morpholino)propyl)-1H-indol-3-yl]-maleinimide, as regioisomeric mixture 1:1, orange crystals, 132°-135° C., prepared by process B by use of the BOC protecting group;

38.) (±)-2-[1-(3-Ethoxy-2-hydroxypropyl)-1H-indol-3-yl]-3-(1H-indol-3-yl)-maleinimide, dark red crystals, 130°-134° C. prepared by process B by use of the BOC protecting group and epibromohydrin as alkylating agent;

39.) (±)-2-[1-(2-hydroxy-3-(1-piperidino)-propyl)-1H-indol-3-yl]-3-(1H-indol-3-yl)-maleinimide, dark red crystals, 142° C., decomp., prepared by process B by use of the BOC protecting group and epibromohydrin as alkylating agent;

40.) (±)-2-[1-(3-diethylamino-2-hydroxypropyl)-5-methoxy-1H-indol-3-yl]-3-(1H-indol-3-yl)-maleinimide and 41.) (±)-2-[1-(3-diethylamino-2-hydroxypropyl)-1H-indol-3-yl]-3-(5-methoxy-1H-indol-3-yl)-maleinimide, as regioisomeric mixture 4:1, dark red crystals, above 150° C. decomp., prepared by process B by use of the BOC protecting group and 1,1-diethyl-3-hydroxyazetidinium-chloride as alkylating agent;

42.) 2-(1H-indol-3-yl)-3-[5-methoxy-1-(3-(1-piperidino)-propyl)-1H-indol-3-yl]-maleinimide, 257°-258° C., and with 43.) 2-(5-methoxy-1H-indol-3-yl)-3-[1-(3-(1-piperidino)-propyl)-1H-indol-3-yl]-maleinimide, as regioisomeric mixture 1:1, orange crystals, 150° C., prepared by process B by use of the BOC protecting group;

44.) 2-[1-(3-diethylaminopropyl)-5-methoxy-1H-indol-3-yl]-3-(5,6-dimethoxy-1-methyl-1H-indol-3-yl)-maleinimide, pale red crystals, 165°-166° C., prepared by process A;

45.) 2-[1-(3-diethylaminopropyl)-5-methoxy-1H-indol-3-yl]-3-(1H-indol-3-yl)-maleinimide and 46.) 2-[1-(3-diethylaminopropyl)-1H-indol-3-yl)-3-(5-methoxy-1H-indol-3-yl)-maleinimide, as regioisomeric mixture 3:2, pale red crystals, 206°-208° C., decomp, prepared by process B by use of the BOC protecting group;

47.) 2-[1-(3-diethylaminopropyl)-1H-indol-3-yl]-3-(5-methoxy-1H-indol-3-yl)-maleinimide and
48.) 2-[1-(3-diethylaminopropyl)-5-methoxy-1H-indol-3-yl]-3-(1H-indol-3-yl)-maleinimide, as regioisomeric mixture 3:1, pale red crystals, 185°-190° C., prepared by process B.
49.) 2-[1-(3-diethylaminopropyl)-5-methoxy-1H-indol-3-yl]-3-(6-methoxy-1H-indol-3-yl)-maleinimide and
50.) 2-[1-(3-diethylaminopropyl)-6-methoxy-1H-indol-3-yl]-3-(5-methoxy-1H-indol-3-yl)-maleinimide, as regioisomeric mixture 5:1, red crystals, 176°-182° C., prepared by process B.
51.) 2-[5-fluoro-1-(3-dimethylaminopropyl)-1H-indol-3-yl]-3-(1H-indol-3-yl)-maleinimide and
52.) 2-(5-fluoro-1H-indol-3-yl)-3-[1-(3-dimethylaminoplopyl)-1H-indol-3-yl]-maleinimide, as regioisomeric mixture 3:1, 230°-235° C.
53.) 2-(5-bromo-1H-indol-3-yl)-3-(1H-indol-3-yl)-maleinamide, m.p. 284° C.
54.) 2-(5-fluoro-1H-indol-3-yl)-3-(1H-indol-3-yl)-maleinimide, m.p. 265° C.
55.) 2-[1-(3-diethylaminopropyl)-5-fluoro-1H-indol-3-yl]-3-(1H-indol-3-yl)-maleinimide.HCl, m.p. 136°-139° C.
56.) (±)-2-[1-(2,3-dihydroxypropyl)-5-methoxy-1H-indol-3-yl]-3-(1H-indol-3-yl)-maleinimide, m.p. 203°-206° C.
57.) (±)-2-[1-(3-ethoxy-2-hydroxypropyl)-5-methoxy-1H-indol-3-yl]-3-(1H-indol-3-yl)-maleinimide, m.p. 185°-187° C.
58.) 2-[1-(2-cyanoethyl)-5-methoxy-1H-indol-3-yl]-3-(1-methyl-1H-indol-3-yl)-maleinimide, m.p.200° C., dec.
59.) 2-[1-(2-cyanoethyl)-1H-indol-3-yl]-3-(1-methyl-1H-indol-3-yl)-maleinimide, m.p. 250°-255° C., dec.
60.) 2-[1-(2-cyanoethyl)-1H-indol-3-yl]-3-(5-methoxy-1-methyl-1H-indol-3-yl)-maleinimide, m.p. 250° C., dec.
61.) 2-(1H-indol-3-yl)-3-[1-(3-diisopropylaminopropyl)-1H-indol-3-yl]-maleinimide, m.p. 167°-170° C.

In analogous manner the following compounds are prepared according to their substituents by one of the disclosed processes:

2-[1-(3-(amidinothio)propyl)-1H-indol-3-yl]-3-(1H-indol-3-yl)-maleinimide;
2-[1-(2-aminoethyl)-1H-indol-3-yl]-3-(1H-indol-3-yl)-maleinimide;
2-[1-(3-aminopropyl)-1H-indol-3-yl]-3-(1H-indol-3-yl)-maleinimide;
2-[1-(2-diethylaminoethyl)-1H-indol-3-yl]-3-(1H-indol-3yl)-maleinimide;
2-[1-(3-ethylaminopropyl)-1H-indol-3-yl]-3-(1H-indol-3-yl)-maleinimide;
(±)-2-[1-(2-hydroxy-3-dimethylaminopropyl)-1H-indol-3-yl]-3-(1H-indol-3-yl)-maleinimide;
(+)-2-[1-(2-hydroxy-3-dimethylaminopropyl)-1H-indol-3-yl]-3-(1H-indol-3-yl)-maleinimide;
(−)-2-[1-(2-hydroxy-3-dimethylaminopropyl)-1H-indol-3-yl]-3-(1H-indol-3-yl)-maleinimide;
(±)-2-[1-[2-hydroxy-3-(4-morpholino) propyl]-1H-indol-3-yl]-3-(1H-indol-3-yl)-maleinimide;
(+)-2-[1-[2-hydroxy-3-(4-morpholino) propyl]-1H-indol-3-yl]-3-(1H-indol-3-yl)-maleinimide;
(−)-2-[1-[2-hydroxy-3-(4-morpholino)propyl]-1H-indol-3-yl]-3-(1H-indol-3-yl)-maleinimide;
2-[1-(3-hydroxypropyl)-1H-indol-3-yl]-3-(1H-indol-3-yl)-maleinimide;
2-(1H-indol-3-yl)-3-[1-(3-isothiocyanatopropyl)-1H-indol-3-yl]-maleinimide;
(±)-2-(1H-indol-3-yl)-3-[1-(2-methoxy-3-dimethylaminopropyl)-1H-indol-3-yl]-maleinimide;
(+)-2-(1H-indol-3-yl)-3-[1-(2-methoxy-3-dimethylaminopropyl)-1H-indol-3-yl]-maleinimide;
(−)-2-(1H-indol-3-yl)-3-[1-(2-methoxy-3-dimethylaminopropyl)-1H-indol-3-yl]-maleinimide;
2-(1H-indol-3-yl)-3-[1-(3-dimethylaminopropyl)-1H-indol-3-yl]-maleinimide;
2-(1H-indol-3-yl)-3-[1-(3-methylaminopropyl)-1H-indol-3-yl]-maleinimide;
2-(1H-indol-3-yl)-3-[1-[3-(2-nitroguanidino) propyl]-1H-indol-3-yl]-maleinimide;
2-(4-acetylamino-1H-indol-3-yl)-3-(1H-indol-3-yl)-maleinimide;
2-(5-acetylamino-1H-indol-3-yl)-3-(1H-indol-3-yl)-maleinimide;
2-(6-acetylamino-1H-indol-3-yl)-3-(1H-indol-3-yl)-maleinimide;
2-(7-acetylamino-1H-indol-3-yl)-3-(1H-indol-3-yl)-maleinimide;
2-(4-amino-1H-indol-3-yl)-3-(1H-indol-3-yl)-maleinimide;
2-(5-amino-1H-indol-3-yl)-3-(1H-indol-3-yl)-maleinimide;
2-(6-amino-1H-indol-3-yl)-3-(1H-indol-3-yl)-maleinimide;
2-(7-amino-1H-indol-3-yl)-3-(1H-indol-3-yl)-maleinimide;
2-(4-benzyloxy-1H-indol-3-yl)-3-(1H-indol-3-yl)-maleinimide;
2-(5-benzyloxy-1H-indol-3-yl)-3-(1H-indol-3-yl)-maleinimide;
2-(6-benzyloxy-1H-indol-3-yl)-3-(1H-indol-3-yl)-maleinimide;
2-(7-benzyloxy-1H-indol-3-yl)-3-(1H-indol-3-yl)-maleinimide;
2-(4-bromo-1H-indol-3-yl)-3-(1H-indol-3-yl)-maleinimide;
2-(6-bromo-1H-indol-3-yl)-3-(1H-indol-3-yl)-maleinimide;
2-(7-bromo-1H-indol-3-yl)-3-(1H-indol-3-yl)-maleinimide;
2-(4-chloro-1H-indol-3-yl)-3-(1H-indol-3-yl)-maleinimide;
2-(5-chloro-1H-indol-3-yl)-3-(1H-indol-3-yl)-maleinimide;
2-(6-chloro-1H-indol-3-yl)-3-(1H-indol-3-yl)-maleinimide;
2-(7-chloro-1H-indol-3-yl)-3-(1H-indol-3-yl)-maleinimide;
2-(4-fluoro-1H-indol-3-yl)-3-(1H-indol-3-yl)-maleinimide;
2-(6-fluoro-1H-indol-3-yl)-3-(1H-indol-3-yl)-maleinimide;
2-(7-fluoro-1H-indol-3-yl)-3-(1H-indol-3-yl)-maleinimide;
2-(4-hydroxy-1H-indol-3-yl)-3-(1H-indol-3-yl)-maleinimide;
2-(5-hydroxy-1H-indol-3-yl)-3-(1H-indol-3-yl)-maleinimide;
2-(6-hydroxy-1H-indol-3-yl)-3-(1H-indol-3-yl)-maleinimide;
2-(7-hydroxy-1H-indol-3-yl)-3-(1H-indol-3-yl)-maleinimide;
2-(4-trifluoromethyl-1H-indol-3-yl)-3-(1H-indol-3-yl)-maleinimide;
2-(5-trifluoromethyl-1H-indol-3-yl)-3-(1H-indol-3-yl)-maleinimide;

2-(6-trifluoromethyl-1H-indol-3-yl)-3-(1H-indol-3-yl)-maleinimide;
2-(7-trifluoromethyl-1H-indol-3-yl)-3-(1H-indol-3-yl)-maleinimide;
2-(1H-indol-3-yl)-3-(4-methoxy-1H-indol-3-yl)-maleinimide;
2-(1H-indol-3-yl)-3-(5-methoxy-1H-indol-3-yl)-maleinimide;
2-(1H-indol-3-yl)-3-(6-methoxy-1H-indol-3-yl)-maleinimide;
2-(1H-indol-3-yl)-3-(7-methoxy-1H-indol-3-yl)-maleinimide;
2-(1H-indol-3-yl)-3-(4,5-methylendioxy-1H-indol-3-yl)-maleinimide;
2-(1H-indol-3-yl)-3-(5,6-methylendioxy-1H-indol-3-yl)-maleinimide;
2-(1H-indol-3-yl)-3-(6,7-methylendioxy-1H-indol-3-yl)-maleinimide;
2-(1H-indol-3-yl)-3-(4-methyl-1H-indol-3-yl)-maleinimide;
2-(1H-indol-3-yl)-3-(5-methyl-1H-indol-3-yl)-maleinimide;
2-(1H-indol-3-yl)-3-(6-methyl-1H-indol-3-yl)-maleinimide;
2-(1H-indol-3-yl)-3-(7-methyl-1H-indol-3-yl)-maleinimide;
2-(1H-indol-3-yl)-3-(4-nitro-1H-indol-3-yl)-maleinimide;
2-(1H-indol-3-yl)-3-(5-nitro-1H-indol-3-yl)-maleinimide;
2-(1H-indol-3-yl)-3-(6-nitro-1H-indol-3-yl)-maleinimide;
2-(1H-indol-3-yl)-3-(7-nitro-1H-indol-3-yl)-maleinimide;
2-(1H-indol-3-yl)-3-(4-methylthio-1H-indol-3-yl)-maleinimide;
2-(1H-indol-3-yl)-3-(5-methylthio-1H-indol-3-yl)-maleinimide;
2-(1H-indol-3-yl)-3-(6-methylthio-1H-indol-3-yl)-maleinimide;
2-(1H-indol-3-yl)-3-(7-methylthio-1H-indol-3-yl)-maleinimide;
2-(1H-indol-3-yl)-3-(4,5-dimethoxy-1H-indol-3-yl)-maleinimide;
2-(1H-indol-3-yl)-3-(5,6-dimethoxy-1H-indol-3-yl)-maleinimide;
2-(1H-indol-3-yl)-3-(6,7-dimethoxy-1H-indol-3-yl)-maleinimide;
2-[4-acetylamino-1-(3-(amidinothio) propyl)-1H-indol-3-yl]-3-(1H-indol-3-yl)-maleinimide;
2-[5-acetylamino-1-(3-(amidinothio)propyl)-1H-indol-3-yl]-3-(1H-indol-3-yl)-maleinimide;
2-[6-acetylamino-1-(3-(amidinothio)propyl)-1H-indol-3-yl]-3-(1H-indol-3-yl)-maleinimide;
2-[7-acetylamino-1-(3-(amidinothio)propyl)-1H-indol-3-yl]-3-(1H-indol-3-yl)-maleinimide;
2-[1-(3-(amidinothio)propyl)-4-amino-1H-indol-3-yl]-3-(1H-indol-3-yl)-maleinimide;
2-[1-(3-(amidinothio)propyl)-5-amino-1H-indol-3-yl]-3-(1H-indol-3-yl)-maleinimide;
2-[1-(3-(amidinothio)propyl)-6-amino-1H-indol-3-yl]-3-(1H-indol-3-yl)-maleinimide;
2-[1-(3-(amidinothio)propyl)-7-amino-1H-indol-3-yl]-3-(1H-indol-3-yl)-maleinimide;
2-[1-(3-(amidinothio)propyl)-4-benzyloxy-1H-indol-3-yl]-3-(1H-indol-3-yl)-maleinimide;
2-[1-(3-(amidinothio)propyl)-5-benzyloxy-1H-indol-3-yl]-3-(1H-indol-3-yl)-maleinimide;
2-[1-(3-(amidinothio)propyl)-6-benzyloxy-1H-indol-3-yl]-3-(1H-indol-3-yl)-maleinimide;
2-[1-(3-(amidinothio)propyl)-7-benzyloxy-1H-indol-3-yl]-3-(1H-indol-3-yl)-maleinimide;
2-[1-(3-(amidinothio)propyl)-4-bromo-1H-indol-3-yl]-3-(1H-indol-3-yl)-maleinimide;
2-[1-(3-(amidinothio)propyl)-5-bromo-1H-indol-3-yl]-3-(1H-indol-3-yl)-maleinimide;
2-[1-(3-(amidinothio)propyl)-6-bromo-1H-indol-3-yl]-3-(1H-indol-3-yl)-maleinimide;
2-[1-(3-(amidinothio)propyl)-7-bromo-1H-indol-3-yl]-3-(1H-indol-3-yl)-maleinimide;
2-[1-(3-(amidinothio)propyl)-4-chloro-1H-indol-3-yl]-3-(1H-indol-3-yl)-maleinimide;
2-[1-(3-(amidinothio)propyl)-5-chloro-1H-indol-3-yl]-3-(1H-indol-3-yl)-maleinimide;
2-[1-(3-(amidinothio)propyl)-6-chloro-1H-indol-3-yl]-3-(1H-indol-3-yl)-maleinimide;
2-[1-(3-(amidinothio)propyl)-7-chloro-1H-indol-3-yl]-3-(1H-indol-3-yl)-maleinimide;
2-[1-(3-(amidinothio)propyl)-4-fluoro-1H-indol-3-yl]-3-(1H-indol-3-yl)-maleinimide;
2-[1-(3-(amidinothio)propyl)-5-fluoro-1H-indol-3-yl]-3-(1H-indol-3-yl)-maleinimide;
2-[1-(3-(amidinothio)propyl)-6-fluoro-1H-indol-3-yl]-3-(1H-indol-3-yl)-maleinimide;
2-[1-(3-(amidinothio)propyl)-7-fluoro-1H-indol-3-yl]-3-(1H-indol-3-yl)-maleinimide;
2-[1-(3-(amidinothio)propyl)-4-hydroxy-1H-indol-3-yl]-3-(1H-indol-3-yl)-maleinimide;
2-[1-(3-(amidinothio)propyl)-5-hydroxy-1H-indol-3-yl]-3-(1H-indol-3-yl)-maleinimide;
2-[1-(3-(amidinothio)propyl)-6-hydroxy-1H-indol-3-yl]-3-(1H-indol-3-yl)-maleinimide;
2-[1-(3-(amidinothio)propyl)-7-hydroxy-1H-indol-3-yl]-3-(1H-indol-3-yl)-maleinimide;
2-[1-(3-(amidinothio)propyl)-4-trifluoromethyl-1H-indol-3-yl]-3-(1H-indol-3-yl)-maleinimide;
2-[1-(3-(amidinothio)propyl)-5-trifluoromethyl-1H-indol-3-yl]-3-(1H-indol-3-yl)-maleinimide;
2-[1-(3-(amidinothio)propyl)-6-trifluoromethyl-1H-indol-3-yl]-3-(1H-indol-3-yl)-maleinimide;
2-[1-(3-(amidinothio)propyl)-7-trifluoromethyl-1H-indol-3-yl]-3-(1H-indol-3-yl)-maleinimide;
2-[1-(3-(amidinothio)propyl)-4-methoxy-1H-indol-3-yl]-3-(1H-indol-3-yl)-maleinimide;
2-[1-(3-(amidinothio)propyl)-5-methoxy-1H-indol-3-yl]-3-(1H-indol-3-yl)-maleinimide;
2-[1-(3-(amidinothio)propyl)-6-methoxy-1H-indol-3-yl]-3-(1H-indol-3-yl)-maleinimide;
2-[1-(3-(amidinothio)propyl)-7-methoxy-1H-indol-3-yl]-3-(1H-indol-3-yl)-maleinimide;
2-[1-(3-(amidinothio)propyl)-4,5-methylendioxy-1H-indol-3-yl]-3-(1H-indol-3-yl)-maleinimide;
2-[1-(3-(amidinothio)propyl)-5,6-methylendioxy-1H-indol-3-yl]-3-(1H-indol-3-yl)-maleinimide;
2-[1-(3-(amidinothio)propyl)-6,7-methylendioxy-1H-indol-3-yl]-3-(1H-indol-3-yl)-maleinimide;
2-[1-(3-(amidinothio)propyl)-4-methyl-1H-indol-3-yl]-3-(1H-indol-3-yl)-maleinimide;
2-[1-(3-(amidinothio)propyl)-5-methyl-1H-indol-3-yl]-3-(1H-indol-3-yl)-maleinimide;
2-[1-(3-(amidinothio)propyl)-6-methyl-1H-indol-3-yl]-3-(1H-indol-3-yl)-maleinimide;
2-[1-(3-(amidinothio)propyl)-7-methyl-1H-indol-3-yl]-3-(1H-indol-3-yl)-maleinimide;
2-[1-(3-(amidinothio)propyl)-4-nitro-1H-indol-3-yl]-3-(1H-indol-3-yl)-maleinimide;

2-[1-(3-(amidinothio)propyl)-5-nitro-1H-indol-3-yl]-3-(1H-indol-3-yl)-maleinimide;
2-[1-(3-(amidinothio)propyl)-6-nitro-1H-indol-3-yl]-3-(1H-indol-3-yl)-maleinimide;
2-[1-(3-(amidinothio)propyl)-7-nitro-1H-indol-3-yl]-3-(1H-indol-3-yl)-maleinimide;
2-[1-(3-(amidinothio)propyl)-4-methylthio-1H-indol-3-yl]-3-(1H-indol-3-yl)-maleinimide;
2-[1-(3-(amidinothio)propyl)-5-methylthio-1H-indol-3-yl]-3-(1H-indol-3-yl)-maleinimide;
2-[1-(3-(amidinothio)propyl)-6-methylthio-1H-indol-3-yl]-3-(1H-indol-3-yl)-maleinimide;
2-[1-(3-(amidinothio)propyl)-7-methylthio-1H-indol-3-yl]-3-(1H-indol-3-yl)-maleinimide;
2-[1-(3-(amidinothio)propyl)-4,5-dimethoxy-1H-indol-3-yl]-3-(1H-indol-3-yl)-maleinimide;
2-[1-(3-(amidinothio)propyl)-5,6-dimethoxy-1H-indol-3-yl]-3-(1H-indol-3-yl)-maleinimide;
2-[1-(3-(amidinothio)propyl)-6,7-dimethoxy-1H-indol-3-yl]-3-(1H-indol-3-yl)-maleinimide;
2-[4-acetylamino-1-(2-aminoethyl)-1H-indol-3-yl]-3-(1H-indol-3-yl)-maleinimide;
2-[5-acetylamino-1-(2-aminoethyl)-1H-indol-3-yl]-3-(1H-indol-3-yl)-maleinimide;
2-[6-acetylamino-1-(2-aminoethyl)-1H-indol-3-yl]-3-(1H-indol-3-yl)-maleinimide;
2-[7-acetylamino-1-(2-aminoethyl)-1H-indol-3-yl]-3-(1H-indol-3-yl)-maleinimide;
2-[4-amino-1-(2-aminoethyl)-1H-indol-3-yl]-3-(1H-indol-3-yl)-maleinimide;
2-[5-amino-1-(2-aminoethyl)-1H-indol-3-yl]-3-(1H-indol-3-yl)-maleinimide;
2-[6-amino-1-(2-aminoethyl)-1H-indol-3-yl]-3-(1H-indol-3-yl)-maleinimide;
2-[7-amino-1-(2-aminoethyl)-1H-indol-3-yl]-3-(1H-indol-3-yl)-maleinimide;
2-[1-(2-aminoethyl)-4-benzyloxy-1H-indol-3-yl]-3-(1H-indol-3-yl)-maleinimide;
2-[1-(2-aminoethyl)-5-benzyloxy-1H-indol-3-yl]-3-(1H-indol-3-yl)-maleinimide;
2-[1-(2-aminoethyl)-6-benzyloxy-1H-indol-3-yl]-3-(1H-indol-3-yl)-maleinimide;
2-[1-(2-aminoethyl)-7-benzyloxy-1H-indol-3-yl]-3-(1H-indol-3-yl)-maleinimide;
2-[1-(2-aminoethyl)-4-bromo-1H-indol-3-yl]-3-(1H-indol-3-yl)-maleinimide;
2-[1-(2-aminoethyl)-5-bromo-1H-indol-3-yl]-3-(1H-indol-3-yl)-maleinimide;
2-[1-(2-aminoethyl)-6-bromo-1H-indol-3-yl]-3-(1H-indol-3-yl)-maleinimide;
2-[1-(2-aminoethyl)-7-bromo-1H-indol-3-yl]-3-(1H-indol-3-yl)-maleinimide;
2-[1-(2-aminoethyl)-4-chloro-1H-indol-3-yl]-3-(1H-indol-3-yl)-maleinimide;
2-[1-(2-aminoethyl)-5-chloro-1H-indol-3-yl]-3-(1H-indol-3-yl)-maleinimide;
2-[1-(2-aminoethyl)-6-chloro-1H-indol-3-yl]-3-(1H-indol-3-yl)-maleinimide;
2-[1-(2-aminoethyl)-7-chloro-1H-indol-3-yl]-3-(1H-indol-3-yl)-maleinimide;
2-[1-(2-aminoethyl)-4-fluoro-1H-indol-3-yl]-3-(1H-indol-3-yl)-maleinimide;
2-[1-(2-aminoethyl)-5-fluoro-1H-indol-3-yl]-3-(1H-indol-3-yl)-maleinimide;
2-[1-(2-aminoethyl)-6-fluoro-1H-indol-3-yl]-3-(1H-indol-3-yl)-maleinimide;
2-[1-(2-aminoethyl)-7-fluoro-1H-indol-3-yl]-3-(1H-indol-3-yl)-maleinimide;
2-[1-(2-aminoethyl)-4-hydroxy-1H-indol-3-yl]-3-(1H-indol-3-yl)-maleinimide;
2-[1-(2-aminoethyl)-5-hydroxy-1H-indol-3-yl]-3-(1H-indol-3-yl)-maleinimide;
2-[1-(2-aminoethyl)-6-hydroxy-1H-indol-3-yl]-3-(1H-indol-3-yl)-maleinimide;
2-[1-(2-aminoethyl)-7-hydroxy-1H-indol-3-yl]-3-(1H-indol-3-yl)-maleinimide;
2-[1-(2-aminoethyl)-4-trifluoromethyl-1H-indol-3-yl]-3-(1H-indol-3-yl)-maleinimide;
2-[1-(2-aminoethyl)-5-trifluoromethyl-1H-indol-3-yl]-3-(1H-indol-3-yl)-maleinimide;
2-[1-(2-aminoethyl)-6-trifluoromethyl-1H-indol-3-yl]-3-(1H-indol-3-yl)-maleinimide;
2-[1-(2-aminoethyl)-7-trifluoromethyl-1H-indol-3-yl]-3-(1H-indol-3-yl)-maleinimide;
2-[1-(2-aminoethyl)-4-methoxy-1H-indol-3-yl]-3-(1H-indol-3-yl)-maleinimide;
2-[1-(2-aminoethyl)-5-methoxy-1H-indol-3-yl]-3-(1H-indol-3-yl)-maleinimide;
2-[1-(2-aminoethyl)-6-methoxy-1H-indol-3-yl]-3-(1H-indol-3-yl)-maleinimide;
2-[1-(2-aminoethyl)-7-methoxy-1H-indol-3-yl]-3-(1H-indol-3-yl)-maleinimide;
2-[1-(2-aminoethyl)-4,5-methylendioxy-1H-indol-3-yl]-3-(1H-indol-3-yl)-maleinimide;
2-[1-(2-aminoethyl)-5,6-methylendioxy-1H-indol-3-yl]-3-(1H-indol-3-yl)-maleinimide;
2-[1-(2-aminoethyl)-6,7-methylendioxy-1H-indol-3-yl]-3-(1H-indol-3-yl)-maleinimide;
2-[1-(2-aminoethyl)-4-methyl-1H-indol-3-yl]-3-(1H-indol-3-yl)-maleinimide;
2-[1-(2-aminoethyl)-5-methyl-1H-indol-3-yl]-3-(1H-indol-3-yl)-maleinimide;
2-[1-(2-aminoethyl)-6-methyl-1H-indol-3-yl]-3-(1H-indol-3-yl)-maleinimide;
2-[1-(2-aminoethyl)-7-methyl-1H-indol-3-yl]-3-(1H-indol-3-yl)-maleinimide;
2-[1-(2-aminoethyl)-4-nitro-1H-indol-3-yl]-3-(1H-indol-3-yl)-maleinimide;
2-[1-(2-aminoethyl)-5-nitro-1H-indol-3-yl]-3-(1H-indol-3-yl)-maleinimide;
2-[1-(2-aminoethyl)-6-nitro-1H-indol-3-yl]-3-(1H-indol-3-yl)-maleinimide;
2-[1-(2-aminoethyl)-7-nitro-1H-indol-3-yl]-3-(1H-indol-3-yl)-maleinimide;
2-[1-(2-aminoethyl)-4-methylthio-1H-indol-3-yl]-3-(1H-indol-3-yl)-maleinimide;
2-[1-(2-aminoethyl)-5-methylthio-1H-indol-3-yl]-3-(1H-indol-3-yl)-maleinimide;
2-[1-(2-aminoethyl)-6-methylthio-1H-indol-3-yl]-3-(1H-indol-3-yl)-maleinimide;
2-[1-(2-aminoethyl)-7-methylthio-1H-indol-3-yl]-3-(1H-indol-3-yl)-maleinimide;
2-[1-(2-aminoethyl)-4,5-dimethoxy-1H-indol-3-yl]-3-(1H-indol-3-yl)-maleinimide;
2-[1-(2-aminoethyl)-5,6-dimethoxy-1H-indol-3-yl]-3-(1H-indol-3-yl)-maleinimide;
2-[1-(2-aminoethyl)-6,7-dimethoxy-1H-indol-3-yl]-3-(1H-indol-3-yl)-maleinimide;
2-[4-acetylamino-1-(3-aminopropyl)-1H-indol-3-yl]-3-(1H-indol-3-yl)-maleinimide;
2-[5-acetylamino-1-(3-aminopropyl)-1H-indol-3-yl]-3-(1H-indol-3-yl)-maleinimide;
2-[6-acetylamino-1-(3-aminopropyl)-1H-indol-3-yl]-3-(1H-indol-3-yl)-maleinimide;
2-[7-acetylamino-1-(3-aminopropyl)-1H-indol-3-yl]-3-(1H-indol-3-yl)-maleinimide;

2-[4-amino-1-(3-aminopropyl)-1H-indol-3-yl]-3-(1H-indol-3-yl)-maleinimide;
2-[5-amino-1-(3-aminopropyl)-1H-indol-3-yl]-3-(1H-indol-3-yl)-maleinimide;
2-[6-amino-1-(3-aminopropyl)-1H-indol-3-yl]-3-(1H-indol-3-yl)-maleinimide;
2-[7-amino-1-(3-aminopropyl)-1H-indol-3-yl]-3-(1H-indol-3-yl)-maleinimide;
2-[1-(3-aminopropyl)-4-benzyloxy-1H-indol-3-yl]-3-(1H-indol-3-yl)-maleinimide;
2-[1-(3-aminopropyl)-5-benzyloxy-1H-indol-3-yl]-3-(1H-indol-3-yl)-maleinimide;
2-[1-(3-aminopropyl)-6-benzyloxy-1H-indol-3-yl]-3-(1H-indol-1-3-yl)-maleinimide;
2-[1-(3-aminopropyl)-7-benzyloxy-1H-indol-3-yl]-3-(1H-indol-3-yl)-maleinimide;
2-[1-(3-aminopropyl)-4-bromo-1H-indol-3-yl]-3-(1H-indol-3-yl])-maleinimide;
2-[1-(3-aminopropyl)-5-bromo-1H-indol-3-yl]-3-(1H-indol-3-yl)-maleinimide;
2-[1-(3-aminopropyl)-6-bromo-1H-indol-3-yl]-3-(1H-indol-3-yl)-maleinimide;
2-[1-(3-aminopropyl)-7-bromo-1H-indol-3-yl]-3-(1H-indol-3-yl)-maleinimide;
2-[1-(3-aminopropyl)-4-chloro-1H-indol-3-yl]-3-(1H-indol-3-yl)-maleinimide;
2-[1-(3-aminopropyl)-5-chloro-1H-indol-3-yl]-3-(1H-indol-3-yl)-maleinimide;
2-[1-(3-aminopropyl)-6-chloro-1H-indol-3-yl]-3-(1H-indol-3-yl)-maleinimide;
2-[1-(3-aminopropyl)-7-chloro-1H-indol-3-yl]-3-(1H-indol-3-yl)-maleinimide;
2-[1-(3-aminopropyl)-4-fluoro-1H-indol-3-yl]-3-(1H-indol-3-yl)-maleinimide;
2-[1-(3-aminopropyl)-5-fluoro-1H-indol-3-yl]-3-(1H-indol-3-yl)-maleinimide;
2-[1-(3-aminopropyl)-6-fluoro-1H-indol-3-yl]-3-(1H-indol-3-yl)-maleinimide;
2-[1-(3-aminopropyl)-7-fluoro-1H-indol-3-yl]-3-(1H-indol-3-yl)-maleinimide;
2-[1-(3-aminopropyl)-4-hydroxy-1H-indol-3-yl]-3-(1H-indol-3-yl)-maleinimide;
2-[1-(3-aminopropyl)-5-hydroxy-1H-indol-3-yl]-3-(1H-indol-3-yl)-maleinimide;
2-[1-(3-aminopropyl)-6-hydroxy-1H-indol-3-yl]-3-(1H-indol-3-yl)-maleinimide;
2-[1-(3-aminopropyl)-7-hydroxy-1H-indol-3-yl]-3-(1H-indol-3-yl)-maleinimide;
2-[1-(3-aminopropyl)-4-trifluoromethyl-1H-indol-3-yl]-3-(1H-indol-3-yl)-maleinimide;
2-[1-(3-aminopropyl)-5-trifluoromethyl-1H-indol-3-yl]-3-(1H-indol-3-yl)-maleinimide;
2-[1-(3-aminopropyl)-6-trifluoromethyl-1H-indol-3-yl]-3-(1H-indol-3-yl)-maleinimide;
2-[1-(3-aminopropyl)-7-trifluoromethyl-1H-indol-3-yl]-3-(1H-indol-3-yl)-maleinimide;
2-[1-(3-aminopropyl)-4-methoxy-1H-indol-3-yl]-3-(1H-indol-3-yl)-maleinimide;
2-[1-(3-aminopropyl)-5-methoxy-1H-indol-3-yl]-3-(1H-indol-3-yl)-maleinimide;
2-[1-(3-aminopropyl)-6-methoxy-1H-indol-3-yl]-3-(1H-indol-3-yl)-maleinimide;
2-[1-(3-aminopropyl)-7-methoxy-1H-indol-3-yl]-3-(1H-indol-3-yl)-maleinimide;
2-[1-(3-aminopropyl)-4,5-methylendioxy-1H-indol-3-yl]-3-(1H-indol-3-yl)-maleinimide;
2-[1-(3-aminopropyl)-5,6-methylendioxy-1H-indol-3-yl]-3-(1H-indol-3-yl)-maleinimide;
2-[1-(3-aminopropyl)-6,7-methylendioxy-1H-indol-3-yl]-3-(1H-indol-3-yl)-maleinimide;
2-[1-(3-aminopropyl)-4-methyl-1H-indol-3-yl]-3-(1H-indol-3-yl)-maleinimide;
2-[1-(3-aminopropyl)-5-methyl-1H-indol-3-yl]-3-(1H-indol-3-yl)-maleinimide;
2-[1-(3-aminopropyl)-6-methyl-1H-indol-3-yl]-3-(1H-indol-3-yl)-maleinimide;
2-[1-(3-aminopropyl)-7-methyl-1H-indol-3-yl]-3-(1H-indol-3-yl)-maleinimide;
2-[1-(3-aminopropyl)-4-nitro-1H-indol-3-yl]-3-(1H-indol-3-yl)-maleinimide;
2-[1-(3-aminopropyl)-5-nitro-1H-indol-3-yl]-3-(1H-indol-3-yl)-maleinimide;
2-[1-(3-aminopropyl)-6-nitro-1H-indol-3-yl]-3-(1H-indol-3-yl)-maleinimide;
2-[1-(3-aminopropyl)-7-nitro-1H-indol-3-yl]-3-(1H-indol-3-yl)-maleinimide;
2-[1-(3-aminopropyl)-4-methylthio-1H-indol-3-yl]-3-(1H-indol-3-yl)-maleinimide;
2-[1-(3-aminopropyl)-5-methylthio-1H-indol-3-yl]-3-(1H-indol-3-yl)-maleinimide;
2-[1-(3-aminopropyl)-6-methylthio-1H-indol-3-yl]-3-(1H-indol-3-yl)-maleinimide;
2-[1-(3-aminopropyl)-7-methylthio-1H-indol-3-yl]-3-(1H-indol-3-yl)-maleinimide;
2-[1-(3-aminopropyl)-4,5-dimethoxy-1H-indol-3-yl]-3-(1H-indol-3-yl)-maleinimide;
2-[1-(3-aminopropyl)-5,6-dimethoxy-1H-indol-3-yl]-3-(1H-indol-3-yl)-maleinimide;
2-[1-(3-aminopropyl)-6,7-dimethoxy-1H-indol-3-yl]-3-(1H-indol-3-yl)-maleinimide;
(±)-2-[4-acetylamino-1-(3-ethoxy-2-hydroxypropyl)-1H-indol-3-yl]-3-(1H-indol-3-yl)-maleinimide;
(±)-2-[5-acetylamino-1-(3-ethoxy-2-hydroxypropyl)-1H-indol-3-yl]-3-(1H-indol-3-yl)-maleinimide;
(±)-2-[6-acetylamino-1-(3-ethoxy-2-hydroxypropyl)-1H-indol-3-yl]-3-(1H-indol-3-yl)-maleinimide;
(±)-2-[7-acetylamino-1-(3-ethoxy-2-hydroxypropyl)-1H-indol-3-yl]-3-(1H-indol-3-yl)-maleinimide;
(±)-2-[4-amino-1-(3-ethoxy-2-hydroxypropyl)-1H-indol-3-yl]-3-(1H-indol-3-yl)-maleinimide;
(±)-2-[5-amino-1-(3-ethoxy-2-hydroxypropyl)-1H-indol-3-yl]-3-(1H-indol-3-yl)-maleinimide;
(±)-2-[6-amino-1-(3-ethoxy-2-hydroxypropyl)-1H-indol-3-yl]-3-(1H-indol-3-yl)-maleinimide;
(±)-2-[7-amino-1-(3-ethoxy-2-hydroxypropyl)-1H-indol-3-yl]-3-(1H-indol-3-yl)-maleinimide;
(±)-2-[4-benzyloxy-1-(3-ethoxy-2-hydroxypropyl)-1H-indol-3-yl]-3-(1H-indol-3-yl)-maleinimide;
(±)-2-[5-benzyloxy-1-(3-ethoxy-2-hydroxypropyl)-1H-indol-3-yl]-3-(1H-indol-3-yl)-maleinimide;
(±)-2-[6-benzyloxy-1-(3-ethoxy-2-hydroxypropyl)-1H-indol-3-yl]-3-(1H-indol-3-yl)-maleinimide;
(±)-2-[7-benzyloxy-1-(3-ethoxy-2-hydroxypropyl)-1H-indol-3-yl]-3-(1H-indol-3-yl)-maleinimide;
(±)-2-[4-bromo-1-(3-ethoxy-2-hydroxypropyl)-1H-indol-3-yl]-3-(1H-indol-3-yl)-maleinimide;
(±)-2-[5-bromo-1-(3-ethoxy-2-hydroxypropyl)-1H-indol-3-yl]-3-(1H-indol-3-yl)-maleinimide;
(±)-2-[6-bromo-1-(3-ethoxy-2-hydroxypropyl)-1H-indol-3-yl]-3-(1H-indol-3-yl)-maleinimide;
(±)-2-[7-bromo-1-(3-ethoxy-2-hydroxypropyl)-1H-indol-3-yl]-3-(1H-indol-3-yl)-maleinimide;
(±)-2-[4-chloro-1-(3-ethoxy-2-hydroxypropyl)-1H-indol-3-yl]-3-(1H-indol-3-yl)-maleinimide;
(±)-2-[5-chloro-1-(3-ethoxy-2-hydroxypropyl)-1H-indol-3-yl]-3-(1H-indol-3-yl)-maleinimide;

(±)-2-[6-chloro-1-(3-ethoxy-2-hydroxypropyl)-1H-indol-3-yl]-3-(1H-indol-3-yl)-maleinimide;
(±)-2-[7-chloro-1-(3-ethoxy-2-hydroxypropyl)-1H-indol-3-yl]-3-(1H-indol-3-yl)-maleinimide;
(±)-2-[1-(3-ethoxy-2-hydroxypropyl)-4-fluoro-1H-indol-3-yl]-3-(1H-indol-3-yl)-maleinimide;
(±)-2-[1-(3-ethoxy-2-hydroxypropyl)-5-fluoro-1H-indol-3-yl]-3-(1H-indol-3-yl)-maleinimide;
(±)-2-[1-(3-ethoxy-2-hydroxypropyl)-6-fluoro-1H-indol-3-yl]-3-(1H-indol-3-yl)-maleinimide;
(±)-2-[1-(3-ethoxy-2-hydroxypropyl)-7-fluoro-1H-indol-3-yl]-3-(1H-indol-3-yl)-maleinimide;
(±)-2-[1-(3-ethoxy-2-hydroxypropyl)-4-hydroxy-1H-indol-3-yl]-3-(1H-indol-3-yl)-maleinimide;
(±)-2-[1-(3-ethoxy-2-hydroxypropyl)-5-hydroxy-1H-indol-3-yl]-3-(1H-indol-3-yl)-maleinimide;
(±)-2-[1-(3-ethoxy-2-hydroxypropyl)-6-hydroxy-1H-indol-3-yl]-3-(1H-indol-3-yl)-maleinimide;
(±)-2-[1-(3-ethoxy-2-hydroxypropyl)-7-hydroxy-1H-indol-3-yl]-3-(1H-indol-3-yl)-maleinimide;
(±)-2-[1-(3-ethoxy-2-hydroxypropyl)-4-trifluoromethyl-1H-indol-3-yl]-3-(1H-indol-3-yl)-maleinimide;
(±)-2-[1-(3-ethoxy-2-hydroxypropyl)-5-trifluoromethyl-1H-indol-3-yl]-3-(1H-indol-3-yl)-maleinimide;
(±)-2-[1-(3-ethoxy-2-hydroxypropyl)-6-trifluoromethyl-1H-indol-3-yl]-3-(1H-indol-3-yl)-maleinimide;
(±)-2-[1-(3-ethoxy-2-hydroxypropyl)-7-trifluoromethyl-1H-indol-3-yl]-3-(1H-indol-3-yl)-maleinimide;
(±)-2-[1-(3-ethoxy-2-hydroxypropyl)-4-methoxy-1H-indol-3-yl]-3-(1H-indol-3-yl)-maleinimide;
(±)-2-[1-(3-ethoxy-2-hydroxypropyl)-6-methoxy-1H-indol-3-yl]-3-(1H-indol-3-yl)-maleinimide;
(±)-2-[1-(3-ethoxy-2-hydroxypropyl)-7-methoxy-1H-indol-3-yl]-3-(1H-indol-3-yl)-maleinimide;
(±)-2-[1-(3-ethoxy-2-hydroxypropyl)-4,5-methylendioxy-1H-indol-3-yl]-3-(1H-indol-3-yl)-maleinimide;
(±)-2-[1-(3-ethoxy-2-hydroxypropyl)-5,6-methylendioxy-1H-indol-3-yl]-3-(1H-indol-3-yl)-maleinimide;
(±)-2-[1-(3-ethoxy-2-hydroxypropyl)-6,7-methylendioxy-1H-indol-3-yl]-3-(1H-indol-3-yl)-maleinimide;
(±)-2-[1-(3-ethoxy-2-hydroxypropyl)-4-methyl-1H-indol-3-yl]-3-(1H-indol-3-yl)-maleinimide;
(±)-2-[1-(3-ethoxy-2-hydroxypropyl)-5-methyl-1H-indol-3-yl]-3-(1H-indol-3-yl)-maleinimide;
(±)-2-[1-(3-ethoxy-2-hydroxypropyl)-6-methyl-1H-indol-3-yl]-3-(1H-indol-3-yl)-maleinimide;
(±)-2-[1-(3-ethoxy-2-hydroxypropyl)-7-methyl-1H-indol-3-yl]-3-(1H-indol-3-yl)-maleinimide;
(±)-2-[1-(3-ethoxy-2-hydroxypropyl)-4-nitro-1H-indol-3-yl]-3-(1H-indol-3-yl)-maleinimide;
(±)-2-[1-(3-ethoxy-2-hydroxypropyl)-5-nitro-1H-indol-3-yl]-3-(1H-indol-3-yl)-maleinimide;
(±)-2-[1-(3-ethoxy-2-hydroxypropyl)-6-nitro-1H-indol-3-yl]-3-(1H-indol-3-yl)-maleinimide;
(±)-2-[1-(3-ethoxy-2-hydroxypropyl)-7-nitro-1H-indol-3-yl]-3-(1H-indol-3-yl)-maleinimide;
(±)-2-[1-(3-ethoxy-2-hydroxypropyl)-4-methylthio-1H-indol-3-yl]-3-(1H-indol-3-yl)-maleinimide;
(±)-2-[1-(3-ethoxy-2-hydroxypropyl)-5-methylthio-1H-indol-3-yl]-3-(1H-indol-3-yl)-maleinimide;
(±)-2-[1-(3-ethoxy-2-hydroxypropyl)-6-methylthio-1H-indol-3-yl]-3-(1H-indol-3-yl)-maleinimide;
(±)-2-[1-(3-ethoxy-2-hydroxypropyl)-7-methylthio-1H-indol-3-yl]-3-(1H-indol-3-yl)-maleinimide;
(±)-2-[1-(3-ethoxy-2-hydroxypropyl)-4,5-dimethoxy-1H-indol-3-yl]-3-(1H-indol-3-yl)-maleinimide;
(±)-2-[1-(3-ethoxy-2-hydroxypropyl)-5,6-dimethoxy-1H-indol-3-yl]-3-(1H-indol-3-yl)-maleinimide;
(±)-2-[1-(3-ethoxy-2-hydroxypropyl)-6,7-dimethoxy-1H-indol-3-yl]-3-(1H-indol-3-yl)-maleinimide;
(+)-2-[4-acetylamino-1-(3-ethoxy-2-hydroxypropyl)-1H-indol-3-yl]-3-(1H-indol-3-yl)-maleinimide;
(+)-2-[5-acetylamino-1-(3-ethoxy-2-hydroxypropyl)-1H-indol-3-yl]-3-(1H-indol-3-yl)-maleinimide;
(+)-2-[6-acetylamino-1-(3-ethoxy-2-hydroxypropyl)-1H-indol-3-yl]-3-(1H-indol-3-yl)-maleinimide;
(+)-2-[7-acetylamino-1-(3-ethoxy-2-hydroxypropyl)-1H-indol-3-yl]-3-(1H-indol-3-yl)-maleinimide;
(+)-2-[4-amino-1-(3-ethoxy-2-hydroxypropyl)-1H-indol-3-yl]-3-(1H-indol-3-yl)-maleinimide;
(+)-2-[5-amino-1-(3-ethoxy-2-hydroxypropyl)-1H-indol-3-yl]-3-(1H-indol-3-yl)-maleinimide;
(+)-2-[6-amino-1-(3-ethoxy-2-hydroxypropyl)-1H-indol-3-yl]-3-(1H-indol-3-yl)-maleinimide;
(+)-2-[7-amino-1-(3-ethoxy-2-hydroxypropyl)-1H-indol-3-yl]-3-(1H-indol-3-yl)-maleinimide;
(+)-2-[4-benzyloxy-1-(3-ethoxy-2-hydroxypropyl)-1H-indol-3-yl]-3-(1H-indol-3-yl)-maleinimide;
(+)-2-[5-benzyloxy-1-(3-ethoxy-2-hydroxypropyl)-1H-indol-3-yl]-3-(1H-indol-3-yl)-maleinimide;
(+)-2-[6-benzyloxy-1-(3-ethoxy-2-hydroxypropyl)-1H-indol-3-yl]-3-(1H-indol-3-yl)-maleinimide;
(+)-2-[7-benzyloxy-1-(3-ethoxy-2-hydroxypropyl)-1H-indol-3-yl]-3-(1H-indol-3-yl)-maleinimide;
(+)-2-[4-bromo-1-(3-ethoxy-2-hydroxypropyl)-1H-indol-3-yl]-3-(1H-indol-3-yl)-maleinimide;
(+)-2-[5-bromo-1-(3-ethoxy-2-hydroxypropyl)-1H-indol-3-yl]-3-(1H-indol-3-yl)-maleinimide;
(+)-2-[6-bromo-1-(3-ethoxy-2-hydroxypropyl)-1H-indol-3-yl]-3-(1H-indol-3-yl)-maleinimide;
(+)-2-[7-bromo-1-(3-ethoxy-2-hydroxypropyl)-1H-indol-3-yl]-3-(1H-indol-3-yl)-maleinimide;
(+)-2-[4-chloro-1-(3-ethoxy-2-hydroxypropyl)-1H-indol-3-yl]-3-(1H-indol-3-yl)-maleinimide;
(+)-2-[5-chloro-1-(3-ethoxy-2-hydroxypropyl)-1H-indol-3-yl]-3-(1H-indol-3-yl)-maleinimide;
(+)-2-[6-chloro-1-(3-ethoxy-2-hydroxypropyl)-1H-indol-3-yl]-3-(1H-indol-3-yl)-maleinimide;
(+)-2-[7-chloro-1-(3-ethoxy-2-hydroxypropyl)-1H-indol-3-yl]-3-(1H-indol-3-yl)-maleinimide;
(+)-2-[1-(3-ethoxy-2-hydroxypropyl)-4-fluoro-1H-indol-3-yl]-3-(1H-indol-3-yl)-maleinimide;
(+)-2-[1-(3-ethoxy-2-hydroxypropyl)-5-fluoro-1H-indol-3-yl]-3-(1H-indol-3-yl)-maleinimide;
(+)-2-[1-(3-ethoxy-2-hydroxypropyl)-6-fluoro-1H-indol-3-yl]-3-(1H-indol-3-yl)-maleinimide;
(+)-2-[1-(3-ethoxy-2-hydroxypropyl)-7-fluoro-1H-indol-3-yl]-3-(1H-indol-3-yl)-maleinimide;
(+)-2-[1-(3-ethoxy-2-hydroxypropyl)-4-hydroxy-1H-indol-3-yl]-3-(1H-indol-3-yl)-maleinimide;
(+)-2-[1-(3-ethoxy-2-hydroxypropyl)-5-hydroxy-1H-indol-3-yl]-3-(1H-indol-3-yl)-maleinimide;
(+)-2-[1-(3-ethoxy-2-hydroxypropyl)-6-hydroxy-1H-indol-3-yl]-3-(1H-indol-3-yl)-maleinimide;
(+)-2-[1-(3-ethoxy-2-hydroxypropyl)-7-hydroxy-1H-indol-3-yl]-3-(1H-indol-3-yl)-maleinimide;
(+)-2-[1-(3-ethoxy-2-hydroxypropyl)-4-trifluoromethyl-1H-indol-3-yl]-3-(1H-indol-3-yl)-maleinimide;
(+)-2-[1-(3-ethoxy-2-hydroxypropyl)-5-trifluoromethyl-1H-indol-3-yl]-3-(1H-indol-3-yl)-maleinimide;
(+)-2-[1-(3-ethoxy-2-hydroxypropyl)-6-trifluoromethyl-1H-indol-3-yl]-3-(1H-indol-3-yl)-maleinimide;
(+)-2-[1-(3-ethoxy-2-hydroxypropyl)-7-trifluoromethyl-1H-indol-3-yl]-3-(1H-indol-3-yl)-maleinimide;
(+)-2-[1-(3-ethoxy-2-hydroxypropyl)-4-methoxy-1H-indol-3-yl]-3-(1H-indol-3-yl)-maleinimide;

(+)-2-[1-(3-ethoxy-2-hydroxypropyl)-5-methoxy-1H-indol-3-yl]-3-(1H-indol-3-yl)-maleinimide;
(+)-2-[1-(3-ethoxy-2-hydroxypropyl)-6-methoxy-1H-indol-3-yl]-3-(1H-indol-3-yl)-maleinimide;
(+)-2-[1-(3-ethoxy-2-hydroxypropyl)-7-methoxy-1H-indol-3-yl]-3-(1H-indol-3-yl)-maleinimide;
(+)-2-[1-(3-ethoxy-2-hydroxypropyl)-4,5-methylendioxy-1H-indol-3-yl]-3-(1H-indol-3-yl)-maleinimide;
(+)-2-[1-(3-ethoxy-2-hydroxypropyl)-5,6-methylendioxy-1H-indol-3-yl]-3-(1H-indol-3-yl)-maleinimide;
(+)-2-[1-(3-ethoxy-2-hydroxypropyl)-6,7-methylendioxy-1H-indol-3-yl]-3-(1H-indol-3-yl)-maleinimide;
(+)-2-[1-(3-ethoxy-2-hydroxypropyl)-4-methyl-1H-indol-3-yl]-3-(1H-indol-3-yl)-maleinimide;
(+)-2-[1-(3-ethoxy-2-hydroxypropyl)-5-methyl-1H-indol-3-yl]-3-(1H-indol-3-yl)-maleinimide;
(+)-2-[1-(3-ethoxy-2-hydroxypropyl)-6-methyl-1H-indol-3-yl]-3-(1H-indol-3-yl)-maleinimide;
(+)-2-[1-(3-ethoxy-2-hydroxypropyl)-7-methyl-1H-indol-3-yl]-3-(1H-indol-3-yl)-maleinimide;
(+)-2-[1-(3-ethoxy-2-hydroxypropyl)-4-nitro-1H-indol-3-yl]-3-(1H-indol-3-yl)-maleinimide;
(+)-2-[1-(3-ethoxy-2-hydroxypropyl)-5-nitro-1H-indol-3-yl]-3-(1H-indol-3-yl)-maleinimide;
(+)-2-[1-(3-ethoxy-2-hydroxypropyl)-6-nitro-1H-indol-3-yl]-3-(1H-indol-3-yl)-maleinimide;
(+)-2-[1-(3-ethoxy-2-hydroxypropyl)-7-nitro-1H-indol-3-yl]-3-(1H-indol-3-yl)-maleinimide;
(+)-2-[1-(3-ethoxy-2-hydroxypropyl)-4-methylthio-1H-indol-3-yl]-3-(1H-indol-3-yl)-maleinimide;
(+)-2-[1-(3-ethoxy-2-hydroxypropyl)-5-methylthio-1H-indol-3-yl]-3-(1H-indol-3-yl)-maleinimide;
(+)-2-[1-(3-ethoxy-2-hydroxypropyl)-6-methylthio-1H-indol-3-yl]-3-(1H-indol-3-yl)-maleinimide;
(+)-2-[1-(3-ethoxy-2-hydroxypropyl)-7-methylthio-1H-indol-3-yl]-3-(1H-indol-3-yl)-maleinimide;
(+)-2-[1-(3-ethoxy-2-hydroxypropyl)-4,5-dimethoxy-1H-indol-3-yl]-3-(1H-indol-3-yl)-maleinimide;
(+)-2-[1-(3-ethoxy-2-hydroxypropyl)-5,6-dimethoxy-1H-indol-3-yl]-3-(1H-indol-3-yl)-maleinimide;
(+)-2-[1-(3-ethoxy-2-hydroxypropyl)-6,7-dimethoxy-1H-indol-3-yl]-3-(1H-indol-3-yl)-maleinimide;
(−)-2-[4-acetylamino-1-(3-ethoxy-2-hydroxypropyl)-1H-indol-3-yl]-3-(1H-indol-3-yl)-maleinimide;
(−)-2-[5-acetylamino-1-(3-ethoxy-2-hydroxypropyl)-1H-indol-3-yl]-3-(1H-indol-3-yl)-maleinimide;
(−)-2-[6-acetylamino-1-(3-ethoxy-2-hydroxypropyl)-1H-indol-3-yl]-3-(1H-indol-3-yl)-maleinimide;
(−)-2-[7-acetylamino-1-(3-ethoxy-2-hydroxypropyl)-1H-indol-3-yl]-3-(1H-indol-3-yl)-maleinimide;
(−)-2-[4-amino-1-(3-ethoxy-2-hydroxypropyl)-1H-indol-3-yl]-3-(1H-indol-3-yl)-maleinimide;
(−)-2-[5-amino-1-(3-ethoxy-2-hydroxypropyl)-1H-indol-3-yl]-3-(1H-indol-3-yl)-maleinimide;
(−)-2-[6-amino-1-(3-ethoxy-2-hydroxypropyl)-1H-indol-3-yl]-3-(1H-indol-3-yl)-maleinimide;
(−)-2-[7-amino-1-(3-ethoxy-2-hydroxypropyl)-1H-indol-3-yl]-3-(1H-indol-3-yl)-maleinimide;
(−)-2-[4-benzyloxy-1-(3-ethoxy-2-hydroxypropyl)-1H-indol-3-yl]-3-(1H-indol-3-yl)-maleinimide;
(−)-2-[5-benzyloxy-1-(3-ethoxy-2-hydroxypropyl)-1H-indol-3-yl]-3-(1H-indol-3-yl)-maleinimide;
(−)-2-[6-benzyloxy-1-(3-ethoxy-2-hydroxypropyl)-1H-indol-3-yl]-3-(1H-indol-3-yl)-maleinimide;
(−)-2-[7-benzyloxy-1-(3-ethoxy-2-hydroxypropyl)-1H-indol-3-yl]-3-(1H-indol-3-yl)-maleinimide;
(−)-2-[4-bromo-1-(3-ethoxy-2-hydroxypropyl)-1H-indol-3-yl]-3-(1H-indol-3-yl)-maleinimide;
(−)-2-[5-bromo-1-(3-ethoxy-2-hydroxypropyl)-1H-indol-3-yl]-3-(1H-indol-3-yl)-maleinimide;
(−)-2-[6-bromo-1-(3-ethoxy-2-hydroxypropyl)-1H-indol-3-yl]-3-(1H-indol-3-yl)-maleinimide;
(−)-2-[7-bromo-1-(3-ethoxy-2-hydroxypropyl)-1H-indol-3-yl]-3-(1H-indol-3-yl)-maleinimide;
(−)-2-[4-chloro-1-(3-ethoxy-2-hydroxypropyl)-1H-indol-3-yl]-3-(1H-indol-3-yl)-maleinimide;
(−)-2-[5-chloro-1-(3-ethoxy-2-hydroxypropyl)-1H-indol-3-yl]-3-(1H-indol-3-yl)-maleinimide;
(−)-2-[6-chloro-1-(3-ethoxy-2-hydroxypropyl)-1H-indol-3-yl]-3-(1H-indol-3-yl)-maleinimide;
(−)-2-[7-chloro-1-(3-ethoxy-2-hydroxypropyl)-1H-indol-3-yl]-3-(1H-indol-3-yl)-maleinimide;
(−)-2-[1-(3-ethoxy-2-hydroxypropyl)-4-fluoro-1H-indol-3-yl]-3-(1H-indol-3-yl)-maleinimide;
(−)-2-[1-(3-ethoxy-2-hydroxypropyl)-5-fluoro-1H-indol-3-yl]-3-(1H-indol-3-yl)-maleinimide;
(−)-2-[1-(3-ethoxy-2-hydroxypropyl)-6-fluoro-1H-indol-3-yl]-3-(1H-indol-3-yl)-maleinimide;
(−)-2-[1-(3-ethoxy-2-hydroxypropyl)-7-fluoro-1H-indol-3-yl]-3-(1H-indol-3-yl)-maleinimide;
(−)-2-[1-(3-ethoxy-2-hydroxypropyl)-4-hydroxy-1H-indol-3-yl]-3-(1H-indol-3-yl)-maleinimide;
(−)-2-[1-(3-ethoxy-2-hydroxypropyl)-5-hydroxy-1H-indol-3-yl]-3-(1H-indol-3-yl)-maleinimide;
(−)-2-[1-(3-ethoxy-2-hydroxypropyl)-6-hydroxy-1H-indol-3-yl]-3-(1H-indol-3-yl)-maleinimide;
(−)-2-[1-(3-ethoxy-2-hydroxypropyl)-7-hydroxy-1H-indol-3-yl]-3-(1H-indol-3-yl)-maleinimide;
(−)-2-[1-(3-ethoxy-2-hydroxypropyl)-4-trifluoromethyl-1H-indol-3-yl]-3-(1H-indol-3-yl)-maleinimide;
(−)-2-[1-(3-ethoxy-2-hydroxypropyl)-5-trifluoromethyl-1H-indol-3-yl]-3-(1H-indol-3-yl)-maleinimide;
(−)-2-[1-(3-ethoxy-2-hydroxypropyl)-6-trifluoromethyl-1H-indol-3-yl]-3-(1H-indol-3-yl)-maleinimide;
(−)-2-[1-(3-ethoxy-2-hydroxypropyl)-7-trifluoromethyl-1H-indol-3-yl]-3-(1H-indol-3-yl)-maleinimide;
(−)-2-[1-(3-ethoxy-2-hydroxypropyl)-4-methoxy-1H-indol-3-yl]-3-(1H-indol-3-yl)-maleinimide;
(−)-2-[1-(3-ethoxy-2-hydroxypropyl)-5-methoxy-1H-indol-3-yl]-3-(1H-indol-3-yl)-maleinimide;
(−)-2-[1-(3-ethoxy-2-hydroxypropyl)-6-methoxy-1H-indol-3-yl]-3-(1H-indol-3-yl)-maleinimide;
(−)-2-[1-(3-ethoxy-2-hydroxypropyl)-7-methoxy-1H-indol-3-yl]-3-(1H-indol-3-yl)-maleinimide;
(−)-2-[1-(3-ethoxy-2-hydroxypropyl)-4,5-methylendioxy-1H-indol-3-yl]-3-(1H-indol-3-yl)-maleinimide;
(−)-2-[1-(3-ethoxy-2-hydroxypropyl)-5,6-methylendioxy-1H-indol-3-yl]-3-(1H-indol-3-yl)-maleinimide;
(−)-2-[1-(3-ethoxy-2-hydroxypropyl)-6,7-methylendioxy-1H-indol-3-yl]-3-(1H-indol-3-yl)-maleinimide;
(−)-2-[1-(3-ethoxy-2-hydroxypropyl)-4-methyl-1H-indol-3-yl]-3-(1H-indol-3-yl)-maleinimide;
(−)-2-[1-(3-ethoxy-2-hydroxypropyl)-5-methyl-1H-indol-3-yl]-3-(1H-indol-3-yl)-maleinimide;
(−)-2-[1-(3-ethoxy-2-hydroxypropyl)-6-methyl-1H-indol-3-yl]-3-(1H-indol-3-yl)-maleinimide;
(−)-2-[1-(3-ethoxy-2-hydroxypropyl)-7-methyl-1H-indol-3-yl]-3-(1H-indol-3-yl)-maleinimide;
(−)-2-[1-(3-ethoxy-2-hydroxypropyl)-4-nitro-1H-indol-3-yl]-3-(1H-indol-3-yl)-maleinimide;
(−)-2-[1-(3-ethoxy-2-hydroxypropyl)-5-nitro-1H-indol-3-yl]-3-(1H-indol-3-yl)-maleinimide;
(−)-2-[1-(3-ethoxy-2-hydroxypropyl)-6-nitro-1H-indol-3-yl]-3-(1H-indol-3-yl)-maleinimide;
(−)-2-[1-(3-ethoxy-2-hydroxypropyl)-7-nitro-1H-indol-3-yl]-3-(1H-indol-3-yl)-maleinimide;

(−)-2-[1-(3-ethoxy-2-hydroxypropyl)-4-methylthio-1H-indol-3-yl]-3-(1H-indol-3-yl)-maleinimide;
(−)-2-[1-(3-ethoxy-2-hydroxypropyl)-5-methylthio-1H-indol-3-yl]-3-(1H-indol-3-yl)-maleinimide;
(−)-2-[1-(3-ethoxy-2-hydroxypropyl)-6-methylthio-1H-indol-3-yl]-3-(1H-indol-3-yl)-maleinimide;
(−)-2-[1-(3-ethoxy-2-hydroxypropyl)-7-methylthio-1H-indol-3-yl]-3-(1H-indol-3-yl)-maleinimide;
(−)-2-[1-(3-ethoxy-2-hydroxypropyl)-4,5-dimethoxy-1H-indol-3-yl]-3-(1H-indol-3-yl)-maleinimide;
(−)-2-[1-(3-ethoxy-2-hydroxypropyl)-5,6-dimethoxy-1H-indol-3-yl]-3-(1H-indol-3-yl)-maleinimide;
(−)-2-[1-(3-ethoxy-2-hydroxypropyl)-6,7-dimethoxy-1H-indol-3-yl]-3-(1H-indol-3-yl)-maleinimide;
2-[4-acetylamino-1-(2-diethylaminoethyl)-1H-indol-3-yl]-3-(1H-indol-3-yl)-maleinimide;
2-[5-acetylamino-1-(2-diethylaminoethyl)-1H-indol-3-yl]-3-(1H-indol-3-yl)-maleinimide;
2-[6-acetylamino-1-(2-diethylaminoethyl)-1H-indol-3-yl]-3-(1H-indol-3-yl)-maleinimide;
2-[7-acetylamino-1-(2-diethylaminoethyl)-1H-indol-3-yl]-3-(1H-indol-3-yl)-maleinimide;
2-[4-amino-1-(2-diethylaminoethyl)-1H-indol-3-yl]-3-(1H-indol-3-yl)-maleinimide;
2-[5-amino-1-(2-diethylaminoethyl)-1H-indol-3-yl]-3-(1H-indol-3-yl)-maleinimide;
2-[6-amino-1-(2-diethylaminoethyl)-1H-indol-3-yl]-3-(1H-indol-3-yl)-maleinimide;
2-[7-amino-1-(2-diethylaminoethyl)-1H-indol-3-yl]-3-(1H-indol-3-yl)-maleinimide;
2-[4-benzyloxy-1-(2-diethylaminoethyl)-1H-indol-3-yl]-3-(1H-indol-3-yl)-maleinimide;
2-[5-benzyloxy-1-(2-diethylaminoethyl)-1H-indol-3-yl]-3-(1H-indol-3-yl)-maleinimide;
2-[6-benzyloxy-1-(2-diethylaminoethyl)-1H-indol-3-yl]-3-(1H-indol-3-yl)-maleinimide;
2-[7-benzyloxy-1-(2-diethylaminoethyl)-1H-indol-3-yl]-3-(1H-indol-3-yl)-maleinimide;
2-[4-bromo-1-(2-diethylaminoethyl)-1H-indol-3-yl]-3-(1H-indol-3-yl)-maleinimide;
2-[5-bromo-1-(2-diethylaminoethyl)-1H-indol-3-yl]-3-(1H-indol-3-yl)-maleinimide;
2-[6-bromo-1-(2-diethylaminoethyl)-1H-indol-3-yl]-3-(1H-indol-3-yl)-maleinimide;
2-[7-bromo-1-(2-diethylaminoethyl)-1H-indol-3-yl]-3-(1H-indol-3-yl)-maleinimide;
2-[4-chloro-1-(2-diethylaminoethyl)-1H-indol-3-yl]-3-(1H-indol-3-yl)-maleinimide;
2-[5-chloro-1-(2-diethylaminoethyl)-1H-indol-3-yl]-3-(1H-indol-3-yl)-maleinimide;
2-[6-chloro-1-(2-diethylaminoethyl)-1H-indol-3-yl]-3-(1H-indol-3-yl)-maleinimide;
2-[7-chloro-1-(2-diethylaminoethyl)-1H-indol-3-yl]-3-(1H-indol-3-yl)-maleinimide;
2-[1-(2-diethylaminoethyl)-4-fluoro-1H-indol-3-yl]-3-(1H-indol-3-yl)-maleinimide;
2-[1-(2-diethylaminoethyl)-5-fluoro-1H-indol-3-yl]-3-(1H-indol-3-yl)-maleinimide;
2-[1-(2-diethylaminoethyl)-6-fluoro-1H-indol-3-yl]-3-(1H-indol-3-yl)-maleinimide;
2-[1-(2-diethylaminoethyl)-7-fluoro-1H-indol-3-yl]-3-(1H-indol-3-yl)-maleinimide;
2-[1-(2-diethylaminoethyl)-4-hydroxy-1H-indol-3-yl]-3-(1H-indol-3-yl)-maleinimide;
2-[1-(2-diethylaminoethyl)-5-hydroxy-1H-indol-3-yl]-3-(1H-indol-3-yl)-maleinimide;
2-[1-(2-diethylaminoethyl)-6-hydroxy-1H-indol-3-yl]-3-(1H-indol-3-yl)-maleinimide;
2-[1-(2-diethylaminoethyl)-7-hydroxy-1H-indol-3-yl]-3-(1H-indol-3-yl)-maleinimide;
2-[1-(2-diethylaminoethyl)-4-trifluoromethyl-1H-indol-3-yl]-3-(1H-indol-3-yl)-maleinimide;
2-[1-(2-diethylaminoethyl)-5-trifluoromethyl-1H-indol-3-yl]-3-(1H-indol-3-yl)-maleinimide;
2-[1-(2-diethylaminoethyl)-6-trifluoromethyl-1H-indol-3-yl]-3-(1H-indol-3-yl)-maleinimide;
2-[1-(2-diethylaminoethyl)-7-trifluoromethyl-1H-indol-3-yl]-3-(1H-indol-3-yl)-maleinimide;
2-[1-(2-diethylaminoethyl)-4-methoxy-1H-indol-3-yl]-3-(1H-indol-3-yl)-maleinimide;
2-[1-(2-diethylaminoethyl)-5-methoxy-1H-indol-3-yl]-3-(1H-indol-3-yl)-maleinimide;
2-[1-(2-diethylaminoethyl)-6-methoxy-1H-indol-3-yl]-3-(1H-indol-3-yl)-maleinimide;
2-[1-(2-diethylaminoethyl)-7-methoxy-1H-indol-3-yl]-3-(1H-indol-3-yl)-maleinimide;
2-[1-(2-diethylaminoethyl)-4,5-methylendioxy-1H-indol-3-yl]-3-(1H-indol-3-yl)-maleinimide;
2-[1-(2-diethylaminoethyl)-5,6-methylendioxy-1H-indol-3-yl]-3-(1H-indol-3-yl)-maleinimide;
2-[1-(2-diethylaminoethyl)-6,7-methylendioxy-1H-indol-3-yl]-3-(1H-indol-3-yl)-maleinimide;
2-[1-(2-diethylaminoethyl)-4-methyl-1H-indol-3-yl]-3-(1H-indol-3-yl)-maleinimide;
2-[1-(2-diethylaminoethyl)-5-methyl-1H-indol-3-yl]-3-(1H-indol-3-yl)-maleinimide;
2-[1-(2-diethylaminoethyl)-6-methyl-1H-indol-3-yl]-3-(1H-indol-3-yl)-maleinimide;
2-[1-(2-diethylaminoethyl)-7-methyl-1H-indol-3-yl]-3-(1H-indol-3-yl)-maleinimide;
2-[1-(2-diethylaminoethyl)-4-nitro-1H-indol-3-yl]-3-(1H-indol-3-yl)-maleinimide;
2-[1-(2-diethylaminoethyl)-5-nitro-1H-indol-3-yl]-3-(1H-indol-3-yl)-maleinimide;
2-[1-(2-diethylaminoethyl)-6-nitro-1H-indol-3-yl]-3-(1H-indol-3-yl)-maleinimide;
2-[1-(2-diethylaminoethyl)-7-nitro-1H-indol-3-yl]-3-(1H-indol-3-yl)-maleinimide;
2-[1-(2-diethylaminoethyl)-4-methylthio-1H-indol-3-yl]-3-(1H-indol-3-yl)-maleinimide;
2-[1-(2-diethylaminoethyl)-5-methylthio-1H-indol-3-yl]-3-(1H-indol-3-yl)-maleinimide;
2-[1-(2-diethylaminoethyl)-6-methylthio-1H-indol-3-yl]-3-(1H-indol-3-yl)-maleinimide;
2-[1-(2-diethylaminoethyl)-7-methylthio-1H-indol-3-yl]-3-(1H-indol-3-yl)-maleinimide;
2-[1-(2-diethylaminoethyl)-4,5-dimethoxy-1H-indol-3-yl]-3-(1H-indol-3-yl)-maleinimide;
2-[1-(2-diethylaminoethyl)-5,6-dimethoxy-1H-indol-3-yl]-3-(1H-indol-3-yl)-maleinimide;
2-[1-(2-diethylaminoethyl)-6,7-dimethoxy-1H-indol-3-yl]-3-(1H-indol-3-yl)-maleinimide;
(±)-2-[4-acetylamino-1-(3-diethylamino-2-hydroxypropyl)-1H-indol-3-yl]-3-(1H-indol-3-yl)-maleinimide;
(±)-2-[5-acetylamino-1-(3-diethylamino-2-hydroxypropyl)-1H-indol-3-yl]-3-(1H-indol-3-yl)-maleinimide;
(±)-2-[6-acetylamino-1-(3-diethylamino-2-hydroxypropyl)-1H-indol-3-yl]-3-(1H-indol-3-yl)-maleinimide;
(±)-2-[7-acetylamino-1-(3-diethylamino-2-hydroxypropyl)-1H-indol-3-yl]-3-(1H-indol-3-yl)-maleinimide;
(±)-2-[4-amino-1-(3-diethylamino-2-hydroxypropyl)-1H-indol-3-yl]-3-(1H-indol-3-yl)-maleinimide;

(±)-2-[5-amino-1-(3-diethylamino-2-hydroxypropyl)-1H-indol-3-yl]-3-(1H-indol-3-yl)-maleinimide;
(±)-2-[6-amino-1-(3-diethylamino-2-hydroxypropyl)-1H-indol-3-yl]-3-(1H-indol-3-yl)-maleinimide;
(±)-2-[7-amino-1-(3-diethylamino-2-hydroxypropyl)-1H-indol-3-yl]-3-(1H-indol-3-yl)-maleinimide;
(±)-2-[4-benzyloxy-1-(3-diethylamino-2-hydroxypropyl)-1H-indol-3-yl]-3-(1H-indol-3-yl)-maleinimide;
(±)-2-[5-benzyloxy-1-(3-diethylamino-2-hydroxypropyl)-1H-indol-3-yl]-3-(1H-indol-3-yl)-maleinimide;
(±)-2-[6-benzyloxy-1-(3-diethylamino-2-hydroxypropyl)-1H-indol-3-yl]-3-(1H-indol-3-yl)-maleinimide;
(±)-2-[7-benzyloxy-1-(3-diethylamino-2-hydroxypropyl)-1H-indol-3-yl]-3-(1H-indol-3-yl)-maleinimide;
(±)-2-[4-bromo-1-(3-diethylamino-2-hydroxypropyl)-1H-indol-3-yl]-3-(1H-indol-3-yl)-maleinimide;
(±)-2-[5-bromo-1-(3-diethylamino-2-hydroxypropyl)-1H-indol-3-yl]-3-(1H-indol-3-yl)-maleinimide;
(±)-2-[6-bromo-1-(3-diethylamino-2-hydroxypropyl)-1H-indol-3-yl]-3-(1H-indol-3-yl)-maleinimide;
(±)-2-[7-bromo-1-(3-diethylamino-2-hydroxypropyl)-1H-indol-3-yl]-3-(1H-indol-3-yl)-maleinimide;
(±)-2-[4-chloro-1-(3-diethylamino-2-hydroxypropyl)-1H-indol-3-yl]-3-(1H-indol-3-yl)-maleinimide;
(±)-2-[5-chloro-1-(3-diethylamino-2-hydroxypropyl)-1H-indol-3-yl]-3-(1H-indol-3-yl)-maleinimide;
(±)-2-[6-chloro-1-(3-diethylamino-2-hydroxypropyl)-1H-indol-3-yl]-3-(1H-indol-3-yl)-maleinimide;
(±)-2-[7-chloro-1-(3-diethylamino-2-hydroxypropyl)-1H-indol-3-yl]-3-(1H-indol-3-yl)-maleinimide;
(±)-2-[1-(3-diethylamino-2-hydroxypropyl)-4-fluoro-1H-indol-3-yl]-3-(1H-indol-3-yl)-maleinimide;
(±)-2-[1-(3-diethylamino-2-hydroxypropyl)-5-fluoro-1H-indol-3-yl]-3-(1H-indol-3-yl)-maleinimide;
(±)-2-[1-(3-diethyl amino-2-hydroxypropyl)-6-fluoro-1H-indol-3-yl]-3-(1H-indol-3-yl)-maleinimide;
(±)-2-[1-(3-diethylamino-2-hydroxypropyl)-7-fluoro-1H-indol-3-yl]-3-(1H-indol-3-yl)-maleinimide;
(±)-2-[1-(3-diethyl amino-2-hydroxypropyl)-4-hydroxy-1H-indol-3-yl]-3-(1H-indol-3-yl)-maleinimide;
(±)-2-[1-(3-diethylamino-2-hydroxypropyl)-5-hydroxy-1H-indol-3-yl]-3-(1H-indol-3-yl)-maleinimide;
(±)-2-[1-(3-diethylamino-2-hydroxypropyl)-6-hydroxy-1H-indol-3-yl]-3-(1H-indol-3-yl)-maleinimide;
(±)-2-[1-(3-diethylamino-2-hydroxypropyl)-7-hydroxy-1H-indol-3-yl]-3-(1H-indol-3-yl)-maleinimide;
(±)-2-[1-(3-diethylamino-2-hydroxypropyl)-4-trifluoromethyl-1H-indol-3-yl]-3-(1H-indol-3-yl)-maleinimide;
(±)-2-[1-(3-diethylamino-2-hydroxypropyl)-5-trifluoromethyl-1H-indol-3-yl]-3-(1H-indol-3-yl)-maleinimide;
(±)-2-[1-(3-diethylamino-2-hydroxypropyl)-6-trifluoromethyl-1H-indol-3-yl]-3-(1H-indol-3-yl)-maleinimide;
(±)-2-[1-(3-diethylamino-2-hydroxypropyl)-7-trifluoromethyl-1H-indol-3-yl]-3-(1H-indol-3-yl)-maleinimide;
(±)-2-[1-(3-diethylamino-2-hydroxypropyl)-4-methoxy-1H-indol-3-yl]-3-(1H-indol-3-yl)-maleinimide;
(±)-2-[1-(3-diethylamino-2-hydroxypropyl)-6-methoxy-1H-indol-3-yl]-3-(1H-indol-3-yl)-maleinimide;
(±)-2-[1-(3-diethylamino-2-hydroxypropyl)-7-methoxy-1H-indol-3-yl]-3-(1H-indol-3-yl)-maleinimide;
(±)-2-[1-(3-diethylamino-2-hydroxypropyl)-4,5-methylendioxy-1H-indol-3-yl]-3-(1H-indol-3-yl)-maleinimide;
(±)-2-[1-(3-diethylamino-2-hydroxypropyl)-5,6-methylendioxy-1H-indol-3-yl]-3-(1H-indol-3-yl)-maleinimide;
(±)-2-[1-(3-diethylamino-2-hydroxypropyl)-6,7-methylendioxy-1H-indol-3-yl]-3-(1H-indol-3-yl)-maleinimide;
(±)-2-[1-(3-diethylamino-2-hydroxypropyl)-4-methyl-1H-indol-3-yl]-3-(1H-indol-3-yl)-maleinimide;
(±)-2-[1-(3-diethylamino-2-hydroxypropyl)-5-methyl-1H-indol-3-yl]-3-(1H-indol-3-yl)-maleinimide;
(±)-2-[1-(3-diethylamino-2-hydroxypropyl)-6-methyl-1H-indol-3-yl]-3-(1H-indol-3-yl)-maleinimide;
(±)-2-[1-(3-diethylamino-2-hydroxypropyl)-7-methyl-1H-indol-3-yl]-3-(1H-indol-3-yl)-maleinimide;
(±)-2-[1-(3-diethylamino-2-hydroxypropyl)-4-nitro-1H-indol-3-yl]-3-(1H-indol-3-yl)-maleinimide;
(±)-2-[1-(3-diethylamino-2-hydroxypropyl)-5-nitro-1H-indol-3-yl]-3-(1H-indol-3-yl)-maleinimide;
(±)-2-[1-(3-diethylamino-2-hydroxypropyl)-6-nitro-1H-indol-3-yl]-3-(1H-indol-3-yl)-maleinimide;
(±)-2-[1-(3-diethylamino-2-hydroxypropyl)-7-nitro-1H-indol-3-yl]-3-(1H-indol-3-yl)-maleinimide;
(±)-2-[1-(3-diethylamino-2-hydroxypropyl)-4-methylthio-1H-indol-3-yl]-3-(1H-indol-3-yl)-maleinimide;
(±)-2-[1-(3-diethylamino-2-hydroxypropyl)-5-methylthio-1H-indol-3-yl]-3-(1H-indol-3-yl)-maleinimide;
(±)-2-[1-(3-diethylamino-2-hydroxypropyl)-6-methylthio-1H-indol-3-yl]-3-(1H-indol-3-yl)-maleinimide;
(±)-2-[1-(3-diethylamino-2-hydroxypropyl)-7-methylthio-1H-indol-3-yl]-3-(1H-indol-3-yl)-maleinimide;
(±)-2-[1-(3-diethylamino-2-hydroxypropyl)-4,5-dimethoxy-1H-indol-3-yl]-3-(1H-indol-3-yl)-maleinimide;
(±)-2-[1-(3-diethylamino-2-hydroxypropyl)-5,6-dimethoxy-1H-indol-3-yl]-3-(1H-indol-3-yl)-maleinimide;
(±)-2-[1-(3-diethylamino-2-hydroxypropyl)-6,7-dimethoxy-1H-indol-3-yl]-3-(1H-indol-3-yl)-maleinimide;
(+)-2-[4-acetylamino-1-(3-diethylamino-2-hydroxypropyl)-1H-indol-3-yl]-3-(1H-indol-3-yl)-maleinimide;
(+)-2-[5-acetylamino-1-(3-diethylamino-2-hydroxypropyl)-1H-indol-3-yl]-3-(1H-indol-3-yl)-maleinimide;
(+)-2-[6-acetylamino-1-(3-diethylamino-2-hydroxypropyl)-1H-indol-3-yl]-3-(1H-indol-3-yl)-maleinimide;
(+)-2-[7-acetylamino-1-(3-diethylamino-2-hydroxypropyl)-1H-indol-3-yl]-3-(1H-indol-3-yl)-maleinimide;
(+)-2-[4-amino-1-(3-diethylamino-2-hydroxypropyl)-1H-indol-3-yl]-3-(1H-indol-3-yl)-maleinimide;
(+)-2-[5-amino-1-(3-diethylamino-2-hydroxypropyl)-1H-indol-3-yl]-3-(1H-indol-3-yl)-maleinimide;
(+)-2-[6-amino-1-(3-diethylamino-2-hydroxypropyl)-1H-indol-3-yl]-3-(1H-indol-3-yl)-maleinimide;
(+)-2-[7-amino-1-(3-diethylamino-2-hydroxypropyl)-1H-indol-3-yl]-3-(1H-indol-3-yl)-maleinimide;
(+)-2-[4-benzyloxy-1-(3-diethylamino-2-hydroxypropyl)-1H-indol-3-yl]-3-(1H-indol-3-yl)-maleinimide;

(+)-2-[5-benzyloxy-1-(3-diethylamino-2-hydroxypropyl)-1H-indol-3-yl]-3-(1H-indol-3-yl)-maleinimide;
(+)-2-[6-benzyloxy-1-(3-diethylamino-2-hydroxypropyl)-1H-indol-3-yl]-3-(1H-indol-3-yl)-maleinimide;
(+)-2-[7-benzyloxy-1-(3-diethylamino-2-hydroxypropyl)-1H-indol-3-yl]-3-(1H-indol-3-yl)-maleinimide;
(+)-2-[4-bromo-1-(3-diethylamino-2-hydroxypropyl)-1H-indol-3-yl]-3-(1H-indol-3-yl)-maleinimide;
(+)-2-[5-bromo-1-(3-diethylamino-2-hydroxypropyl)-1H-indol-3-yl]-3-(1H-indol-3-yl)-maleinimide;
(+)-2-[6-bromo-1-(3-diethylamino-2-hydroxypropyl)-1H-indol-3-yl]-3-(1H-indol-3-yl)-maleinimide;
(+)-2-[7-bromo-1-(3-diethylamino-2-hydroxypropyl)-1H-indol-3-yl]-3-(1H-indol-3-yl)-maleinimide;
(+)-2-[4-chloro-1-(3-diethylamino-2-hydroxypropyl)-1H-indol-3-yl]-3-(1H-indol-3-yl)-maleinimide;
(+)-2-[5-chloro-1-(3-diethylamino-2-hydroxypropyl)-1H-indol-3-yl]-3-(1H-indol-3-yl)-maleinimide;
(+)-2-[6-chloro-1-(3-diethylamino-2-hydroxypropyl)-1H-indol-3-yl]-3-(1H-indol-3-yl)-maleinimide;
(+)-2-[7-chloro-1-(3-diethylamino-2-hydroxypropyl)-1H-indol-3-yl]-3-(1H-indol-3-yl)-maleinimide;
(+)-2-[1-(3-diethylamino-2-hydroxypropyl)-4-fluoro-1H-indol-3-yl]-3-(1H-indol-3-yl)-maleinimide;
(+)-2-[1-(3-diethylamino-2-hydroxypropyl)-5-fluoro-1H-indol-3-yl]-3-(1H-indol-3-yl)-maleinimide;
(+)-2-[1-(3-diethylamino-2-hydroxypropyl)-6-fluoro-1H-indol-3-yl]-3-(1H-indol-3-yl)-maleinimide;
(+)-2-[1-(3-diethylamino-2-hydroxypropyl)-7-fluoro-1H-indol-3-yl]-3-(1H-indol-3-yl)-maleinimide;
(+)-2-[1-(3-diethylamino-2-hydroxypropyl)-4-hydroxy-1H-indol-3-yl]-3-(1H-indol-3-yl)-maleinimide;
(+)-2-[1-(3-diethylamino-2-hydroxypropyl)-5-hydroxy-1H-indol-3-yl]-3-(1H-indol-3-yl)-maleinimide;
(+)-2-[1-(3-diethylamino-2-hydroxypropyl)-6-hydroxy-1H-indol-3-yl]-3-(1H-indol-3-yl)-maleinimide;
(+)-2-[1-(3-diethylamino-2-hydroxypropyl)-7-hydroxy-1H-indol-3-yl]-3-(1H-indol-3-yl)-maleinimide;
(+)-2-[1-(3-diethylamino-2-hydroxypropyl)-4-trifluoromethyl-1H-indol-3-yl]-3-(1H-indol-3-yl)-maleinimide;
(+)-2-[1-(3-diethylamino-2-hydroxypropyl)-5-trifluoromethyl-1H-indol-3-yl]-3-(1H-indol-3-yl)-maleinimide;
(+)-2-[1-(3-diethylamino-2-hydroxypropyl)-6-trifluoromethyl-1H-indol-3-yl]-3-(1H-indol-3-yl)-maleinimide;
(+)-2-[1-(3-diethylamino-2-hydroxypropyl)-7-trifluoromethyl-1H-indol-3-yl]-3-(1H-indol-3-yl)-maleinimide;
(+)-2-[1-(3-diethylamino-2-hydroxypropyl)-4-methoxy-1H-indol-3-yl]-3-(1H-indol-3-yl)-maleinimide;
(+)-2-[1-(3-diethylamino-2-hydroxypropyl)-5-methoxy-1H-indol-3-yl]-3-(1H-indol-3-yl)-maleinimide;
(+)-2-[1-(3-diethylamino-2-hydroxypropyl)-6-methoxy-1H-indol-3-yl]-3-(1H-indol-3-yl)-maleinimide;
(+)-2-[1-(3-diethylamino-2-hydroxypropyl)-7-methoxy-1H-indol-3-yl]-3-(1H-indol-3-yl)-maleinimide;
(+)-2-[1-(3-diethylamino-2-hydroxypropyl)-4,5-methylendioxy-1H-indol-3-yl]-3-(1H-indol-3-yl)-maleinimide;
(+)-2-[1-(3-diethylamino-2-hydroxypropyl)-5,6-methylendioxy-1H-indol-3-yl]-3-(1H-indol-3-yl)-maleinimide;
(+)-2-[1-(3-diethylamino-2-hydroxypropyl)-6,7-methylendioxy-1H-indol-3-yl]-3-(1H-indol-3-yl)-maleinimide;
(+)-2-[1-(3-diethylamino-2-hydroxypropyl)-4-methyl-1H-indol-3-yl]-3-(1H-indol-3-yl)-maleinimide;
(+)-2-[1-(3-diethylamino-2-hydroxypropyl)-5-methyl-1H-indol-3-yl]-3-(1H-indol-3-yl)-maleinimide;
(+)-2-[1-(3-diethylamino-2-hydroxypropyl)-6-methyl-1H-indol-3-yl]-3-(1H-indol-3-yl)-maleinimide;
(+)-2-[1-(3-diethylamino-2-hydroxypropyl)-7-methyl-1H-indol-3-yl]-3-(1H-indol-3-yl)-maleinimide;
(+)-2-[1-(3-diethylamino-2-hydroxypropyl)-4-nitro-1H-indol-3-yl]-3-(1H-indol-3-yl)-maleinimide;
(+)-2-[1-(3-diethylamino-2-hydroxypropyl)-5-nitro-1H-indol-3-yl]-3-(1H-indol-3-yl)-maleinimide;
(+)-2-[1-(3-diethylamino-2-hydroxypropyl)-6-nitro-1H-indol-3-yl]-3-(1H-indol-3-yl)-maleinimide;
(+)-2-[1-(3-diethylamino-2-hydroxypropyl)-7-nitro-1H-indol-3-yl]-3-(1H-indol-3-yl)-maleinimide;
(+)-2-[1-(3-diethylamino-2-hydroxypropyl)-4-methylthio-1H-indol-3-yl]-3-(1H-indol-3-yl)-maleinimide;
(+)-2-[1-(3-diethylamino-2-hydroxypropyl)-5-methylthio-1H-indol-3-yl]-3-(1H-indol-3-yl)-maleinimide;
(+)-2-[1-(3-diethylamino-2-hydroxypropyl)-6-methylthio-1H-indol-3-yl]-3-(1H-indol-3-yl)-maleinimide;
(+)-2-[1-(3-diethylamino-2-hydroxypropyl)-7-methylthio-1H-indol-3-yl]-3-(1H-indol-3-yl)-maleinimide;
(+)-2-[1-(3-diethylamino-2-hydroxypropyl)-4,5-dimethoxy-1H-indol-3-yl]-3-(1H-indol-3-yl)-maleinimide;
(+)-2-[1-(3-diethylamino-2-hydroxypropyl)-5,6-dimethoxy-1H-indol-3-yl]-3-(1H-indol-3-yl)-maleinimide;
(+)-2-[1-(3-diethylamino-2-hydroxypropyl)-6,7-dimethoxy-1H-indol-3-yl]-3-(1H-indol-3-yl)-maleinimide;
(−)-2-[4-acetylamino-1-(3-diethylamino-2-hydroxypropyl)-1H-indol-3-yl]-3-(1H-indol-3-yl)-maleinimide;
(−)-2-[5-acetylamino-1-(3-diethylamino-2-hydroxypropyl)-1H-indol-3-yl]-3-(1H-indol-3-yl)-maleinimide;
(−)-2-[6-acetylamino-1-(3-diethylamino-2-hydroxypropyl)-1H-indol-3-yl]-3-(1H-indol-3-yl)-maleinimide;
(−)-2-[7-acetylamino-1-(3-diethylamino-2-hydroxypropyl)-1H-indol-3-yl]-3-(1H-indol-3-yl)-maleinimide;
(−)-2-[4-amino-1-(3-diethylamino-2-hydroxypropyl)-1H-indol-3-yl]-3-(1H-indol-3-yl)-maleinimide;
(−)-2-[5-amino-1-(3-diethylamino-2-hydroxypropyl)-1H-indol-3-yl]-3-(1H-indol-3-yl)-maleinimide;
(−)-2-[6-amino-1-(3-diethylamino-2-hydroxypropyl)-1H-indol-3-yl]-3-(1H-indol-3-yl)-maleinimide;
(−)-2-[7-amino-1-(3-diethylamino-2-hydroxypropyl)-1H-indol-3-yl]-3-(1H-indol-3-yl)-maleinimide;
(−)-2-[4-benzyloxy-1-(3-diethylamino-2-hydroxypropyl)-1H-indol-3-yl]-3-(1H-indol-3-yl)-maleinimide;
(−)-2-[5-benzyloxy-1-(3-diethylamino-2-hydroxypropyl)-1H-indol-3-yl]-3-(1H-indol-3-yl)-maleinimide;
(−)-2-[6-benzyloxy-1-(3-diethylamino-2-hydroxypropyl)-1H-indol-3-yl]-3-(1H-indol-3-yl)-maleinimide;
(−)-2-[7-benzyloxy-1-(3-diethylamino-2-hydroxypropyl)-1H-indol-3-yl]-3-(1H-indol-3-yl)-maleinimide;

(−)-2-[4-bromo-1-(3-diethylamino-2-hydroxypropyl)-1H-indol-3-yl]-3-(1H-indol-3-yl)-maleinimide;
(−)-2-[5-bromo-1-(3-diethylamino-2-hydroxypropyl)-1H-indol-3-yl]-3-(1H-indol-3-yl)-maleinimide;
(−)-2-[6-bromo-1-(3-diethylamino-2-hydroxypropyl)-1H-indol-3-yl]-3-(1H-indol-3-yl)-maleinimide;
(−)-2-[7-bromo-1-(3-diethylamino-2-hydroxypropyl)-1H-indol-3-yl]-3-(1H-indol-3-yl)-maleinimide;
(−)-2-[4-chloro-1-(3-diethylamino-2-hydroxypropyl)-1H-indol-3-yl]-3-(1H-indol-3-yl)-maleinimide;
(−)-2-[5-chloro-1-(3-diethylamino-2-hydroxypropyl)-1H-indol-3-yl]-3-(1H-indol-3-yl)-maleinimide;
(−)-2-[6-chloro-1-(3-diethylamino-2-hydroxypropyl)-1H-indol-3-yl]-3-(1H-indol-3-yl)-maleinimide;
(−)-2-[7-chloro-1-(3-diethylamino-2-hydroxypropyl)-1H-indol-3-yl]-3-(1H-indol-3-yl)-maleinimide;
(−)-2-[1-(3-diethylamino-2-hydroxypropyl)-4-fluoro-1H-indol-3-yl]-3-(1H-indol-3-yl)-maleinimide;
(−)-2-[1-(3-diethylamino-2-hydroxypropyl)-5-fluoro-1H-indol-3-yl]-3-(1H-indol-3-yl)-maleinimide;
(−)-2-[1-(3-diethylamino-2-hydroxypropyl)-6-fluoro-1H-indol-3-yl]-3-(1H-indol-3-yl)-maleinimide;
(−)-2-[1-(3-diethylamino-2-hydroxypropyl)-7-fluoro-1H-indol-3-yl]-3-(1H-indol-3-yl)-maleinimide;
(−)-2-[1-(3-diethylamino-2-hydroxypropyl)-4-hydroxy-1H-indol-3-yl]-3-(1H-indol-3-yl)-maleinimide;
(−)-2-[1-(3-diethylamino-2-hydroxypropyl)-5-hydroxy-1H-indol-3-yl]-3-(1H-indol-3-yl)-maleinimide;
(−)-2-[1-(3-diethylamino-2-hydroxypropyl)-6-hydroxy-1H-indol-3-yl]-3-(1H-indol-3-yl)-maleinimide;
(−)-2-[1-(3-diethylamino-2-hydroxypropyl)-7-hydroxy-1H-indol-3-yl]-3-(1H-indol-3-yl)-maleinimide;
(−)-2-[1-(3-diethylamino-2-hydroxypropyl)-4-trifluoromethyl-1H-indol-3-yl]-3-(1H-indol-3-yl)-maleinimide;
(−)-2-[1-(3-diethylamino-2-hydroxypropyl)-5-trifluoromethyl-1H-indol-3-yl]-3-(1H-indol-3-yl)-maleinimide;
(−)-2-[1-(3-diethylamino-2-hydroxypropyl)-6-trifluoromethyl-1H-indol-3-yl]-3-(1H-indol-3-yl)-maleinimide;
(−)-2-[1-(3-diethylamino-2-hydroxypropyl)-7-trifluoromethyl-1H-indol-3-yl]-3-(1H-indol-3-yl)-maleinimide;
(−)-2-[1-(3-diethylamino-2-hydroxypropyl)-4-methoxy-1H-indol-3-yl]-3-(1H-indol-3-yl)-maleinimide;
(−)-2-[1-(3-diethylamino-2-hydroxypropyl)-5-methoxy-1H-indol-3-yl]-3-(1H-indol-3-yl)-maleinimide;
(−)-2-[1-(3-diethylamino-2-hydroxypropyl)-6-methoxy-1H-indol-3-yl]-3-(1H-indol-3-yl)-maleinimide;
(−)-2-[1-(3-diethylamino-2-hydroxypropyl)-7-methoxy-1H-indol-3-yl]-3-(1H-indol-3-yl)-maleinimide;
(−)-2-[1-(3-diethylamino-2-hydroxypropyl)-4,5-methylendioxy-1H-indol-3-yl]-3-(1H-indol-3-yl)-maleinimide;
(−)-2-[1-(3-diethylamino-2-hydroxypropyl)-5,6-methylendioxy-1H-indol-3-yl]-3-(1H-indol-3-yl)-maleinimide;
(−)-2-[1-(3-diethylamino-2-hydroxypropyl)-6,7-methylendioxy-1H-indol-3-yl]-3-(1H-indol-3-yl)-maleinimide;
(−)-2-[1-(3-diethylamino-2-hydroxypropyl)-4-methyl-1H-indol-3-yl]-3-(1H-indol-3-yl)-maleinimide;
(−)-2-[1-(3-diethylamino-2-hydroxypropyl)-5-methyl-1H-indol-3-yl]-3-(1H-indol-3-yl)-maleinimide;
(−)-2-[1-(3-diethylamino-2-hydroxypropyl)-6-methyl-1H-indol-3-yl]-3-(1H-indol-3-yl)-maleinimide;
(−)-2-[1-(3-diethylamino-2-hydroxypropyl)-7-methyl-1H-indol-3-yl]-3-(1H-indol-3-yl)-maleinimide;
(−)-2-[1-(3-diethylamino-2-hydroxypropyl)-4-nitro-1H-indol-3-yl]-3-(1H-indol-3-yl)-maleinimide;
(−)-2-[1-(3-diethylamino-2-hydroxypropyl)-5-nitro-1H-indol-3-yl]-3-(1H-indol-3-yl)-maleinimide;
(−)-2-[1-(3-diethylamino-2-hydroxypropyl)-6-nitro-1H-indol-3-yl]-3-(1H-indol-3-yl)-maleinimide;
(−)-2-[1-(3-diethylamino-2-hydroxypropyl)-7-nitro-1H-indol-3-yl]-3-(1H-indol-3-yl)-maleinimide;
(−)-2-[1-(3-diethylamino-2-hydroxypropyl)-4-methylthio-1H-indol-3-yl]-3-(1H-indol-3-yl)-maleinimide;
(−)-2-[1-(3-diethylamino-2-hydroxypropyl)-5-methylthio-1H-indol-3-yl]-3-(1H-indol-3-yl)-maleinimide;
(−)-2-[1-(3-diethylamino-2-hydroxypropyl)-6-methylthio-1H-indol-3-yl]-3-(1H-indol-3-yl)-maleinimide;
(−)-2-[1-(3-diethylamino-2-hydroxypropyl)-7-methylthio-1H-indol-3-yl]-3-(1H-indol-3-yl)-maleinimide;
(−)-2-[1-(3-diethylamino-2-hydroxypropyl)-4,5-dimethoxy-1H-indol-3-yl]-3-(1H-indol-3-yl)-maleinimide;
(−)-2-[1-(3-diethylamino-2-hydroxypropyl)-5,6-dimethoxy-1H-indol-3-yl]-3-(1H-indol-3-yl)-maleinimide;
(−)-2-[1-(3-diethylamino-2-hydroxypropyl)-6,7-dimethoxy-1H-indol-3-yl]-3-(1H-indol-3-yl)-maleinimide;
2-[4-acetylamino-1-(3-diethylaminopropyl)-1H-indol-3-yl]-3-(1H-indol-3-yl)-maleinimide;
2-[5-acetylamino-1-(3-diethylaminopropyl)-1H-indol-3-yl]-3-(1H-indol-3-yl)-maleinimide;
2-[6-acetylamino-1-(3-diethylaminopropyl)-1H-indol-3-yl]-3-(1H-indol-3-yl)-maleinimide;
2-[7-acetylamino-1-(3-diethylaminopropyl)-1H-indol-3-yl]-3-(1H-indol-3-yl)-maleinimide;
2-[4-amino-1-(3-diethylaminopropyl)-1H-indol-3-yl]-3-(1H-indol-3-yl)-maleinimide;
2-[5-amino-1-(3-diethylaminopropyl)-1H-indol-3-yl]-3-(1H-indol-3-yl)-maleinimide;
2-[6-amino-1-(3-diethylaminopropyl)-1H-indol-3-yl]-3-(1H-indol-3-yl)-maleinimide;
2-[7-amino-1-(3-diethylaminopropyl)-1H-indol-3-yl]-3-(1H-indol-3-yl)-maleinimide;
2-[4-benzyloxy-1-(3-diethylaminopropyl)-1H-indol-3-yl]-3-(1H-indol-3-yl)-maleinimide;
2-[5-benzyloxy-1-(3-diethylaminopropyl)-1H-indol-3-yl]-3-(1H-indol-3-yl)-maleinimide;
2-[6-benzyloxy-1-(3-diethylaminopropyl)-1H-indol-3-yl]-3-(1H-indol-3-yl)-maleinimide;
2-[7-benzyloxy-1-(3-diethylaminopropyl)-1H-indol-3-yl]-3-(1H-indol-3-yl)-maleinimide;
2-[4-bromo-1-(3-diethylaminopropyl)-1H-indol-3-yl]-3-(1H-indol-3-yl)-maleinimide;
2-[5-bromo-1-(3-diethylaminopropyl)-1H-indol-3-yl]-3-(1H-indol-3-yl)-maleinimide;
2-[6-bromo-1-(3-diethylaminopropyl)-1H-indol-3-yl]-3-(1H-indol-3-yl)-maleinimide;
2-[7-bromo-1-(3-diethylaminopropyl)-1H-indol-3-yl]-3-(1H-indol-3-yl)-maleinimide;
2-[4-chloro-1-(3-diethylaminopropyl)-1H-indol-3-yl]-3-(1H-indol-3-yl)-maleinimide;
2-[5-chloro-1-(3-diethylaminopropyl)-1H-indol-3-yl]-3-(1H-indol-3-yl)-maleinimide;
2-[6-chloro-1-(3-diethylaminopropyl)-1H-indol-3-yl]-3-(1H-indol-3-yl)-maleinimide;
2-[7-chloro-1-(3-diethylaminopropyl)-1H-indol-3-yl]-3-(1H-indol-3-yl)-maleinimide;

2-[1-(3-diethylaminopropyl)-4-fluoro-1H-indol-3-yl]-3-(1H-indol-3-yl)-maleinimide;
2-[1-(3-diethylaminopropyl)-6-fluoro-1H-indol-3-yl]-3-(1H-indol-3-yl)-maleinimide;
2-[1-(3-diethylaminopropyl)-7-fluoro-1H-indol-3-yl]-3-(1H-indol-3-yl)-maleinimide;
2-[1-(3-diethylaminopropyl)-4-hydroxy-1H-indol-3-yl]-3-(1H-indol-3-yl)-maleinimide;
2-[1-(3-diethylaminopropyl)-5-hydroxy-1H-indol-3-yl]-3-(1H-indol-3-yl)-maleinimide;
2-[1-(3-diethylaminopropyl)-6-hydroxy-1H-indol-3-yl]-3-(1H-indol-3-yl)-maleinimide;
2-[1-(3-diethylaminopropyl)-7-hydroxy-1H-indol-3-yl]-3-(1H-indol-3-yl)-maleinimide;
2-[1-(3-diethylaminopropyl)-4-trifluoromethyl-1H-indol-3-yl]-3-(1H-indol-3-yl)-maleinimide;
2-[1-(3-diethylaminopropyl)-5-trifluoromethyl-1H-indol-3-yl]-3-(1H-indol-3-yl)-maleinimide;
2-[1-(3-diethylaminopropyl)-6-trifluoromethyl-1H-indol-3-yl]-3-(1H-indol-3-yl)-maleinimide;
2-[1-(3-diethylaminopropyl)-7-trifluoromethyl-1H-indol-3-yl]-3-(1H-indol-3-yl)-maleinimide;
2-[1-(3-diethylaminopropyl)-4-methoxy-1H-indol-3-yl]-3-(1H-indol-3-yl)-maleinimide;
2-[1-(3-diethylaminopropyl)-6-methoxy-1H-indol-3-yl]-3-(1H-indol-3-yl)-maleinimide;
2-[1-(3-diethylaminopropyl)-7-methoxy-1H-indol-3-yl]-3-(1H-indol-3-yl)-maleinimide;
2-[1-(3-diethylaminopropyl)-4,5-methylendioxy-1H-indol-3-yl]-3-(1H-indol-3-yl)-maleinimide;
2-[1-(3-diethylaminopropyl)-5,6-methylendioxy-1H-indol-3-yl]-3-(1H-indol-3-yl)-maleinimide;
2-[1-(3-diethylaminopropyl)-6,7-methylendioxy-1H-indol-3-yl]-3-(1H-indol-3-yl)-maleinimide;
2-[1-(3-diethylaminopropyl)-4-methyl-1H-indol-3-yl]-3-(1H-indol-3-yl)-maleinimide;
2-[1-(3-diethylaminopropyl)-5-methyl-1H-indol-3-yl]-3-(1H-indol-3-yl)-maleinimide;
2-[1-(3-diethylaminopropyl)-6-methyl-1H-indol-3-yl]-3-(1H-indol-3-yl)-maleinimide;
2-[1-(3-diethylaminopropyl)-7-methyl-1H-indol-3-yl]-3-(1H-indol-3-yl)-maleinimide;
2-[1-(3-diethylaminopropyl)-4-nitro-1H-indol-3-yl]-3-(1H-indol-3-yl)-maleinimide;
2-[1-(3-diethylaminopropyl)-5-nitro-1H-indol-3-yl]-3-(1H-indol-3-yl)-maleinimide;
2-[1-(3-diethylaminopropyl)-6-nitro-1H-indol-3-yl]-3-(1H-indol-3-yl)-maleinimide;
2-[1-(3-diethylaminopropyl)-7-nitro-1H-indol-3-yl]-3-(1H-indol-3-yl)-maleinimide;
2-[1-(3-diethylaminopropyl)-4-methylthio-1H-indol-3-yl]-3-(1H-indol-3-yl)-maleinimide;
2-[1-(3-diethylaminopropyl)-5-methylthio-1H-indol-3-yl]-3-(1H-indol-3-yl)-maleinimide;
2-[1-(3-diethylaminopropyl)-6-methylthio-1H-indol-3-yl]-3-(1H-indol-3-yl)-maleinimide;
2-[1-(3-diethylaminopropyl)-7-methylthio-1H-indol-3-yl]-3-(1H-indol-3-yl)-maleinimide;
2-[1-(3-diethylaminopropyl)-4,5-dimethoxy-1H-indol-3-yl]-3-(1H-indol-3-yl)-maleinimide;
2-[1-(3-diethylaminopropyl)-5,6-dimethoxy-1H-indol-3-yl]-3-(1H-indol-3-yl)-maleinimide;
2-[1-(3-diethylaminopropyl)-6,7-dimethoxy-1H-indol-3-yl]-3-(1H-indol-3-yl)-maleinimide;
2-[4-acetylamino-1-(3-ethylaminopropyl)-1H-indol-3-yl]-3-(1H-indol-3-yl)-maleinimide;
2-[5-acetylamino-1-(3-ethylaminopropyl)-1H-indol-3-yl]-3-(1H-indol-3-yl)-maleinimide;
2-[6-acetylamino-1-(3-ethylaminopropyl)-1H-indol-3-yl]-3-(1H-indol-3-yl)-maleinimide;
2-[7-acetylamino-1-(3-ethylaminopropyl)-1H-indol-3-yl]-3-(1H-indol-3-yl)-maleinimide;
2-[4-amino-1-(3-ethylaminopropyl)-1H-indol-3-yl]-3-(1H-indol-3-yl)-maleinimide;
2-[5-amino-1-(3-ethylaminopropyl)-1H-indol-3-yl]-3-(1H-indol-3-yl)-maleinimide;
2-[6-amino-1-(3-ethylaminopropyl)-1H-indol-3-yl]-3-(1H-indol-3-yl)-maleinimide;
2-[7-amino-1-(3-ethylaminopropyl)-1H-indol-3-yl]-3-(1H-indol-3-yl)-maleinimide;
2-[4-benzyloxy-1-(3-ethylaminopropyl)-1H-indol-3-yl]-3-(1H-indol-3-yl)-maleinimide;
2-[5-benzyloxy-1-(3-ethylaminopropyl)-1H-indol-3-yl]-3-(1H-indol-3-yl)-maleinimide;
2-[6-benzyloxy-1-(3-ethylaminopropyl)-1H-indol-3-yl]-3-(1H-indol-3-yl)-maleinimide;
2-[7-benzyloxy-1-(3-ethylaminopropyl)-1H-indol-3-yl]-3-(1H-indol-3-yl)-maleinimide;
2-[4-bromo-1-(3-ethylaminopropyl)-1H-indol-3-yl]-3-(1H-indol-3-yl)-maleinimide;
2-[5-bromo-1-(3-ethylaminopropyl)-1H-indol-3-yl]-3-(1H-indol-3-yl)-maleinimide;
2-[6-bromo-1-(3-ethylaminopropyl)-1H-indol-3-yl]-3-(1H-indol-3-yl)-maleinimide;
2-[7-bromo-1-(3-ethylaminopropyl)-1H-indol-3-yl]-3-(1H-indol-3-yl)-maleinimide;
2-[4-chloro-1-(3-ethylaminopropyl)-1H-indol-3-yl]-3-(1H-indol-3-yl)-maleinimide;
2-[5-chloro-1-(3-ethylaminopropyl)-1H-indol-3-yl]-3-(1H-indol-3-yl)-maleinimide;
2-[6-chloro-1-(3-ethylaminopropyl)-1H-indol-3-yl]-3-(1H-indol-3-yl)-maleinimide;
2-[7-chloro-1-(3-ethylaminopropyl)-1H-indol-3-yl]-3-(1H-indol-3-yl)-maleinimide;
2-[1-(3-ethylaminopropyl)-4-fluoro-1H-indol-3-yl]-3-(1H-indol-3-yl)-maleinimide;
2-[1-(3-ethylaminopropyl)-5-fluoro-1H-indol-3-yl]-3-(1H-indol-3-yl)-maleinimide;
2-[1-(3-ethylaminopropyl)-6-fluoro-1H-indol-3-yl]-3-(1H-indol-3-yl)-maleinimide;
2-[1-(3-ethylaminopropyl)-7-fluoro-1H-indol-3-yl]-3-(1H-indol-3-yl)-maleinimide;
2-[1-(3-ethylaminopropyl)-4-hydroxy-1H-indol-3-yl]-3-(1H-indol-3-yl)-maleinimide;
2-[1-(3-ethylaminopropyl)-5-hydroxy-1H-indol-3-yl]-3-(1H-indol-3-yl)-maleinimide;
2-[1-(3-ethylaminopropyl)-6-hydroxy-1H-indol-3-yl]-3-(1H-indol-3-yl)-maleinimide;
2-[1-(3-ethylaminopropyl)-7-hydroxy-1H-indol-3-yl]-3-(1H-indol-3-yl)-maleinimide;
2-[1-(3-ethylaminopropyl)-4-trifluoromethyl-1H-indol-3-yl]-3-(1H-indol-3-yl)-maleinimide;
2-[1-(3-ethylaminopropyl)-5-trifluoromethyl-1H-indol-3-yl]-3-(1H-indol-3-yl)-maleinimide;
2-[1-(3-ethylaminopropyl)-6-trifluoromethyl-1H-indol-3-yl]-3-(1H-indol-3-yl)-maleinimide;
2-[1-(3-ethylaminopropyl)-7-trifluoromethyl-1H-indol-3-yl]-3-(1H-indol-3-yl)-maleinimide;
2-[1-(3-ethylaminopropyl)-4-methoxy-1H-indol-3-yl]-3-(1H-indol-3-yl)-maleinimide;
2-[1-(3-ethylaminopropyl)-5-methoxy-1H-indol-3-yl]-3-(1H-indol-3-yl)-maleinimide;
2-[1-(3-ethylaminopropyl)-6-methoxy-1H-indol-3-yl]-3-(1H-indol-3-yl)-maleinimide;
2-[1-(3-ethylaminopropyl)-7-methoxy-1H-indol-3-yl]-3-(1H-indol-3-yl)-maleinimide;

2-[1-(3-ethylaminopropyl)-4,5-methylendioxy-1H-indol-3-yl]-3-(1H-indol-3-yl)-maleinimide;
2-[1-(3-ethylaminopropyl)-5,6-methylendioxy-1H-indol-3-yl]-3-(1H-indol-3-yl)-maleinimide;
2-[1-(3-ethylaminopropyl)-6,7-methylendioxy-1H-indol-3-yl]-3-(1H-indol-3-yl)-maleinimide;
2-[1-(3-ethylaminopropyl)-4-methyl-1H-indol-3-yl]-3-(1H-indol-3-yl)-maleinimide;
2-[1-(3-ethylaminopropyl)-5-methyl-1H-indol-3-yl]-3-(1H-indol-3-yl)-maleinimide;
2-[1-(3-ethylaminopropyl)-6-methyl-1H-indol-3-yl]-3-(1H-indol-3-yl)-maleinimide;
2-[1-(3-ethylaminopropyl)-7-methyl-1H-indol-3-yl]-3-(1H-indol-3-yl)-maleinimide;
2-[1-(3-ethylaminopropyl)-4-nitro-1H-indol-3-yl]-3-(1H-indol-3-yl)-maleinimide;
2-[1-(3-ethylaminopropyl)-5-nitro-1H-indol-3-yl]-3-(1H-indol-3-yl)-maleinimide;
2-[1-(3-ethylaminopropyl)-6-nitro-1H-indol-3-yl]-3-(1H-indol-3-yl)-maleinimide;
2-[1-(3-ethylaminopropyl)-7-nitro-1H-indol-3-yl]-3-(1H-indol-3-yl)-maleinimide;
2-[1-(3-ethylaminopropyl)-4-methylthio-1H-indol-3-yl]-3-(1H-indol-3-yl)-maleinimide;
2-[1-(3-ethylaminopropyl)-5-methylthio-1H-indol-3-yl]-3-(1H-indol-3-yl)-maleinimide;
2-[1-(3-ethylaminopropyl)-6-methylthio-1H-indol-3-yl]-3-(1H-indol-3-yl)-maleinimide;
2-[1-(3-ethylaminopropyl)-7-methylthio-1H-indol-3-yl]-3-(1H-indol-3-yl)-maleinimide;
2-[1-(3-ethylaminopropyl)-4,5-dimethoxy-1H-indol-3-yl]-3-(1H-indol-3-yl)-maleinimide;
2-[1-(3-ethylaminopropyl)-5,6-dimethoxy-1H-indol-3-yl]-3-(1H-indol-3-yl)-maleinimide;
2-[1-(3-ethylaminopropyl)-6,7-dimethoxy-1H-indol-3-yl]-3-(1H-indol-3-yl)-maleinimide;
(±)-2-[4-acetylamino-1-(2-hydroxy-3-dimethylaminopropyl)-1H-indol-3-yl]-3-(1H-indol-3-yl)-maleinimide;
(±)-2-[5-acetylamino-1-(2-hydroxy-3-dimethylaminopropyl)-1H-indol-3-yl]-3-(1H-indol-3-yl)-maleinimide;
(±)-2-[6-acetylamino-1-(2-hydroxy-3-dimethylaminopropyl)-1H-indol-3-yl]-3-(1H-indol-3-yl)-maleinimide;
(±)-2-[7-acetylamino-1-(2-hydroxy-3-dimethylaminopropyl)-1H-indol-3-yl]-3-(1H-indol-3-yl)-maleinimide;
(±)-2-[4-amino-1-(2-hydroxy-3-dimethylaminopropyl)-1H-indol-3-yl]-3-(1H-indol-3-yl)-maleinimide;
(±)-2-[5-amino-1-(2-hydroxy-3-dimethylaminopropyl)-1H-indol-3-yl]-3-(1H-indol-3-yl)-maleinimide;
(±)-2-[6-amino-1-(2-hydroxy-3-dimethylaminopropyl)-1H-indol-3-yl]-3-(1H-indol-3-yl)-maleinimide;
(±)-2-[7-amino-1-(2-hydroxy-3-dimethylaminopropyl)-1H-indol-3-yl]-3-(1H-indol-3-yl)-maleinimide;
(±)-2-[4-benzyloxy-1-(2-hydroxy-3-dimethylaminopropyl)-1H-indol-3-yl]-3-(1H-indol-3-yl)-maleinimide;
(±)-2-[5-benzyloxy-1-(2-hydroxy-3-dimethylaminopropyl)-1H-indol-3-yl]-3-(1H-indol-3-yl)-maleinimide;
(±)-2-[6-benzyloxy-1-(2-hydroxy-3-dimethylaminopropyl)-1H-indol-3-yl]-3-(1H-indol-3-yl)-maleinimide;
(±)-2-[7-benzyloxy-1-(2-hydroxy-3-dimethylaminopropyl)-1H-indol-3-yl]-3-(1H-indol-3-yl)-maleinimide;
(±)-2-[4-bromo-1-(2-hydroxy-3-dimethylaminopropyl)-1H-indol-3-yl]-3-(1H-indol-3-yl)-maleinimide;
(±)-2-[5-bromo-1-(2-hydroxy-3-dimethylaminopropyl)-1H-indol-3-yl]-3-(1H-indol-3-yl)-maleinimide;
(±)-2-[6-bromo-1-(2-hydroxy-3-dimethylaminopropyl)-1H-indol-3-yl]-3-(1H-indol-3-yl)-maleinimide;
(±)-2-[7-bromo-1-(2-hydroxy-3-dimethylaminopropyl)-1H-indol-3-yl]-3-(1H-indol-3-yl)-maleinimide;
(±)-2-[4-chloro-1-(2-hydroxy-3-dimethylaminopropyl)-1H-indol-3-yl]-3-(1H-indol-3-yl)-maleinimide;
(±)-2-[5-chloro-1-(2-hydroxy-3-dimethylaminopropyl)-1H-indol-3-yl]-3-(1H-indol-3-yl)-maleinimide;
(±)-2-[6-chloro-1-(2-hydroxy-3-dimethylaminopropyl)-1H-indol-3-yl]-3-(1H-indol-3-yl)-maleinimide;
(±)-2-[7-chloro-1-(2-hydroxy-3-dimethylaminopropyl)-1H-indol-3-yl]-3-(1H-indol-3-yl)-maleinimide;
(±)-2-[4-fluoro-1-(2-hydroxy-3-dimethylaminopropyl)-1H-indol-3-yl]-3-(1H-indol-3-yl)-maleinimide;
(±)-2-[5-fluoro-1-(2-hydroxy-3-dimethylaminopropyl)-1H-indol-3-yl]-3-(1H-indol-3-yl)-maleinimide;
(±)-2-[6-fluoro-1-(2-hydroxy-3-dimethylaminopropyl)-1H-indol-3-yl]-3-(1H-indol-3-yl)-maleinimide;
(±)-2-[7-fluoro-1-(2-hydroxy-3-dimethylaminopropyl)-1H-indol-3-yl]-3-(1H-indol-3-yl)-maleinimide;
(±)-2-[4-hydroxy-1-(2-hydroxy-3-dimethylaminopropyl)-1H-indol-3-yl]-3-(1H-indol-3-yl)-maleinimide;
(±)-2-[5-hydroxy-1-(2-hydroxy-3-dimethylaminopropyl)-1H-indol-3-yl]-3-(1H-indol-3-yl)-maleinimide;
(±)-2-[6-hydroxy-1-(2-hydroxy-3-dimethylaminopropyl)-1H-indol-3-yl]-3-(1H-indol-3-yl)-maleinimide;
(±)-2-[7-hydroxy-1-(2-hydroxy-3-dimethylaminopropyl)-1H-indol-3-yl]-3-(1H-indol-3-yl)-maleinimide;
(±)-2-[4-trifluoromethyl-1-(2-hydroxy-3-dimethylaminopropyl)-1H-indol-3-yl]-3-(1H-indol-3-yl)-maleinimide;
(±)-2-[5-trifluoromethyl-1-(2-hydroxy-3-dimethylaminopropyl)-1H-indol-3-yl]-3-(1H-indol-3-yl)-maleinimide;
(±)-2-[6-trifluoromethyl-1-(2-hydroxy-3-dimethylaminopropyl)-1H-indol-3-yl]-3-(1H-indol-3-yl)-maleinimide;
(±)-2-[7-trifluoromethyl-1-(2-hydroxy-3-dimethylaminopropyl)-1H-indol-3-yl]-3-(1H-indol-3-yl)-maleinimide;
(±)-2-[1-(2-hydroxy-3-dimethylaminopropyl)-4-methoxy-1H-indol-3-yl]-3-(1H-indol-3-yl)-maleinimide;
(±)-2-[1-(2-hydroxy-3-dimethylaminopropyl)-5-methoxy-1H-indol-3-yl]-3-(1H-indol-3-yl)-maleinimide;
(±)-2-[1-(2-hydroxy-3-dimethylaminopropyl)-6-methoxy-1H-indol-3-yl]-3-(1H-indol-3-yl)-maleinimide;
(±)-2-[1-(2-hydroxy-3-dimethylaminopropyl)-7-methoxy-1H-indol-3-yl]-3-(1H-indol-3-yl)-maleinimide;
(±)-2-[1-(2-hydroxy-3-dimethylaminopropyl)-4,5-methylendioxy-1H-indol-3-yl]-3-(1H-indol-3-yl)-maleinimide;
(±)-2-[1-(2-hydroxy-3-dimethylaminopropyl)-5,6-methylendioxy-1H-indol-3-yl]-3-(1H-indol-3-yl)-maleinimide;

(±)-2-[1-(2-hydroxy-3-dimethylaminopropyl)-6,7-methylendioxy-1H-indol-3-yl]-3-(1H-indol-3-yl)-maleinimide;
(±)-2-[1-(2-hydroxy-3-dimethylaminopropyl)-4-methyl-1H-indol-3-yl]-3-(1H-indol-3-yl)-maleinimide;
(±)-2-[1-(2-hydroxy-3-dimethylaminopropyl)-5-methyl-1H-indol-3-yl]-3-(1H-indol-3-yl)-maleinimide;
(±)-2-[1-(2-hydroxy-3-dimethylaminopropyl)-6-methyl-1H-indol-3-yl]-3-(1H-indol-3-yl)-maleinimide;
(±)-2-[1-(2-hydroxy-3-dimethylaminopropyl)-7-methyl-1H-indol-3-yl]-3-(1H-indol-3-yl)-maleinimide;
(±)-2-[1-(2-hydroxy-3-dimethylaminopropyl)-4-nitro-1H-indol-3-yl]-3-(1H-indol-3-yl)-maleinimide;
(±)-2-[1-(2-hydroxy-3-dimethylaminopropyl)-5-nitro-1H-indol-3-yl]-3-(1H-indol-3-yl)-maleinimide;
(±)-2-[1-(2-hydroxy-3-dimethylaminopropyl)-6-nitro-1H-indol-3-yl]-3-(1H-indol-3-yl)-maleinimide;
(±)-2-[1-(2-hydroxy-3-dimethylaminopropyl)-7-nitro-1H-indol-3-yl]-3-(1H-indol-3-yl)-maleinimide;
(±)-2-[1-(2-hydroxy-3-dimethylaminopropyl)-4-methylthio-1H-indol-3-yl]-3-(1H-indol-3-yl)-maleinimide;
(±)-2-[1-(2-hydroxy-3-dimethylaminopropyl)-5-methylthio-1H-indol-3-yl]-3-(1H-indol-3-yl)-maleinimide;
(±)-2-[1-(2-hydroxy-3-dimethylaminopropyl)-6-methylthio-1H-indol-3-yl]-3-(1H-indol-3-yl)-maleinimide;
(±)-2-[1-(2-hydroxy-3-dimethylaminopropyl)-7-methylthio-1H-indol-3-yl]-3-(1H-indol-3-yl)-maleinimide;
(±)-2-[1-(2-hydroxy-3-dimethylaminopropyl)-4,5-dimethoxy-1H-indol-3-yl]-3-(1H-indol-3-yl)-maleinimide;
(±)-2-[1-(2-hydroxy-3-dimethylaminopropyl)-5,6-dimethoxy-1H-indol-3-yl]-3-(1H-indol-3-yl)-maleinimide;
(±)-2-[1-(2-hydroxy-3-dimethylaminopropyl)-6,7-dimethoxy-1H-indol-3-yl]-3-(1H-indol-3-yl)-maleinimide;
(+)-2-[4-acetylamino-1-(2-hydroxy-3-dimethylaminopropyl)-1H-indol-3-yl]-3-(1H-indol-3-yl)-maleinimide;
(+)-2-[5-acetylamino-1-(2-hydroxy-3-dimethylaminopropyl)-1H-indol-3-yl]-3-(1H-indol-3-yl)-maleinimide;
(+)-2-[6-acetylamino-1-(2-hydroxy-3-dimethylaminopropyl)-1H-indol-3-yl]-3-(1H-indol-3-yl)-maleinimide;
(+)-2-[7-acetylamino-1-(2-hydroxy-3-dimethylaminopropyl)-1H-indol-3-yl]-3-(1H-indol-3-yl)-maleinimide;
(+)-2-[4-amino-1-(2-hydroxy-3-dimethylaminopropyl)-1H-indol-3-yl]-3-(1H-indol-3-yl)-maleinimide;
(+)-2-[5-amino-1-(2-hydroxy-3-dimethylaminopropyl)-1H-indol-3-yl]-3-(1H-indol-3-yl)-maleinimide;
(+)-2-[6-amino-1-(2-hydroxy-3-dimethylaminopropyl)-1H-indol-3-yl]-3-(1H-indol-3-yl)-maleinimide;
(+)-2-[7-amino-1-(2-hydroxy-3-dimethylaminopropyl)-1H-indol-3-yl]-3-(1H-indol-3-yl)-maleinimide;
(+)-2-[4-benzyloxy-1-(2-hydroxy-3-dimethylaminopropyl)-1H-indol-3-yl]-3-(1H-indol-3-yl)-maleinimide;
(+)-2-[5-benzyloxy-1-(2-hydroxy-3-dimethylaminopropyl)-1H-indol-3-yl]-3-(1H-indol-3-yl)-maleinimide;
(+)-2-[6-benzyloxy-1-(2-hydroxy-3-dimethylaminopropyl)-1H-indol-3-yl]-3-(1H-indol-3-yl)-maleinimide;
(+)-2-[7-benzyloxy-1-(2-hydroxy-3-dimethylaminopropyl)-1H-indol-3-yl]-3-(1H-indol-3-yl)-maleinimide;
(+)-2-[4-bromo-1-(2-hydroxy-3-dimethylaminopropyl)-1H-indol-3-yl]-3-(1H-indol-3-yl)-maleinimide;
(+)-2-[5-bromo-1-(2-hydroxy-3-dimethylaminopropyl)-1H-indol-3-yl]-3-(1H-indol-3-yl)-maleinimide;
(+)-2-[6-bromo-1-(2-hydroxy-3-dimethylaminopropyl)-1H-indol-3-yl]-3-(1H-indol-3-yl)-maleinimide;
(+)-2-[7-bromo-1-(2-hydroxy-3-dimethylaminopropyl)-1H-indol-3-yl]-3-(1H-indol-3-yl)-maleinimide;
(+)-2-[4-chloro-1-(2-hydroxy-3-dimethylaminopropyl)-1H-indol-3-yl]-3-(1H-indol-3-yl)-maleinimide;
(+)-2-[5-chloro-1-(2-hydroxy-3-dimethylaminopropyl)-1H-indol-3-yl]-3-(1H-indol-3-yl)-maleinimide;
(+)-2-[6-chloro-1-(2-hydroxy-3-dimethylaminopropyl)-1H-indol-3-yl]-3-(1H-indol-3-yl)-maleinimide;
(+)-2-[7-chloro-1-(2-hydroxy-3-dimethylaminopropyl)-1H-indol-3-yl]-3-(1H-indol-3-yl)-maleinimide;
(+)-2-[4-fluoro-1-(2-hydroxy-3-dimethylaminopropyl)-1H-indol-3-yl]-3-(1H-indol-3-yl)-maleinimide;
(+)-2-[5-fluoro-1-(2-hydroxy-3-dimethylaminopropyl)-1H-indol-3-yl]-3-(1H-indol-3-yl)-maleinimide;
(+)-2-[6-fluoro-1-(2-hydroxy-3-dimethylaminopropyl)-1H-indol-3-yl]-3-(1H-indol-3-yl)-maleinimide;
(+)-2-[7-fluoro-1-(2-hydroxy-3-dimethylaminopropyl)-1H-indol-3-yl]-3-(1H-indol-3-yl)-maleinimide;
(+)-2-[4-hydroxy-1-(2-hydroxy-3-dimethylaminopropyl)-1H-indol-3-yl]-3-(1H-indol-3-yl)-maleinimide;
(+)-2-[5-hydroxy-1-(2-hydroxy-3-dimethylaminopropyl)-1H-indol-3-yl]-3-(1H-indol-3-yl)-maleinimide;
(+)-2-[6-hydroxy-1-(2-hydroxy-3-dimethylaminopropyl)-1H-indol-3-yl]-3-(1H-indol-3-yl)-maleinimide;
(+)-2-[7-hydroxy-1-(2-hydroxy-3-dimethylaminopropyl)-1H-indol-3-yl]-3-(1H-indol-3-yl)-maleinimide;
(+)-2-[4-trifluoromethyl-1-(2-hydroxy-3-dimethylaminopropyl)-1H-indol-3-yl]-3-(1H-indol-3-yl)-maleinimide;
(+)-2-[5-trifluoromethyl-1-(2-hydroxy-3-dimethylaminopropyl)-1H-indol-3-yl]-3-(1H-indol-3-yl)-maleinimide;
(+)-2-[6-trifluoromethyl-1-(2-hydroxy-3-dimethylaminopropyl)-1H-indol-3-yl]-3-(1H-indol-3(yl)-maleinimide;
(+)-2-[7-trifluoromethyl-1-(2-hydroxy-3-dimethylaminopropyl)-1H-indol-3-yl]-3-(1H-indol-3-yl)-maleinimide;
(+)-2-[1-(2-hydroxy-3-dimethylaminopropyl)-4-methoxy-1H-indol-3-yl]-3-(1H-indol-3-yl)-maleinimide;
(+)-2-[1-(2-hydroxy-3-dimethylaminopropyl)-5-methoxy-1H-indol-3-yl]-3-(1H-indol-3-yl)-maleinimide;
(+)-2-[1-(2-hydroxy-3-dimethylaminopropyl)-6-methoxy-1H-indol-3-yl]-3-(1H-indol-3-yl)-maleinimide;
(+)-2-[1-(2-hydroxy-3-dimethylaminopropyl)-7-methoxy-1H-indol-3-yl]-3-(1H-indol-3-yl)-maleinimide;
(+)-2-[1-(2-hydroxy-3-dimethylaminopropyl)-4,5-methylendioxy-1H-indol-3-yl]-3-(1H-indol-3-yl)-maleinimide;
(+)-2-[1-(2-hydroxy-3-dimethylaminopropyl)-5,6-methylendioxy-1H-indol-3-yl]-3-(1H-indol-3-yl)-maleinimide;

(+)-2-[1-(2-hydroxy-3-dimethylaminopropyl)-6,7-methylendioxy-1H-indol-3-yl]-3-(1H-indol-3-yl)-maleinimide;
(+)-2-[1-(2-hydroxy-3-dimethylaminopropyl)-4-methyl-1H-indol-3-yl]-3-(1H-indol-3-yl)-maleinimide;
(+)-2-[1-(2-hydroxy-3-dimethylaminopropyl)-5-methyl-1H-indol-3-yl]-3-(1H-indol-3-yl)-maleinimide;
(+)-2-[1-(2-hydroxy-3-dimethylaminopropyl)-6-methyl-1H-indol-3-yl]-3-(1H-indol-3-yl)-maleinimide;
(+)-2-[1-(2-hydroxy-3-dimethylaminopropyl)-7-methyl-1H-indol-3-yl]-3-(1H-indol-3-yl)-maleinimide;
(+)-2-[1-(2-hydroxy-3-dimethylaminopropyl)-4-nitro-1H-indol-3-yl]-3-(1H-indol-3-yl)-maleinimide;
(+)-2-[1-(2-hydroxy-3-dimethylaminopropyl)-5-nitro-1H-indol-3-yl]-3-(1H-indol-3-yl)-maleinimide;
(+)-2-[1-(2-hydroxy-3-dimethylaminopropyl)-6-nitro-1H-indol-3-yl]-3-(1H-indol-3-yl)-maleinimide;
(+)-2-[1-(2-hydroxy-3-dimethylaminopropyl)-7-nitro-1H-indol-3-yl]-3-(1H-indol-3-yl)-maleinimide;
(+)-2-[1-(2-hydroxy-3-dimethylaminopropyl)-4-methylthio-1H-indol-3-yl]-3-(1H-indol-3-yl)-maleinimide;
(+)-2-[1-(2-hydroxy-3-dimethylaminopropyl)-5-methylthio-1H-indol-3-yl]-3-(1H-indol-3-yl)-maleinimide;
(+)-2-[1-(2-hydroxy-3-dimethylaminopropyl)-6-methylthio-1H-indol-3-yl]-3-(1H-indol-3-yl)-maleinimide;
(+)-2-[1-(2-hydroxy-3-dimethylaminopropyl)-7-methylthio-1H-indol-3-yl]-3-(1H-indol-3-yl)-maleinimide;
(+)-2-[1-(2-hydroxy-3-dimethylaminopropyl)-4,5-dimethoxy-1H-indol-3-yl]-3-(1H-indol-3-yl)-maleinimide;
(+)-2-[1-(2-hydroxy-3-dimethylaminopropyl)-5,6-dimethoxy-1H-indol-3-yl]-3-(1H-indol-3-yl)-maleinimide;
(+)-2-[1-(2-hydroxy-3-dimethylaminopropyl)-6,7-dimethoxy-1H-indol-3-yl]-3-(1H-indol-3-yl)-maleinimide;
(−)-2-[4-acetylamino-1-(2-hydroxy-3-dimethylaminopropyl)-1H-indol-3-yl]-3-(1H-indol-3-yl)-maleinimide;
(−)-2-[5-acetylamino-1-(2-hydroxy-3-dimethylaminopropyl)-1H-indol-3-yl]-3-(1H-indol-3-yl)-maleinimide;
(−)-2-[6-acetylamino-1-(2-hydroxy-3-dimethylaminopropyl)-1H-indol-3-yl]-3-(1H-indol-3-yl)-maleinimide;
(−)-2-[7-acetylamino-1-(2-hydroxy-3-dimethylaminopropyl)-1H-indol-3-yl]-3-(1H-indol-3-yl)-maleinimide;
(−)-2-[4-amino-1-(2-hydroxy-3-dimethylaminopropyl)-1H-indol-3-yl]-3-(1H-indol-3-yl)-maleinimide;
(−)-2-[5-amino-1-(2-hydroxy-3-dimethylaminopropyl)-1H-indol-3-yl]-3-(1H-indol-3-yl)-maleinimide;
(−)-2-[6-amino-1-(2-hydroxy-3-dimethylaminopropyl)-1H-indol-3-yl]-3-(1H-indol-3-yl)-maleinimide;
(−)-2-[7-amino-1-(2-hydroxy-3-dimethylaminopropyl)-1H-indol-3-yl]-3-(1H-indol-3-yl)-maleinimide;
(−)-2-[4-benzyloxy-1-(2-hydroxy-3-dimethylaminopropyl)-1H-indol-3-yl]-3-(1H-indol-3-yl)-maleinimide;
(−)-2-[5-benzyloxy-1-(2-hydroxy-3-dimethylaminopropyl)-1H-indol-3-yl]-3-(1H-indol-3-yl)-maleinimide;
(−)-2-[6-benzyloxy-1-(2-hydroxy-3-dimethylaminopropyl)-1H-indol-3-yl]-3-(1H-indol-3-yl)-maleinimide;
(−)-2-[7-benzyloxy-1-(2-hydroxy-3-dimethylaminopropyl)-1H-indol-3-yl]-3-(1H-indol-3-yl)-maleinimide;
(−)-2-[4-bromo-1-(2-hydroxy-3-dimethylaminopropyl)-1H-indol-3-yl]-3-(1H-indol-3-yl)-maleinimide;
(−)-2-[5-bromo-1-(2-hydroxy-3-dimethylaminopropyl)-1H-indol-3-yl]-3-(1H-indol-3-yl)-maleinimide;
(−)-2-[6-bromo-1-(2-hydroxy-3-dimethylaminopropyl)-1H-indol-3-yl]-3-(1H-indol-3-yl)-maleinimide;
(−)-2-[7-bromo-1-(2-hydroxy-3-dimethylaminopropyl)-1H-indol-3-yl]-3-(1H-indol-3-yl)-maleinimide;
(−)-2-[4-chloro-1-(2-hydroxy-3-dimethylaminopropyl)-1H-indol-3-yl]-3-(1H-indol-3-yl)-maleinimide;
(−)-2-[5-chloro-1-(2-hydroxy-3-dimethylaminopropyl)-1H-indol-3-yl]-3-(1H-indol-3-yl)-maleinimide;
(−)-2-[6-chloro-1-(2-hydroxy-3-dimethylaminopropyl)-1H-indol-3-yl]-3-(1H-indol-3-yl)-maleinimide;
(−)-2-[7-chloro-1-(2-hydroxy-3-dimethylaminopropyl)-1H-indol-3-yl]-3-(1H-indol-3-yl)-maleinimide;
(−)-2-[4-fluoro-1-(2-hydroxy-3-dimethylaminopropyl)-1H-indol-3-yl]-3-(1H-indol-3-yl)-maleinimide;
(−)-2-[5-fluoro-1-(2-hydroxy-3-dimethylaminopropyl)-1H-indol-3-yl]-3-(1H-indol-3-yl)-maleinimide;
(−)-2-[6-fluoro-1-(2-hydroxy-3-dimethylaminopropyl)-1H-indol-3-yl]-3-(1H-indol-3-yl)-maleinimide;
(−)-2-[7-fluoro-1-(2-hydroxy-3-dimethylaminopropyl)-1H-indol-3-yl]-3-(1H-indol-3-yl)-maleinimide;
(−)-2-[4-hydroxy-1-(2-hydroxy-3-dimethylaminopropyl)-1H-indol-3-yl]-3-(1H-indol-3-yl)-maleinimide;
(−)-2-[5-hydroxy-1-(2-hydroxy-3-dimethylaminopropyl)-1H-indol-3-yl]-3-(1H-indol-3-yl)-maleinimide;
(−)-2-[6-hydroxy-1-(2-hydroxy-3-dimethylaminopropyl)-1H-indol-3-yl]-3-(1H-indol-3-yl)-maleinimide;
(−)-2-[7-hydroxy-1-(2-hydroxy-3-dimethylaminopropyl)-1H-indol-3-yl]-3-(1H-indol-3-yl)-maleinimide;
(−)-2-[4-trifluoromethyl-1-(2-hydroxy-3-dimethylaminopropyl)-1H-indol-3-yl]-3-(1H-indol-3-yl)-maleinimide;
(−)-2-[5-trifluoromethyl-1-(2-hydroxy-3-dimethylaminopropyl)-1H-indol-3-yl]-3-(1H-indol-3-yl)-maleinimide;
(−)-2-[6-trifluoromethyl-1-(2-hydroxy-3-dimethylaminopropyl)-1H-indol-3-yl]-3-(1H-indol-3-yl)-maleinimide;
(−)-2-[7-trifluoromethyl-1-(2-hydroxy-3-dimethylaminopropyl)-1H-indol-3-yl]-3-(1H-indol-3-yl)-maleinimide;
(−)-2-[1-(2-hydroxy-3-dimethylaminopropyl)-4-methoxy-1H-indol-3-yl]-3-(1H-indol-3-yl)-maleinimide;
(−)-2-[1-(2-hydroxy-3-dimethylaminopropyl)-5-methoxy-1H-indol-3-yl]-3-(1H-indol-3-yl)-maleinimide;
(−)-2-[1-(2-hydroxy-3-dimethylaminopropyl)-6-methoxy-1H-indol-3-yl]-3-(1H-indol-3-yl)-maleinimide;
(−)-2-[1-(2-hydroxy-3-dimethylaminopropyl)-7-methoxy-1H-indol-3-yl]-3-(1H-indol-3-yl)-maleinimide;
(−)-2-[1-(2-hydroxy-3-dimethylaminopropyl)-4,5-methylendioxy-1H-indol-3-yl]-3-(1H-indol-3-yl)-maleinimide;
(−)-2-[1-(2-hydroxy-3-dimethylaminopropyl)-5,6-methylendioxy-1H-indol-3-yl]-3-(1H-indol-3-yl)-maleinimide;

(−)-2-[1-(2-hydroxy-3-dimethylaminopropyl)-6,7-methylendioxy-1H-indol-3-yl]-3-(1H-indol-3-yl)-maleinimide;

(−)-2-[1-(2-hydroxy-3-dimethylaminopropyl)-4-methyl-1H-indol-3-yl]-3-(1H-indol-3-yl)-maleinimide;

(−)-2-[1-(2-hydroxy-3-dimethylaminopropyl)-5-methyl-1H-indol-3-yl]-3-(1H-indol-3-yl)-maleinimide;

(−)-2-[1-(2-hydroxy-3-dimethylaminopropyl)-6-methyl-1H-indol-3-yl]-3-(1H-indol-3-yl)-maleinimide;

(−)-2-[1-(2-hydroxy-3-dimethylaminopropyl)-7-methyl-1H-indol-3-yl]-3-(1H-indol-3-yl)-maleinimide;

(−)-2-[1-(2-hydroxy-3-dimethylaminopropyl)-4-nitro-1H-indol-3-yl]-3-(1H-indol-3-yl)-maleinimide;

(−)-2-[1-(2-hydroxy-3-dimethylaminopropyl)-5-nitro-1H-indol-3-yl]-3-(1H-indol-3-yl)-maleinimide;

(−)-2-[1-(2-hydroxy-3-dimethylaminopropyl)-6-nitro-1H-indol-3-yl]-3-(1H-indol-3-yl)-maleinimide;

(−)-2-[1-(2-hydroxy-3-dimethylaminopropyl)-7-nitro-1H-indol-3-yl]-3-(1H-indol-3-yl)-maleinimide;

(−)-2-[1-(2-hydroxy-3-dimethylaminopropyl)-4-methylthio-1H-indol-3-yl]-3-(1H-indol-3-yl)-maleinimide;

(−)-2-[1-(2-hydroxy-3-dimethylaminopropyl)-5-methylthio-1H-indol-3-yl]-3-(1H-indol-3-yl)-maleinimide;

(−)-2-[1-(2-hydroxy-3-dimethylaminopropyl)-6-methylthio-1H-indol-3-yl]-3-(1H-indol-3-yl)-maleinimide;

(−)-2-[1-(2-hydroxy-3-dimethylaminopropyl)-7-methylthio-1H-indol-3-yl]-3-(1H-indol-3-yl)-maleinimide;

(−)-2-[1-(2-hydroxy-3-dimethylaminopropyl)-4,5-dimethoxy-1H-indol-3-yl]-3-(1H-indol-3-yl)-maleinimide;

(−)-2-[1-(2-hydroxy-3-dimethylaminopropyl)-5,6-dimethoxy-1H-indol-3-yl]-3-(1H-indol-3-yl)-maleinimide;

(−)-2-[1-(2-hydroxy-3-dimethylaminopropyl)-6,7-dimethoxy-1H-indol-3-yl]-3-(1H-indol-3-yl)-maleinimide;

(±)-2-[4-acetylamino-1-(2-hydroxy-3-(4morpholino)-propyl)-1H-indol-3-yl]-3-(1H-indol-3-yl)-maleinimide;

(±)-2-[5-acetylamino-1-(2-hydroxy-3-(4-morpholino)-propyl)-1H-indol-3-yl]-3-(1H-indol-3-yl)-maleinimide;

(±)-2-[6-acetylamino-1-(2-hydroxy-3-(4-morpholino)-propyl)-1H-indol-3-yl]-3-(1H-indol-3-yl)-maleinimide;

(±)-2-[7-acetyl amino-1-(2-hydroxy-3-(4-morpholino)-propyl)-1H-indol-3-yl]-3-(1H-indol-3-yl)-maleinimide;

(±)-2-[4-amino-1-(2-hydroxy-3-(4-morpholino)propyl)-1H-indol-3-yl]-3-(1H-indol-3-yl)-maleinimide;

(±)-2-[5-amino-1-(2-hydroxy-3-(4-morpholino)propyl)-1H-indol-3-yl]-3-(1H-indol-3-yl)-maleinimide;

(±)-2-[6-amino-1-(2-hydroxy-3-(4-morpholino)propyl)-1H-indol-3-yl]-3-(1H-indol-3-yl)-maleinimide;

(±)-2-[7-amino-1-(2-hydroxy-3-(4-morpholino)propyl)-1H-indol-3-yl]-3-(1H-indol-3-yl)-maleinimide;

(±)-2-[4-benzyloxy-1-(2-hydroxy-3-(4-morpholino)-propyl)-1H-indol-3-yl]-3-(1H-indol-3-yl)-maleinimide;

(±)-2-[5-benzyloxy-1-(2-hydroxy-3-(4-morpholino)-propyl)-1H-indol-3-yl]-3-(1H-indol-3-yl)-maleinimide;

(±)-2-[6-benzyloxy-1-(2-hydroxy-3-(4-morpholino)-propyl)-1H-indol-3-yl]-3-(1H-indol-3-yl)-maleinimide;

(±)-2-[7-benzyloxy-1-(2-hydroxy-3-(4-morpholino)-propyl)-1H-indol-3-yl]-3-(1H-indol-3-yl)-maleinimide;

(±)-2-[4-bromo-1-(2-hydroxy-3-(4-morpholino)-propyl)-1H-indol-3-yl]-3-(1H-indol-3-yl)-maleinimide;

(±)-2-[5-bromo-1-(2-hydroxy-3-(4-morpholino)-propyl)-1H-indol-3-yl]-3-(1H-indol-3-yl)-maleinimide;

(±)-2-[6-bromo-1-(2-hydroxy-3-(4-morpholino)-propyl)-1H-indol-3-yl]-3-(1H-indol-3-yl)-maleinimide;

(±)-2-[7-bromo-1-(2-hydroxy-3-(4-morpholino)-propyl)-1H-indol-3-yl]-3-(1H-indol-3-yl)-maleinimide;

(±)-2-[4-chloro-1-(2-hydroxy-3-(4-morpholino)-propyl)-1H-indol-3-yl]-3-(1H-indol-3-yl)-maleinimide;

(±)-2-[5-chloro-1-(2-hydroxy-3-(4-morpholino)-propyl)-1H-indol-3-yl]-3-(1H-indol-3-yl)-maleinimide;

(±)-2-[6-chloro-1-(2-hydroxy-3-(4-morpholino)-propyl)-1H-indol-3-yl]-3-(1H-indol-3-yl)-maleinimide;

(±)-2-[7-chloro-1-(2-hydroxy-3-(4-morpholino)-propyl)-1H-indol-3-yl]-3-(1H-indol-3-yl)-maleinimide;

(±)-2-[4-fluoro-1-(2-hydroxy-3-(4-morpholino)propyl)-1H-indol-3-yl]-3-(1H-indol-3-yl)-maleinimide;

(±)-2-[5-fluoro-1-(2-hydroxy-3-(4-morpholino)propyl)-1H-indol-3-yl]-3-(1H-indol-3-yl)-maleinimide;

(±)-2-[6-fluoro-1-(2-hydroxy-3-(4-morpholino)propyl)-1H-indol-3-yl]-3-(1H-indol-3-yl)-maleinimide;

(±)-2-[7-fluoro-1-(2-hydroxy-3-(4-morpholino)propyl)-1H-indol-3-yl]-3-(1H-indol-3-yl)-maleinimide;

(±)-2-[4-hydroxy-1-(2-hydroxy-3-(4-morpholino)-propyl)-1H-indol-3-yl]-3-(1H-indol-3-yl)-maleinimide;

(±)-2-[5-hydroxy-1-(2-hydroxy-3-(4-morpholino)-propyl)-1H-indol-3-yl]-3-(1H-indol-3-yl)-maleinimide;

(±)-2-[6-hydroxy-1-(2-hydroxy-3-(4-morpholino)-propyl)-1H-indol-3-yl]-3-(1H-indol-3-yl)-maleinimide;

(±)-2-[7-hydroxy-1-(2-hydroxy-3-(4-morpholino)-propyl)-1H-indol-3-yl]-3-(1H-indol-3-yl)-maleinimide;

(±)-2-[4-trifluoromethyl-1-(2-hydroxy-3-(4-morpholino)propyl)-1H-indol-3-yl]-3-(1H-indol-3-yl)-maleinimide;

(±)-2-[5-trifluoromethyl-1-(2-hydroxy-3-(4-morpholino)propyl)-1H-indol-3-yl]-3-(1H-indol-3-yl)-maleinimide;

(±)-2-[6-trifluoromethyl-1-(2-hydroxy-3-(4-morpholino)propyl)-1H-indol-3-yl]-3-(1H-indol-3-yl)-maleinimide;

(±)-2-[7-trifluoromethyl-1-(2-hydroxy-3-(4-morpholino)propyl)-1H-indol-3-yl]-3-(1H-indol-3-yl)-maleinimide;

(±)-2-[1-(2-hydroxy-3-(4-morpholino)propyl)-4-methoxy-1H-indol-3-yl]-3-(1H-indol-3-yl)-maleinimide;

(±)-2-[1-(2-hydroxy-3-(4-morpholino propyl)-5-methoxy-1H-indol-3-yl]-3-(1H-indol-3-yl)-maleinimide;

(±)-2-[1-(2-hydroxy-3-(4-morpholino)propyl)-6-methoxy-1H-indol-3-yl]-3-(1H-indol-3-yl)-maleinimide;

(±)-2-[1-(2-hydroxy-3-(4-morpholino)propyl)-7-methoxy-1H-indol-3-yl]-3-(1H-indol-3-yl)-maleinimide;

(±)-2-[1-(2-hydroxy-3-(4-morpholino)propyl)-4,5-methylendioxy-1H-indol-3-yl]-3-(1H-indol-3-yl)-maleinimide;

(±)-2-[1-(2-hydroxy-3-(4-morpholino)propyl)-5,6-methylendioxy-1H-indol-3-yl]-3-(1H-indol-3-yl)-maleinimide;

(±)-2-[1-(2-hydroxy-3-(4-morpholino)propyl)-6,7-methylendioxy-1H-indol-3-yl]-3-(1H-indol-3-yl)-maleinimide;

(±)-2-[1-(2-hydroxy-3-(4-morpholino)propyl)-4-methyl-1H-indol-3-yl]-3-(1H-indol-3-yl)-maleinimide;

(±)-2-[1-(2-hydroxy-3-(4-morpholino)propyl)-5-methyl-1H-indol-3-yl]-3-(1H-indol-3-yl)-maleinimide;

(±)-2-[1-(2-hydroxy-3-(4-morpholino)propyl)-6-methyl-1H-indol-3-yl]-3-(1H-indol-3-yl)-maleinimide;

(±)-2-[1-(2-hydroxy-3-(4-morpholino)propyl)-7-methyl-1H-indol-3-yl]-3-(1H-indol-3-yl)-maleinimide;

(±)-2-[1-(2-hydroxy-3-(4-morpholino)propyl)-4-nitro-1H-indol-3-yl]-3-(1H-indol-3-yl)-maleinimide;

(±)-2-[1-(2-hydroxy-3-(4-morpholino)propyl)-5-nitro-1H-indol-3-yl]-3-(1H-indol-3-yl)-maleinimide;

(±)-2-[1-(2-hydroxy-3-(4-morpholino)propyl)-6-nitro-1H-indol-3-yl]-3-(1H-indol-3-yl)-maleinimide;

(±)-2-[1-(2-hydroxy-3-(4-morpholino)propyl)-7-nitro-1H-indol-3-yl]-3-(1H-indol-3-yl)-maleinimide;

(±)-2-[1-(2-hydroxy-3-(4-morpholino)propyl)-4-methylthio-1H-indol-3-yl]-3-(1H-indol-3-yl)-maleinimide;

(±)-2-[1-(2-hydroxy-3-(4-morpholino)propyl)-5-methylthio-1H-indol-3-yl]-3-(1H-indol-3-yl)-maleinimide;

(±)-2-[1-(2-hydroxy-3-(4-morpholino)propyl)-6-methylthio-1H-indol-3-yl]-3-(1H-indol-3-yl)-maleinimide;

(±)-2-[1-(2-hydroxy-3-(4-morpholino)propyl)-7-methylthio-1H-indol-3-yl]-3-(1H-indol-3-yl)-maleinimide;

(±)-2-[1-(2-hydroxy-3-(4-morpholino)propyl)-4,5-dimethoxy-1H-indol-3-yl]-3-(1H-indol-3-yl)-maleinimide;

(±)-2-[1-(2-hydroxy-3-(4-morpholino)propyl)-5,6-dimethoxy-1H-indol-3-yl]-3-(1H-indol-3-yl)-maleinimide;

(±)-2-[1-(2-hydroxy-3-(4-morpholino)propyl)-6,7-dimethoxy-1H-indol-3-yl]-3-(1H-indol-3-yl)-maleinimide;

(+)-2-[4-acetylamino-1-(2-hydroxy-3-(4-morpholino)propyl)-1H-indol-3-yl]-3-(1H-indol-3-yl)-maleinimide;

(+)-2-[5-acetylamino-1-(2-hydroxy-3-(4-morpholino)propyl)-1H-indol-3-yl]-3-(1H-indol-3-yl)-maleinimide;

(+)-2-[6-acetylamino-1-(2-hydroxy-3-(4-morpholino)propyl)-1H-indol-3-yl]-3-(1H-indol-3-yl)-maleinimide;

(+)-2-[7-acetylamino-1-(2-hydroxy-3-(4-morpholino)propyl)-1H-indol-3-yl]-3-(1H-indol-3-yl)-maleinimide;

(+)-2-[4-amino-1-(2-hydroxy-3-(4-morpholino)propyl)-1H-indol-3-yl]-3-(1H-indol-3-yl)-maleinimide;

(+)-2-[5-amino-1-(2-hydroxy-3-(4-morpholino)propyl)-1H-indol-3-yl]-3-(1H-indol-3-yl)-maleinimide;

(+)-2-[6-amino-1-(2-hydroxy-3-(4-morpholino)propyl)-1H-indol-3-yl]-3-(1H-indol-3-yl)-maleinimide;

(+)-2-[7-amino-1-(2-hydroxy-3-(4-morpholino)propyl)-1H-indol-3-yl]-3-(1H-indol-3-yl)-maleinimide;

(+)-2-[4-benzyloxy-1-(2-hydroxy-3-(4-morpholino)propyl)-1H-indol-3-yl]-3-(1H-indol-3-yl)-maleinimide;

(+)-2-[5-benzyloxy-1-(2-hydroxy-3-(4-morpholino)propyl)-1H-indol-3-yl]-3-(1H-indol-3-yl)-maleinimide;

(+)-2-[6-benzyloxy-1-(2-hydroxy-3-(4-morpholino)propyl)-1H-indol-3-yl]-3-(1H-indol-3-yl)-maleinimide;

(+)-2-[7-benzyloxy-1-(2-hydroxy-3-(4-morpholino)propyl)-1H-indol-3-yl]-3-(1H-indol-3-yl)-maleinimide;

(+)-2-[4-bromo-1-(2-hydroxy-3-(4-morpholino)propyl)-1H-indol-3-yl]-3-(1H-indol-3-yl)-maleinimide;

(+)-2-[5-bromo-1-(2-hydroxy-3-(4-morpholino)propyl)-1H-indol-3-yl]-3-(1H-indol-3-yl)-maleinimide;

(+)-2-[6-bromo-1-(2-hydroxy-3-(4-morpholino)propyl)-1H-indol-3-yl]-3-(1H-indol-3-yl)-maleinimide;

(+)-2-[7-bromo-1-(2-hydroxy-3-(4-morpholino propyl)-1H-indol-3-yl]-3-(1H-indol-3-yl)-maleinimide;

(+)-2-[4-chloro-1-(2-hydroxy-3-(4-morpholino)propyl)-1H-indol-3-yl]-3-(1H-indol-3-yl)-maleinimide;

(+)-2-[5-chloro-1-(2-hydroxy-3-(4-morpholino)propyl)-1H-indol-3-yl]-3-(1H-indol-3-yl)-maleinimide;

(+)-2-[6-chloro-1-(2-hydroxy-3-(4-morpholino)propyl)-1H-indol-3-yl]-3-(1H-indol-3-yl)-maleinimide;

(+)-2-[7-chloro-1-(2-hydroxy-3-(4-morpholino)propyl)-1H-indol-3-yl]-3-(1H-indol-3-yl)-maleinimide;

(+)-2-[4-fluoro-1-(2-hydroxy-3-(4-morpholino)propyl)-1H-indol-3-yl]-3-(1H-indol-3-yl)-maleinimide;

(+)-2-[5-fluoro-1-(2-hydroxy-3-(4-morpholino)propyl)-1H-indol-3-yl]-3-(1H-indol-3-yl)-maleinimide;

(+)-2-[6-fluoro-1-(2-hydroxy-3-(4-morpholino)propyl)-1H-indol-3-yl]-3-(1H-indol-3-yl)-maleinimide;

(+)-2-[7-fluoro-1-(2-hydroxy-3-(4-morpholino)propyl)-1H-indol-3-yl]-3-(1H-indol-3-yl)-maleinimide;

(+)-2-[4-hydroxy-1-(2-hydroxy-3-(4-morpholino)propyl)-1H-indol-3-yl]-3-(1H-indol-3-yl)-maleinimide;

(+)-2-[5-hydroxy-1-(2-hydroxy-3-(4-morpholino)propyl)-1H-indol-3-yl]-3-(1H-indol-3-yl)-maleinimide;

(+)-2-[6-hydroxy-1-(2-hydroxy-3-(4-morpholino)propyl)-1H-indol-3-yl]-3-(1H-indol-3-yl)-maleinimide;

(+)-2-[7-hydroxy-1-(2-hydroxy-3-(4-morpholino)propyl)-1H-indol-3-yl]-3-(1H-indol-3-yl)-maleinimide;

(+)-2-[4-trifluoromethyl-1-(2-hydroxy-3-(4-morpholino)propyl)-1H-indol-3-yl]-3-(1H-indol-3-yl)-maleinimide;

(+)-2-[5-trifluoromethyl-1-(2-hydroxy-3-(4-morpholino)propyl)-1H-indol-3-yl]-3-(1H-indol-3-yl)-maleinimide;

(+)-2-[6-trifluoromethyl-1-(2-hydroxy-3-(4-morpholino)propyl)-1H-indol-3-yl]-3-(1H-indol-3-yl)-maleinimide;

(+)-2-[7-trifluoromethyl-1-(2-hydroxy-3-(4-morpholino)propyl)-1H-indol-3-yl]-3-(1H-indol-3-yl)-maleinimide;

(+)-2-[1-(2-hydroxy-3-(4-morpholino)propyl)-4-methoxy-1H-indol-3-yl]-3-(1H-indol-3-yl)-maleinimide;

(+)-2-[1-(2-hydroxy-3-(4-morpholino)propyl)-5-methoxy-1H-indol-3-yl]-3-(1H-indol-3-yl)-maleinimide;

(+)-2-[1-(2-hydroxy-3-(4-morpholino)propyl)-6-methoxy-1H-indol-3-yl]-3-(1H-indol-3-yl)-maleinimide;

(+)-2-[1-(2-hydroxy-3-(4-morpholino)propyl)-7-methoxy-1H-indol-3-yl]-3-(1H-indol-3-yl)-maleinimide;

(+)-2-[1-(2-hydroxy-3-(4-morpholino)propyl)-4,5-methylendioxy-1H-indol-3-yl]-3-(1H-indol-3-yl)-maleinimide;

(+)-2-[1-(2-hydroxy-3-(4-morpholino)propyl)-5,6-methylendioxy-1H-indol-3-yl]-3-(1H-indol-3-yl)-maleinimide;

(+)-2-[1-(2-hydroxy-3-(4-morpholino)propyl)-6,7-methylendioxy-1H-indol-3-yl]-3-(1H-indol-3-yl)-maleinimide;

(+)-2-[1-(2-hydroxy-3-(4-morpholino)propyl)-4-methyl-1H-indol-3-yl]-3-(1H-indol-3-yl)-maleinimide;

(+)-2-[1-(2-hydroxy-3-(4-morpholino)propyl)-5-methyl-1H-indol-3-yl]-3-(1H-indol-3-yl)-maleinimide;

(+)-2-[1-(2-hydroxy-3-(4-morpholino)propyl)-6-methyl-1H-indol-3-yl]-3-(1H-indol-3-yl)-maleinimide;

(+)-2-[1-(2-hydroxy-3-(4-morpholino)propyl)-7-methyl-1H-indol-3-yl]-3-(1H-indol-3-yl)-maleinimide;

(+)-2-[1-(2-hydroxy-3-(4-morpholino)propyl)-4-nitro-1H-indol-3-yl]-3-(1H-indol-3-yl)-maleinimide;

(+)-2-[1-(2-hydroxy-3-(4-morpholino)propyl)-5-nitro-1H-indol-3-yl]-3-(1H-indol-3-yl)-maleinimide;

(+)-2-[1-(2-hydroxy-3-(4-morpholino)propyl)-6-nitro-1H-indol-3-yl]-3-(1H-indol-3-yl)-maleinimide;

(+)-2-[1-(2-hydroxy-3-(4-morpholino)propyl)-7-nitro-1H-indol-3-yl]-3-(1H-indol-3-yl)-maleinimide;

(+)-2-[1-(2-hydroxy-3-(4-morpholino)propyl)-4-methylthio-1H-indol-3-yl]-3-(1H-indol-3-yl)-maleinimide;

(+)-2-[1-(2-hydroxy-3-(4-morpholino)propyl)-5-methylthio-1H-indol-3-yl]-3-(1H-indol-3-yl)-maleinimide;

(+)-2-[1-(2-hydroxy-3-(4-morpholino)propyl)-6-methylthio-1H-indol-3-yl]-3-(1H-indol-3-yl)-maleinimide;

(+)-2-[1-(2-hydroxy-3-(4-morpholino)propyl)-7-methylthio-1H-indol-3-yl]-3-(1H-indol-3-yl)-maleinimide;

(+)-2-[1-(2-hydroxy-3-(4-morpholino)propyl)-4,5-dimethoxy-1H-indol-3-yl]-3-(1H-indol-3-yl)-maleinimide;

(+)-2-[1-(2-hydroxy-3-(4-morpholino)propyl)-5,6-dimethoxy-1H-indol-3-yl]-3-(1H-indol-3-yl)-maleinimide;

(+)-2-[1-(2-hydroxy-3-(4-morpholino)propyl)-6,7-dimethoxy-1H-indol-3-yl]-3-(1H-indol-3-yl)-maleinimide;

(−)-2-[4-acetylamino-1-(2-hydroxy-3-(4-morpholino)propyl)-1H-indol-3-yl]-3-(1H-indol-3-yl)-maleinimide;

(−)-2-[5-acetylamino-1-(2-hydroxy-3-(4-morpholino)propyl)-1H-indol-3-yl]-3-(1H-indol-3-yl)-maleinimide;

(−)-2-[6-acetylamino-1-(2-hydroxy-3-(4-morpholino)propyl)-1H-indol-3-yl]-3-(1H-indol-3-yl)-maleinimide;

(−)-2-[7-acetylamino-1-(2-hydroxy-3-(4-morpholino)propyl)-1H-indol-3-yl]-3-(1H-indol-3-yl)-maleinimide;

(−)-2-[4-amino-1-(2-hydroxy-3-(4-morpholino)propyl)-1H-indol-3-yl]-3-(1H-indol-3-yl)-maleinimide;

(−)-2-[5-amino-1-(2-hydroxy-3-(4-morpholino)propyl)-1H-indol-3-yl]-3-(1H-indol-3-yl)-maleinimide;

(−)-2-[6-amino-1-(2-hydroxy-3-(4-morpholino)propyl)-1H-indol-3-yl]-3-(1H-indol-3-yl)-maleinimide;

(−)-2-[7-amino-1-(2-hydroxy-3-(4-morpholino)propyl)-1H-indol-3-yl]-3-(1H-indol-3-yl)-maleinimide;

(−)-2-[4-benzyloxy-1-(2-hydroxy-3-(4-morpholino)propyl)-1H-indol-3-yl]-3-(1H-indol-3-yl)-maleinimide;

(−)-2-[5-benzyloxy-1-(2-hydroxy-3-(4-morpholino)propyl)-1H-indol-3-yl]-3-(1H-indol-3-yl)-maleinimide;

(−)-2-[6-benzyloxy-1-(2-hydroxy-3-(4-morpholino)propyl)-1H-indol-3-yl]-3-(1H-indol-3-yl)-maleinimide;

(−)-2-[7-benzyloxy-1-(2-hydroxy-3-(4-morpholino)propyl)-1H-indol-3-yl]-3-(1H-indol-3-yl)-maleinimide;

(−)-2-[4-bromo-1-(2-hydroxy-3-(4-morpholino)propyl)-1H-indol-3-yl]-3-(1H-indol-3-yl)-maleinimide;

(−)-2-[5-bromo-1-(2-hydroxy-3-(4-morpholino)propyl)-1H-indol-3-yl]-3-(1H-indol-3-yl)-maleinimide;

(−)-2-[6-bromo-1-(2-hydroxy-3-(4-morpholino)propyl)-1H-indol-3-yl]-3-(1H-indol-3-yl)-maleinimide;

(−)-2-[7-bromo-1-(2-hydroxy-3-(4-morpholino)propyl)-1H-indol-3-yl]-3-(1H-indol-3-yl)-maleinimide;

(−)-2-[4-chloro-1-(2-hydroxy-3-(4-morpholino)propyl)-1H-indol-3-yl]-3-(1H-indol-3-yl)-maleinimide;

(−)-2-[5-chloro-1-(2-hydroxy-3-(4-morpholino)propyl)-1H-indol-3-yl]-3-(1H-indol-3-yl)-maleinimide;

(−)-2-[6-chloro-1-(2-hydroxy-3-(4-morpholino)propyl)-1H-indol-3-yl]-3-(1H-indol-3-yl)-maleinimide;

(−)-2-[7-chloro-1-(2-hydroxy-3-(4-morpholino)propyl)-1H-indol-3-yl]-3-(1H-indol-3-yl)-maleinimide;

(−)-2-[4-fluoro-1-(2-hydroxy-3-(4-morpholino)propyl)-1H-indol-3-yl]-3-(1H-indol-3-yl)-maleinimide;

(−)-2-[5-fluoro-1-(2-hydroxy-3-(4-morpholino)propyl)-1H-indol-3-yl]-3-(1H-indol-3-yl)-maleinimide;

(−)-2-[6-fluoro-1-(2-hydroxy-3-(4-morpholino)propyl)-1H-indol-3-yl]-3-(1H-indol-3-yl)-maleinimide;

(−)-2-[7-fluoro-1-(2-hydroxy-3-(4-morpholino)propyl)-1H-indol-3-yl]-3-(1H-indol-3-yl)-maleinimide;

(−)-2-[4-hydroxy-1-(2-hydroxy-3-(4-morpholino)propyl)-1H-indol-3-yl]-3-(1H-indol-3-yl)-maleinimide;

(−)-2-[5-hydroxy-1-(2-hydroxy-3-(4-morpholino)propyl)-1H-indol-3-yl]-3-(1H-indol-3-yl)-maleinimide;

(−)-2-[6-hydroxy-1-(2-hydroxy-3-(4-morpholino)propyl)-1H-indol-3-yl]-3-(1H-indol-3-yl)-maleinimide;

(−)-2-[7-hydroxy-1-(2-hydroxy-3-(4-morpholino)propyl)-1H-indol-3-yl]-3-(1H-indol-3-yl)-maleinimide;

(−)-2-[4-trifluoromethyl-1-(2-hydroxy-3-(4-morpholino)propyl)-1H-indol-3-yl]-3-(1H-indol-3-yl)-maleinimide;

(−)-2-[5-trifluoromethyl-1-(2-hydroxy-3-(4-morpholino)propyl)-1H-indol-3-yl]-3-(1H-indol-3-yl)-maleinimide;

(−)-2-[6-trifluoromethyl-1-(2-hydroxy-3-(4-morpholino)propyl)-1H-indol-3-yl]-3-(1H-indol-3-yl)-maleinimide;

(−)-2-[7-trifluoromethyl-1-(2-hydroxy-3-(4-morpholino)propyl)-1H-indol-3-yl]-3-(1H-indol-3-yl)-maleinimide;
(−)-2-[1-(2-hydroxy-3-(4-morpholino)propyl)-4-methoxy-1H-indol-3-yl]-3-(1H-indol-3-yl)-maleinimide;
(−)-2-[1-(2-hydroxy-3-(4-morpholino)propyl)-5-methoxy-1H-indol-3-yl]-3-(1H-indol-3-yl)-maleinimide;
(−)-2-[1-(2-hydroxy-3-(4-morpholino)propyl)-6-methoxy-1H-indol-3-yl]-3-(1H-indol-3-yl)-maleinimide;
(−)-2-[1-(2-hydroxy-3-(4-morpholino)propyl)-7-methoxy-1H-indol-3-yl]-3-(1H-indol-3-yl)-maleinimide;
(−)-2-[1-(2-hydroxy-3-(4-morpholino)propyl)-4,5-methylendioxy-1H-indol-3-yl]-3-(1H-indol-3-yl)-maleinimide;
(−)-2-[1-(2-hydroxy-3-(4-morpholino)propyl)-5,6-methylendioxy-1H-indol-3-yl]-3-(1H-indol-3-yl)-maleinimide;
(−)-2-[1-(2-hydroxy-3-(4-morpholino)propyl)-6,7-methylendioxy-1H-indol-3-yl]-3-(1H-indol-3-yl)-maleinimide;
(−)-2-[1-(2-hydroxy-3-(4-morpholino)propyl)-4-methyl-1H-indol-3-yl]-3-(1H-indol-3-yl)-maleinimide;
(−)-2-[1-(2-hydroxy-3-(4-morpholino)propyl)-5-methyl-1H-indol-3-yl]-3-(1H-indol-3-yl)-maleinimide;
(−)-2-[1-(2-hydroxy-3-(4-morpholino)propyl)-6-methyl-1H-indol-3-yl]-3-(1H-indol-3-yl)-maleinimide;
(−)-2-[1-(2-hydroxy-3-(4-morpholino)propyl)-7-methyl-1H-indol-3-yl]-3-(1H-indol-3-yl)-maleinimide;
(−)-2-[1-(2-hydroxy-3-(4-morpholino)propyl)-4-nitro-1H-indol-3-yl]-3-(1H-indol-3-yl)-maleinimide;
(−)-2-[1-(2-hydroxy-3-(4-morpholino)propyl)-5-nitro-1H-indol-3-yl]-3-(1H-indol-3-yl)-maleinimide;
(−)-2-[1-(2-hydroxy-3-(4-morpholino)propyl)-6-nitro-1H-indol-3-yl]-3-(1H-indol-3-yl)-maleinimide;
(−)-2-[1-(2-hydroxy-3-(4-morpholino)propyl)-7-nitro-1H-indol-3-yl]-3-(1H-indol-3-yl)-maleinimide;
(−)-2-[1-(2-hydroxy-3-(4-morpholino)propyl)-4-methylthio-1H-indol-3-yl]-3-(1H-indol-3-yl)-maleinimide;
(−)-2-[1-(2-hydroxy-3-(4-morpholino)propyl)-5-methylthio-1H-indol-3-yl]-3-(1H-indol-3-yl)-maleinimide;
(−)-2-[1-(2-hydroxy-3-(4-morpholino)propyl)-6-methylthio-1H-indol-3-yl]-3-(1H-indol-3-yl)-maleinimide;
(−)-2-[1-(2-hydroxy-3-(4-morpholino)propyl)-7-methylthio-1H-indol-3-yl]-3-(1H-indol-3-yl)-maleinimide;
(−)-2-[1-(2-hydroxy-3-(4-morpholino)propyl)-4,5-dimethoxy-1H-indol-3-yl]-3-(1H-indol-3-yl)-maleinimide;
(−)-2-[1-(2-hydroxy-3-(4-morpholino)propyl)-5,6-dimethoxy-1H-indol-3-yl]-3-(1H-indol-3-yl)-maleinimide;
(−)-2-[1-(2-hydroxy-3-(4-morpholino)propyl)-6,7-dimethoxy-1H-indol-3-yl]-3-(1H-indol-3-yl)-maleinimide;
(±)-2-[4-acetylamino-1-(2-hydroxy-3-(1-piperidino)propyl)-1H-indol-3-yl]-3-(1H-indol-3-yl)-maleinimide;
(±)-2-[5-acetylamino-1-(2-hydroxy-3-(1-piperidino)propyl)-1H-indol-3-yl]-3-(1H-indol-3-yl)-maleinimide;
(±)-2-[6-acetylamino-1-(2-hydroxy-3-(1-piperidino)propyl)-1H-indol-3-yl]-3-(1H-indol-3-yl)-maleinimide;
(±)-2-[7-acetylamino-1-(2-hydroxy-3-(1-piperidino)propyl)-1H-indol-3-yl]-3-(1H-indol-3-yl)-maleinimide;
(±)-2-[4-amino-1-(2-hydroxy-3-(1-piperidino)propyl)-1H-indol-3-yl]-3-(1H-indol-3-yl)-maleinimide;
(±)-2-[5-amino-1-(2-hydroxy-3-(1-piperidino)propyl)-1H-indol-3-yl]-3-(1H-indol-3-yl)-maleinimide;
(±)-2-[6-amino-1-(2-hydroxy-3-(1-piperidino)propyl)-1H-indol-3-yl]-3-(1H-indol-3-yl)-maleinimide;
(±)-2-[7-amino-1-(2-hydroxy-3-(1-piperidino)propyl)-1H-indol-3-yl]-3-(1H-indol-3-yl)-maleinimide;
(±)-2-[4-benzyloxy-1-(2-hydroxy-3-(1-piperidino)propyl)-1H-indol-3-yl]-3-(1H-indol-3-yl)-maleinimide;
(±)-2-[5-benzyloxy-1-(2-hydroxy-3-(1-piperidino)propyl)-1H-indol-3-yl]-3-(1H-indol-3-yl)-maleinimide;
(±)-2-[6-benzyloxy-1-(2-hydroxy-3-(1-piperidino)propyl)-1H-indol-3-yl]-3-(1H-indol-3-yl)-maleinimide;
(±)-2-[7-benzyloxy-1-(2-hydroxy-3-(1-piperidino)propyl)-1H-indol-3-yl]-3-(1H-indol-3-yl)-maleinimide;
(±)-2-[4-bromo-1-(2-hydroxy-3-(1-piperidino)propyl)-1H-indol-3-yl]-3-(1H-indol-3-yl)-maleinimide;
(±)-2-[5-bromo-1-(2-hydroxy-3-(1-piperidino)propyl)-1H-indol-3-yl]-3-(1H-indol-3-yl)-maleinimide;
(±)-2-[6-bromo-1-(2-hydroxy-3-(1-piperidino)propyl)-1H-indol-3-yl]-3-(1H-indol-3-yl)-maleinimide;
(±)-2-[7-bromo-1-(2-hydroxy-3-(1-piperidino)propyl)-1H-indol-3-yl]-3-(1H-indol-3-yl)-maleinimide;
(±)-2-[4-chloro-1-(2-hydroxy-3-(1-piperidino)propyl)-1H-indol-3-yl]-3-(1H-indol-3-yl)-maleinimide;
(±)-2-[5-chloro-1-(2-hydroxy-3-(1-piperidino)propyl)-1H-indol-3-yl]-3-(1H-indol-3-yl)-maleinimide;
(±)-2-[6-chloro-1-(2-hydroxy-3-(1-piperidino)propyl)-1H-indol-3-yl]-3-(1H-indol-3-yl)-maleinimide;
(±)-2-[7-chloro-1-(2-hydroxy-3-(1-piperidino)propyl)-1H-indol-3-yl]-3-(1H-indol-3-yl)-maleinimide;
(±)-2-[4-fluoro-1-(2-hydroxy-3-(1-piperidino)propyl)-1H-indol-3-yl]-3-(1H-indol-3-yl)-maleinimide;
(±)-2-[5-fluoro-1-(2-hydroxy-3-(1-piperidino)propyl)-1H-indol-3-yl]-3-(1H-indol-3-yl)-maleinimide;
(±)-2-[6-fluoro-1-(2-hydroxy-3-(1-piperidino)propyl)-1H-indol-3-yl]-3-(1H-indol-3-yl)-maleinimide;
(±)-2-[7-fluoro-1-(2-hydroxy-3-(1-piperidino)propyl)-1H-indol-3-yl]-3-(1H-indol-3-yl)-maleinimide;
(±)-2-[4-hydroxy-1-(2-hydroxy-3-(1-piperidino)propyl)-1H-indol-3-yl]-3-(1H-indol-3-yl)-maleinimide;
(±)-2-[5-hydroxy-1-(2-hydroxy-3-(1-piperidino)propyl)-1H-indol-3-yl]-3-(1H-indol-3-yl)-maleinimide;
(±)-2-[6-hydroxy-1-(2-hydroxy-3-(1-piperidino)propyl)-1H-indol-3-yl]-3-(1H-indol-3-yl)-maleinimide;
(±)-2-[7-hydroxy-1-(2-hydroxy-3-(1-piperidino)propyl)-1H-indol-3-yl]-3-(1H-indol-3-yl)-maleinimide;
(±)-2-[4-trifluoromethyl-1-(2-hydroxy-3-(1-piperidino)propyl)-1H-indol-3-yl]-3-(1H-indol-3-yl)-maleinimide;
(±)-2-[5-trifluoromethyl-1-(2-hydroxy-3-(1-piperidino)propyl)-1H-indol-3-yl]-3-(1H-indol-3-yl)-maleinimide;
(±)-2-[6-trifluoromethyl-1-(2-hydroxy-3-(1-piperidino)propyl)-1H-indol-3-yl]-3-(1H-indol-3-yl)-maleinimide;

(±)-2-[7-trifluoromethyl-1-(2-hydroxy-3-(1-piperidino)propyl)-1H-indol-3-yl]-3-(1H-indol-3-yl)-maleinimide;
(±)-2-[1-(2-hydroxy-3-(1-piperidino)propyl)-4-methoxy-1H-indol-3-yl]-3-(1H-indol-3-yl)-maleinimide;
(±)-2-[1-(2-hydroxy-3-(1-piperidino)propyl)-5-methoxy-1H-indol-3-yl]-3-(1H-indol-3-yl)-maleinimide;
(±)-2-[1-(2-hydroxy-3-(1-piperidino)propyl)-6-methoxy-1H-indol-3-yl]-3-(1H-indol-3-yl)-maleinimide;
(±)-2-[1-(2-hydroxy-3-(1-piperidino)propyl)-7-methoxy-1H-indol-3-yl]-3-(1H-indol-3-yl)-maleinimide;
(±)-2-[1-(2-hydroxy-3-(1-piperidino)propyl)-4,5-methylendioxy-1H-indol-3-yl]-3-(1H-indol-3-yl)-maleinimide;
(±)-2-[1-(2-hydroxy-3-(1-piperidino)propyl)-5,6-methylendioxy-1H-indol-3-yl]-3-(1H-indol-3-yl)-maleinimide;
(±)-2-[1-(2-hydroxy-3-(1-piperidino)propyl)-6,7-methylendioxy-1H-indol-3-yl]-3-(1H-indol-3-yl)-maleinimide;
(±)-2-[1-(2-hydroxy-3-(1-piperidino)propyl)-4-methyl-1H-indol-3-yl]-3-(1H-indol-3-yl)-maleinimide;
(±)-2-[1-(2-hydroxy-3-(1-piperidino)propyl)-5-methyl-1H-indol-3-yl]-3-(1H-indol-3-yl)-maleinimide;
(±)-2-[1-(2-hydroxy-3-(1-piperidino)propyl)-6-methyl-1H-indol-3-yl]-3-(1H-indol-3-yl)-maleinimide;
(±)-2-[1-(2-hydroxy-3-(1-piperidino)propyl)-7-methyl-1H-indol-3-yl]-3-(1H-indol-3-yl)-maleinimide;
(±)-2-[1-(2-hydroxy-3-(1-piperidino)propyl)-4-nitro-1H-indol-3-yl]-3-(1H-indol-3-yl)-maleinimide;
(±)-2-[1-(2-hydroxy-3-(1-piperidino)propyl)-5-nitro-1H-indol-3-yl]-3-(1H-indol-3-yl)-maleinimide;
(±)-2-[1-(2-hydroxy-3-(1-piperidino)propyl)-6-nitro-1H-indol-3-yl]-3-(1H-indol-3-yl)-maleinimide;
(±)-2-[1-(2-hydroxy-3-(1-piperidino)propyl)-7-nitro-1H-indol-3-yl]-3-(1H-indol-3-yl)-maleinimide;
(±)-2-[1-(2-hydroxy-3-(1-piperidino)propyl)-4-methylthio-1H-indol-3-yl]-3-(1H-indol-3-yl)-maleinimide;
(±)-2-[1-(2-hydroxy-3-(1-piperidino)propyl)-5-methylthio-1H-indol-3-yl]-3-(1H-indol-3-yl)-maleinimide;
(±)-2-[1-(2-hydroxy-3-(1-piperidino)propyl)-6-methylthio-1H-indol-3-yl]-3-(1H-indol-3-yl)-maleinimide;
(±)-2-[1-(2-hydroxy-3-(1-piperidino)propyl)-7-methylthio-1H-indol-3-yl]-3-(1H-indol-3-yl)-maleinimide;
(±)-2-[1-(2-hydroxy-3-(1-piperidino)propyl)-4,5-dimethoxy-1H-indol-3-yl]-3-(1H-indol-3-yl)-maleinimide;
(±)-2-[1-(2-hydroxy-3-(1-piperidino)propyl)-5,6-dimethoxy-1H-indol-3-yl]-3-(1H-indol-3-yl)-maleinimide;
(±)-2-[1-(2-hydroxy-3-(1-piperidino)propyl)-6,7-dimethoxy-1H-indol-3-yl]-3-(1H-indol-3-yl)-maleinimide;
(+)-2-[4-acetyl amino-1-(2-hydroxy-3-(1-piperidino)propyl)-1H-indol-3-yl]-3-(1H-indol-3-yl)-maleinimide;
(+)-2-[5-acetylamino-1-(2-hydroxy-3-(1-piperidino)propyl)-1H-indol-3-yl]-3-(1H-indol-3-yl)-maleinimide;
(+)-2-[6-acetylamino-1-(2-hydroxy-3-(1-piperidino)propyl)-1H-indol-3-yl]-3-(1H-indol-3-yl)-maleinimide;
(+)-2-[7-acetylamino-1-(2-hydroxy-3-(1-piperidino)propyl)-1H-indol-3-yl]-3-(1H-indol-3-yl)-maleinimide;
(+)-2-[4-amino-1-(2-hydroxy-3-(1-piperidino)propyl)-1H-indol-3-yl]-3-(1H-indol-3-yl)-maleinimide;
(+)-2-[5-amino-1-(2-hydroxy-3-(1-piperidino)propyl)-1H-indol-3-yl]-3-(1H-indol-3-yl)-maleinimide;
(+)-2-[6-amino-1-(2-hydroxy-3-(1-piperidino)propyl)-1H-indol-3-yl]-3-(1H-indol-3-yl)-maleinimide;
(+)-2-[7-amino-1-(2-hydroxy-3-(1-piperidino)propyl)-1H-indol-3-yl]-3-(1H-indol-3-yl)-maleinimide;
(+)-2-[4-benzyloxy-1-(2-hydroxy-3-(1-piperidino)propyl)-1H-indol-3-yl]-3-(1H-indol-3-yl)-maleinimide;
(+)-2-[5-benzyloxy-1-(2-hydroxy-3-(1-piperidino)propyl)-1H-indol-3-yl]-3-(1H-indol-3-yl)-maleinimide;
(+)-2-[6-benzyloxy-1-(2-hydroxy-3-(1-piperidino)propyl)-1H-indol-3-yl]-3-(1H-indol-3-yl)-maleinimide;
(+)-2-[7-benzyloxy-1-(2-hydroxy-3-(1-piperidino)propyl)-1H-indol-3-yl]-3-(1H-indol-3-yl)-maleinimide;
(+)-2-[4-bromo-1-(2-hydroxy-3-(1-piperidino)propyl)-1H-indol-3-yl]-3-(1H-indol-3-yl)-maleinimide;
(+)-2-[5-bromo-1-(2-hydroxy-3-(1-piperidino)propyl)-1H-indol-3-yl]-3-(1H-indol-3-yl)-maleinimide;
(+)-2-[6-bromo-1-(2-hydroxy-3-(1-piperidino)propyl)-1H-indol-3-yl]-3-(1H-indol-3-yl)-maleinimide;
(+)-2-[7-bromo-1-(2-hydroxy-3-(1-piperidino)propyl)-1H-indol-3-yl]-3-(1H-indol-3-yl)-maleinimide;
(+)-2-[4-chloro-1-(2-hydroxy-3-(1-piperidino)propyl)-1H-indol-3-yl]-3-(1H-indol-3-yl)-maleinimide;
(+)-2-[5-chloro-1-(2-hydroxy-3-(1-piperidino)propyl)-1H-indol-3-yl]-3-(1H-indol-3-yl)-maleinimide;
(+)-2-[6-chloro-1-(2-hydroxy-3-(1-piperidino)propyl)-1H-indol-3-yl]-3-(1H-indol-3-yl)-maleinimide;
(+)-2-[7-chloro-1-(2-hydroxy-3-(1-piperidino)propyl)-1H-indol-3-yl]-3-(1H-indol-3-yl)-maleinimide;
(+)-2-[4-fluoro-1-(2-hydroxy-3-(1-piperidino)propyl)-1H-indol-3-yl]-3-(1H-indol-3-yl)-maleinimide;
(+)-2-[5-fluoro-1-(2-hydroxy-3-(1-piperidino)propyl)-1H-indol-3-yl]-3-(1H-indol-3-yl)-maleinimide;
(+)-2-[6-fluoro-1-(2-hydroxy-3-(1-piperidino)propyl)-1H-indol-3-yl]-3-(1H-indol-3-yl)-maleinimide;
(+)-2-[7-fluoro-1-(2-hydroxy-3-(1-piperidino)propyl)-1H-indol-3-yl]-3-(1H-indol-3-yl)-maleinimide;
(+)-2-[4-hydroxy-1-(2-hydroxy-3-(1-piperidino)propyl)-1H-indol-3-yl]-3-(1H-indol-3-yl)-maleinimide;
(+)-2-[5-hydroxy-1-(2-hydroxy-3-(1-piperidino)propyl)-1H-indol-3-yl]-3-(1H-indol-3-yl)-maleinimide;
(+)-2-[6-hydroxy-1-(2-hydroxy-3-(1-piperidino)propyl)-1H-indol-3-yl]-3-(1H-indol-3-yl)-maleinimide;
(+)-2-[7-hydroxy-1-(2-hydroxy-3-(1-piperidino)propyl)-1H-indol-3-yl]-3-(1H-indol-3-yl)-maleinimide;
(+)-2-[4-trifluoromethyl-1-(2-hydroxy-3-(1-piperidino)propyl)-1H-indol-3-yl]-3-(1H-indol-3-yl)-maleinimide;
(+)-2-[5-trifluoromethyl-1-(2-hydroxy-3-(1-piperidino)propyl)-1H-indol-3-yl]-3-(1H-indol-3-yl)-maleinimide;
(+)-2-[6-trifluoromethyl-1-(2-hydroxy-3-(1-piperidino)propyl)-1H-indol-3-yl]-3-(1H-indol-3-yl)-maleinimide;
(+)-2-[7-trifluoromethyl-1-(2-hydroxy-3-(1-piperidino)propyl)-1H-indol-3-yl]-3-(1H-indol-3-yl)-maleinimide;

(+)-2-[1-(2-hydroxy-3-(1-piperidino)propyl)-4-methoxy-1H-indol-3-yl]-3-(1H-indol-3-yl)-maleinimide;
(+)-2-[1-(2-hydroxy-3-(1-piperidino)propyl)-5-methoxy-1H-indol-3-yl]-3-(1H-indol-3-yl)-maleinimide;
(+)-2-[1-(2-hydroxy-3-(1-piperidino)propyl)-6-methoxy-1H-indol-3-yl]-3-(1H-indol-3-yl)-maleinimide;
(+)-2-[1-(2-hydroxy-3-(1-piperidino)propyl)-7-methoxy-1H-indol-3-yl]-3-(1H-indol-3-yl)-maleinimide;
(+)-2-[1-(2-hydroxy-3-(1-piperidino)propyl)-4,5-methylendioxy-1H-indol-3-yl]-3-(1H-indol-3-yl)-maleinimide;
(+)-2-[1-(2-hydroxy-3-(1-piperidino)propyl)-5,6-methylendioxy-1H-indol-3-yl]-3-(1H-indol-3-yl)-maleinimide;
(+)-2-[1-(2-hydroxy-3-(1-piperidino)propyl)-6,7-methylendioxy-1H-indol-3-yl]-3-(1H-indol-3-yl)-maleinimide;
(+)-2-[1-(2-hydroxy-3-(1-piperidino)propyl)-4-methyl-1H-indol-3-yl]-3-(1H-indol-3-yl)-maleinimide;
(+)-2-[1-(2-hydroxy-3-(1-piperidino)propyl)-5-methyl-1H-indol-3-yl]-3-(1H-indol-3-yl)-maleinimide;
(+)-2-[1-(2-hydroxy-3-(1-piperidino)propyl)-6-methyl-1H-indol-3-yl]-3-(1H-indol-3-yl)-maleinimide;
(+)-2-[1-(2-hydroxy-3-(1-piperidino)propyl)-7-methyl-1H-indol-3-yl]-3-(1H-indol-3-yl)-maleinimide;
(+)-2-[1-(2-hydroxy-3-(1-piperidino)propyl)-4-nitro-1H-indol-3-yl]-3-(1H-indol-3-yl)-maleinimide;
(+)-2-[1-(2-hydroxy-3-(1-piperidino)propyl)-5-nitro-1H-indol-3-yl]-3-(1H-indol-3-yl)-maleinimide;
(+)-2-[1-(2-hydroxy-3-(1-piperidino)propyl)-6-nitro-1H-indol-3-yl]-3-(1H-indol-3-yl)-maleinimide;
(+)-2-[1-(2-hydroxy-3-(1-piperidino)propyl)-7-nitro-1H-indol-3-yl]-3-(1H-indol-3-yl)-maleinimide;
(+)-2-[1-(2-hydroxy-3-(1-piperidino)propyl)-4-methylthio-1H-indol-3-yl]-3-(1H-indol-3-yl)-maleinimide;
(+)-2-[1-(2-hydroxy-3-(1-piperidino)propyl)-5-methylthio-1H-indol-3-yl]-3-(1H-indol-3-yl)-maleinimide;
(+)-2-[1-(2-hydroxy-3-(1-piperidino)propyl)-6-methylthio-1H-indol-3-yl]-3-(1H-indol-3-yl)-maleinimide;
(+)-2-[1-(2-hydroxy-3-(1-piperidino)propyl)-7-methylthio-1H-indol-3-yl]-3-(1H-indol-3-yl)-maleinimide;
(+)-2-[1-(2-hydroxy-3-(1-piperidino)propyl)-4,5-dimethoxy-1H-indol-3-yl]-3-(1H-indol-3-yl)-maleinimide;
(+)-2-[1-(2-hydroxy-3-(1-piperidino)propyl)-5,6-dimethoxy-1H-indol-3-yl]-3-(1H-indol-3-yl)-maleinimide;
(+)-2-[1-(2-hydroxy-3-(1-piperidino)propyl)-6,7-dimethoxy-1H-indol-3-yl]-3-(1H-indol-3-yl)-maleinimide;
(−)-2-[4-acetylamino-1-(2-hydroxy-3-(1-piperidino)propyl)-1H-indol-3-yl]-3-(1H-indol-3-yl)-maleinimide;
(−)-2-[5-acetylamino-1-(2-hydroxy-3-(1-piperidino)propyl)-1H-indol-3-yl]-3-(1H-indol-3-yl)-maleinimide;
(−)-2-[6-acetylamino-1-(2-hydroxy-3-(1-piperidino)propyl)-1H-indol-3-yl]-3-(1H-indol-3-yl)-maleinimide;
(−)-2-[7-acetylamino-1-(2-hydroxy-3-(1-piperidino)propyl)-1H-indol-3-yl]-3-(1H-indol-3-yl)-maleinimide;
(−)-2-[4-amino-1-(2-hydroxy-3-(1-piperidino)propyl)-1H-indol-3-yl]-3-(1H-indol-3-yl)-maleinimide;
(−)-2-[5-amino-1-(2-hydroxy-3-(1-piperidino)propyl)-1H-indol-3-yl]-3-(1H-indol-3-yl)-maleinimide;
(−)-2-[6-amino-1-(2-hydroxy-3-(1-piperidino)propyl)-1H-indol-3-yl]-3-(1H-indol-3-yl)-maleinimide;
(−)-2-[7-amino-1-(2-hydroxy-3-(1-piperidino)propyl)-1H-indol-3-yl]-3-(1H-indol-3-yl)-maleinimide;
(−)-2-[4-benzyloxy-1-(2-hydroxy-3-(1-piperidino)propyl)-1H-indol-3-yl]-3-(1H-indol-3-yl)-maleinimide;
(−)-2-[5-benzyloxy-1-(2-hydroxy-3-(1-piperidino)propyl)-1H-indol-3-yl]-3-(1H-indol-3-yl)-maleinimide;
(−)-2-[6-benzyloxy-1-(2-hydroxy-3-(1-piperidino)propyl)-1H-indol-3-yl]-3-(1H-indol-3-yl)-maleinimide;
(−)-2-[7-benzyloxy-1-(2-hydroxy-3-(1-piperidino)propyl)-1H-indol-3-yl]-3-(1H-indol-3-yl)-maleinimide;
(−)-2-[4-bromo-1-(2-hydroxy-3-(1-piperidino)propyl)-1H-indol-3-yl]-3-(1H-indol-3-yl)-maleinimide;
(−)-2-[5-bromo-1-(2-hydroxy-3-(1-piperidino)propyl)-1H-indol-3-yl]-3-(1H-indol-3-yl)-maleinimide;
(−)-2-[6-bromo-1-(2-hydroxy-3-(1-piperidino)propyl)-1H-indol-3-yl]-3-(1H-indol-3-yl)-maleinimide;
(−)-2-[7-bromo-1-(2-hydroxy-3-(1-piperidino)propyl)-1H-indol-3-yl]-3-(1H-indol-3-yl)-maleinimide;
(−)-2-[4-chloro-1-(2-hydroxy-3-(1-piperidino)propyl)-1H-indol-3-yl]-3-(1H-indol-3-yl)-maleinimide;
(−)-2-[5-chloro-1-(2-hydroxy-3-(1-piperidino)propyl)-1H-indol-3-yl]-3-(1H-indol-3-yl)-maleinimide;
(−)-2-[6-chloro-1-(2-hydroxy-3-(1-piperidino)propyl)-1H-indol-3-yl]-3-(1H-indol-3-yl)-maleinimide;
(−)-2-[7-chloro-1-(2-hydroxy-3-(1-piperidino)propyl)-1H-indol-3-yl]-3-(1H-indol-3-yl)-maleinimide;
(−)-2-[4-fluoro-1-(2-hydroxy-3-(1-piperidino)propyl)-1H-indol-3-yl]-3-(1H-indol-3-yl)-maleinimide;
(−)-2-[5-fluoro-1-(2-hydroxy-3-(1-piperidino)propyl)-1H-indol-3-yl]-3-(1H-indol-3-yl)-maleinimide;
(−)-2-[6-fluoro-1-(2-hydroxy-3-(1-piperidino)propyl)-1H-indol-3-yl]-3-(1H-indol-3-yl)-maleinimide;
(−)-2-[7-fluoro-1-(2-hydroxy-3-(1-piperidino)propyl)-1H-indol-3-yl]-3-(1H-indol-3-yl)-maleinimide;
(−)-2-[4-hydroxy-1-(2-hydroxy-3-(1-piperidino)propyl)-1H-indol-3-yl]-3-(1H-indol-3-yl)-maleinimide;
(−)-2-[5-hydroxy-1-(2-hydroxy-3-(1-piperidino)propyl)-1H-indol-3-yl]-3-(1H-indol-3-yl)-maleinimide;
(−)-2-[6-hydroxy-1-(2-hydroxy-3-(1-piperidino)propyl)-1H-indol-3-yl]-3-(1H-indol-3-yl)-maleinimide;
(−)-2-[7-hydroxy-1-(2-hydroxy-3-(1-piperidino)propyl)-7-hydroxy-1H-indol-3-yl]-3-(1H-indol-3-yl)-maleinimide;
(−)-2-[4-trifluoromethyl-1-(2-hydroxy-3-(1-piperidino)propyl)-4-trifluoromethyl-1H-indol-3-yl]-3-(1H-indol-3-yl)-maleinimide;
(−)-2-[5-trifluoromethyl-1-(2-hydroxy-3-(1-piperidino)propyl)-1H-indol-3-yl]-3-(1H-indol-3-yl)-maleinimide;
(−)-2-[6-trifluoromethyl-1-(2-hydroxy-3-(1-piperidino)propyl)-6-trifluoromethyl-1H-indol-3-yl]-3-(1H-indol-3-yl)-maleinimide;
(−)-2-[7-trifluoromethyl-1-(2-hydroxy-3-(1-piperidino)propyl)-1H-indol-3-yl]-3-(1H-indol-3-yl)-maleinimide;
(−)-2-[1-(2-hydroxy-3-(1-piperidino)propyl)-4-methoxy-1H-indol-3-yl]-3-(1H-indol-3-yl)-maleinimide;

(−)-2-[1-(2-hydroxy-3-(1-piperidino)propyl)-5-methoxy-1H-indol-3-yl]-3-(1H-indol-3-yl)-maleinimide;
(−)-2-[1-(2-hydroxy-3-(1-piperidino)propyl)-6-methoxy-1H-indol-3-yl]-3-(1H-indol-3-yl)-maleinimide;
(−)-2-[1-(2-hydroxy-3-(1-piperidino)propyl)-7-methoxy-1H-indol-3-yl]-3-(1H-indol-3-yl)-maleinimide;
(−)-2-[1-(2-hydroxy-3-(1-piperidino)propyl)-4,5-methylendioxy-1H-indol-3-yl]-3-(1H-indol-3-yl)-maleinimide;
(−)-2-[1-(2-hydroxy-3-(1-piperidino)propyl)-5,6-methylendioxy-1H-indol-3-yl]-3-(1H-indol-3-yl)-maleinimide;
(−)-2-[1-(2-hydroxy-3-(1-piperidino)propyl)-6,7-methylendioxy-1H-indol-3-yl]-3-(1H-indol-3-yl)-maleinimide;
(−)-2-[1-(2-hydroxy-3-(1-piperidino)propyl)-4-methyl-1H-indol-3-yl]-3-(1H-indol-3-yl)-maleinimide;
(−)-2-[1-(2-hydroxy-3-(1-piperidino)propyl)-5-methyl-1H-indol-3-yl]-3-(1H-indol-3-yl)-maleinimide;
(−)-2-[1-(2-hydroxy-3-(1-piperidino)propyl)-6-methyl-1H-indol-3-yl]-3-(1H-indol-3-yl)-maleinimide;
(−)-2-[1-(2-hydroxy-3-(1-piperidino)propyl)-7-methyl-1H-indol-3-yl]-3-(1H-indol-3-yl)-maleinimide;
(−)-2-[1-(2-hydroxy-3-(1-piperidino)propyl)-4-nitro-1H-indol-3-yl]-3-(1H-indol-3-yl)-maleinimide;
(−)-2-[1-(2-hydroxy-3-(1-piperidino)propyl)-5-nitro-1H-indol-3-yl]-3-(1H-indol-3-yl)-maleinimide;
(−)-2-[1-(2-hydroxy-3-(1-piperidino)propyl)-6-nitro-1H-indol-3-yl]-3-(1H-indol-3-yl)-maleinimide;
(−)-2-[1-(2-hydroxy-3-(1-piperidino)propyl)-7-nitro-1H-indol-3-yl]-3-(1H-indol-3-yl)-maleinimide;
(−)-2-[1-(2-hydroxy-3-(1-piperidino)propyl)-4-methylthio-1H-indol-3-yl]-3-(1H-indol-3-yl)-maleinimide;
(−)-2-[1-(2-hydroxy-3-(1-piperidino)propyl)-5-methylthio-1H-indol-3-yl]-3-(1H-indol-3-yl)-maleinimide;
(−)-2-[1-(2-hydroxy-3-(1-piperidino)propyl)-6-methylthio-1H-indol-3-yl]-3-(1H-indol-3-yl)-maleinimide;
(−)-2-[1-(2-hydroxy-3-(1-piperidino)propyl)-7-methylthio-1H-indol-3-yl]-3-(1H-indol-3-yl)-maleinimide;
(−)-2-[1-(2-hydroxy-3-(1-piperidino)propyl)-4,5-dimethoxy-1H-indol-3-yl]-3-(1H-indol-3-yl)-maleinimide;
(−)-2-[1-(2-hydroxy-3-(1-piperidino)propyl)-5,6-dimethoxy-1H-indol-3-yl]-3-(1H-indol-3-yl)-maleinimide;
(−)-2-[1-(2-hydroxy-3-(1-piperidino)propyl)-6,7-dimethoxy-1H-indol-3-yl]-3-(1H-indol-3-yl)-maleinimide;
(±)-2-[4-acetylamino-1-(2,3-dihydroxypropyl)-1H-indol-3-yl]-3-(1H-indol-3-yl)-maleinimide;
(±)-2-[5-acetylamino-1-(2,3-dihydroxypropyl)-1H-indol-3-yl]-3-(1H-indol-3-yl)-maleinimide;
(±)-2-[6-acetylamino-1-(2,3-dihydroxypropyl)-1H-indol-3-yl]-3-(1H-indol-3-yl)-maleinimide;
(±)-2-[7-acetylamino-1-(2,3-dihydroxypropyl)-1H-indol-3-yl]-3-(1H-indol-3-yl)-maleinimide;
(±)-2-[4-amino-1-(2,3-dihydroxypropyl)-1H-indol-3-yl]-3-(1H-indol-3-yl)-maleinimide;
(±)-2-[5-amino-1-(2,3-dihydroxypropyl)-1H-indol-3-yl]-3-(1H-indol-3-yl)-maleinimide;
(±)-2-[6-amino-1-(2,3-dihydroxypropyl)-1H-indol-3-yl]-3-(1H-indol-3-yl)-maleinimide;
(±)-2-[7-amino-1-(2,3-dihydroxypropyl)-1H-indol-3-yl]-3-(1H-indol-3-yl)-maleinimide;
(±)-2-[4-benzyloxy-1-(2,3-dihydroxypropyl)-1H-indol-3-yl]-3-(1H-indol-3-yl)-maleinimide;
(±)-2-[5-benzyloxy-1-(2,3-dihydroxypropyl)-1H-indol-3-yl]-3-(1H-indol-3-yl)-maleinimide;
(±)-2-[6-benzyloxy-1-(2,3-dihydroxypropyl)-1H-indol-3-yl]-3-(1H-indol-3-yl)-maleinimide;
(±)-2-[7-benzyloxy-1-(2,3-dihydroxypropyl)-1H-indol-3-yl]-3-(1H-indol-3-yl)-maleinimide;
(±)-2-[4-bromo-1-(2,3-dihydroxypropyl)-1H-indol-3-yl]-3-(1H-indol-3-yl)-maleinimide;
(±)-2-[5-bromo-1-(2,3-dihydroxypropyl)-1H-indol-3-yl]-3-(1H-indol-3-yl)-maleinimide;
(±)-2-[6-bromo-1-(2,3-dihydroxypropyl)-1H-indol-3-yl]-3-(1H-indol-3-yl)-maleinimide;
(±)-2-[7-bromo-1-(2,3-dihydroxypropyl)-1H-indol-3-yl]-3-(1H-indol-3-yl)-maleinimide;
(±)-2-[4-chloro-1-(2,3-dihydroxypropyl)-1H-indol-3-yl]-3-(1H-indol-3-yl)-maleinimide;
(±)-2-[5-chloro-1-(2,3-dihydroxypropyl)-1H-indol-3-yl]-3-(1H-indol-3-yl)-maleinimide;
(±)-2-[6-chloro-1-(2,3-dihydroxypropyl)-1H-indol-3-yl]-3-(1H-indol-3-yl)-maleinimide;
(±)-2-[7-chloro-1-(2,3-dihydroxypropyl)-1H-indol-3-yl]-3-(1H-indol-3-yl)-maleinimide;
(±)-2-[4-fluoro-1-(2,3-dihydroxypropyl)-1H-indol-3-yl]-3-(1H-indol-3-yl)-maleinimide;
(±)-2-[5-fluoro-1-(2,3-dihydroxypropyl)-1H-indol-3-yl]-3-(1H-indol-3-yl)-maleinimide;
(±)-2-[6-fluoro-1-(2,3-dihydroxypropyl)-1H-indol-3-yl]-3-(1H-indol-3-yl)-maleinimide;
(±)-2-[7-fluoro-1-(2,3-dihydroxypropyl)-1H-indol-3-yl]-3-(1H-indol-3-yl)-maleinimide;
(±)-2-[4-hydroxy-1-(2,3-dihydroxypropyl)-1H-indol-3-yl]-3-(1H-indol-3-yl)-maleinimide;
(±)-2-[5-hydroxy-1-(2,3-dihydroxypropyl)-1H-indol-3-yl]-3-(1H-indol-3-yl)-maleinimide;
(±)-2-[6-hydroxy-1-(2,3-dihydroxypropyl)-1H-indol-3-yl]-3-(1H-indol-3-yl)-maleinimide;
(±)-2-[7-hydroxy-1-(2,3-dihydroxypropyl)-1H-indol-3-yl]-3-(1H-indol-3-yl)-maleinimide;
(±)-2-[4-trifluoromethyl-1-(2,3-dihydroxypropyl)-1H-indol-3-yl]-3-(1H-indol-3-yl)-maleinimide;
(±)-2-[5-trifluoromethyl-1-(2,3-dihydroxypropyl)-1H-indol-3-yl]-3-(1H-indol-3-yl)-maleinimide;
(±)-2-[6-trifluoromethyl-1-(2,3-dihydroxypropyl)-1H-indol-3-yl]-3-(1H-indol-3-yl)-maleinimide;
(±)-2-[7-trifluoromethyl-1-(2,3-dihydroxypropyl)-1H-indol-3-yl]-3-(1H-indol-3-yl)-maleinimide;
(±)-2-[1-(2,3-dihydroxypropyl)-4-methoxy-1H-indol-3-yl]-3-(1H-indol-3-yl)-maleinimide;
(±)-2-[1-(2,3-dihydroxypropyl)-6-methoxy-1H-indol-3-yl]-3-(1H-indol-3-yl)-maleinimide;
(±)-2-[1-(2,3-dihydroxypropyl)-7-methoxy-1H-indol-3-yl]-3-(1H-indol-3-yl)-maleinimide;
(±)-2-[1-(2,3-dihydroxypropyl)-4,5-methylendioxy-1H-indol-3-yl]-3-(1H-indol-3-yl)-maleinimide;
(±)-2-[1-(2,3-dihydroxypropyl)-5,6-methylendioxy-1H-indol-3-yl]-3-(1H-indol-3-yl)-maleinimide;
(±)-2-[1-(2,3-dihydroxypropyl)-6,7-methylendioxy-1H-indol-3-yl]-3-(1H-indol-3-yl)-maleinimide;
(±)-2-[1-(2,3-dihydroxypropyl)-4-methyl-1H-indol-3-yl]-3-(1H-indol-3-yl)-maleinimide;
(±)-2-[1-(2,3-dihydroxypropyl)-5-methyl-1H-indol-3-yl]-3-(1H-indol-3-yl)-maleinimide;
(±)-2-[1-(2,3-dihydroxypropyl)-6-methyl-1H-indol-3-yl]-3-(1H-indol-3-yl)-maleinimide;
(±)-2-[1-(2,3-dihydroxypropyl)-7-methyl-1H-indol-3-yl]-3-(1H-indol-3-yl)-maleinimide;
(±)-2-[1-(2,3-dihydroxypropyl)-4-nitro-1H-indol-3-yl]-3-(1H-indol-3-yl)-maleinimide;
(±)-2-[1-(2,3-dihydroxypropyl)-5-nitro-1H-indol-3-yl]-3-(1H-indol-3-yl)-maleinimide;

(±)-2-[1-(2,3-dihydroxypropyl)-6-nitro-1H-indol-3-yl]-
3-(1H-indol-3-yl)-maleinimide;
(±)-2-[1-(2,3-dihydroxypropyl)-7-nitro-1H-indol-3-yl]-
3-(1H-indol-3-yl)-maleinimide;
(±)-2-[1-(2,3-dihydroxypropyl)-4-methylthio-1H-indol-
3-yl]-3-(1H-indol-3-yl)-maleinimide;
(±)-2-[1-(2,3-dihydroxypropyl)-5-methylthio-1H-indol-
3-yl]-3-(1H-indol-3-yl)-maleinimide;
(±)-2-[1-(2,3-dihydroxypropyl)-6-methylthio-1H-indol-
3-yl]-3-(1H-indol-3-yl)-maleinimide;
(±)-2-[1-(2,3-dihydroxypropyl)-7-methylthio-1H-indol-
3-yl]-3-(1H-indol-3-yl)-maleinimide;
(±)-2-[1-(2,3-dihydroxypropyl)-4,5-dimethoxy-1H-
indol-3-yl]-3-(1H-indol-3-yl)-maleinimide;
(±)-2-[1-(2,3-dihydroxypropyl)-5,6-dimethoxy-1H-
indol-3-yl]-3-(1H-indol-3-yl)-maleinimide;
(±)-2-[1-(2,3-dihydroxypropyl)-6,7-dimethoxy-1H-
indol-3-yl]-3-(1H-indol-3-yl)-maleinimide;
(+)-2-[4-acetylamino-1-(2,3-dihydroxypropyl)-1H-
indol-3-yl]-3-(1H-indol-3-yl)-maleinimide;
(+)-2-[5-acetylamino-1-(2,3-dihydroxypropyl)-1H-
indol-3-yl]-3-(1H-indol-3-yl)-maleinimide;
(+)-2-[6-acetylamino-1-(2,3-dihydroxypropyl)-1H-
indol-3-yl]-3-(1H-indol-3-yl)-maleinimide;
(+)-2-[7-acetylamino-1-(2,3-dihydroxypropyl)-1H-
indol-3-yl]-3-(1H-indol-3-yl)-maleinimide;
(+)-2-[4-amino-1-(2,3-dihydroxypropyl)-1H-indol-3-
yl]-3-(1H-indol-3-yl)-maleinimide;
(+)-2-[5-amino-1-(2,3-dihydroxypropyl)-1H-indol-3-
yl]-3-(1H-indol-3-yl)-maleinimide;
(+)-2-[6-amino-1-(2,3-dihydroxypropyl)-1H-indol-3-
yl]-3-(1H-indol-3-yl)-maleinimide;
(+)-2-[7-amino-1-(2,3-dihydroxypropyl)-1H-indol-3-
yl]-3-(1H-indol-3-yl)-maleinimide;
(+)-2-[4-benzyloxy-1-(2,3-dihydroxypropyl)-1H-indol-
3-yl]-3-(1H-indol-3-yl)-maleinimide;
(+)-2-[5-benzyloxy-1-(2,3-dihydroxypropyl)-1H-indol-
3-yl]-3-(1H-indol-3-yl)-maleinimide;
(+)-2-[6-benzyloxy-1-(2,3-dihydroxypropyl)-1H-indol-
3-yl]-3-(1H-indol-3-yl)-maleinimide;
(+)-2-[7-benzyloxy-1-(2,3-dihydroxypropyl)-1H-indol-
3-yl]-3-(1H-indol-3-yl)-maleinimide;
(+)-2-[4-bromo-1-(2,3-dihydroxypropyl)-1H-indol-3-
yl]-3-(1H-indol-3-yl)-maleinimide;
(+)-2-[5-bromo-1-(2,3-dihydroxypropyl)-1H-indol-3-
yl]-3-(1H-indol-3-yl)-maleinimide;
(+)-2-[6-bromo-1-(2,3-dihydroxypropyl)-1H-indol-3-
yl]-3-(1H-indol-3-yl)-maleinimide;
(+)-2-[7-bromo-1-(2,3-dihydroxypropyl)-1H-indol-3-
yl]-3-(1H-indol-3-yl)-maleinimide;
(+)-2-[4-chloro-1-(2,3-dihydroxypropyl)-1H-indol-3-
yl]-3-(1H-indol-3-yl)-maleinimide;
(+)-2-[5-chloro-1-(2,3-dihydroxypropyl)-1H-indol-3-
yl]-3-(1H-indol-3-yl)-maleinimide;
(+)-2-[6-chloro-1-(2,3-dihydroxypropyl)-1H-indol-3-
yl]-3-(1H-indol-3-yl)-maleinimide;
(+)-2-[7-chloro -1-(2,3-dihydroxypropyl)-1 H-indol-3-
yl]-3-(1H-indol-3-yl)-maleinimide;
(+)-2-[4-fluoro-1-(2,3-dihydroxypropyl)-1H-indol-3-
yl]-3-(1H-indol-3-yl)-maleinimide;
(+)-2-[5-fluoro-1-(2,3-dihydroxypropyl)-1H-indol-3-
yl]-3-(1H-indol-3-yl)-maleinimide;
(+)-2-[6-fluoro-1-(2,3-dihydroxypropyl)-1H-indol-3-
yl]-3-(1H-indol-3-yl)-maleinimide;
(+)-2-[7-fluoro-1-(2,3-dihydroxypropyl)-1H-indol-3-
yl]-3-(1H-indol-3-yl)-maleinimide;
(+)-2-[4-hydroxy-1-(2,3-dihydroxypropyl)-1H-indol-3-
yl]-3-(1H-indol-3-yl)-maleinimide;

(+)-2-[5-hydroxy-1-(2,3-dihydroxypropyl)-1H-indol-3-
yl]-3-(1H-indol-3-yl)-maleinimide;
(+)-2-[6-hydroxy-1-(2,3-dihydroxypropyl)-1H-indol-3-
yl]-3-(1H-indol-3-yl)-maleinimide;
(+)-2-[7-hydroxy-1-(2,3-dihydroxypropyl)-1H-indol-3-
yl]-3-(1H-indol-3-yl)-maleinimide;
(+)-2-[4-trifluoromethyl-1-(2,3-dihydroxypropyl)-1H-
indol-3-yl]-3-(1H-indol-3-yl)-maleinimide;
(+)-2-[5-trifluoromethyl-1-(2,3-dihydroxypropyl)-1H-
indol-3-yl]-3-(1H-indol-3-yl)-maleinimide;
(+)-2-[6-trifluoromethyl-1-(2,3-dihydroxypropyl)-1H-
indol-3-yl]-3-(1H-indol-3-yl)-maleinimide;
(+)-2-[7-trifluoromethyl-1-(2,3-dihydroxypropyl)-1H-
indol-3-yl]-3-(1H-indol-3-yl)-maleinimide;
(+)-2-[1-(2,3-dihydroxypropyl)-4-methoxy-1H-indol-3-
yl]-3-(1H-indol-3-yl)-maleinimide;
(+)-2-[1-(2,3-dihydroxypropyl)-5-methoxy-1H-indol-3-
yl]-3-(1H-indol-3-yl)-maleinimide;
(+)-2-[1-(2,3-dihydroxypropyl)-6-methoxy-1H-indol-3-
yl]-3-(1H-indol-3-yl)-maleinimide;
(+)-2-[1-(2,3-dihydroxypropyl)-7-methoxy-1H-indol-3-
yl]-3-(1H-indol-3-yl)-maleinimide;
(+)-2-[1-(2,3-dihydroxypropyl)-4,5-methylendioxy-1H-
indol-3-yl]-3-(1H-indol-3-yl)-maleinimide;
(+)-2-[1-(2,3-dihydroxypropyl)-5,6-methylendioxy-1H-
indol-3-yl]-3-(1H-indol-3-yl)-maleinimide;
(+)-2-[1-(2,3-dihydroxypropyl)-6,7-methylendioxy-1H-
indol-3-yl]-3-(1H-indol-3-yl)-maleinimide;
(+)-2-[1-(2,3-dihydroxypropyl)-4-methyl-1H-indol-3-
yl]-3-(1H-indol-3-yl)-maleinimide;
(+)-2-[1-(2,3-dihydroxypropyl)-5-methyl-1H-indol-3-
yl]-3-(1H-indol-3-yl)-maleinimide;
(+)-2-[1-(2,3-dihydroxypropyl)-6-methyl-1H-indol-3-
yl]-3-(1H-indol-3-yl)-maleinimide;
(+)-2-[1-(2,3-dihydroxypropyl)-7-methyl-1H-indol-3-
yl]-3-(1H-indol-3-yl)-maleinimide;
(+)-2-[1-(2,3-dihydroxypropyl)-4-nitro-1H-indol-3-yl]-
3-(1H-indol-3-yl)-maleinimide;
(+)-2-[1-(2,3-dihydroxypropyl)-5-nitro-1H-indol-3-yl]-
3-(1H-indol-3-yl)-maleinimide;
(+)-2-[1-(2,3-dihydroxypropyl)-6-nitro-1H-indol-3-yl]-
3-(1H-indol-3-yl)-maleinimide;
(+)-2-[1-(2,3-dihydroxypropyl)-7-nitro-1H-indol-3-yl]-
3-(1H-indol-3-yl)-maleinimide;
(+)-2-[1-(2,3-dihydroxypropyl)-4-methylthio-1H-indol-
3-yl]-3-(1H-indol-3-yl)-maleinimide;
(+)-2-[1-(2,3-dihydroxypropyl)-5-methylthio-1H-indol-
3-yl]-3-(1H-indol-3-yl)-maleinimide;
(+)-2-[1-(2,3-dihydroxypropyl)-6-methylthio-1H-indol-
3-yl]-3-(1H-indol-3-yl)-maleinimide;
(+)-2-[1-(2,3-dihydroxypropyl)-7-methylthio-1H-indol-
3-yl]-3-(1H-indol-3-yl)-maleinimide;
(+)-2-[1-(2,3-dihydroxypropyl)-4,5-dimethoxy-1H-
indol-3-yl]-3-(1H-indol-3-yl)-maleinimide;
(+)-2-[1-(2,3-dihydroxypropyl)-5,6-dimethoxy-1H-
indol-3-yl]-3-(1H-indol-3-yl)-maleinimide;
(+)-2-[1-(2,3-dihydroxypropyl)-6,7-dimethoxy-1H-
indol-3-yl]-3-(1H-indol-3-yl)-maleinimide;
(−)-2-[4-acetylamino-1-(2,3-dihydroxypropyl)-1H-
indol-3-yl]-3-(1H-indol-3-yl)-maleinimide;
(−)-2-[5-acetylamino-1-(2,3-dihydroxypropyl)-1H-
indol-3-yl]-3-(1H-indol-3-yl)-maleinimide;
(−)-2-[6-acetylamino-1-(2,3-dihydroxypropyl)-1H-
indol-3-yl]-3-(1H-indol-3-yl)-maleinimide;
(−)-2-[7-acetylamino-1-(2,3-dihydroxypropyl)-1H-
indol-3-yl]-3-(1H-indol-3-yl)-maleinimide;
(−)-2-[4-amino-1-(2,3-dihydroxypropyl)-1H-indol-3-
yl]-3-(1H-indol-3-yl)-maleinimide;

(−)-2-[5-amino-1-(2,3-dihydroxypropyl)-1H-indol-3-yl]-3-(1H-indol-3-yl)-maleinimide;
(−)-2-[6-amino-1-(2,3-dihydroxypropyl)-1H-indol-3-yl]-3-(1H-indol-3-yl)-maleinimide;
(−)-2-[7-amino-1-(2,3-dihydroxypropyl)-1H-indol-3-yl]-3-(1H-indol-3-yl)-maleinimide;
(−)-2-[4-benzyloxy-1-(2,3-dihydroxypropyl)-1H-indol-3-yl]-3-(1H-indol-3-yl)-maleinimide;
(−)-2-[5-benzyloxy-1-(2,3-dihydroxypropyl)-1H-indol-3-yl]-3-(1H-indol-3-yl)-maleinimide;
(−)-2-[6-benzyloxy-1-(2,3-dihydroxypropyl)-1H-indol-3-yl]-3-(1H-indol-3-yl)-maleinimide;
(−)-2-[7-benzyloxy-1-(2,3-dihydroxypropyl)-1H-indol-3-yl]-3-(1H-indol-3-yl)-maleinimide;
(−)-2-[4-bromo-1-(2,3-dihydroxypropyl)-1H-indol-3-yl]-3-(1H-indol-3-yl)-maleinimide;
(−)-2-[5-bromo-1-(2,3-dihydroxypropyl)-1H-indol-3-yl]-3-(1H-indol-3-yl)-maleinimide;
(−)-2-[6-bromo-1-(2,3-dihydroxypropyl)-1H-indol-3-yl]-3-(1H-indol-3-yl)-maleinimide;
(−)-2-[7-bromo-1-(2,3-dihydroxypropyl)-1H-indol-3-yl]-3-(1H-indol-3-yl)-maleinimide;
(−)-2-[4-chloro-1-(2,3-dihydroxypropyl)-1H-indol-3-yl]-3-(1H-indol-3-yl)-maleinimide;
(−)-2-[5-chloro-1-(2,3-dihydroxypropyl)-1H-indol-3-yl]-3-(1H-indol-3-yl)-maleinimide;
(−)-2-[6-chloro-1-(2,3-dihydroxypropyl)-1H-indol-3-yl]-3-(1H-indol-3-yl)-maleinimide;
(−)-2-[7-chloro-1-(2,3-dihydroxypropyl)-1H-indol-3-yl]-3-(1H-indol-3-yl)-maleinimide;
(−)-2-[4-fluoro-1-(2,3-dihydroxypropyl)-1H-indol-3-yl]-3-(1H-indol-3-yl)-maleinimide;
(−)-2-[5-fluoro-1-(2,3-dihydroxypropyl)-1H-indol-3-yl]-3-(1H-indol-3-yl)-maleinimide;
(−)-2-[6-fluoro-1-(2,3-dihydroxypropyl)-1H-indol-3-yl]-3-(1H-indol-3-yl)-maleinimide;
(−)-2-[7-fluoro-1-(2,3-dihydroxypropyl)-1H-indol-3-yl]-3-(1H-indol-3-yl)-maleinimide;
(−)-2-[4-hydroxy-1-(2,3-dihydroxypropyl)-1H-indol-3-yl]-3-(1H-indol-3-yl)-maleinimide;
(−)-2-[5-hydroxy-1-(2,3-dihydroxypropyl)-1H-indol-3-yl]-3-(1H-indol-3-yl)-maleinimide;
(−)-2-[6-hydroxy-1-(2,3-dihydroxypropyl)-1H-indol-3-yl]-3-(1H-indol-3-yl)-maleinimide;
(−)-2-[7-hydroxy-1-(2,3-dihydroxypropyl)-1H-indol-3-yl]-3-(1H-indol-3-yl)-maleinimide;
(−)-2-[4-trifluoromethyl-1-(2,3-dihydroxypropyl)-1H-indol-3-yl]-3-(1H-indol-3-yl)-maleinimide;
(−)-2-[5-trifluoromethyl-1-(2,3-dihydroxypropyl)-1H-indol-3-yl]-3-(1H-indol-3-yl)-maleinimide;
(−)-2-[6-trifluoromethyl-1-(2,3-dihydroxypropyl)-1H-indol-3-yl]-3-(1H-indol-3-yl)-maleinimide;
(−)-2-[7-trifluoromethyl-1-(2,3-dihydroxypropyl)-1H-indol-3-yl]-3-(1H-indol-3-yl)-maleinimide;
(−)-2-[1-(2,3-dihydroxypropyl)-4-methoxy-1H-indol-3-yl]-3-(1H-indol-3-yl)-maleinimide;
(−)-2-[1-(2,3-dihydroxypropyl)-5-methoxy-1H-indol-3-yl]-3-(1H-indol-3-yl)-maleinimide;
(−)-2-[1-(2,3-dihydroxypropyl)-6-methoxy-1H-indol-3-yl]-3-(1H-indol-3-yl)-maleinimide;
(−)-2-[1-(2,3-dihydroxypropyl)-7-methoxy-1H-indol-3-yl]-3-(1H-indol-3-yl)-maleinimide;
(−)-2-[1-(2,3-dihydroxypropyl)-4,5-methylendioxy-1H-indol-3-yl]-3-(1H-indol-3-yl)-maleinimide;
(−)-2-[1-(2,3-dihydroxypropyl)-5,6-methylendioxy-1H-indol-3-yl]-3-(1H-indol-3-yl)-maleinimide;
(−)-2-[1-(2,3-dihydroxypropyl)-6,7-methylendioxy-1H-indol-3-yl]-3-(1H-indol-3-yl)-maleinimide;
(−)-2-[1-(2,3-dihydroxypropyl)-4-methyl-1H-indol-3-yl]-3-(1H-indol-3-yl)-maleinimide;
(−)-2-[1-(2,3-dihydroxypropyl)-5-methyl-1H-indol-3-yl]-3-(1H-indol-3-yl)-maleinimide;
(−)-2-[1-(2,3-dihydroxypropyl)-6-methyl-1H-indol-3-yl]-3-(1H-indol-3-yl)-maleinimide;
(−)-2-[1-(2,3-dihydroxypropyl)-7-methyl-1H-indol-3-yl]-3-(1H-indol-3-yl)-maleinimide;
(−)-2-[1-(2,3-dihydroxypropyl)-4-nitro-1H-indol-3-yl]-3-(1H-indol-3-yl)-maleinimide;
(−)-2-[1-(2,3-dihydroxypropyl)-5-nitro-1H-indol-3-yl]-3-(1H-indol-3-yl)-maleinimide;
(−)-2-[1-(2,3-dihydroxypropyl)-6-nitro-1H-indol-3-yl]-3-(1H-indol-3-yl)-maleinimide;
(−)-2-[1-(2,3-dihydroxypropyl)-7-nitro-1H-indol-3-yl]-3-(1H-indol-3-yl)-maleinimide;
(−)-2-[1-(2,3-dihydroxypropyl)-4-methylthio-1H-indol-3-yl]-3-(1H-indol-3-yl)-maleinimide;
(−)-2-[1-(2,3-dihydroxypropyl)-5-methylthio-1H-indol-3-yl]-3-(1H-indol-3-yl)-maleinimide;
(−)-2-[1-(2,3-dihydroxypropyl)-6-methylthio-1H-indol-3-yl]-3-(1H-indol-3-yl)-maleinimide;
(−)-2-[1-(2,3-dihydroxypropyl)-7-methylthio-1H-indol-3-yl]-3-(1H-indol-3-yl)-maleinimide;
(−)-2-[1-(2,3-dihydroxypropyl)-4,5-dimethoxy-1H-indol-3-yl]-3-(1H-indol-3-yl)-maleinimide;
(−)-2-[1-(2,3-dihydroxypropyl)-5,6-dimethoxy-1H-indol-3-yl]-3-(1H-indol-3-yl)-maleinimide;
(−)-2-[1-(2,3-dihydroxypropyl)-6,7-dimethoxy-1H-indol-3-yl]-3-(1H-indol-3-yl)-maleinimide;
2-[4-acetylamino-1-(3-hydroxypropyl)-1H-indol-3-yl]-3-(1H-indol-3-yl)-maleinimide;
2-[5-acetylamino-1-(3-hydroxypropyl)-1H-indol-3-yl]-3-(1H-indol-3-yl)-maleinimide;
2-[6-acetylamino-1-(3-hydroxypropyl)-1H-indol-3-yl]-3-(1H-indol-3-yl)-maleinimide;
2-[7-acetylamino-1-(3-hydroxypropyl)-1H-indol-3-yl]-3-(1H-indol-3-yl)-maleinimide;
2-[4-amino-1-(3-hydroxypropyl)-1H-indol-3-yl]-3-(1H-indol-3-yl)-maleinimide;
2-[5-amino-1-(3-hydroxypropyl)-1H-indol-3-yl]-3-(1H-indol-3-yl)-maleinimide;
2-[6-amino-1-(3-hydroxypropyl)-1H-indol-3-yl]-3-(1H-indol-3-yl)-maleinimide;
2-[7-amino-1-(3-hydroxypropyl)-1H-indol-3-yl]-3-(1H-indol-3-yl)-maleinimide;
2-[4-benzyloxy-1-(3-hydroxypropyl)-1H-indol-3-yl]-3-(1H-indol-3-yl)-maleinimide;
2-[5-benzyloxy-1-(3-hydroxypropyl)-1H-indol-3-yl]-3-(1H-indol-3-yl)-maleinimide;
2-[6-benzyloxy-1-(3-hydroxypropyl)-1H-indol-3-yl]-3-(1H-indol-3-yl)-maleinimide;
2-[7-benzyloxy-1-(3-hydroxypropyl)-1H-indol-3-yl]-3-(1H-indol-3-yl)-maleinimide;
2-[4-bromo-1-(3-hydroxypropyl)-1H-indol-3-yl]-3-(1H-indol-3-yl)-maleinimide;
2-[5-bromo-1-(3-hydroxypropyl)-1H-indol-3-yl]-3-(1H-indol-3-yl)-maleinimide;
2-[6-bromo-1-(3-hydroxypropyl)-1H-indol-3-yl]-3-(1H-indol-3-yl)-maleinimide;
2-[7-bromo-1-(3-hydroxypropyl)-1H-indol-3-yl]-3-(1H-indol-3-yl)-maleinimide;
2-[4-chloro-1-(3-hydroxypropyl)-1H-indol-3-yl]-3-(1H-indol-3-yl)-maleinimide;
2-[5-chloro-1-(3-hydroxypropyl)-1H-indol-3-yl]-3-(1H-indol-3-yl)-maleinimide;
2-[6-chloro-1-(3-hydroxypropyl)-1H-indol-3-yl]-3-(1H-indol-3-yl)-maleinimide;

2-[7-chloro-1-(3-hydroxypropyl)-1H-indol-3-yl]-3-(1H-indol-3-yl)-maleinimide;
2-[4-fluoro-1-(3-hydroxypropyl)-1H-indol-3-yl]-3-(1H-indol-3-yl)-maleinimide;
2-[5-fluoro-1-(3-hydroxypropyl)-1H-indol-3-yl]-3-(1H-indol-3-yl)-maleinimide;
2-[6-fluoro-1-(3-hydroxypropyl)-1H-indol-3-yl]-3-(1H-indol-3-yl)-maleinimide;
2-[7-fluoro-1-(3-hydroxypropyl)-1H-indol-3-yl]-3-(1H-indol-3-yl)-maleinimide;
2-[4-hydroxy-1-(3-hydroxypropyl)-1H-indol-3-yl]-3-(1H-indol-3-yl)-maleinimide;
2-[5-hydroxy-1-(3-hydroxypropyl)-1H-indol-3-yl]-3-(1H-indol-3-yl)-maleinimide;
2-[6-hydroxy-1-(3-hydroxypropyl)-1H-indol-3-yl]-3-(1H-indol-3-yl)-maleinimide;
2-[7-hydroxy-1-(3-hydroxypropyl)-1H-indol-3-yl]-3-(1H-indol-3-yl)-maleinimide;
2-[4-trifluoromethyl-1-(3-hydroxypropyl)-1H-indol-3-yl]-3-(1H-indol-3-yl)-maleinimide;
2-[5-trifluoromethyl-1-(3-hydroxypropyl)-5-trifluoromethyl-1H-indol-3-yl]-3-(1H-indol-3-yl)-maleinimide;
2-[6-trifluoromethyl-1-(3-hydroxypropyl)-6-trifluoromethyl-1H-indol-3-yl]-3-(1H-indol-3-yl)-maleinimide;
2-[7-trifluoromethyl-1-(3-hydroxypropyl)-1H-indol-3-yl]-3-(1H-indol-3-yl)-maleinimide;
2-[1-(3-hydroxypropyl)-4-methoxy-1H-indol-3-yl]-3-(1H-indol-3-yl)-maleinimide;
2-[1-(3-hydroxypropyl)-5-methoxy-1H-indol-3-yl]-3-(1H-indol-3-yl)-maleinimide;
2-[1-(3-hydroxypropyl)-6-methoxy-1H-indol-3-yl]-3-(1H-indol-3-yl)-maleinimide;
2-[1-(3-hydroxypropyl)-7-methoxy-1H-indol-3-yl]-3-(1H-indol-3-yl)-maleinimide;
2-[1-(3-hydroxypropyl)-4,5-methylendioxy-1H-indol-3-yl]-3-(1H-indol-3-yl)-maleinimide;
2-[1-(3-hydroxypropyl)-5,6-methylendioxy-1H-indol-3-yl]-3-(1H-indol-3-yl)-maleinimide;
2-[1-(3-hydroxypropyl)-6,7-methylendioxy-1H-indol-3-yl]-3-(1H-indol-3-yl)-maleinimide;
2-[1-(3-hydroxypropyl)-4-methyl-1H-indol-3-yl]-3-(1H-indol-3-yl)-maleinimide;
2-[1-(3-hydroxypropyl)-5-methyl-1H-indol-3-yl]-3-(1H-indol-3-yl)-maleinimide;
2-[1-(3-hydroxypropyl)-6-methyl-1H-indol-3-yl]-3-(1H-indol-3-yl)-maleinimide;
2-[1-(3-hydroxypropyl)-7-methyl-1H-indol-3-yl]-3-(1H-indol-3-yl)-maleinimide;
2-[1-(3-hydroxypropyl)-4-nitro-1H-indol-3-yl]-3-(1H-indol-3-yl)-maleinimide;
2-[1-(3-hydroxypropyl)-5-nitro-1H-indol-3-yl]-3-(1H-indol-3-yl)-maleinimide;
2-[1-(3-hydroxypropyl)-6-nitro-1H-indol-3-yl]-3-(1H-indol-3-yl)-maleinimide;
2-[1-(3-hydroxypropyl)-7-nitro-1H-indol-3-yl]-3-(1H-indol-3-yl)-maleinimide;
2-[1-(3-hydroxypropyl)-4-methylthio-1H-indol-3-yl]-3-(1H-indol-3-yl)-maleinimide;
2-[1-(3-hydroxypropyl)-5-methylthio-1H-indol-3-yl]-3-(1H-indol-3-yl)-maleinimide;
2-[1-(3-hydroxypropyl)-6-methylthio-1H-indol-3-yl]-3-(1H-indol-3-yl)-maleinimide;
2-[1-(3-hydroxypropyl)-7-methylthio-1H-indol-3-yl]-3-(1H-indol-3-yl)-maleinimide;
2-[1-(3-hydroxypropyl)-4,5-dimethoxy-1H-indol-3-yl]-3-(1H-indol-3-yl)-maleinimide;
2-[1-(3-hydroxypropyl)-5,6-dimethoxy-1H-indol-3-yl]-3-(1H-indol-3-yl)-maleinimide;
2-[1-(3-hydroxypropyl)-6,7-dimethoxy-1H-indol-3-yl]-3-(1H-indol-3-yl)-maleinimide;
2-[4-acetylamino-1-(3-isothiocyanatopropyl)-1H-indol-3-yl]-3-(1H-indol-3-yl)-maleinimide;
2-[5-acetylamino-1-(3-isothiocyanatopropyl)-1H-indol-3-yl]-3-(1H-indol-3-yl)-maleinimide;
2-[6-acetylamino-1-(3-isothiocyanatopropyl)-1H-indol-3-yl]-3-(1H-indol-3-yl)-maleinimide;
2-[7-acetylamino-1-(3-isothiocyanatopropyl)-1H-indol-3-yl]-3-(1H-indol-3-yl)-maleinimide;
2-[4-amino-1-(3-isothiocyanatopropyl)-1H-indol-3-yl]-3-(1H-indol-3-yl)-maleinimide;
2-[5-amino-1-(3-isothiocyanatopropyl)-1H-indol-3-yl]-3-(1H-indol-3-yl)-maleinimide;
2-[6-amino-1-(3-isothiocyanatopropyl)-1H-indol-3-yl]-3-(1H-indol-3-yl)-maleinimide;
2-[7-amino-1-(3-isothiocyanatopropyl)-1H-indol-3-yl]-3-(1H-indol-3-yl)-maleinimide;
2-[4-benzyloxy-1-(3-isothiocyanatopropyl)-1H-indol-3-yl]-3-(1H-indol-3-yl)-maleinimide;
2-[5-benzyloxy-1-(3-isothiocyanatopropyl)-1H-indol-3-yl]-3-(1H-indol-3-yl)-maleinimide;
2-[6-benzyloxy-1-(3-isothiocyanatopropyl)-1H-indol-3-yl]-3-(1H-indol-3-yl)-maleinimide;
2-[7-benzyloxy-1-(3-isothiocyanatopropyl)-1H-indol-3-yl]-3-(1H-indol-3-yl)-maleinimide;
2-[4-bromo-1-(3-isothiocyanatopropyl)-1H-indol-3-yl]-3-(1H-indol-3-yl)-maleinimide;
2-[5-bromo-1-(3-isothiocyanatopropyl)-1H-indol-3-yl]-3-(1H-indol-3-yl)-maleinimide;
2-[6-bromo-1-(3-isothiocyanatopropyl)-1H-indol-3-yl]-3-(1H-indol-3-yl)-maleinimide;
2-[7-bromo-1-(3-isothiocyanatopropyl)-1H-indol-3-yl]-3-(1H-indol-3-yl)-maleinimide;
2-[4-chloro-1-(3-isothiocyanatopropyl)-1H-indol-3-yl]-3-(1H-indol-3-yl)-maleinimide;
2-[5-chloro-1-(3-isothiocyanatopropyl)-1H-indol-3-yl]-3-(1H-indol-3-yl)-maleinimide;
2-[6-chloro-1-(3-isothiocyanatopropyl)-1H-indol-3-yl]-3-(1H-indol-3-yl)-maleinimide;
2-[7-chloro-1-(3-isothiocyanatopropyl)-1H-indol-3-yl]-3-(1H-indol-3-yl)-maleinimide;
2-[4-fluoro-1-(3-isothiocyanatopropyl)-1H-indol-3-yl]-3-(1H-indol-3-yl)-maleinimide;
2-[5-fluoro-1-(3-isothiocyanatopropyl)-1H-indol-3-yl]-3-(1H-indol-3-yl)-maleinimide;
2-[6-fluoro-1-(3-isothiocyanatopropyl)-1H-indol-3-yl]-3-(1H-indol-3-yl)-maleinimide;
2-[7-fluoro-1-(3-isothiocyanatopropyl)-1H-indol-3-yl]-3-(1H-indol-3-yl)-maleinimide;
2-[4-hydroxy-1-(3-isothiocyanatopropyl)-1H-indol-3-yl]-3-(1H-indol-3-yl)-maleinimide;
2-[5-hydroxy-1-(3-isothiocyanatopropyl)-1H-indol-3-yl]-3-(1H-indol-3-yl)-maleinimide;
2-[6-hydroxy-1-(3-isothiocyanatopropyl)-1H-indol-3-yl]-3-(1H-indol-3-yl)-maleinimide;
2-[7-hydroxy-1-(3-isothiocyanatopropyl)-1H-indol-3-yl]-3-(1H-indol-3-yl)-maleinimide;
2-[4-trifluoromethyl-1-(3-isothiocyanatopropyl)-1H-indol-3-yl]-3-(1H-indol-3-yl)-maleinimide;
2-[5-trifluoromethyl-1-(3-isothiocyanatopropyl)-1H-indol-3-yl]-3-(1H-indol-3-yl)-maleinimide;
2-[6-trifluoromethyl-1-(3-isothiocyanatopropyl)-1H-indol-3-yl]-3-(1H-indol-3-yl)-maleinimide;
2-[7-trifluoromethyl-1-(3-isothiocyanatopropyl)-1H-indol-3-yl]-3-(1H-indol-3-yl)-maleinimide;

2-(1H-indol-3-yl)-3-[1-(3-isothiocyanatopropyl)-4-methoxy-1H-indol-3-yl]-maleinimide;
2-(1H-indol-3-yl)-3-[1-(3-isothiocyanatopropyl)-5-methoxy-1H-indol-3-yl]-maleinimide;
2-(1H-indol-3-yl)-3-[1-(3-isothiocyanatopropyl)-6-methoxy-1H-indol-3-yl]-maleinimide;
2-(1H-indol-3-yl)-3-[1-(3-isothiocyanatopropyl)-7-methoxy-1H-indol-3-yl]-maleinimide;
2-(1H-indol-3-yl)-3-[1-(3-isothiocyanatopropyl)-4,5-methylendioxy-1H-indol-3-yl-maleinimide;
2-(1H-indol-3-yl)-3-[1-(3-isothiocyanatopropyl)-5,6-methylendioxy-1H-indol-3-yl]-maleinimide;
2-(1H-indol-3-yl)-3-[1-(3-isothiocyanatopropyl)-6,7-methylendioxy-1H-indol-3-yl]-maleinimide;
2-(1H-indol-3-yl)-3-[1-(3-isothiocyanatopropyl)-4-methyl-1H-indol-3-yl]-maleinimide;
2-(1H-indol-3-yl)-3-[1-(3-isothiocyanatopropyl)-5-methyl-1H-indol-3-yl]-maleinimide;
2-(1H-indol-3-yl)-3-[1-(3-isothiocyanatopropyl)-6-methyl-1H-indol-3-yl]-maleinimide;
2-(1H-indol-3-yl)-3-[1-(3-isothiocyanatopropyl)-7-methyl-1H-indol-3-yl]-maleinimide;
2-(1H-indol-3-yl)-3-[1-(3-isothiocyanatopropyl)-4-nitro-1H-indol-3-yl]-maleinimide;
2-(1H-indol-3-yl)-3-[1-(3-isothiocyanatopropyl)-5-nitro-1H-indol-3-yl]-maleinimide;
2-(1H-indol-3-yl)-3-[1-(3-isothiocyanatopropyl)-6-nitro-1H-indol-3-yl]-maleinimide;
2-(1H-indol-3-yl)-3-[1-(3-isothiocyanatopropyl)-7-nitro-1H-indol-3-yl]-maleinimide;
2-(1H-indol-3-yl)-3-[1-(3-isothiocyanatopropyl)-4-methylthio-1H-indol-3-yl]-maleinimide;
2-(1H-indol-3-yl)-3-[1-(3-isothiocyanatopropyl)-5-methylthio-1H-indol-3-yl]-maleinimide;
2-(1H-indol-3-yl)-3-[1-(3-isothiocyanatopropyl)-6-methylthio-1H-indol-3-yl]-maleinimide;
2-(1H-indol-3-yl)-3-[1-(3-isothiocyanatopropyl)-7-methylthio-1H-indol-3-yl]-maleinimide;
2-(1H-indol-3-yl)-3-[1-(3-isothiocyanatopropyl)-4,5-dimethoxy-1H-indol-3-yl]-maleinimide;
2-(1H-indol-3-yl)-3-[1-(3-isothiocyanatopropyl)-5,6-dimethoxy-1H-indol-3-yl]-maleinimide;
2-(1H-indol-3-yl)-3-[1-(3-isothiocyanatopropyl)-6,7-dimethoxy-1H-indol-3-yl]-maleinimide;
(±)-2-[4-acetylamino-1-(2-methoxy-3-dimethylaminopropyl)-1H-indol-3-yl]-3-(1H-indol-3-yl)-maleinimide;
(±)-2-[5-acetylamino-1-(2-methoxy-3-dimethylaminopropyl)-1H-indol-3-yl]-3-(1H-indol-3-yl)-maleinimide;
(±)-2-[6-acetylamino-1-(2-methoxy-3-dimethylaminopropyl)-1H-indol-3-yl]-3-(1H-indol-3-yl)-maleinimide;
(±)-2-[7-acetylamino-1-(2-methoxy-3-dimethylaminopropyl)-1H-indol-3-yl]-3-(1H-indol-3-yl)-maleinimide;
(±)-2-[4-amino-1-(2-methoxy-3-dimethylaminopropyl)-1H-indol-3-yl]-3-(1H-indol-3-yl)-maleinimide;
(±)-2-[5-amino-1-(2-methoxy-3-dimethylaminopropyl)-1H-indol-3-yl]-3-(1H-indol-3-yl)-maleinimide;
(±)-2-[6-amino-1-(2-methoxy-3-dimethylaminopropyl)-1H-indol-3-yl]-3-(1H-indol-3-yl)-maleinimide;
(±)-2-[7-amino-1-(2-methoxy-3-dimethylaminopropyl)-1H-indol-3-yl]-3-(1H-indol-3-yl)-maleinimide;
(±)-2-[4-benzyloxy-1-(2-methoxy-3-dimethylaminopropyl)-1H-indol-3-yl]-3-(1H-indol-3-yl)-maleinimide;
(±)-2-[5-benzyloxy-1-(2-methoxy-3-dimethylaminopropyl)-1H-indol-3-yl]-3-(1H-indol-3-yl)-maleinimide;
(±)-2-[6-benzyloxy-1-(2-methoxy-3-dimethylaminopropyl)-1H-indol-3-yl]-3-(1H-indol-3-yl)-maleinimide;
(±)-2-[7-benzyloxy-1-(2-methoxy-3-dimethylaminopropyl)-1H-indol-3-yl]-3-(1H-indol-3-yl)-maleinimide;
(±)-2-[4-bromo-1-(2-methoxy-3-dimethylaminopropyl)-1H-indol-3-yl]-3-(1H-indol-3-yl)-maleinimide;
(±)-2-[5-bromo-1-(2-methoxy-3-dimethylaminopropyl)-1H-indol-3-yl]-3-(1H-indol-3-yl)-maleinimide;
(±)-2-[6-bromo-1-(2-methoxy-3-dimethylaminopropyl)-1H-indol-3-yl]-3-(1H-indol-3-yl)-maleinimide;
(±)-2-[7-bromo-1-(2-methoxy-3-dimethylaminopropyl)-1H-indol-3-yl]-3-(1H-indol-3-yl)-maleinimide;
(±)-2-[4-chloro-1-(2-methoxy-3-dimethylaminopropyl)-1H-indol-3-yl]-3-(1H-indol-3-yl)-maleinimide;
(±)-2-[5-chloro-1-(2-methoxy-3-dimethylaminopropyl)-1H-indol-3-yl]-3-(1H-indol-3-yl)-maleinimide;
(±)-2-[6-chloro-1-(2-methoxy-3-dimethylaminopropyl)-1H-indol-3-yl]-3-(1H-indol-3-yl)-maleinimide;
(±)-2-[7-chloro-1-(2-methoxy-3-dimethylaminopropyl)-1H-indol-3-yl]-3-(1H-indol-3-yl)-maleinimide;
(±)-2-[4-fluoro-1-(2-methoxy-3-dimethylaminopropyl)-1H-indol-3-yl]-3-(1H-indol-3-yl)-maleinimide;
(±)-2-[5-fluoro-1-(2-methoxy-3-dimethylaminopropyl)-1H-indol-3-yl]-3-(1H-indol-3-yl)-maleinimide;
(±)-2-[6-fluoro-1-(2-methoxy-3-dimethylaminopropyl)-1H-indol-3-yl]-3-(1H-indol-3-yl)-maleinimide;
(±)-2-[7-fluoro-1-(2-methoxy-3-dimethylaminopropyl)-1H-indol-3-yl]-3-(1H-indol-3-yl)-maleinimide;
(±)-2-[4-hydroxy-1-(2-methoxy-3-dimethylaminopropyl)-1H-indol-3-yl]-3-(1H-indol-3-yl)-maleinimide;
(±)-2-[5-hydroxy-1-(2-methoxy-3-dimethylaminopropyl)-1H-indol-3-yl]-3-(1H-indol-3-yl)-maleinimide;
(±)-2-[6-hydroxy-1-(2-methoxy-3-dimethylaminopropyl)-1H-indol-3-yl]-3-(1H-indol-3-yl)-maleinimide;
(±)-2-[7-hydroxy-1-(2-methoxy-3-dimethylaminopropyl)-1H-indol-3-yl]-3-(1H-indol-3-yl)-maleinimide;
(±)-2-[4-trifluoromethyl-1-(2-methoxy-3-dimethylaminopropyl)-1H-indol-3-yl]-3-(1H-indol-3-yl)-maleinimide;
(±)-2-[5-trifluoromethyl-1-(2-methoxy-3-dimethylaminopropyl)-1H-indol-3-yl]-3-(1H-indol-3-yl)-maleinimide;
(±)-2-[6-trifluoromethyl-1-(2-methoxy-3-dimethylaminopropyl)-1H-indol-3-yl]-3-(1H-indol-3-yl)-maleinimide;
(±)-2-[7-trifluoromethyl-1-(2-methoxy-3-dimethylaminopropyl)-1H-indol-3-yl]-3-(1H-indol-3-yl)-maleinimide;
(±)-2-(1H-indol-3-yl)-3-[4-methoxy-1-(2-methoxy-3-dimethylaminopropyl)-1H-indol-3-yl]-maleinimide;

(±)-2-(1H-indol-3-yl)-3-[5-methoxy-1-(2-methoxy-3-dimethylaminopropyl)-1H-indol-3-yl]-maleinimide;
(±)-2-(1H-indol-3-yl)-3-[6-methoxy-1-(2-methoxy-3-dimethylaminopropyl)-1H-indol-3-yl]-maleinimide;
(±)-2-(1H-indol-3-yl)-3-[7-methoxy-1-(2-methoxy-3-dimethylaminopropyl)-1H-indol-3-yl]-maleinimide;
(±)-2-(1H-indol-3-yl)-3-[1-(2-methoxy-3-dimethylaminopropyl)-4,5-methylendioxy-1H-indol-3-yl]-maleinimide;
(±)-2-(1H-indol-3-yl)-3-[1-(2-methoxy-3-dimethylaminopropyl)-5,6-methylendioxy-1H-indol-3-yl]-maleinimide;
(±)-2-(1H-indol-3-yl)-3-[1-(2-methoxy-3-dimethylaminopropyl)-6,7-methylendioxy-1H-indol-3-yl]-maleinimide;
(±)-2-(1H-indol-3-yl)-3-[1-(2-methoxy-3-dimethylaminopropyl)-4-methyl-1H-indol-3-yl]-maleinimide;
(±)-2-(1H-indol-3-yl)-3-[1-(2-methoxy-3-dimethylaminopropyl)-5-methyl-1H-indol-3-yl]-maleinimide;
(±)-2-(1H-indol-3-yl)-3-[1-(2-methoxy-3-dimethylaminopropyl)-6-methyl-1H-indol-3-yl]-maleinimide;
(±)-2-(1H-indol-3-yl)-3-[1-(2-methoxy-3-dimethylaminopropyl)-7-methyl-1H-indol-3-yl]-maleinimide;
(±)-2-(1H-indol-3-yl)-3-[1-(2-methoxy-3-dimethylaminopropyl)-4-nitro-1H-indol-3-yl]-maleinimide;
(±)-2-(1H-indol-3-yl)-3-[1-(2-methoxy-3-dimethylaminopropyl)-5-nitro-1H-indol-3-yl]-maleinimide;
(±)-2-(1H-indol-3-yl)-3-[1-(2-methoxy-3-dimethylaminopropyl)-6-nitro-1H-indol-3-yl]-maleinimide;
(±)-2-(1H-indol-3-yl)-3-[1-(2-methoxy-3-dimethylaminopropyl)-7-nitro-1H-indol-3-yl]-maleinimide;
(±)-2-(1H-indol-3-yl)-3-[1-(2-methoxy-3-dimethylaminopropyl)-4-methylthio-1H-indol-3-yl]-maleinimide;
(±)-2-(1H-indol-3-yl)-3-[1-(2-methoxy-3-dimethylaminopropyl)-5-methylthio-1H-indol-3-yl]-maleinimide;
(±)-2-(1H-indol-3-yl)-3-[1-(2-methoxy-3-dimethylaminopropyl)-6-methylthio-1H-indol-3-yl]-maleinimide;
(±)-2-(1H-indol-3-yl)-3-[1-(2-methoxy-3-dimethylaminopropyl)-7-methylthio-1H-indol-3-yl]-maleinimide;
(±)-2-(1H-indol-3-yl)-3-[4,5-dimethoxy-1-(2-methoxy-3-dimethylaminopropyl)-1H-indol-3-yl]-maleinimide;
(±)-2-(1H-indol-3-yl)-3-[5,6-dimethoxy-1-(2-methoxy-3-dimethylaminopropyl)-1H-indol-3-yl]-maleinimide;
(±)-2-(1H-indol-3-yl)-3-[6,7-dimethoxy-1-(2-methoxy-3-dimethylaminopropyl)-1H-indol-3-yl]-maleinimide;
(+)-2-[4-acetylamino-1-(2-methoxy-3-dimethylaminopropyl)-1H-indol-3-yl]-3-(1H-indol-3-yl)-maleinimide;
(+)-2-[5-acetylamino-1-(2-methoxy-3-dimethylaminopropyl)-1H-indol-3-yl]-3-(1H-indol-3-yl)-maleinimide;
(+)-2-[6-acetylamino-1-(2-methoxy-3-dimethylaminopropyl)-1H-indol-3-yl]-3-(1H-indol-3-yl)-maleinimide;
(+)-2-[7-acetylamino-1-(2-methoxy-3-dimethylaminopropyl)-1H-indol-3-yl]-3-(1H-indol-3-yl)-maleinimide;
(+)-2-[4-amino-1-(2-methoxy-3-dimethylaminopropyl)-1H-indol-3-yl]-3-(1H-indol-3-yl)-maleinimide;
(+)-2-[5-amino-1-(2-methoxy-3-dimethylaminopropyl)-1H-indol-3-yl]-3-(1H-indol-3-yl)-maleinimide;
(+)-2-[6-amino-1-(2-methoxy-3-dimethylaminopropyl)-1H-indol-3-yl]-3-(1H-indol-3-yl)-maleinimide;
(+)-2-[7-amino-1-(2-methoxy-3-dimethylaminopropyl)-1H-indol-3-yl]-3-(1H-indol-3-yl)-maleinimide;
(+)-2-[4-benzyloxy-1-(2-methoxy-3-dimethylaminopropyl)-1H-indol-3-yl]-3-(1H-indol-3-yl)-maleinimide;
(+)-2-[5-benzyloxy-1-(2-methoxy-3-dimethylaminopropyl)-1H-indol-3-yl]-3-(1H-indol-3-yl)-maleinimide;
(+)-2-[6-benzyloxy-1-(2-methoxy-3-dimethylaminopropyl)-1H-indol-3-yl]-3-(1H-indol-3-yl)-maleinimide;
(+)-2-[7-benzyloxy-1-(2-methoxy-3-dimethylaminopropyl)-1H-indol-3-yl]-3-(1H-indol-3-yl)-maleinimide;
(+)-2-[4-bromo-1-(2-methoxy-3-dimethylaminopropyl)-1H-indol-3-yl]-3-(1H-indol-3-yl)-maleinimide;
(+)-2-[5-bromo-1-(2-methoxy-3-dimethylaminopropyl)-1H-indol-3-yl]-3-(1H-indol-3-yl)-maleinimide;
(+)-2-[6-bromo-1-(2-methoxy-3-dimethylaminopropyl)-1H-indol-3-yl]-3-(1H-indol-3-yl)-maleinimide;
(+)-2-[7-bromo-1-(2-methoxy-3-dimethylaminopropyl)-1H-indol-3-yl]-3-(1H-indol-3-yl)-maleinimide;
(+)-2-[4-chloro-1-(2-methoxy-3-dimethylaminopropyl)-1H-indol-3-yl]-3-(1H-indol-3-yl)-maleinimide;
(+)-2-[5-chloro-1-(2-methoxy-3-dimethylaminopropyl)-1H-indol-3-yl]-3-(1H-indol-3-yl)-maleinimide;
(+)-2-[6-chloro-1-(2-methoxy-3-dimethylaminopropyl)-1H-indol-3-yl]-3-(1H-indol-3-yl)-maleinimide;
(+)-2-[7-chloro-1-(2-methoxy-3-dimethylaminopropyl)-1H-indol-3-yl]-3-(1H-indol-3-yl)-maleinimide;
(+)-2-[4-fluoro-1-(2-methoxy-3-dimethylaminopropyl)-1H-indol-3-yl]-3-(1H-indol-3-yl)-maleinimide;
(+)-2-[5-fluoro-1-(2-methoxy-3-dimethylaminopropyl)-1H-indol-3-yl]-3-(1H-indol-3-yl)-maleinimide;
(+)-2-[6-fluoro-1-(2-methoxy-3-dimethylaminopropyl)-1H-indol-3-yl]-3-(1H-indol-3-yl)-maleinimide;
(+)-2-[7-fluoro-1-(2-methoxy-3-dimethylaminopropyl)-1H-indol-3-yl]-3-(1H-indol-3-yl)-maleinimide;
(+)-2-[4-hydroxy-1-(2-methoxy-3-dimethylaminopropyl)-1H-indol-3-yl]-3-(1H-indol-3-yl)-maleinimide;
(+)-2-[5-hydroxy-1-(2-methoxy-3-dimethylaminopropyl)-1H-indol-3-yl]-3-(1H-indol-3-yl)-maleinimide;
(+)-2-[6-hydroxy-1-(2-methoxy-3-dimethylaminopropyl)-1H-indol-3-yl]-3-(1H-indol-3-yl)-maleinimide;
(+)-2-[7-hydroxy-1-(2-methoxy-3-dimethylaminopropyl)-1H-indol-3-yl]-3-(1H-indol-3-yl)-maleinimide;

(+)-2-[4-trifluoromethyl-1-(2-methoxy-3-dimethylaminopropyl)-1H-indol-3-yl]-3-(1H-indol-3-yl)-maleinimide;
(+)-2-[5-trifluoromethyl-1-(2-methoxy-3-dimethylaminopropyl)-1H-indol-3-yl]-3-(1H-indol-3-yl)-maleinimide;
(+)-2-[6-trifluoromethyl-1-(2-methoxy-3-dimethylaminopropyl)-1H-indol-3-yl]-3-(1H-indol-3-yl)-maleinimide;
(+)-2-[7-trifluoromethyl-1-(2-methoxy-3-dimethylaminopropyl)-1H-indol-3-yl]-3-(1H-indol-3-yl)-maleinimide;
(+)-2-(1H-indol-3-yl)-3-[4-methoxy-1-(2-methoxy-3-dimethylaminopropyl)-1H-indol-3-yl]-maleinimide;
(+)-2-(1H-indol-3-yl)-3-[5-methoxy-1-(2-methoxy-3-dimethylaminopropyl)-1H-indol-3-yl]-maleinimide;
(+)-2-(1H-indol-3-yl)-3-[6-methoxy-1-(2-methoxy-3-dimethylaminopropyl)-1 H-indol-3-yl]-maleinimide;
(+)-2-(1H-indol-3-yl)-3-[7-methoxy-1-(2-methoxy-3-dimethylaminopropyl)-1H-indol-3-yl]-maleinimide;
(+)-2-(1H-indol-3-yl)-3-[1-(2-methoxy-3-dimethylaminopropyl)-4,5-methylendioxy-1H-indol-3-yl]-maleinimide;
(+)-2-(1H-indol-3-yl)-3-[1-(2-methoxy-3-dimethylaminopropyl)-5,6-methylendioxy-1H-indol-3-yl]-maleinimide;
(+)-2-(1H-indol-3-yl)-3-[1-(2-methoxy-3-dimethylaminopropyl)-6,7-methylendioxy-1H-indol-3-yl]-maleinimide;
(+)-2-(1H-indol-3-yl)-3-[1-(2-methoxy-3-dimethylaminopropyl)-4-methyl-1H-indol-3-yl]-maleinimide;
(+)-2-(1H-indol-3-yl)-3-[1-(2-methoxy-3-dimethylaminopropyl)-5-methyl-1H-indol-3-yl]-maleinimide;
(+)-2-(1H-indol-3-yl)-3-[1-(2-methoxy-3-dimethylaminopropyl)-6-methyl-1H-indol-3-yl]-maleinimide;
(+)-2-(1H-indol-3-yl)-3-[1-(2-methoxy-3-dimethylaminopropyl)-7-methyl-1H-indol-3-yl]-maleinimide;
(+)-2-(1H-indol-3-yl)-3-[1-(2-methoxy-3-dimethylaminopropyl)-4-nitro-1H-indol-3-yl]-maleinimide;
(+)-2-(1H-indol-3-yl)-3-[1-(2-methoxy-3-dimethylaminopropyl)-5-nitro-1H-indol-3-yl]-maleinimide;
(+)-2-(1H-indol-3-yl)-3-[1-(2-methoxy-3-dimethylaminopropyl)-6-nitro-1H-indol-3-yl]-maleinimide;
(+)-2-(1H-indol-3-yl)-3-[1-(2-methoxy-3-dimethylaminopropyl)-7-nitro-1H-indol-3-yl]-maleinimide;
(+)-2-(1H-indol-3-yl)-3-[1-(2-methoxy-3-dimethylaminopropyl)-4-methylthio-1H-indol-3-yl]-maleinimide;
(+)-2-(1H-indol-3-yl)-3-[1-(2-methoxy-3-dimethylaminopropyl)-5-methylthio-1H-indol-3-yl]-maleinimide;
(+)-2-(1H-indol-3-yl)-3-[1-(2-methoxy-3-dimethylaminopropyl)-6-methylthio-1H-indol-3-yl]-maleinimide;
(+)-2-(1H-indol-3-yl)-3-[1-(2-methoxy-3-dimethylaminopropyl)-7-methylthio-1H-indol-3-yl]-maleinimide;
(+)-2-(1H-indol-3-yl)-3-[4,5-dimethoxy-1-(2-methoxy-3-dimethylaminopropyl)-1H-indol-3-yl]-maleinimide;
(+)-2-(1H-indol-3-yl)-3-[5,6-dimethoxy-1-(2-methoxy-3-dimethylaminopropyl)-1H-indol-3-yl]-maleinimide;
(+)-2-(1H-indol-3-yl)-3-[6,7-dimethoxy-1-(2-methoxy-3-dimethylaminopropyl)-1H-indol-3-yl]-maleinimide;
(−)-2-[4-acetylamino-1-(2-methoxy-3-dimethylaminopropyl)-1H-indol-3-yl]-3-(1H-indol-3-yl)-maleinimide;
(−)-2-[5-acetylamino-1-(2-methoxy-3-dimethylaminopropyl)-1H-indol-3-yl]-3-(1H-indol-3-yl)-maleinimide;
(−)-2-[6-acetylamino-1-(2-methoxy-3-dimethylaminopropyl)-1H-indol-3-yl]-3-(1H-indol-3-yl)-maleinimide;
(−)-2-[7-acetylamino-1-(2-methoxy-3-dimethylaminopropyl)-1H-indol-3-yl]-3-(1H-indol-3-yl)-maleinimide;
(−)-2-[4-amino-1-(2-methoxy-3-dimethylaminopropyl)-1H-indol-3-yl]-3-(1H-indol-3-yl)-maleinimide;
(−)-2-[5-amino-1-(2-methoxy-3-dimethylaminopropyl)-1H-indol-3-yl]-3-(1H-indol-3-yl)-maleinimide;
(−)-2-[6-amino-1-(2-methoxy-3-dimethylaminopropyl)-1H-indol-3-yl]-3-(1H-indol-3-yl)-maleinimide;
(−)-2-[7-amino-1-(2-methoxy-3-dimethylaminopropyl)-1H-indol-3-yl]-3-(1H-indol-3-yl)-maleinimide;
(−)-2-[4-benzyloxy-1-(2-methoxy-3-dimethylaminopropyl)-1H-indol-3-yl]-3-(1H-indol-3-yl)-maleinimide;
(−)-2-[5-benzyloxy-1-(2-methoxy-3-dimethylaminopropyl)-1H-indol-3-yl]-3-(1H-indol-3-yl)-maleinimide;
(−)-2-[6-benzyloxy-1-(2-methoxy-3-dimethylaminopropyl)-1H-indol-3-yl]-3-(1H-indol-3-yl)-maleinimide;
(−)-2-[7-benzyloxy-1-(2-methoxy-3-dimethylaminopropyl)-1H-indol-3-yl]-3-(1H-indol-3-yl)-maleinimide;
(−)-2-[4-bromo-1-(2-methoxy-3-dimethylaminopropyl)-1H-indol-3-yl]-3-(1H-indol-3-yl)-maleinimide;
(−)-2-[5-bromo-1-(2-methoxy-3-dimethylaminopropyl)-1H-indol-3-yl]-3-(1H-indol-3-yl)-maleinimide;
(−)-2-[6-bromo-1-(2-methoxy-3-dimethylaminopropyl)-1H-indol-3-yl]-3-(1H-indol-3-yl)-maleinimide;
(−)-2-[7-bromo-1-(2-methoxy-3-dimethylaminopropyl)-1H-indol-3-yl]-3-(1H-indol-3-yl)-maleinimide;
(−)-2-[4-chloro-1-(2-methoxy-3-dimethylaminopropyl)-1H-indol-3-yl]-3-(1H-indol-3-yl)-maleinimide;
(−)-2-[5-chloro-1-(2-methoxy-3-dimethylaminopropyl)-1H-indol-3-yl]-3-(1H-indol-3-yl)-maleinimide;
(−)-2-[6-chloro-1-(2-methoxy-3-dimethylaminopropyl)-1H-indol-3-yl]-3-(1H-indol-3-yl)-maleinimide;
(−)-2-[7-chloro-1-(2-methoxy-3-dimethylaminopropyl)-1H-indol-3-yl]-3-(1H-indol-3-yl)-maleinimide;
(−)-2-[4-fluoro-1-(2-methoxy-3-dimethylaminopropyl)-1H-indol-3-yl]-3-(1H-indol-3-yl)-maleinimide;
(−)-2-[5-fluoro-1-(2-methoxy-3-dimethylaminopropyl)-1H-indol-3-yl]-3-(1H-indol-3-yl)-maleinimide;
(−)-2-[6-fluoro-1-(2-methoxy-3-dimethylaminopropyl)-1H-indol-3-yl]-3-(1H-indol-3-yl)-maleinimide;
(−)-2-[7-fluoro-1-(2-methoxy-3-dimethylaminopropyl)-1H-indol-3-yl]-3-(1H-indol-3-yl)-maleinimide;

(−)-2-[4-hydroxy-1-(2-methoxy-3-dimethylaminopropyl)-1H-indol-3-yl]-3-(1H-indol-3-yl)-maleinimide;
(−)-2-[5-hydroxy-1-(2-methoxy-3-dimethylaminopropyl)-1H-indol-3-yl]-3-(1H-indol-3-yl)-maleinimide;
(−)-2-[6-hydroxy-1-(2-methoxy-3-dimethylaminopropyl)-1H-indol-3-yl]-3-(1H-indol-3-yl)-maleinimide;
(−)-2-[7-hydroxy-1-(2-methoxy-3-dimethylaminopropyl)-1H-indol-3-yl]-3-(1H-indol-3-yl)-maleinimide;
(−)-2-[4-trifluoromethyl-1-(2-methoxy-3-dimethylaminopropyl)-1H-indol-3-yl]-3-(1H-indol-3-yl)-maleinimide;
(−)-2-[5-trifluoromethyl-1-(2-methoxy-3-dimethylaminopropyl)-1H-indol-3-yl]-3-(1H-indol-3-yl)-maleinimide;
(−)-2-[6-trifluoromethyl-1-(2-methoxy-3-dimethylaminopropyl)-1H-indol-3-yl]-3-(1H-indol-3-yl)-maleinimide;
(−)-2-[7-trifluoromethyl-1-(2-methoxy-3-dimethylaminopropyl)-1H-indol-3-yl]-3-(1H-indol-3-yl)-maleinimide;
(−)-2-(1H-indol-3-yl)-3-[4-methoxy-1-(2-methoxy-3-dimethylaminopropyl)-1H-indol-3-yl]-maleinimide;
(−)-2-(1H-indol-3-yl)-3-[5-methoxy-1-(2-methoxy-3-dimethylaminopropyl)-1H-indol-3-yl]-maleinimide;
(−)-2-(1H-indol-3-yl)-3-[6-methoxy-1-(2-methoxy-3-dimethylaminopropyl)-1H-indol-3-yl]-maleinimide;
(−)-2-(1H-indol-3-yl)-3-[7-methoxy-1-(2-methoxy-3-dimethylaminopropyl)-1H-indol-3-yl]-maleinimide;
(−)-2-(1H-indol-3-yl)-3-[1-(2-methoxy-3-dimethylaminopropyl)-4,5-methylendioxy-1H-indol-3-yl]-maleinimide;
(−)-2-(1H-indol-3-yl)-3-[1-(2-methoxy-3-dimethylaminopropyl)-5,6-methylendioxy-1H-indol-3-yl]-maleinimide;
(−)-2-(1H-indol-3-yl)-3-[1-(2-methoxy-3-dimethylaminopropyl)-6,7-methylendioxy-1H-indol-3-yl]-maleinimide;
(−)-2-(1H-indol-3-yl)-3-[1-(2-methoxy-3-dimethylaminopropyl)-4-methyl-1H-indol-3-yl]-maleinimide;
(−)-2-(1H-indol-3-yl)-3-[1-(2-methoxy-3-dimethylaminopropyl)-5-methyl-1H-indol-3-yl]-maleinimide;
(−)-2-(1H-indol-3-yl)-3-[1-(2-methoxy-3-dimethylaminopropyl)-6-methyl-1H-indol-3-yl]-maleinimide;
(−)-2-(1H-indol-3-yl)-3-[1-(2-methoxy-3-dimethylaminopropyl)-7-methyl-1H-indol-3-yl]-maleinimide;
(−)-2-(1H-indol-3-yl)-3-[1-(2-methoxy-3-dimethylaminopropyl)-4-nitro-1H-indol-3-yl]-maleinimide;
(−)-2-(1H-indol-3-yl)-3-[1-(2-methoxy-3-dimethylaminopropyl)-5-nitro-1H-indol-3-yl]-maleinimide;
(−)-2-(1H-indol-3-yl)-3-[1-(2-methoxy-3-dimethylaminopropyl)-6-nitro-1H-indol-3-yl]-maleinimide;
(−)-2-(1H-indol-3-yl)-3-[1-(2-methoxy-3-dimethylaminopropyl)-7-nitro-1H-indol-3-yl]-maleinimide;
(−)-2-(1H-indol-3-yl)-3-[1-(2-methoxy-3-dimethylaminopropyl)-4-methylthio-1H-indol-3-yl]-maleinimide;
(−)-2-(1H-indol-3-yl)-3-[1-(2-methoxy-3-dimethylaminopropyl)-5-methylthio-1H-indol-3-yl]-maleinimide;
(−)-2-(1H-indol-3-yl)-3-[1-(2-methoxy-3-dimethylaminopropyl)-6-methylthio-1H-indol-3-yl]-maleinimide;
(−)-2-(1H-indol-3-yl)-3-[1-(2-methoxy-3-dimethylaminopropyl)-7-methylthio-1H-indol-3-yl]-maleinimide;
(−)-2-(1H-indol-3-yl)-3-[4,5-dimethoxy-1-(2-methoxy-3-dimethylaminopropyl)-1H-indol-3-yl]-maleinimide;
(−)-2-(1H-indol-3-yl)-3-[5,6-dimethoxy-1-(2-methoxy-3-dimethylaminopropyl)-1H-indol-3-yl]-maleinimide;
(−)-2-(1H-indol-3-yl)-3-[6,7-dimethoxy-1-(2-methoxy-3-dimethylaminopropyl)-1H-indol-3-yl]-maleinimide;
2-[4-acetylamino-1-(2-dimethylaminoethyl)-1H-indol-3-yl]-3-(1H-indol-3-yl)-maleinimide;
2-[5-acetylamino-1-(2-dimethylaminoethyl)-1H-indol-3-yl]-3-(1H-indol-3-yl)-maleinimide;
2-[6-acetylamino-1-(2-dimethylaminoethyl)-1H-indol-3-yl]-3-(1H-indol-3-yl)-maleinimide;
2-[7-acetylamino-1-(2-dimethylaminoethyl)-1H-indol-3-yl]-3-(1H-indol-3-yl)-maleinimide;
2-[4-amino-1-(2-dimethylaminoethyl)-1H-indol-3-yl]-3-(1H-indol-3-yl)-maleinimide;
2-[5-amino-1-(2-dimethylaminoethyl)-1H-indol-3-yl]-3-(1H-indol-3-yl)-maleinimide;
2-[6-amino-1-(2-dimethylaminoethyl)-1H-indol-3-yl]-3-(1H-indol-3-yl)-maleinimide;
2-[7-amino-1-(2-dimethylaminoethyl)-1H-indol-3-yl]-3-(1H-indol-3-yl)-maleinimide;
2-[4-benzyloxy-1-(2-dimethylaminoethyl)-1H-indol-3-yl]-3-(1H-indol-3-yl)-maleinimide;
2-[5-benzyloxy-1-(2-dimethylaminoethyl)-1H-indol-3-yl]-3-(1H-indol-3-yl)-maleinimide;
2-[6-benzyloxy-1-(2-dimethylaminoethyl)-1H-indol-3-yl]-3-(1H-indol-3-yl)-maleinimide;
2-[7-benzyloxy-1-(2-dimethylaminoethyl)-1H-indol-3-yl]-3-(1H-indol-3-yl)-maleinimide;
2-[4-bromo-1-(2-dimethylaminoethyl)-1H-indol-3-yl]-3-(1H-indol-3-yl)-maleinimide;
2-[5-bromo-1-(2-dimethylaminoethyl)-1H-indol-3-yl]-3-(1H-indol-3-yl)-maleinimide;
2-[6-bromo-1-(2-dimethylaminoethyl)-1H-indol-3-yl]-3-(1H-indol-3-yl)-maleinimide;
2-[7-bromo-1-(2-dimethylaminoethyl)-1H-indol-3-yl]-3-(1H-indol-3-yl)-maleinimide;
2-[4-chloro-1-(2-dimethylaminoethyl)-1H-indol-3-yl]-3-(1H-indol-3-yl)-maleinimide;
2-[5-chloro-1-(2-dimethylaminoethyl)-1H-indol-3-yl]-3-(1H-indol-3-yl)-maleinimide;
2-[6-chloro-1-(2-dimethylaminoethyl)-1H-indol-3-yl]-3-(1H-indol-3-yl)-maleinimide;
2-[7-chloro-1-(2-dimethylaminoethyl)-1H-indol-3-yl]-3-(1H-indol-3-yl)-maleinimide;
2-[4-fluoro-1-(2-dimethylaminoethyl)-1H-indol-3-yl]-3-(1H-indol-3-yl)-maleinimide;
2-[5-fluoro-1-(2-dimethylaminoethyl)-1H-indol-3-yl]-3-(1H-indol-3-yl)-maleinimide;
2-[6-fluoro-1-(2-dimethylaminoethyl)-1H-indol-3-yl]-3 (1H-indol-3-yl)-maleinimide;
2-[7-fluoro-1-(2-dimethylaminoethyl)-1H-indol-3-yl]-3-(1H-indol-3-yl)-maleinimide;
2-[4-hydroxy-1-(2-dimethylaminoethyl)-1H-indol-3-yl]-3-(1H-indol-3-yl)-maleinimide;
2-[5-hydroxy-1-(2-dimethylaminoethyl)-1H-indol-3-yl]-3-(1H-indol-3-yl)-maleinimide;

2-[6-hydroxy-1-(2-dimethylaminoethyl)-1H-indol-3-yl]-3-(1H-indol-3-yl)-maleinimide;
2-[7-hydroxy-1-(2-dimethylaminoethyl)-1H-indol-3-yl]-3-(1H-indol-3-yl)-maleinimide;
2-[4-trifluoromethyl-1-(2-dimethylaminoethyl)-1H-indol-3-yl]-3-(1H-indol-3-yl)-maleinimide;
2-[5-trifluoromethyl-1-(2-dimethylaminoethyl)-1H-indol-3-yl]-3-(1H-indol-3-yl)-maleinimide;
2-[6-trifluoromethyl-1-(2-dimethylaminoethyl)-1H-indol-3-yl]-3-(1H-indol-3-yl)-maleinimide;
2-[7-trifluoromethyl-1-(2-dimethylaminoethyl)-1H-indol-3-yl]-3-(1H-indol-3-yl)-maleinimide;
2-(1H-indol-3-yl)-3-[4-methoxy-1-(2-dimethylaminoethyl)-1H-indol-3-yl]-maleinimide;
2-(1H-indol-3-yl)-3-[5-methoxy-1-(2-dimethylaminoethyl)-1H-indol-3-yl]-maleinimide;
2-(1H-indol-3-yl)-3-[6-methoxy-1-(2-dimethylaminoethyl)-1H-indol-3-yl]-maleinimide;
2-(1H-indol-3-yl)-3-[7-methoxy-1-(2-dimethylaminoethyl)-1H-indol-3-yl]-maleinimide;
2-(1H-indol-3-yl)-3-[1-(2-dimethylaminoethyl)-4,5-methylendioxy-1H-indol-3-yl]-maleinimide;
2-(1H-indol-3-yl)-3-[1-(2-dimethylaminoethyl)-5,6-methylendioxy-1H-indol-3-yl]-maleinimide;
2-(1H-indol-3-yl)-3-[1-(2-dimethylaminoethyl)-6,7-methylendioxy-1H-indol-3-yl]-maleinimide;
2-(1H-indol-3-yl)-3-[4-methyl-1-(2-dimethylaminoethyl)-1H-indol-3-yl]-maleinimide;
2-(1H-indol-3-yl)-3-[5-methyl-1-(2-dimethylaminoethyl)-1H-indol-3-yl]-maleinimide;
2-(1H-indol-3-yl)-3-[6-methyl-1-(2-dimethylaminoethyl)-1H-indol-3-yl]-maleinimide;
2-(1H-indol-3-yl)-3-[7-methyl-1-(2-dimethylaminoethyl)-1H-indol-3-yl]-maleinimide;
2-(1H-indol-3-yl)-3-[1-(2-dimethylaminoethyl)-4-nitro-1H-indol-3-yl]-maleinimide;
2-(1H-indol-3-yl)-3-[1-(2-dimethylaminoethyl)-5-nitro-1H-indol-3-yl]-maleinimide;
2-(1H-indol-3-yl)-3-[1-(2-dimethylaminoethyl)-6-nitro-1H-indol-3-yl]-maleinimide;
2-(1H-indol-3-yl)-3-[1-(2-dimethylaminoethyl)-7-nitro-1H-indol-3-yl]-maleinimide;
2-(1H-indol-3-yl)-3-[1-(2-dimethylaminoethyl)-4-methylthio-1H-indol-3-yl]-maleinimide;
2-(1H-indol-3-yl)-3-[1-(2-dimethylaminoethyl)-5-methylthio-1H-indol-3-yl]-maleinimide;
2-(1H-indol-3-yl)-3-[1-(2-dimethylaminoethyl)-6-methylthio-1H-indol-3-yl]-maleinimide;
2-(1H-indol-3-yl)-3-[1-(2-dimethylaminoethyl)-7-methylthio-1H-indol-3-yl]-maleinimide;
2-(1H-indol-3-yl)-3-[4,5-dimethoxy-1-(2-dimethylaminoethyl)-1H-indol-3-yl]-maleinimide;
2-(1H-indol-3-yl)-3-[5,6-dimethoxy-1-(2-dimethylaminoethyl)-1H-indol-3-yl]-maleinimide;
2-(1H-indol-3-yl)-3-[6,7-dimethoxy-1-(2-dimethylaminoethyl)-1H-indol-3-yl]-maleinimide;
2-[4-acetylamino-1-(3-dimethylaminopropyl)-1H-indol-3-yl]-3-(1H-indol-3-yl)-maleinimide;
2-[5-acetylamino-1-(3-dimethylaminopropyl)-1H-indol-3-yl]-3-(1H-indol-3-yl)-maleinimide;
2-[6-acetylamino-1-(3-dimethylaminopropyl)-1H-indol-3-yl]-3-(1H-indol-3-yl)-maleinimide;
2-[7-acetylamino-1-(3-dimethylaminopropyl)-1H-indol-3-yl]-3-(1H-indol-3-yl)-maleinimide;
2-[4-amino-1-(3-dimethylaminopropyl)-1H-indol-3-yl]-3-(1H-indol-3-yl)-maleinimide;
2-[5-amino-1-(3-dimethylaminopropyl)-1H-indol-3-yl]-3-(1H-indol-3-yl)-maleinimide;
2-[6-amino-1-(3-dimethylaminopropyl)-1H-indol-3-yl]-3-(1H-indol-3-yl)-maleinimide;
2-[7-amino-1-(3-dimethylaminopropyl)-1H-indol-3-yl]-3-(1H-indol-3-yl)-maleinimide;
2-[4-benzyloxy-1-(3-dimethylaminopropyl)-1H-indol-3-yl]-3-(1H-indol-3-yl)-maleinimide;
2-[5-benzyloxy-1-(3-dimethylaminopropyl)-1H-indol-3-yl]-3-(1H-indol-3-yl)-maleinimide;
2-[6-benzyloxy-1-(3-dimethylaminopropyl)-1H-indol-3-yl]-3-(1H-indol-3-yl)-maleinimide;
2-[7-benzyloxy-1-(3-dimethylaminopropyl)-1H-indol-3-yl]-3-(1H-indol-3-yl)-maleinimide;
2-[4-bromo-1-(3-dimethylaminopropyl)-1H-indol-3-yl]-3-(1H-indol-3-yl)-maleinimide;
2-[5-bromo-1-(3-dimethylaminopropyl)-1H-indol-3-yl]-3-(1H-indol-3-yl)-maleinimide;
2-[6-bromo-1-(3-dimethylaminopropyl)-1H-indol-3-yl]-3-(1H-indol-3-yl)-maleinimide;
2-[7-bromo-1-(3-dimethylaminopropyl)-1H-indol-3-yl]-3-(1H-indol-3-yl)-maleinimide;
2-[4-chloro-1-(3-dimethylaminopropyl)-1H-indol-3-yl]-3-(1H-indol-3-yl)-maleinimide;
2-[5-chloro-1-(3-dimethylaminopropyl)-1H-indol-3-yl]-3-(1H-indol-3-yl)-maleinimide;
2-[6-chloro-1-(3-dimethylaminopropyl)-1H-indol-3-yl]-3-(1H-indol-3-yl)-maleinimide;
2-[7-chloro-1-(3-dimethylaminopropyl)-1H-indol-3-yl]-3-(1H-indol-3-yl)-maleinimide;
2-[4-fluoro-1-(3-dimethylaminopropyl)-1H-indol-3-yl]-3-(1H-indol-3-yl)-maleinimide;
2-[6-fluoro-1-(3-dimethylaminopropyl)-1H-indol-3-yl]-3-(1H-indol-3-yl)-maleinimide;
2-[7-fluoro-1-(3-dimethylaminopropyl)-1H-indol-3-yl]-3-(1H-indol-3-yl)-maleinimide;
2-[4-hydroxy-1-(3-dimethylaminopropyl)-1H-indol-3-yl]-3-(1H-indol-3-yl)-maleinimide;
2-[5-hydroxy-1-(3-dimethylaminopropyl)-1H-indol-3-yl]-3-(1H-indol-3-yl)-maleinimide;
2-[6-hydroxy-1-(3-dimethylaminopropyl)-1H-indol-3-yl]-3-(1H-indol-3-yl)-maleinimide;
2-[7-hydroxy-1-(3-dimethylaminopropyl)-1H-indol-3-yl]-3-(1H-indol-3-yl)-maleinimide;
2-[4-trifluoromethyl-1-(3-dimethylaminopropyl)-1H-indol-3-yl]-3-(1H-indol-3-yl)-maleinimide;
2-[5-trifluoromethyl-1-(3-dimethylaminopropyl)-1H-indol-3-yl]-3-(1H-indol-3-yl)-maleinimide;
2-[6-trifluoromethyl-1-(3-dimethylaminopropyl)-1H-indol-3-yl]-3-(1H-indol-3-yl)-maleinimide;
2-[7-trifluoromethyl-1-(3-dimethylaminopropyl)-1H-indol-3-yl]-3-(1H-indol-3-yl)-maleinimide;
2-(1H-indol-3-yl)-3-[4-methoxy-1-(3-dimethylaminopropyl)-1H-indol-3-yl]-maleinimide;
2-(1H-indol-3-yl)-3-[6-methoxy-1-(3-dimethylaminopropyl)-1H-indol-3-yl]-maleinimide;
2-(1H-indol-3-yl)-3-[7-methoxy-1-(3-dimethylaminopropyl)-1H-indol-3-yl]-maleinimide;
2-(1H-indol-3-yl)-3-[1-(3-dimethylaminopropyl)-4,5-methylendioxy-1H-indol-3-yl]-maleinimide;
2-(1H-indol-3-yl)-3-[1-(3-dimethylaminopropyl)-5,6-methylendioxy-1H-indol-3-yl]-maleinimide;
2-(1H-indol-3-yl)-3-[1-(3-dimethylaminopropyl)-6,7-methylendioxy-1H-indol-3-yl]-maleinimide;
2-(1H-indol-3-yl)-3-[4-methyl-1-(3-dimethylaminopropyl)-1H-indol-3-yl]-maleinimide;
2-(1H-indol-3-yl)-3-[5-methyl-1-(3-dimethylaminopropyl)-1H-indol-3-yl]-maleinimide;
2-(1H-indol-3-yl)-3-[6-methyl-1-(3-dimethylaminopropyl)-1H-indol-3-yl]-maleinimide;

2-(1H-indol-3-yl)-3-[7-methyl-1-(3-dimethylaminopropyl)-1H-indol-3-yl]-maleinimide;
2-(1H-indol-3-yl)-3-[1-(3-dimethylaminopropyl)-4-nitro-1H-indol-3-yl]-maleinimide;
2-(1H-indol-3-yl)-3-[1-(3-dimethylaminopropyl)-5-nitro-1H-indol-3-yl]-maleinimide;
2-(1H-indol-3-yl)-3-[1-(3-dimethylaminopropyl)-6-nitro-1H-indol-3-yl]-maleinimide;
2-(1H-indol-3-yl)-3-[1-(3-dimethylaminopropyl)-7nitro-1H-indol-3-yl]-maleinimide;
2-(1H-indol-3-yl)-3-[1-(3-dimethylaminopropyl)-4-methylthio-1H-indol-3-yl]-maleinimide;
2-(1H-indol-3-yl)-3-[1-(3-dimethylaminopropyl)-5-methylthio-1H-indol-3-yl]-maleinimide;
2-(1H-indol-3-yl)-3-[1-(3-dimethylaminopropyl)-6-methylthio-1H-indol-3-yl]-maleinimide;
2-(1H-indol-3-yl)-3-[1-(3-dimethylaminopropyl)-7-methylthio-1H-indol-3-yl]-maleinimide;
2-(1H-indol-3-yl)-3-[4,5-dimethoxy-1-(3-dimethylaminopropyl)-1H-indol-3-yl]-maleinimide;
2-(1H-indol-3-yl)-3-[5,6-dimethoxy-1-(3-dimethylaminopropyl)-1H-indol-3-yl]-maleinimide;
2-(1H-indol-3-yl)-3-[6,7-dimethoxy-1-(3-dimethylaminopropyl)-1H-indol-3-yl]-maleinimide;
2-[4-acetylamino-1-(3-methylaminopropyl)-1H-indol-3-yl]-3-(1H-indol-3-yl)-maleinimide;
2-[5-acetylamino-1-(3-methylaminopropyl)-1H-indol-3-yl]-3-(1H-indol-3-yl)-maleinimide;
2-[6-acetylamino-1-(3-methylaminopropyl)-1H-indol-3-yl]-3-(1H-indol-3-yl)-maleinimide;
2-[7-acetylamino-1-(3-methylaminopropyl)-1H-indol-3-yl]-3-(1H-indol-3-yl)-maleinimide;
2-[4-amino-1-(3-methylaminopropyl)-1H-indol-3-yl]-3-(1H-indol-3-yl)-maleinimide;
2-[5-amino-1-(3-methylaminopropyl)-1H-indol-3-yl]-3-(1H-indol-3-yl)-maleinimide;
2-[6-amino-1-(3-methylaminopropyl)-1H-indol-3-yl]-3-(1H-indol-3-yl)-maleinimide;
2-[7-amino-1-(3-methylaminopropyl)-1H-indol-3-yl]-3-(1H-indol-3-yl)-maleinimide;
2-[4-benzyloxy-1-(3-methylaminopropyl)-1H-indol-3-yl]-3-(1H-indol-3-yl)-maleinimide;
2-[4-benzyloxy-1-(3-methylaminopropyl)-1H-indol-3-yl]-3-(1H-indol-3-yl)-maleinimide;
2-[6-benzyloxy-1-(3-methylaminopropyl)-1H-indol-3-yl]-3-(1H-indol-3-yl)-maleinimide;
2-[7-benzyloxy-1-(3-methylaminopropyl)-1H-indol-3-yl]-3-(1H-indol-3-yl)-maleinimide;
2-[4-bromo-1-(3-methylaminopropyl)-1H-indol-3-yl]-3-(1H-indol-3-yl)-maleinimide;
2-[5-bromo-1-(3-methylaminopropyl)-1H-indol-3-yl]-3-(1H-indol-3-yl)-maleinimide;
2-[6-bromo-1-(3-methylaminopropyl)-1H-indol-3-yl]-3-(1H-indol-3-yl)-maleinimide;
2-[7-bromo-1-(3-methylaminopropyl)-1H-indol-3-yl]-3-(1H-indol-3-yl)-maleinimide;
2-[4-chloro-1-(3-methylaminopropyl)-1H-indol-3-yl]-3-(1H-indol-3-yl)-maleinimide;
2-[5-chloro-1-(3-methylaminopropyl)-1H-indol-3-yl]-3-(1H-indol-3-yl)-maleinimide;
2-[6-chloro-1-(3-methylaminopropyl)-1H-indol-3-yl]-3-(1H-indol-3-yl)-maleinimide;
2-[7-chloro-1-(3-methylaminopropyl)-1H-indol-3-yl]-3-(1H-indol-3-yl)-maleinimide;
2-[4-fluoro-1-(3-methylaminopropyl)-1H-indol-3-yl]-3-(1H-indol-3-yl)-maleinimide;
2-[5-fluoro-1-(3-methylaminopropyl)-1H-indol-3-yl]-3-(1H-indol-3-yl)-maleinimide;
2-[6-fluoro-1-(3-methylaminopropyl)-1H-indol-3-yl]-3-(1H-indol-3-yl)-maleinimide;
2-[7-fluoro-1-(3-methylaminopropyl)-1H-indol-3-yl]-3-(1H-indol-3-yl)-maleinimide;
2-[4-hydroxy-1-(3-methylaminopropyl)-1H-indol-3-yl]-3-(1H-indol-3-yl)-maleinimide;
2-[5-hydroxy-1-(3-methylaminopropyl)-1H-indol-3-yl]-3-(1H-indol-3-yl)-maleinimide;
2-[6-hydroxy-1-(3-methylaminopropyl)-1H-indol-3-yl]-3-(1H-indol-3-yl)-maleinimide;
2-[7-hydroxy-1-(3-methylaminopropyl)-1H-indol-3-yl]-3-(1H-indol-3-yl)-maleinimide;
2-[4-trifluoromethyl-1-(3-methylaminopropyl)-1H-indol-3-yl]-3-(1H-indol-3-yl)-maleinimide;
2-[5-trifluoromethyl-1-(3-methylaminopropyl)-1H-indol-3-yl]-3-(1H-indol-3-yl)-maleinimide;
2-[6-trifluoromethyl -1-(3-methylaminopropyl)-1H-indol-3-yl]-3-(1H-indol-3-yl)-maleinimide;
2-[7-trifluoromethyl-1-(3-methylaminopropyl)-1H-indol-3-yl]-3-(1H-indol-3-yl)-maleinimide;
2-(1H-indol-3-yl)-3-[4-methoxy-1-(3-methylaminopropyl)-1H-indol-3-yl]-maleinimide;
2-(1H-indol-3-yl)-3-[5-methoxy-1-(3-methylaminopropyl)-1H-indol-3-yl]-maleinimide;
2-(1H-indol-3-yl)-3-[6-methoxy-1-(3-methylaminopropyl)-1H-indol-3-yl]-maleinimide;
2-(1H-indol-3-yl)-3-[7-methoxy-1-(3-methylaminopropyl)-1 H-indol-3-yl]-maleinimide;
2-(1H-indol-3-yl)-3-[1-(3-methylaminopropyl)-4,5-methylendioxy-1H-indol-3-yl]-maleinimide;
2-(1H-indol-3-yl)-3-[1-(3-methylaminopropyl)-5,6-methylendioxy-1H-indol-3-yl]-maleinimide;
2-(1H-indol-3-yl)-3-[1-(3-methylaminopropyl)-6,7-methylendioxy-1H-indol-3-yl]-maleinimide;
2-(1H-indol-3-yl)-3-[4-methyl-1-(3-methylaminopropyl)-1H-indol-3-yl]-maleinimide;
2-(1H-indol-3-yl)-3-[5-methyl-1-(3-methylaminopropyl)-1H-indol-3-yl]-maleinimide;
2-(1H-indol-3-yl)-3-[6-methyl-1-(3-methylaminopropyl)-1H-indol-3-yl]-maleinimide;
2-(1H-indol-3-yl)-3-[7-methyl-1-(3-methylaminopropyl)-1H-indol-3-yl]-maleinimide;
2-(1H-indol-3-yl)-3-[1-(3-methylaminopropyl)-4-nitro-1H-indol-3-yl]-maleinimide;
2-(1H-indol-3-yl)-3-[1-(3-methylaminopropyl)-5-nitro-1H-indol-3-yl]-maleinimide;
2-(1H-indol-3-yl)-3-[1-(3-methylaminopropyl)-6-nitro-1H-indol-3-yl]-maleinimide;
2-(1H-indol-3-yl)-3-[1-(3-methylaminopropyl)-7-nitro-1H-indol-3-yl]-maleinimide;
2-(1H-indol-3-yl)-3-[1-(3-methylaminopropyl)-4-methylthio-1H-indol-3-yl]-maleinimide;
2-(1H-indol-3-yl)-3-[1-(3-methylaminopropyl)-5-methylthio-1H-indol-3-yl]-maleinimide;
2-(1H-indol-3-yl)-3-[1-(3-methylaminopropyl)-6-methylthio-1H-indol-3-yl]-maleinimide;
2-(1H-indol-3-yl)-3-[1-(3-methylaminopropyl)-7-methylthio-1H-indol-3-yl]-maleinimide;
2-(1H-indol-3-yl)-3-[4,5-dimethoxy-1-(3methylaminopropyl)-1H-indol-3-yl]-maleinimide;
2-(1H-indol-3-yl)-3-[5,6-dimethoxy-1-(3-methylaminopropyl)-1H-indol-3-yl]-maleinimide;
2-(1H-indol-3-yl)-3-[6,7-dimethoxy-1-(3-methylaminopropyl)-1H-indol-3-yl]-maleinimide;
2-[4-acetylamino-1-(3-(4-morpholino)propyl)-1H-indol-3-yl]-3-(1H-indol-3-yl)-maleinimide;
2-[5-acetylamino-1-(3-(4-morpholino)propyl)-1H-indol-3-yl]-3-(1H-indol-3-yl)-maleinimide;

2-[6-acetylamino-1-(3-(4-morpholino)propyl)-1H-indol-3-yl]-3-(1H-indol-3-yl)-maleinimide;
2-[7-acetylamino-1-(3-(4-morpholino)propyl)-1H-indol-3-yl]-3-(1H-indol-3-yl)-maleinimide;
2-[4-amino-1-(3-(4-morpholino)propyl)-1H-indol-3-yl]-3-(1H-indol-3-yl)-maleinimide;
2-[5-amino-1-(3-(4-morpholino)propyl)-1H-indol-3-yl]-3-(1H-indol-3-yl)-maleinimide;
2-[6-amino-1-(3-(4-morpholino)propyl)-1H-indol-3-yl]-3-(1H-indol-3-yl)-maleinimide;
2-[7-amino-1-(3-(4-morpholino)propyl)-1H-indol-3-yl]-3-(1H-indol-3-yl)-maleinimide;
2-[4-benzyloxy-1-(3-(4-morpholino)propyl)-1H-indol-3-yl]-3-(1H-indol-3-yl)-maleinimide;
2-[5-benzyloxy-1-(3-(4-morpholino)propyl)-1H-indol-3-yl]-3-(1H-indol-3-yl)-maleinimide;
2-[6-benzyloxy-1-(3-(4-morpholino)propyl)-1H-indol-3-yl]-3-(1H-indol-3-yl)-maleinimide;
2-[7-benzyloxy-1-(3-(4-morpholino)propyl)-1H-indol-3-yl]-3-(1H-indol-3-yl)-maleinimide;
2-[4-bromo-1-(3-(4-morpholino)propyl)-1H-indol-3-yl]-3-(1H-indol-3-yl)-maleinimide;
2-[5-bromo-1-(3-(4-morpholinopropyl)-1H-indol-3-yl]-3-(1H-indol-3-yl)-maleinimide;
2-[6-bromo-1-(3-(4-morpholinopropyl)-1H-indol-3-yl]-3-(1H-indol-3-yl)-maleinimide;
2-[7-bromo-1-(3-(4-morpholino)propyl)-1H-indol-3-yl]-3-(1H-indol-3-yl)-maleinimide;
2-[4-chloro-1-(3-(4-morpholino)propyl)-1H-indol-3-yl]-3-(1H-indol-3-yl)-maleinimide;
2-[5-chloro-1-(3-(4-morpholino)propyl)-1H-indol-3-yl]-3-(1H-indol-3-yl)-maleinimide;
2-[6-chloro-1-(3-(4-morpholino)propyl)-1H-indol-3-yl]-3-(1H-indol-3-yl)-maleinimide;
2-[7-chloro-1-(3-(4-morpholino)propyl)-1H-indol-3-yl]-3-(1H-indol-3-yl)-maleinimide;
2-[4-fluoro-1-(3-(4-morpholino)propyl)-1H-indol-3-yl]-3-(1H-indol-3-yl)-maleinimide;
2-[5-fluoro-1-(3-(4-morpholino)propyl)-1H-indol-3-yl]-3-(1H-indol-3-yl)-maleinimide;
2-[6-fluoro-1-(3-(4-morpholino)propyl)-1H-indol-3-yl]-3-(1H-indol-3-yl)-maleinimide;
2-[7-fluoro-1-(3-(4-morpholino)propyl)-1H-indol-3-yl]-3-(1H-indol-3-yl)-maleinimide;
2-[4-hydroxy-1-(3-(4-morpholino)propyl)-1H-indol-3-yl]-3-(1H-indol-3-yl)-maleinimide;
2-[5-hydroxy-1-(3-(4-morpholino)propyl)-1H-indol-3-yl]-3-(1H-indol-3-yl)-maleinimide;
2-[6-hydroxy-1-(3-(4-morpholino)propyl)-1H-indol-3-yl]-3-(1H-indol-3-yl)-maleinimide;
2-[7-hydroxy-1-(3-(4-morpholino)propyl)-1H-indol-3-yl]-3-(1H-indol-3-yl)-maleinimide;
2-[4-trifluoromethyl-1-(3-(4-morpholinopropyl)-1H-indol-3-yl]-3-(1H-indol-3-yl)-maleinimide;
2-[5-trifluoromethyl-1-(3-(4-morpholino)propyl)-1H-indol-3-yl]-3-(1H-indol-3-yl)-maleinimide;
2-[6-trifluoromethyl-1-(3-(4-morpholino)propyl)-1H-indol-3-yl]-3-(1H-indol-3-yl)-maleinimide;
2-[7-trifluoromethyl-1-(3-(4-morpholino)propyl)-1H-indol-3-yl]-3-(1H-indol-3-yl)-maleinimide;
2-(1H-indol-3-yl)-3-[4-methoxy-1-(3-(4-morpholino)propyl)-1H-indol-3-yl]-maleinimide;
2-(1H-indol-3-yl)-3-[6-methoxy-1-(3-(4-morpholino)propyl)-1H-indol-3-yl]-maleinimide;
2-(1H-indol-3-yl)-3-[7-methoxy-1-(3-(4-morpholino)propyl)-1H-indol-3-yl]-maleinimide;
2-(1H-indol-3-yl)-3-[4,5-methylendioxy-1-(3-(4-morpholino)propyl)-1H-indol-3-yl]-maleinimide;
2-(1H-indol-3-yl)-3-[5,6-methylendioxy-1-(3-(4-morpholino)propyl)-1H-indol-3-yl]-maleinimide;
2-(1H-indol-3-yl)-3-[6,7-methylendioxy-1-(3-(4-morpholino)propyl)-1H-indol-3-yl]-maleinimide;
2-(1H-indol-3-yl)-3-[4-methyl-1-(3-(4-morpholino)propyl)-1H-indol-3-yl]-maleinimide;
2-(1H-indol-3-yl)-3-[5-methyl-1-(3-(4-morpholino)propyl)-1H-indol-3-yl]-maleinimide;
2-(1H-indol-3-yl)-3-[6-methyl-1-(3-(4-morpholino)propyl)-1H-indol-3-yl]-maleinimide;
2-(1H-indol-3-yl)-3-[7-methyl-1-(3-(4-morpholino)propyl)-1H-indol-3-yl]-maleinimide;
2-(1H-indol-3-yl)-3-[1-(3-(4-morpholino)propyl)-4-nitro-1H-indol-3-yl]-maleinimide;
2-(1H-indol-3-yl)-3-[1-(3-(4-morpholino)propyl)-5-nitro-1H-indol-3-yl]-maleinimide;
2-(1H-indol-3-yl)-3-[1-(3-(4-morpholino)propyl)-6-nitro-1H-indol-3-yl]-maleinimide;
2-(1H-indol-3-yl)-3-[1-(3-(4-morpholino)propyl)-7-nitro-1H-indol-3-yl]-maleinimide;
2-(1H-indol-3-yl)-3-[4-methylthio-1-(3-(4-morpholino)propyl)-1H-indol-3-yl]-maleinimide;
2-(1H-indol-3-yl)-3-[5-methylthio-1-(3-(4-morpholino)propyl)-1H-indol-3-yl]-maleinimide;
2-(1H-indol-3-yl)-3-[6-methylthio-1-(3-(4-morpholino)propyl)-1H-indol-3-yl]-maleinimide;
2-(1H-indol-3-yl)-3-[7-methylthio-1-(3-(4-morpholino)propyl)-1H-indol-3-yl]-maleinimide;
2-(1H-indol-3-yl)-3-[4,5-dimethoxy-1-(3-(4-morpholino)propyl)-1H-indol-3-yl]-maleinimide;
2-(1H-indol-3-yl)-3-[5,6-dimethoxy-1-(3-(4-morpholino)propyl)-1H-indol-3-yl]-maleinimide;
2-(1H-indol-3-yl)-3-[6,7-dimethoxy-1-(3-(4-morpholino)propyl)-1H-indol-3-yl]-maleinimide;
2-[4-acetylamino-1-(3-(2-nitroguanidino)propyl)-1H-indol-3-yl]-3-(1H-indol-3-yl)-maleinimide;
2-[5-acetylamino-1-(3-(2-nitroguanidino)propyl)-1H-indol-3-yl]-3-(1H-indol-3-yl)-maleinimide;
2-[6-acetylamino-1-(3-(2-nitroguanidino)propyl)-1H-indol-3-yl]-3-(1H-indol-3-yl)-maleinimide;
2-[7-acetylamino-1-(3-(2-nitroguanidino)propyl)-1H-indol-3-yl]-3-(1H-indol-3-yl)-maleinimide;
2-[4-amino-1-(3-(2-nitroguanidino)propyl)-1H-indol-3-yl]-3-(1H-indol-3-yl)-maleinimide;
2-[5-amino-1-(3-(2-nitroguanidino)propyl)-1H-indol-3-yl]-3-(1H-indol-3-yl)-maleinimide;
2-[6-amino-1-(3-(2-nitroguanidino)propyl)-1H-indol-3-yl]-3-(1H-indol-3-yl)-maleinimide;
2-[7-amino-1-(3-(2-nitroguanidino)propyl)-1H-indol-3-yl]-3-(1H-indol-3-yl)-maleinimide;
2-[4-benzyloxy-1-(3-(2-nitroguanidino)propyl)-1H-indol-3-yl]-3-(1H-indol-3-yl)-maleinimide;
2-[5-benzyloxy-1-(3-(2-nitroguanidino)propyl)-1H-indol-3-yl]-3-(1H-indol-3-yl)-maleinimide;
2-[6-benzyloxy-1-(3-(2-nitroguanidino)propyl)-1H-indol-3-yl]-3-(1H-indol-3-yl)-maleinimide;
2-[7-benzyloxy-1-(3-(2-nitroguanidino)propyl)-1H-indol-3-yl]-3-(1H-indol-3-yl)-maleinimide;
2-[4-bromo-1-(3-(2-nitroguanidino)propyl)-1H-indol-3-yl]-3-(1H-indol-3-yl)-maleinimide;
2-[5-bromo-1-(3-(2-nitroguanidino)propyl)-1H-indol-3-yl]-3-(1H-indol-3-yl)-maleinimide;
2-[6-bromo-1-(3-(2-nitroguanidino)propyl)-1H-indol-3-yl]-3-(1H-indol-3-yl)-maleinimide;
2-[7-bromo-1-(3-(2-nitroguanidino)propyl)-1H-indol-3-yl]-3-(1H-indol-3-yl)-maleinimide;
2-[4-chloro-1-(3-(2-nitroguanidino)propyl)-1H-indol-3-yl]-3-(1H-indol-3-yl)-maleinimide;

2-[5-chloro-1-(3-(2-nitroguanidino)propyl)-1H-indol-3-yl]-3-(1H-indol-3-yl)-maleinimide;
2-[6-chloro-1-(3-(2-nitroguanidino)propyl)-1H-indol-3-yl]-3-(1H-indol-3-yl)-maleinimide;
2-[7-chloro-1-(3-(2-nitroguanidino)propyl)-1H-indol-3-yl]-3-(1H-indol-3-yl)-maleinimide;
2-[4-fluoro-1-(3-(2-nitroguanidino)propyl)-1H-indol-3-yl]-3-(1H-indol-3-yl)-maleinimide;
2-[5-fluoro-1-(3-(2-nitroguanidino)propyl)-1H-indol-3-yl]-3-(1H-indol-3-yl)-maleinimide;
2-[6-fluoro-1-(3-(2-nitroguanidino)propyl)-1H-indol-3-yl]-3-(1H-indol-3-yl)-maleinimide;
2-[7-fluoro-1-(3-(2-nitroguanidino)propyl)-1H-indol-3-yl]-3-(1H-indol-3-yl)-maleinimide;
2-[4-hydroxy-1-(3-(2-nitroguanidino)propyl)-1H-indol-3-yl]-3-(1H-indol-3-yl)-maleinimide;
2-[5-hydroxy-1-(3-(2-nitroguanidino)propyl)-1H-indol-3-yl]-3-(1H-indol-3-yl)-maleinimide;
2-[6-hydroxy-1-(3-(2-nitroguanidino)propyl)-1H-indol-3-yl]-3-(1H-indol-3-yl)-maleinimide;
2-[7-hydroxy-1-(3-(2-nitroguanidino)propyl)-1H-indol-3-yl]-3-(1H-indol-3-yl)-maleinimide;
2-[4-trifluoromethyl-1-(3-(2-nitroguanidino)propyl)-1H-indol-3-yl]-3-(1H-indol-3-yl)-maleinimide;
2-[5-trifluoromethyl-1-(3-(2-nitroguanidino)propyl)-1H-indol-3-yl]-3-(1H-indol-3-yl)-maleinimide;
2-[6-trifluoromethyl-1-(3-(2-nitroguanidino)propyl)-1H-indol-3-yl]-3-(1H-indol-3-yl)-maleinimide;
2-[7-trifluoromethyl-1-(3-(2-nitroguanidino)propyl)-1H-indol-3-yl]-3-(1H-indol-3-yl)-maleinimide;
2-(1H-indol-3-yl)-3-[4-methoxy-1-(3-(2-nitroguanidino)propyl)-1H-indol-3-yl]-maleinimide;
2-(1H-indol-3-yl)-3-[5-methoxy-1-(3-(2-nitroguanidino)propyl)-1H-indol-3-yl]-maleinimide;
2-(1H-indol-3-yl)-3-[6-methoxy-1-(3-(2-nitroguanidino)propyl)-1H-indol-3-yl]-maleinimide;
2-(1H-indol-3-yl)-3-[7-methoxy-1-(3-(2-nitroguanidino)propyl)-1H-indol-3-yl]-maleinimide;
2-(1H-indol-3-yl)-3-[4,5-methylendioxy-1-(3-(2-nitroguanidino)propyl)-1H-indol-3-yl]-maleinimide;
2-(1H-indol-3-yl)-3-[5,6-methylendioxy-1-(3-(2-nitroguanidino)propyl)-1H-indol-3-yl]-maleinimide;
2-(1H-indol-3-yl)-3-[6,7-methylendioxy-1-(3-(2-nitroguanidino)propyl)-1H-indol-3-yl]-maleinimide;
2-(1H-indol-3-yl)-3-[4-methyl-1-(3-(2-nitroguanidino)propyl)-1H-indol-3-yl]-maleinimide;
2-(1H-indol-3-yl)-3-[5-methyl-1-(3-(2-nitroguanidino)propyl)-1H-indol-3-yl]-maleinimide;
2-(1H-indol-3-yl)-3-[6-methyl-1-(3-(2-nitroguanidino)propyl)-1H-indol-3-yl]-maleinimide;
2-(1H-indol-3-yl)-3-[7-methyl-1-(3-(2-nitroguanidino)propyl)-1H-indol-3-yl]-maleinimide;
2-(1H-indol-3-yl)-3-[4-nitro-1-(3-(2-nitroguanidino)propyl)-1H-indol-3-yl]-maleinimide;
2-(1H-indol-3-yl)-3-[5-nitro-1-(3-(2-nitroguanidino)propyl)-1H-indol-3-yl]-maleinimide;
2-(1H-indol-3-yl)-3-[6-nitro-1-(3-(2-nitroguanidino)propyl)-1H-indol-3-yl]-maleinimide;
2-(1H-indol-3-yl)-3-[7-nitro-1-(3-(2-nitroguanidino)propyl)-1H-indol-3-yl]-maleinimide;
2-(1H-indol-3-yl)-3-[4-methylthio-1-(3-(2-nitroguanidino)propyl)-1H-indol-3-yl]-maleinimide;
2-(1H-indol-3-yl)-3-[5-methylthio-1-(3-(2-nitroguanidino)propyl)-1H-indol-3-yl]-maleinimide;
2-(1H-indol-3-yl)-3-[6-methylthio-1-(3-(2-nitroguanidino)propyl)-1H-indol-3-yl]-maleinimide;
2-(1H-indol-3-yl)-3-[7-methylthio-1-(3-(2-nitroguanidino)propyl)-1H-indol-3-yl]-maleinimide;
2-(1H-indol-3-yl)-3-[4,5-dimethoxy-1-(3-(2-nitroguanidino)propyl)-1H-indol-3-yl]-maleinimide;
2-(1H-indol-3-yl)-3-[5,6-dimethoxy-1-(3-(2-nitroguanidino)propyl)-1H-indol-3-yl]-maleinimide;
2-(1H-indol-3-yl)-3-[6,7-dimethoxy-1-(3-(2-nitroguanidino)propyl)-1H-indol-3-yl]-maleinimide;
2-[4-acetylamino-1-(3-(1-piperidino)propyl)-1H-indol-3-yl]-3-(1H-indol-3-yl)-maleinimide;
2-[5-acetylamino-1-(3-(1-piperidino)propyl)-1H-indol-3-yl]-3-(1H-indol-3-yl)-maleinimide;
2-[6-acetylamino-1-(3-(1-piperidino)propyl)-1H-indol-3-yl]-3-(1H-indol-3-yl)-maleinimide;
2-[7-acetylamino-1-(3-(1-piperidino)propyl)-1H-indol-3-yl]-3-(1H-indol-3-yl)-maleinimide;
2-[4-amino-1-(3-(1-piperidino)propyl)-1H-indol-3-yl]-3-(1H-indol-3-yl)-maleinimide;
2-[5-amino-1-(3-(1-piperidino)propyl)-1H-indol-3-yl]-3-(1H-indol-3-yl)-maleinimide;
2-[6-amino-1-(3-(1-piperidino)propyl)-1H-indol-3-yl]-3-(1H-indol-3-yl)-maleinimide;
2-[7-amino-1-(3-(1-piperidino)propyl)-1H-indol-3-yl]-3-(1H-indol-3-yl)-maleinimide;
2-[4-benzyloxy-1-(3-(1-piperidino)propyl)-1H-indol-3-yl]-3-(1H-indol-3-yl)-maleinimide;
2-[5-benzyloxy-1-(3-(1-piperidino)propyl)-1H-indol-3-yl]-3-(1H-indol-3-yl)-maleinimide;
2-[6-benzyloxy-1-(3-(1-piperidino)propyl)-1H-indol-3-yl]-3-(1H-indol-3-yl)-maleinimide;
2-[7-benzyloxy-1-(3-(1-piperidino)propyl)-1H-indol-3-yl]-3-(1H-indol-3-yl)-maleinimide;
2-[4-bromo-1-(3-(1-piperidino)propyl)-1H-indol-3-yl]-3-(1H-indol-3-yl)-maleinimide;
2-[5-bromo-1-(3-(1-piperidino)propyl)-1H-indol-3-yl]-3-(1H-indol-3-yl)-maleinimide;
2-[6-bromo-1-(3-(1-piperidino)propyl)-1H-indol-3-yl]-3-(1H-indol-3-yl)-maleinimide;
2-[7-bromo-1-(3-(1-piperidino)propyl)-1H-indol-3-yl]-3-(1H-indol-3-yl)-maleinimide;
2-[4-chloro-1-(3-(1-piperidino)propyl)-1H-indol-3-yl]-3-(1H-indol-3-yl)-maleinimide;
2-[5-chloro-1-(3-(1-piperidino)propyl)-1H-indol-3-yl]-3-(1H-indol-3-yl)-maleinimide;
2-[6-chloro-1-(3-(1-piperidino)propyl)-1H-indol-3-yl]-3-(1H-indol-3-yl)-maleinimide;
2-[7-chloro-1-(3-(1-piperidino)propyl)-1H-indol-3-yl]-3-(1H-indol-3-yl)-maleinimide;
2-[4-fluoro-1-(3-(1-piperidino)propyl)-1H-indol-3-yl]-3-(1H-indol-3-yl)-maleinimide;
2-[5-fluoro-1-(3-(1-piperidino)propyl)-1H-indol-3-yl]-3-(1H-indol-3-yl)-maleinimide;
2-[6-fluoro-1-(3-(1-piperidino)propyl)-1H-indol-3-yl]-3-(1H-indol-3-yl)-maleinimide;
2-[7-fluoro-1-(3-(1-piperidino)propyl)-1H-indol-3-yl]-3-(1H-indol-3-yl)-maleinimide;
2-[4-hydroxy-1-(3-(1-piperidino)propyl)-1H-indol-3-yl]-3-(1H-indol-3-yl)-maleinimide;
2-[5-hydroxy-1-(3-(1-piperidino)propyl)-1H-indol-3-yl]-3-(1H-indol-3-yl)-maleinimide;
2-[6-hydroxy-1-(3-(1-piperidino)propyl)-1H-indol-3-yl]-3-(1H-indol-3-yl)-maleinimide;
2-[7-hydroxy-1-(3-(1-piperidino)propyl)-1H-indol-3-yl]-3-(1H-indol-3-yl)-maleinimide;
2-[4-trifluoromethyl-1-(3-(1-piperidino)propyl)-1H-indol-3-yl]-3-(1H-indol-3-yl)-maleinimide;
2-[5-trifluoromethyl-1-(3-(1-piperidino)propyl)-1H-indol-3-yl]-3-(1H-indol-3-yl)-maleinimide;
2-[6-trifluoromethyl-1-(3-(1-piperidino)propyl)-1H-indol-3-yl]-3-(1H-indol-3-yl)-maleinimide;

2-[7-trifluoromethyl-1-(3-(1-piperidino)propyl)-1H-indol-3-yl]-3-(1H-indol-3-yl)-maleinimide;
2-(1H-indol-3-yl)-3-[4-methoxy-1-(3-(1-piperidino)propyl)-1H-indol-3-yl]-maleinimide;
2-(1H-indol-3-yl)-3-[5-methoxy-1-(3-(1-piperidino)propyl)-1H-indol-3-yl]-maleinimide;
2-(1H-indol-3-yl)-3-[6-methoxy-1-(3-(1-piperidino)propyl)-1H-indol-3-yl]-maleinimide;
2-(1H-indol-3-yl)-3-[7-methoxy-1-(3-(1-piperidino)propyl)-1H-indol-3-yl]-maleinimide;
2-(1H-indol-3-yl)-3-[4,5-methylendioxy-1-(3-(1-piperidino)propyl)-1H-indol-3-yl]-maleinimide;
2-(1H-indol-3-yl)-3-[5,6-methylendioxy-1-(3-(1-piperidino)propyl)-1H-indol-3-yl]-maleinimide;
2-(1H-indol-3-yl)-3-[6,7-methylendioxy-1-(3-(1-piperidino)propyl)-1H-indol-3-yl]-maleinimide;
2-(1H-indol-3-yl)-3-[4-methyl-1-(3-(1-piperidino)propyl)-1H-indol-3-yl]-maleinimide;
2-(1H-indol-3-yl)-3-[5-methyl-1-(3-(1-piperidino)propyl)-1H-indol-3-yl]-maleinimide;
2-(1H-indol-3-yl)-3-[6-methyl-1-(3-(1-piperidino)propyl)-1H-indol-3-yl]-maleinimide;
2-(1H-indol-3-yl)-3-[7-methyl-1-(3-(1-piperidino)propyl)-1H-indol-3-yl]-maleinimide;
2-(1H-indol-3-yl)-3-[4-nitro-1-(3-(1-piperidino)propyl)-1H-indol-3-yl]-maleinimide;
2-(1H-indol-3-yl)-3-[5-nitro-1-(3-(1-piperidino)propyl)-1H-indol-3-yl]-maleinimide;
2-(1H-indol-3-yl)-3-[6-nitro-1-(3-(1-piperidino)propyl)-1H-indol-3-yl]-maleinimide;
2-(1H-indol-3-yl)-3-[7-nitro-1-(3-(1-piperidino)propyl)-1H-indol-3-yl]-maleinimide;
2-(1H-indol-3-yl)-3-[4-methylthio-1-(3-(1-piperidino)propyl)-1H-indol-3-yl]-maleinimide;
2-(1H-indol-3-yl)-3-[5-methylthio-1-(3-(1-piperidino)propyl)-1H-indol-3-yl]-maleinimide;
2-(1H-indol-3-yl)-3-[6-methylthio-1-(3-(1-piperidino)propyl)-1H-indol-3-yl]-maleinimide;
2-(1H-indol-3-yl)-3-[7-methylthio-1-(3-(1-piperidino)propyl)-1H-indol-3-yl]-maleinimide;
2-(1H-indol-3-yl)-3-[4,5-dimethoxy-1-(3-(1-piperidino)propyl)-1H-indol-3-yl]-maleinimide;
2-(1H-indol-3-yl)-3-[5,6-dimethoxy-1-(3-(1-piperidino)propyl)-1H-indol-3-yl]-maleinimide;
2-(1H-indol-3-yl)-3-[6,7-dimethoxy-1-(3-(1-piperidino)propyl)-1H-indol-3-yl]-maleinimide;
bis-2,3-(4-acetylamino-1H-indol-3-yl)-maleinimide;
bis-2,3-(5-acetylamino-1H-indol-3-yl)-maleinimide;
bis-2,3-(6-acetylamino-1H-indol-3-yl)-maleinimide;
bis-2,3-(7-acetylamino-1H-indol-3-yl)-maleinimide;
bis-2,3-(4-amino-1H-indol-3-yl)-maleinimide;
bis-2,3-(5-amino-1H-indol-3-yl)-maleinimide;
bis-2,3-(6-amino-1H-indol-3-yl)-maleinimide;
bis-2,3-(7-amino-1H-indol-3-yl)-maleinimide;
bis-2,3-(4-benzyloxy-1H-indol-3-yl)-maleinimide;
bis-2,3-(6-benzyloxy-1H-indol-3-yl)-maleinimide;
bis-2,3-(7-benzyloxy-1H-indol-3-yl)-maleinimide;
bis-2,3-(4-bromo-1H-indol-3-yl)-maleinimide;
bis-2,3-(6-bromo-1H-indol-3-yl)-maleinimide;
bis-2,3-(7-bromo-1H-indol-3-yl)-maleinimide;
bis-2,3-(4-chloro-1H-indol-3-yl)-maleinimide;
bis-2,3-(6-chloro-1H-indol-3-yl)-maleinimide;
bis-2,3-(7-chloro-1H-indol-3-yl)-maleinimide;
bis-2,3-(4-fluoro-1H-indol-3-yl)-maleinimide;
bis-2,3-(6-fluoro-1H-indol-3-yl)-maleinimide;
bis-2,3-(7-fluoro-1H-indol-3-yl)-maleinimide;
bis-2,3-(4-hydroxy-1H-indol-3-yl)-maleinimide;
bis-2,3-(5-hydroxy-1H-indol-3-yl)-maleinimide;
bis-2,3-(6-hydroxy-1H-indol-3-yl)-maleinimide;
bis-2,3-(7-hydroxy-1H-indol-3-yl)-maleinimide;
bis-2,3-(4-trifluoromethyl-1H-indol-3-yl)-maleinimide;
bis-2,3-(5-trifluoromethyl-1H-indol-3-yl)-maleinimide;
bis-2,3-(6-trifluoromethyl-1H-indol-3-yl)-maleinimide;
bis-2,3-(7-trifluoromethyl-1H-indol-3-yl)-maleinimide;
bis-2,3-(4-methoxy-1H-indol-3-yl)-maleinimide;
bis-2,3-(6-methoxy-1H-indol-3-yl)-maleinimide;
bis-2,3-(7-methoxy-1H-indol-3-yl)-maleinimide;
bis-2,3-(4,5-methylendioxy-1H-indol-3-yl)-maleinimide;
bis-2,3-(6,7-methylendioxy-1H-indol-3-yl)-maleinimide;
bis-2,3-(4-methyl-1H-indol-3-yl)-maleinimide;
bis-2,3-(6-methyl-1H-indol-3-yl)-maleinimide;
bis-2,3-(7-methyl-1H-indol-3-yl)-maleinimide;
bis-2,3-(4-nitro-1H-indol-3-yl)-maleinimide;
bis-2,3-(5-nitro-1H-indol-3-yl)-maleinimide;
bis-2,3-(6-nitro-1H-indol-3-yl)-maleinimide;
bis-2,3-(7-nitro-1H-indol-3-yl)-maleinimide;
bis-2,3-(4-methylthio-1H-indol-3-yl)-maleinimide;
bis-2,3-(5-methylthio-1H-indol-3-yl)-maleinimide;
bis-2,3-(6-methylthio-1H-indol-3-yl)-maleinimide;
bis-2,3-(7-methylthio-1H-indol-3-yl)-maleinimide;
bis-2,3-(4,5-dimethoxy-1H-indol-3-yl)-maleinimide;
bis-2,3-(5,6-dimethoxy-1H-indol-3-yl)-maleinimide;
bis-2,3-(6,7-dimethoxy-1H-indol-3-yl)-maleinimide;
2-[5-acetylamino-1-(3-(amidinothio)propyl)-1H-indol-3-yl]-3-(5-acetylamino-1H-indol-3-yl)-maleinimide;
2-[1-(3-(amidinothio)propyl)-5-amino-1H-indol-3-yl]-3-(5-amino-1H-indol-3-yl)-maleinimide;
2-[1-(3-(amidinothio)propyl)-5-benzyloxy-1H-indol-3-yl]-3-(5-benzyloxy-1H-indol-3-yl)-maleinimide;
2-[1-(3-(amidinothio)propyl)-5-bromo-1H-indol-3-yl]-3-(5-bromo-1H-indol-3-yl)-maleinimide;
2-[1-(3-(amidinothio)propyl)-5-chloro-1H-indol-3-yl]-3-(5-chloro-1H-indol-3-yl)-maleinimide;
2-[1-(3-(amidinothio)propyl)-5-fluoro-1H-indol-3-yl]-3-(5-fluoro-1H-indol-3-yl)-maleinimide;
2-[1-(3-(amidinothio)propyl)-5-hydroxy-1H-indol-3-yl]-3-(5-hydroxy-1H-indol-3-yl)-maleinimide;
2-[1-(3-(amidinothio)propyl)-5-trifluoromethyl-1H-indol-3-yl]-3-(5-trifluoromethyl-1H-indol-3-yl)-maleinimide;
2-[1-(3-(amidinothio)propyl)-5-methoxy-1H-indol-3-yl]-3-(5-methoxy-1H-indol-3-yl)-maleinimide;
2-[1-(3-(amidinothio)propyl)-4,5-methylendioxy-1H-indol-3-yl]-3-(4,5-methylendioxy-1H-indol-3-yl)-maleinimide;
2-[1-(3-(amidinothio)propyl)-5,6-methylendioxy-1H-indol-3-yl]-3-(5,6-methylendioxy-1H-indol-3-yl)-maleinimide;
2-[1-(3-(amidinothio)propyl)-5-methyl-1H-indol-3-yl]-3-(5-methyl-1H-indol-3-yl)-maleinimide;
2-[1-(3-(amidinothio)propyl)-5-nitro-1H-indol-3-yl]-3-(5-nitro-1H-indol-3-yl)-maleinimide;
2-[1-(3-(amidinothio)propyl)-5-methylthio-1H-indol-3-yl]-3-(5-methylthio-1H-indol-3-yl)-maleinimide;
2-[1-(3-(amidinothio)propyl)-4,5-dimethoxy-1H-indol-3-yl]-3-(4,5-dimethoxy-1H-indol-3-yl)-maleinimide;
2-[1-(3-(amidinothio)propyl)-5,6-dimethoxy-1H-indol-3-yl]-3-(5,6-dimethoxy-1H-indol-3-yl)-maleinimide;
2-[5-acetylamino-1-(2-aminoethyl)-1H-indol-3-yl]-3-(5-acetylamino-1H-indol-3-yl)-maleinimide;
2-[5-amino-1-(2-aminoethyl)-1H-indol-3-yl]-3-(5-amino-1H-indol-3-yl)-maleinimide;
2-[1-(2-aminoethyl)-5-benzyloxy-1H-indol-3-yl]-3-(5-benzyloxy-1H-indol-3-yl)-maleinimide;
2-[1-(2-aminoethyl)-5-bromo-1H-indol-3-yl]-3-(5-bromo-1H-indol-3-yl)-maleinimide;

2-[1-(2-aminoethyl)-5-chloro-1H-indol-3-yl]-3-(5-chloro-1H-indol-3-yl)-maleinimide;
2-[1-(2-aminoethyl)-5-fluoro-1H-indol-3-yl]-3-(5-fluoro-1H-indol-3-yl)-maleinimide;
2-[1-(2-aminoethyl)-5-hydroxy-1H-indol-3-yl]-3-(5-hydroxy-1H-indol-3-yl)-maleinimide;
2-[1-(2-aminoethyl)-5-trifluoromethyl-1H-indol-3-yl]-3-(5-trifluoromethyl-1H-indol-3-yl)-maleinimide;
2-[1-(2-aminoethyl)-5-methoxy-1H-indol-3-yl]-3-(5-methoxy-1H-indol-3-yl)-maleinimide;
2-[1-(2-aminoethyl)-4,5-methylendioxy-1H-indol-3-yl]-3-(4,5-methylendioxy-1H-indol-3-yl)-maleinimide;
2-[1-(2-aminoethyl)-5,6-methylendioxy-1H-indol-3-yl]-3-(5,6-methylendioxy-1H-indol-3-yl)-maleinimide;
2-[1-(2-aminoethyl)-5-methyl-1H-indol-3-yl]-3-(5-methyl-1H-indol-3-yl)-maleinimide;
2-[1-(2-aminoethyl)-5-nitro-1H-indol-3-yl]-3-(5-nitro-1H-indol-3-yl)-maleinimide;
2-[1-(2-aminoethyl)-5-methylthio-1H-indol-3-yl]-3-(5-methylthio-1H-indol-3-yl)-maleinimide;
2-[1-(2-aminoethyl)-4,5-dimethoxy-1H-indol-3-yl]-3-(4,5-dimethoxy-1H-indol-3-yl)-maleinimide;
2-[1-(2-aminoethyl)-5,6-dimethoxy-1H-indol-3-yl]-3-(5,6-dimethoxy-1H-indol-3-yl)-maleinimide;
2-[5-acetylamino-1-(3-aminopropyl)-1H-indol-3-yl]-3-(5-acetylamino-1H-indol-3-yl)-maleinimide;
2-[5-amino-1-(3-aminopropyl)-1H-indol-3-yl]-3-(5-amino-1H-indol-3-yl)-maleinimide;
2-[1-(3-aminopropyl)-5-benzyloxy-1H-indol-3-yl]-3-(5-benzyloxy-1H-indol-3-yl)-maleinimide;
2-[1-(3-aminopropyl)-5-bromo-1H-indol-3-yl]-3-(5-bromo-1H-indol-3-yl)-maleinimide;
2-[1-(3-aminopropyl)-5-chloro-1H-indol-3-yl]-3-(5-chloro-1H-indol-3-yl)-maleinimide;
2-[1-(3-aminopropyl)-5-fluoro-1H-indol-3-yl]-3-(5-fluoro-1H-indol-3-yl)-maleinimide;
2-[1-(3-aminopropyl)-5-hydroxy-1H-indol-3-yl]-3-(5-hydroxy-1H-indol-3-yl)-maleinimide;
2-[1-(3-aminopropyl)-5-trifluoromethyl-1H-indol-3-yl]-3-(5-trifluoromethyl-1H-indol-3-yl)-maleinimide;
2-[1-(3-aminopropyl)-5-methoxy-1H-indol-3-yl]-3-(5-methoxy-1H-indol-3-yl)-maleinimide;
2-[1-(3-aminopropyl)-4,5-methylendioxy-1H-indol-3-yl]-3-(4,5-methylendioxy-1H-indol-3-yl)-maleinimide;
2-[1-(3-aminopropyl)-5,6-methylendioxy-1H-indol-3-yl]-3-(5,6-methylendioxy-1H-indol-3-yl)-maleinimide;
2-[1-(3-aminopropyl)-5-methyl-1H-indol-3-yl]-3-(5-methyl-1H-indol-3-yl)-maleinimide;
2-[1-(3-aminopropyl)-5-nitro-1H-indol-3-yl]-3-(5-nitro-1H-indol-3-yl)-maleinimide;
2-[1-(3-aminopropyl)-5-methylthio-1H-indol-3-yl]-3-(5-methylthio-1H-indol-3-yl)-maleinimide;
2-[1-(3-aminopropyl)-4,5-dimethoxy-1H-indol-3-yl]-3-(4,5-dimethoxy-1H-indol-3-yl)-maleinimide;
2-[1-(3-aminopropyl)-5,6-dimethoxy-1H-indol-3-yl]-3-(5,6-dimethoxy-1H-indol-3-yl)-maleinimide;
(±)-2-[5-acetylamino-1-(3-ethoxy-2-hydroxypropyl)-1H-indol-3-yl]-3-(5-acetylamino-1H-indol-3-yl)-maleinimide;
(±)-2-[5-amino-1-(3-ethoxy-2-hydroxypropyl)-1H-indol-3-yl]-3-(5-amino-1H-indol-3-yl)-maleinimide;
(±)-2-[5-benzyloxy-1-(3-ethoxy-2-hydroxypropyl)-1H-indol-3-yl]-3-(5-benzyloxy-1H-indol-3-yl)-maleinimide;
(±)-2-[5-bromo-1-(3-ethoxy-2-hydroxypropyl)-1H-indol-3-yl]-3-(5-bromo-1H-indol-3-yl)-maleinimide;
(±)-2-[5-chloro-1-(3-ethoxy-2-hydroxypropyl)-1H-indol-3-yl]-3-(5-chloro-1H-indol-3-yl)-maleinimide;
(±)-2-[1-(3-ethoxy-2-hydroxypropyl)-5-fluoro-1H-indol-3-yl]-3-(5-fluoro-1H-indol-3-yl)-maleinimide;
(±)-2-[1-(3-ethoxy-2-hydroxypropyl)-5-hydroxy-1H-indol-3-yl]-3-(5-hydroxy-1H-indol-3-yl)-maleinimide;
(±)-2-[1-(3-ethoxy-2-hydroxypropyl)-5-trifluoromethyl-1H-indol-3-yl]-3-(5-trifluoromethyl-1H-indol-3-yl)-maleinimide;
(±)-2-[1-(3-ethoxy-2-hydroxypropyl)-5-methoxy-1H-indol-3-yl]-3-(5-methoxy-1H-indol-3-yl)-maleinimide;
(±)-2-[1-(3-ethoxy-2-hydroxypropyl)-4,5-methylendioxy-1H-indol-3-yl]-3-(4,5-methylendioxy-1H-indol-3-yl)-maleinimide;
(±)-2-[1-(3-ethoxy-2-hydroxypropyl)-5,6-methylendioxy-1H-indol-3-yl]-3-(5,6-methylendioxy-1H-indol-3-yl)-maleinimide;
(±)-2-[1-(3-ethoxy-2-hydroxypropyl)-5-methyl-1H-indol-3-yl]-3-(5-methyl-1H-indol-3-yl)-maleinimide;
(±)-2-[1-(3-ethoxy-2-hydroxypropyl)-5-nitro-1H-indol-3-yl]-3-(5-nitro-1H-indol-3-yl)-maleinimide;
(±)-2-[1-(3-ethoxy-2-hydroxypropyl)-5-methylthio-1H-indol-3-yl]-3-(5-methylthio-1H-indol-3-yl)-maleinimide;
(±)-2-[1-(3-ethoxy-2-hydroxypropyl)-4,5-dimethoxy-1H-indol-3-yl]-3-(4,5-dimethoxy-1H-indol-3-yl)-maleinimide;
(±)-2-[1-(3-ethoxy-2-hydroxypropyl)-5,6-dimethoxy-1H-indol-3-yl]-3-(5,6-dimethoxy-1H-indol-3-yl)-maleinimide;
(+)-2-[5-acetylamino-1-(3-ethoxy-2-hydroxypropyl)-1H-indol-3-yl]-3-(5-acetylamino-1H-indol-3-yl)-maleinimide;
(+)-2-[5-amino-1-(3-ethoxy-2-hydroxypropyl)-1H-indol-3-yl]-3-(5-amino-1H-indol-3-yl)-maleinimide;
(+)-2-[5-benzyloxy-1-(3-ethoxy-2-hydroxypropyl)-1H-indol-3-yl]-3-(5-benzyloxy-1H-indol-3-yl)-maleinimide;
(+)-2-[5-bromo-1-(3-ethoxy-2-hydroxypropyl)-1H-indol-3-yl]-3-(5-bromo-1H-indol-3-yl)-maleinimide;
(+)-2-[5-chloro-1-(3-ethoxy-2-hydroxypropyl)-1H-indol-3-yl]-3-(5-chloro-1H-indol-3-yl)-maleinimide;
(+)-2-[1-(3-ethoxy-2-hydroxypropyl)-5-fluoro-1H-indol-3-yl]-3-(5-fluoro-1H-indol-3-yl)-maleinimide;
(+)-2-[1-(3-ethoxy-2-hydroxypropyl)-5-hydroxy-1H-indol-3-yl]-3-(5-hydroxy-1H-indol-3-yl)-maleinimide;
(+)-2-[1-(3-ethoxy-2-hydroxypropyl)-5-trifluoromethyl-1-indol-3-yl]-3-(5-trifluoromethyl-1H-indol-3-yl)-maleinimide;
(+)-2-[1-(3-ethoxy-2-hydroxypropyl)-5-methoxy-1H-indol-3-yl]-3-(5-methoxy-1H-indol-3-yl)-maleinimide;
(+)-2-[1-(3-ethoxy-2-hydroxypropyl)-4,5-methylendioxy-1H-indol-3-yl]-3-(4,5-methylendioxy-1H-indol-3-yl)-maleinimide;
(+)-2-[1-(3-ethoxy-2-hydroxypropyl)-5,6-methylendioxy-1H-indol-3-yl]-3-(5,6-methylendioxy-1H-indol-3-yl)-maleinimide;
(+)-2-[1-(3-ethoxy-2-hydroxypropyl)-5-methyl-1H-indol-3-yl]-3-(5-methyl-1H-indol-3-yl)-maleinimide;
(+)-2-[1-(3-ethoxy-2-hydroxypropyl)-5-nitro-1H-indol-3-yl]-3-(5-nitro-1H-indol-3-yl)-maleinimide;
(+)-2-[1-(3-ethoxy-2-hydroxypropyl)-5-methylthio-1H-indol-3-yl]-3-(5-methylthio-1H-indol-3-yl)-maleinimide;
(+)-2-[1-(3-ethoxy-2-hydroxypropyl)-4,5-dimethoxy-1H-indol-3-yl]-3-(4,5-dimethoxy-1H-indol-3-yl)-maleinimide;

(+)-2-[1-(3-ethoxy-2-hydroxypropyl)-5,6-dimethoxy-1H-indol-3-yl]-3-(5,6-dimethoxy-1H-indol-3-yl)-maleinimide;
(−)-2-[5-acetylamino-1-(3-ethoxy-2-hydroxypropyl)-1H-indol-3-yl]-3-(5-acetylamino-1H-indol-3-yl)-maleinimide;
(−)-2-[5-amino-1-(3-ethoxy-2-hydroxypropyl)-1H-indol-3-yl]-3-(5-amino-1H-indol-3-yl)-maleinimide;
(−)-2-[5-benzyloxy-1-(3-ethoxy-2-hydroxypropyl)-1H-indol-3-yl]-3-(5-benzyloxy-1H-indol-3-yl)-maleinimide;
(−)-2-[5-bromo-1-(3-ethoxy-2-hydroxypropyl)-1H-indol-3-yl]-3-(5-bromo-1H-indol-3-yl)-maleinimide;
(−)-2-[5-chloro-1-(3-ethoxy-2-hydroxypropyl)-1H-indol-3-yl]-3-(5-chloro-1H-indol-3-yl)-maleinimide;
(−)-2-[1-(3-ethoxy-2-hydroxypropyl)-5-fluoro-1H-indol-3-yl]-3-(5-fluoro-1H-indol-3-yl)-maleinimide;
(−)-2-[1-(3-ethoxy-2-hydroxypropyl)-5-hydroxy-1H-indol-3-yl]-3-(5-hydroxy-1H-indol-3-yl)-maleinimide;
(−)-2-[1-(3-ethoxy-2-hydroxypropyl)-5-trifluoromethyl-1H-indol-3-yl]-3-(5-trifluoromethyl-1H-indol-3-yl)-maleinimide;
(−)-2-[1-(3-ethoxy-2-hydroxypropyl)-5-methoxy-1H-indol-3-yl]-3-(5-methoxy-1H-indol-3-yl)-maleinimide;
(−)-2-[1-(3-ethoxy-2-hydroxypropyl)-4,5-methylendioxy-1H-indol-3-yl]-3-(4,5-methylendioxy-1H-indol-3-yl)-maleinimide;
(−)-2-[1-(3-ethoxy-2-hydroxypropyl)-5,6-methylendioxy-1H-indol-3-yl]-3-(5,6-methylendioxy-1H-indol-3-yl)-maleinimide;
(−)-2-[1-(3-ethoxy-2-hydroxypropyl)-5-methyl-1H-indol-3-yl]-3-(5-methyl-1H-indol-3-yl)-maleinimide;
(−)-2-[1-(3-ethoxy-2-hydroxypropyl)-5-nitro-1H-indol-3-yl]-3-(5-nitro-1H-indol-3-yl)-maleinimide;
(−)-2-[1-(3-ethoxy-2-hydroxypropyl)-5-methylthio-1H-indol-3-yl]-3-(5-methylthio-1H-indol-3-yl)-maleinimide;
(−)-2-[1-(3-ethoxy-2-hydroxypropyl)-4,5-dimethoxy-1H-indol-3-yl]-3-(4,5-dimethoxy-1H-indol-3-yl)-maleinimide;
(−)-2-[1-(3-ethoxy-2-hydroxypropyl)-5,6-dimethoxy-1H-indol-3-yl]-3-(5,6-dimethoxy-1H-indol-3-yl)-maleinimide;
2-[5-acetylamino-1-(2-diethylaminoethyl)-1H-indol-3-yl]-3-(5-acetylamino-1H-indol-3-yl)-maleinimide;
2-[5-amino-1-(2-diethylaminoethyl)-1H-indol-3-yl]-3-(5-amino-1H-indol-3-yl)-maleinimide;
2-[5-benzyloxy-1-(2-diethylaminoethyl)-1H-indol-3-yl]-3-(5-benzyloxy-1H-indol-3-yl)-maleinimide;
2-[5-bromo-1-(2-diethylaminoethyl)-1H-indol-3-yl]-3-(5-bromo-1H-indol-3-yl)-maleinimide;
2-[5-chloro-1-(2-diethylaminoethyl)-1H-indol-3-yl]-3-(5-chloro-1H-indol-3-yl)-maleinimide;
2-[1-(2-diethylaminoethyl)-5-fluoro-1H-indol-3-yl]-3-(5-fluoro-1H-indol-3-yl)-maleinimide;
2-[1-(2-diethylaminoethyl)-5-hydroxy-1H-indol-3-yl]-3-(5-hydroxy-1H-indol-3-yl)-maleinimide;
2-[1-(2-diethylaminoethyl)-5-trifluoromethyl-1H-indol-3-yl]-3-(5-trifluoromethyl-1H-indol-3-yl)-maleinimide;
2-[1-(2-diethylaminoethyl)-5-methoxy-1H-indol-3-yl]-3-(5-methoxy-1H-indol-3-yl)-maleinimide;
2-[1-(2-diethylaminoethyl)-4,5-methylendioxy-1H-indol-3-yl]-3-(4,5-methylendioxy-1H-indol-3-yl)-maleinimide;
2-[1-(2-diethylaminoethyl)-5,6-methylendioxy-1H-indol-3-yl]-3-(5,6-methylendioxy-1H-indol-3-yl)-maleinimide;
2-[1-(2-diethylaminoethyl)-5-methyl-1H-indol-3-yl]-3-(5-methyl-1H-indol-3-yl)-maleinimide;
2-[1-(2-diethylaminoethyl)-5-nitro-1H-indol-3-yl]-3-(5-nitro-1H-indol-3-yl)-maleinimide;
2-[1-(2-diethylaminoethyl)-5-methylthio-1H-indol-3-yl]-3-(5-methylthio-1H-indol-3-yl)-maleinimide;
2-[1-(2-diethylaminoethyl)-4,5-dimethoxy-1H-indol-3-yl]-3-(4,5-dimethoxy-1H-indol-3-yl)-maleinimide;
2-[1-(2-diethylaminoethyl)-5,6-dimethoxy-1H-indol-3-yl]-3-(5,6-dimethoxy-1H-indol-3-yl)-maleinimide;
(±)-2-[5-acetylamino-1-(3-diethylamino-2-hydroxypropyl)-1H-indol-3-yl]-3-(5-acetylamino-1H-indol-3-yl)-maleinimide;
(±)-2-[5-amino-1-(3-diethylamino-2-hydroxypropyl)-1H-indol-3-yl]-3-(5-amino-1H-indol-3-yl)-maleinimide;
(±)-2-[5-benzyloxy-1-(3-diethylamino-2-hydroxypropyl)-1H-indol-3-yl]-3-(5-benzyloxy-1H-indol-3-yl)-maleinimide;
(±)-2-[5-bromo-1-(3-diethylamino-2-hydroxypropyl)-1H-indol-3-yl]-3-(5-bromo-1H-indol-3-yl)-maleinimide;
(±)-2-[5-chloro-1-(3-diethylamino-2-hydroxypropyl)-1H-indol-3-yl]-3-(5-chloro-1H-indol-3-yl)-maleinimide;
(±)-2-[1-(3-diethylamino-2-hydroxypropyl)-5-fluoro-1H-indol-3-yl]-3-(5-fluoro-1H-indol-3-yl)-maleinimide;
(±)-2-[1-(3-diethylamino-2-hydroxypropyl)-5-hydroxy-1H-indol-3-yl]-3-(5-hydroxy-1H-indol-3-yl)-maleinimide;
(±)-2-[1-(3-diethylamino-2-hydroxypropyl)-5-trifluoromethyl-1H-indol-3-yl]-3-(5-trifluoromethyl-1H-indol-3-yl)-maleinimide;
(±)-2-[1-(3-diethylamino-2-hydroxypropyl)-4,5-methylendioxy-1H-indol-3-yl]-3-(4,5-methylendioxy-1H-indol-3-yl)-maleinimide;
(±)-2-[1-(3-diethylamino-2-hydroxypropyl)-5,6-methylendioxy-1H-indol-3-yl]-3-(5,6-methylendioxy-1H-indol-3-yl)-maleinimide;
(±)-2-[1-(3-diethylamino-2-hydroxypropyl)-5-methyl-1H-indol-3-yl]-3-(5-methyl-1H-indol-3-yl)-maleinimide;
(±)-2-[1-(3-diethylamino-2-hydroxypropyl)-5-nitro-1H-indol-3-yl]-3-(5-nitro-1H-indol-3-yl)-maleinimide;
(±)-2-[1-(3-diethylamino-2-hydroxypropyl)-5-methylthio-1H-indol-3-yl]-3-(5-methylthio-1H-indol-3-yl)-maleinimide;
(±)-2-[1-(3-diethylamino-2-hydroxypropyl)-4,5-dimethoxy-1H-indol-3-yl]-3-(4,5-dimethoxy-1H-indol-3-yl)-maleinimide;
(±)-2-[1-(3-diethylamino-2-hydroxypropyl)-5,6-dimethoxy-1H-indol-3-yl]-3-(5,6-dimethoxy-1H-indol-3-yl)-maleinimide;
(+)-2-[5-acetylamino-1-(3-diethylamino-2-hydroxypropyl)-1H-indol-3-yl]-3-(5-acetylamino-1H-indol-3-yl)-maleinimide;
(+)-2-[5-amino-1-(3-diethylamino-2-hydroxypropyl)-1H-indol-3-yl]-3-(5-amino-1H-indol-3-yl)-maleinimide;
(+)-2-[5-benzyloxy-1-(3-diethylamino-2-hydroxypropyl)-1H-indol-3-yl]-3-(5-benzyloxy-1H-indol-3-yl)-maleinimide;
(+)-2-[5-bromo-1-(3-diethylamino-2-hydroxypropyl)-1H-indol-3-yl]-3-(5-bromo-1H-indol-3-yl)-maleinimide;

(+)-2-[5-chloro-1-(3-diethylamino-2-hydroxypropyl)-1H-indol-3-yl]-3-(5-chloro-1H-indol-3-yl)-maleinimide;

(+)-2-[1-(3-diethylamino-2-hydroxypropyl)-5-fluoro-1H-indol-3-yl]-3-(5-fluoro-1H-indol-3-yl)-maleinimide;

(+)-2-[1-(3-diethylamino-2-hydroxypropyl)-5-hydroxy-1H-indol-3-yl]-3-(5-hydroxy-1H-indol-3-yl)-maleinimide;

(+)-2-[1-(3-diethylamino-2-hydroxypropyl)-5-trifluoromethyl-1H-indol-3-yl]-3-(5-trifluoromethyl-1H-indol-3-yl)-maleinimide;

(+)-2-[1-(3-diethylamino-2-hydroxypropyl)-5-methoxy-1H-indol-3-yl]-3-(5-methoxy-1H-indol-3-yl)-maleinimide;

(+)-2-[1-(3-diethylamino-2-hydroxypropyl)-4,5-methylendioxy-1H-indol-3-yl]-3-(4,5-methylendioxy-1H-indol-3-yl)-maleinimide;

(+)-2-[1-(3-diethylamino-2-hydroxypropyl)-5,6-methylendioxy-1H-indol-3-yl]-3-(5,6-methylendioxy-1H-indol-3-yl)-maleinimide;

(+)-2-[1-(3-diethylamino-2-hydroxypropyl)-5-methyl-1H-indol-3-yl]-3-(5-methyl-1H-indol-3-yl)-maleinimide;

(+)-2-[1-(3-diethylamino-2-hydroxypropyl)-5-nitro-1H-indol-3-yl]-3-(5-nitro-1H-indol-3-yl)-maleinimide;

(+)-2-[1-(3-diethylamino-2-hydroxypropyl)-5-methylthio-1H-indol-3-yl]-3-(5-methylthio-1H-indol-3-yl)-maleinimide;

(+)-2-[1-(3-diethylamino-2-hydroxypropyl)-4,5-dimethoxy-1H-indol-3-yl]-3-(4,5-dimethoxy-1H-indol-3-yl)-maleinimide;

(+)-2-[1-(3-diethylamino-2-hydroxypropyl)-5,6-dimethoxy-1H-indol-3-yl]-3-(5,6-dimethoxy-1H-indol-3-yl)-maleinimide;

(−)-2-[5-acetylamino-1-(3-diethylamino-2-hydroxypropyl)-1H-indol-3-yl]-3-(5-acetylamino-1H-indol-3-yl)-maleinimide;

(−)-2-[5-amino-1-(3-diethylamino-2-hydroxypropyl)-1H-indol-3-yl]-3-(5-amino-1H-indol-3-yl)-maleinimide;

(−)-2-[5-benzyloxy-1-(3-diethylamino-2-hydroxypropyl)-1H-indol-3-yl]-3-(5-benzyloxy-1H-indol-3-yl)-maleinimide;

(−)-2-[5-bromo-1-(3-diethylamino-2-hydroxypropyl)-1H-indol-3-yl]-3-(5-bromo-1H-indol-3-yl)-maleinimide;

(−)-2-[5-chloro-1-(3-diethylamino-2-hydroxypropyl)-1H-indol-3-yl]-3-(5-chloro-1H-indol-3-yl)-maleinimide;

(−)-2-[1-(3-diethylamino-2-hydroxypropyl)-5-fluoro-1H-indol-3-yl]-3-(5-fluoro-1H-indol-3-yl)-maleinimide;

(−)-2-[1-(3-diethylamino-2-hydroxypropyl)-5-hydroxy-1H-indol-3-yl]-3-(5-hydroxy-1H-indol-3-yl)-maleinimide;

(−)-2-[1-(3-diethylamino-2-hydroxypropyl)-5-trifluoromethyl-1H-indol-3-yl]-3-(5-trifluoromethyl-1H-indol-3-yl)-maleinimide;

(−)-2-[1-(3-diethylamino-2-hydroxypropyl)-5-methoxy-1H-indol-3-yl]-3-(5-methoxy-1H-indol-3-yl)-maleinimide;

(−)-2-[1-(3-diethylamino-2-hydroxypropyl)-4,5-methylendioxy-1H-indol-3-yl]-3-(4,5-methylendioxy-1H-indol-3-yl)-maleinimide;

(−)-2-[1-(3-diethylamino-2-hydroxypropyl)-5,6-methylendioxy-1H-indol-3-yl]-3-(5,6-methylendioxy-1H-indol-3-yl)-maleinimide;

(−)-2-[1-(3-diethylamino-2-hydroxypropyl)-5-methyl-1H-indol-3-yl]-3-(5-methyl-1H-indol-3-yl)-maleinimide;

(−)-2-[1-(3-diethylamino-2-hydroxypropyl)-5-nitro-1H-indol-3-yl]-3-(5-nitro-1H-indol-3-yl)-maleinimide;

(−)-2-[1-(3-diethylamino-2-hydroxypropyl)-5-methylthio-1H-indol-3-yl]-3-(5-methylthio-1H-indol-3-yl)-maleinimide;

(−)-2-[1-(3-diethylamino-2-hydroxypropyl)-4,5-dimethoxy-1H-indol-3-yl]-3-(4,5-dimethoxy-1H-indol-3-yl)-maleinimide;

(−)-2-[1-(3-diethylamino-2-hydroxypropyl)-5,6-dimethoxy-1H-indol-3-yl]-3-(5,6-dimethoxy-1H-indol-3-yl)-maleinimide;

2-[5-acetylamino-1-(3-diethylaminopropyl)-1H-indol-3-yl]-3-(5-acetylamino-1H-indol-3-yl)-maleinimide;

2-[5-amino-1-(3-diethylaminopropyl)-1H-indol-3-yl]-3-(5-amino-1H-indol-3-yl)-maleinimide;

2-[5-benzyloxy-1-(3-diethylaminopropyl)-1H-indol-3-yl]-3-(5-benzyloxy-1H-indol-3-yl)-maleinimide;

2-[5-bromo-1-(3-diethylaminopropyl)-1H-indol-3-yl]-3-(5-bromo-1H-indol-3-yl)-maleinimide;

2-[5-chloro-1-(3-diethylaminopropyl)-1H-indol-3-yl]-3-(5-chloro-1H-indol-3-yl)-maleinimide;

2-[1-(3-diethylaminopropyl)-5-fluoro-1H-indol-3-yl]-3-(5-fluoro-1H-indol-3-yl)-maleinimide;

2-[1-(3-diethylaminopropyl)-5-hydroxy-1H-indol-3-yl]-3-(5-hydroxy-1H-indol-3-yl)-maleinimide;

2-[1-(3-diethylaminopropyl)-5-trifluoromethyl-1H-indol-3-yl]-3-(5-trifluoromethyl-1H-indol-3-yl)-maleinimide;

2-[1-(3-diethylaminopropyl)-5-methoxy-1H-indol-3-yl]-3-(5-methoxy-1H-indol-3-yl)-maleinimide;

2-[1-(3-diethylaminopropyl)-4,5-methylendioxy-1H-indol-3-yl]-3-(4,5-methylendioxy-1H-indol-3-yl)-maleinimide;

2-[1-(3-diethylaminopropyl)-5,6-methylendioxy-1H-indol-3-yl]-3-(5,6-methylendioxy-1H-indol-3-yl)-maleinimide;

2-[1-(3-diethylaminopropyl)-5-methyl-1H-indol-3-yl]-3-(5-methyl-1H-indol-3-yl)-maleinimide;

2-[1-(3-diethylaminopropyl)-5-nitro-1H-indol-3-yl]-3-(5-nitro-1H-indol-3-yl)-maleinimide;

2-[1-(3-diethylaminopropyl)-5-methylthio-1H-indol-3-yl]-3-(5-methylthio-1H-indol-3-yl)-maleinimide;

2-[1-(3-diethylaminopropyl)-4,5-dimethoxy-1H-indol-3-yl]-3-(4,5-dimethoxy-1H-indol-3-yl)-maleinimide;

2-[1-(3-diethylaminopropyl)-5,6-dimethoxy-1H-indol-3-yl]-3-(5,6-dimethoxy-1H-indol-3-yl)-maleinimide;

2-[5-acetylamino-1-(3-ethylaminopropyl)-1H-indol-3-yl]-3-(5-acetylamino-1H-indol-3-yl)-maleinimide;

2-[5-amino-1-(3-ethylaminopropyl)-1H-indol-3-yl]-3-(5-amino-1H-indol-3-yl)-maleinimide;

2-[5-benzyloxy-1-(3-ethylaminopropyl)-1H-indol-3-yl]-3-(5-benzyloxy-1H-indol-3-yl)-maleinimide;

2-[5-bromo-1-(3-ethylaminopropyl)-1H-indol-3-yl]-3-(5-bromo-1H-indol-3-yl)-maleinimide;

2-[5-chloro-1-(3-ethylaminopropyl)-1H-indol-3-yl]-3-(5-chloro-1H-indol-3-yl)-maleinimide;

2-[1-(3-ethylaminopropyl)-5-fluoro-1H-indol-3-yl]-3-(5-fluoro-1H-indol-3-yl)-maleinimide;

2-[1-(3-ethylaminopropyl)-5-hydroxy-1H-indol-3-yl]-3-(5-hydroxy-1H-indol-3-yl)-maleinimide;

2-[1-(3-ethylaminopropyl)-5-trifluoromethyl-1H-indol-3-yl]-3-(5-trifluoromethyl-1H-indol-3-yl)-maleinimide;

2-[1-(3-ethylaminopropyl)-5-methoxy-1H-indol-3-yl]-3-(5-methoxy-1H-indol-3-yl)-maleinimide;

2-[1-(3-ethylaminopropyl)-4,5-methylendioxy-1H-indol-3-yl]-3-(4,5-methylendioxy-1H-indol-3-yl)-maleinimide;
2-[1-(3-ethylaminopropyl)-5,6-methylendioxy-1H-indol-3-yl]-3-(5,6-methylendioxy-1H-indol-3-yl)-maleinimide;
2-[1-(3-ethylaminopropyl)-5-methyl-1H-indol-3-yl]-3-(5-methyl-1H-indol-3-yl)-maleinimide;
2-[1-(3-ethylaminopropyl)-5-nitro-1H-indol-3-yl]-3-(5-nitro-1H-indol-3-yl)-maleinimide;
2-[1-(3-ethylaminopropyl)-5-methylthio-1H-indol-3-yl]-3-(5-methylthio-1H-indol-3-yl)-maleinimide;
2-[1-(3-ethylaminopropyl)-4,5-dimethoxy-1H-indol-3-yl]-3-(4,5-dimethoxy-1H-indol-3-yl)-maleinimide;
2-[1-(3-ethylaminopropyl)-5,6-dimethoxy-1H-indol-3-yl]-3-(5,6-dimethoxy-1H-indol-3-yl)-maleinimide;
(±)-2-[5-acetylamino-1-(2-hydroxy-3-dimethylaminopropyl)-1H-indol-3-yl]-3-(5-acetylamino-1H-indol-3-yl)-maleinimide;
(±)-2-[5-amino-1-(2-hydroxy-3-dimethylaminopropyl)-1H-indol-3-yl]-3-(5-amino-1H-indol-3-yl)-maleinimide;
(±)-2-[5-benzyloxy-1-(2-hydroxy-3-dimethylaminopropyl)-1H-indol-3-yl]-3-(5-benzyloxy-1H-indol-3-yl)-maleinimide;
(±)-2-[5-bromo-1-(2-hydroxy-3-dimethylaminopropyl)-1H-indol-3-yl]-3-(5-bromo-1H-indol-3-yl)-maleinimide;
(±)-2-[5-chloro-1-(2-hydroxy-3-dimethylaminopropyl)-1H-indol-3-yl]-3-(5-chloro-1H-indol-3-yl)-maleinimide;
(±)-2-[5-fluoro-1-(2-hydroxy-3-dimethylaminopropyl)-1H-indol-3-yl]-3-(5-fluoro-1H-indol-3-yl)-maleinimide;
(±)-2-[5-hydroxy-1-(2-hydroxy-3-dimethylaminopropyl)-1H-indol-3-yl]-3-(5-hydroxy-1H-indol-3-yl)-maleinimide;
(±)-2-[5-trifluoromethyl-1-(2-hydroxy-3-dimethylaminopropyl)-1H-indol-3-yl]-3-(5-trifluoromethyl-1H-indol-3-yl)-maleinimide;
(±)-2-[1-(2-hydroxy-3-dimethylaminopropyl)-5-methoxy-1H-indol-3-yl]-3-(5-methoxy-1H-indol-3-yl)-maleinimide;
(±)-2-[1-(2-hydroxy-3-dimethylaminopropyl)-4,5-methylendioxy-1H-indol-3-yl]-3-(4,5-methylendioxy-1H-indol-3-yl)-maleinimide;
(±)-2-[1-(2-hydroxy-3-dimethylaminopropyl)-5,6-methylendioxy-1H-indol-3-yl]-3-(5,6-methylendioxy-1H-indol-3-yl)-maleinimide;
(±)-2-[1-(2-hydroxy-3-dimethylaminopropyl)-5-methyl-1H-indol-3-yl]-3-(5-methyl-1H-indol-3-yl)-maleinimide;
(±)-2-[1-(2-hydroxy-3-dimethylaminopropyl)-5-nitro-1H-indol-3-yl]-3-(5-nitro-1H-indol-3-yl)-maleinimide;
(±)-2-[1-(2-hydroxy-3-dimethylaminopropyl)-5-methylthio-1H-indol-3-yl]-3-(5-methylthio-1H-indol-3-yl)-maleinimide;
(±)-2-[1-(2-hydroxy-3-dimethylaminopropyl)-4,5-dimethoxy-1H-indol-3-yl]-3-(4,5-dimethoxy-1H-indol-3-yl)-maleinimide;
(±)-2-[1-(2-hydroxy-3-dimethylaminopropyl)-5,6-dimethoxy-1H-indol-3-yl]-3-(5,6-dimethoxy-1H-indol-3-yl)-maleinimide;
(+)-2-[5-acetylamino-1-(2-hydroxy-3-dimethylaminopropyl)-1H-indol-3-yl]-3-(5-acetylamino-1H-indol-3-yl)-maleinimide;
(+)-2-[5-amino-1-(2-hydroxy-3-dimethylaminopropyl)-1H-indol-3-yl]-3-(5-amino-1H-indol-3-yl)-maleinimide;
(+)-2-[5-benzyloxy-1-(2-hydroxy-3-dimethylaminopropyl)-1H-indol-3-yl]-3-(5-benzyloxy-1H-indol-3-yl)-maleinimide;
(+)-2-[5-bromo-1-(2-hydroxy-3-dimethylaminopropyl)-1H-indol-3-yl]-3-(5-bromo-1H-indol-3-yl)-maleinimide;
(+)-2-[5-chloro-1-(2-hydroxy-3-dimethylaminopropyl)-1H-indol-3-yl]-3-(5-chloro-1H-indol-3-yl)-maleinimide;
(+)-2-[5-fluoro-1-(2-hydroxy-3-dimethylaminopropyl)-1H-indol-3-yl]-3-(5-fluoro-1H-indol-3-yl)-maleinimide;
(+)-2-[5-hydroxy-1-(2-hydroxy-3-dimethylaminopropyl)-1H-indol-3-yl]-3-(5-hydroxy-1H-indol-3-yl)-maleinimide;
(+)-2-[5-trifluoromethyl-1-(2-hydroxy-3-dimethylaminopropyl)-1H-indol-3-yl]-3-(5-trifluoromethyl-1H-indol-3-yl)-maleinimide;
(+)-2-[1-(2-hydroxy-3-dimethylaminopropyl)-5-methoxy-1H-indol-3-yl]-3-(5-methoxy-1H-indol-3-yl)-maleinimide;
(+)-2-[1-(2-hydroxy-3-dimethylaminopropyl)-4,5-methylendioxy-1H-indol-3-yl]-3-(4,5-methylendioxy-1H-indol-3-yl)-maleinimide;
(+)-2-[1-(2-hydroxy-3-dimethylaminopropyl)-5,6-methylendioxy-1H-indol-3-yl]-3-(5,6-methylendioxy-1H-indol-3-yl)-maleinimide;
(+)-2-[1-(2-hydroxy-3-dimethylaminopropyl)-5-methyl-1H-indol-3-yl]-3-(5-methyl-1H-indol-3-yl)-maleinimide;
(+)-2-[1-(2-hydroxy-3-dimethylaminopropyl)-5-nitro-1H-indol-3-yl]-3-(5-nitro-1H-indol-3-yl)-maleinimide;
(+)-2-[1-(2-hydroxy-3-dimethylaminopropyl)-5-methylthio-1H-indol-3-yl]-3-(5-methylthio-1H-indol-3-yl)-maleinimide;
(+)-2-[1-(2-hydroxy-3-dimethylaminopropyl)-4,5-dimethoxy-1H-indol-3-yl]-3-(4,5-dimethoxy-1H-indol-3-yl)-maleinimide;
(+)-2-[1-(2-hydroxy-3-dimethylaminopropyl)-5,6-dimethoxy-1H-indol-3-yl]-3-(5,6-dimethoxy-1H-indol-3-yl)-maleinimide;
(−)-2-[5-acetylamino-1-(2-hydroxy-3-dimethylaminopropyl)-1H-indol-3-yl]-3-(5-acetylamino-1H-indol-3-yl)-maleinimide;
(−)-2-[5-amino-1-(2-hydroxy-3-dimethylaminopropyl)-1H-indol-3-yl]-3-(5-amino-1H-indol-3-yl)-maleinimide;
(−)-2-[5-benzyloxy-1-(2-hydroxy-3-dimethylaminopropyl)-1H-indol-3-yl]-3-(5-benzyloxy-1H-indol-3-yl)-maleinimide;
(−)-2-[5-bromo-1-(2-hydroxy-3-dimethylaminopropyl)-1H-indol-3-yl]-3-(5-bromo-1H-indol-3-yl)-maleinimide;
(−)-2-[5-chloro-1-(2-hydroxy-3-dimethylaminopropyl)-1H-indol-3-yl]-3-(5-chloro-1H-indol-3-yl)-maleinimide;
(−)-2-[5-fluoro-1-(2-hydroxy-3-dimethylaminopropyl)-1H-indol-3-yl]-3-(5-fluoro-1H-indol-3-yl)-maleinimide;
(−)-2-[5-hydroxy-1-(2-hydroxy-3-dimethylaminopropyl)-1H-indol-3-yl]-3-(5-hydroxy-1H-indol-3-yl)-maleinimide;
(−)-2-[5-trifluoromethyl-1-(2-hydroxy-3-dimethylaminopropyl)-1H-indol-3-yl]-3-(5-trifluoromethyl-1H-indol-3-yl)-maleinimide;

(−)-2-[1-(2-hydroxy-3-dimethylaminopropyl)-5-methoxy-1H-indol-3-yl]-3-(5-methoxy-1H-indol-3-yl)-maleinimide;

(−)-2-[1-(2-hydroxy-3-dimethylaminopropyl)-4,5-methylendioxy-1H-indol-3-yl]-3-(4,5-methylendioxy-1H-indol-3-yl)-maleinimide;

(−)-2-[1-(2-hydroxy-3-dimethylaminopropyl)-5,6-methylendioxy-1H-indol-3-yl]-3-(5,6-methylendioxy-1H-indol-3-yl)-maleinimide;

(−)-2-[1-(2-hydroxy-3-dimethylaminopropyl)-5-methyl-1H-indol-3-yl]-3-(5-methyl-1H-indol-3-yl)-maleinimide;

(−)-2-[1-(2-hydroxy-3-dimethylaminopropyl)-5-nitro-1H-indol-3-yl]-3-(5-nitro-1H-indol-3-yl)-maleinimide;

(−)-2-[1-(2-hydroxy-3-dimethylaminopropyl)-5-methylthio-1H-indol-3-yl]-3-(5-methylthio-1H-indol-3-yl)-maleinimide;

(−)-2-[1-(2-hydroxy-3-dimethylaminopropyl)-4,5-dimethoxy-1H-indol-3-yl]-3-(4,5-dimethoxy-1H-indol-3-yl)-maleinimide;

(−)-2-[1-(2-hydroxy-3-dimethylaminopropyl)-5,6-dimethoxy-1H-indol-3-yl]-3-(5,6-dimethoxy-1H-indol-3-yl)-maleinimide;

(±)-2-[5-acetylamino-1-(2-hydroxy-3-(4-morpholino)propyl)-1H-indol-3-yl]-3-(5-acetylamino-1H-indol-3-yl)-maleinimide;

(±)-2-[5-amino-1-(2-hydroxy-3-(4-morpholino)propyl)-1H-indol-3-yl]-3-(5-amino-1H-indol-3-yl)-maleinimide;

(±)-2-[5-benzyloxy-1-(2-hydroxy-3-(4-morpholino)propyl)-1H-indol-3-yl]-3-(5-benzyloxy-1H-indol-3-yl)-maleinimide;

(±)-2-[5-bromo-1-(2-hydroxy-3-(4-morpholino)propyl)-1H-indol-3-yl]-3-(5-bromo-1H-indol-3-yl)-maleinimide;

(±)-2-[5-chloro-1-(2-hydroxy-3-(4-morpholino)propyl)-1H-indol-3-yl]-3-(5-chloro-1H-indol-3-yl)-maleinimide;

(±)-2-[5-fluoro-1-(2-hydroxy-3-(4-morpholino)propyl)-1H-indol-3-yl]-3-(5-fluoro-1H-indol-3-yl)-maleinimide;

(±)-2-[5-hydroxy-1-(2-hydroxy-3-(4-morpholinopropyl)-1H-indol-3-yl]-3-(5-hydroxy-1H-indol-3-yl)-maleinimide;

(±)-2-[5-trifluoromethyl-1-(2-hydroxy-3-(4-morpholino)propyl)-1H-indol-3-yl]-3-(5-trifluoromethyl-1H-indol-3-yl)-maleinimide;

(±)-2-[1-(2-hydroxy-3-(4-morpholino)propyl)-5-methoxy-1H-indol-3-yl]-3-(5-methoxy-1H-indol-3-yl)-maleinimide;

(±)-2-[1-(2-hydroxy-3-(4-morpholino)propyl)-4,5-methylendioxy-1H-indol-3-yl]-3-(4,5-methylendioxy-1H-indol-3-yl)-maleinimide;

(±)-2-[1-(2-hydroxy-3-(4-morpholino)propyl)-5,6-methylendioxy-1H-indol-3-yl]-3-(5,6-methylendioxy-1H-indol-3-yl)-maleinimide;

(±)-2-[1-(2-hydroxy-3-(4-morpholinopropyl)-5-methyl-1H-indol-3-yl]-3-(5-methyl-1H-indol-3-yl)-maleinimide;

(±)-2-[1-(2-hydroxy-3-(4-morpholino)propyl)-5-nitro-1H-indol-3-yl]-3-(5-nitro-1H-indol-3-yl)-maleinimide;

(±)-2-[1-(2-hydroxy-3-(4-morpholino)propyl)-5-methylthio-1H-indol-3-yl]-3-(5-methylthio-1H-indol-3-yl)-maleinimide;

(±)-2-[1-(2-hydroxy-3-(4-morpholino)propyl)-4,5-dimethoxy-1H-indol-3-yl]-3-(4,5-dimethoxy-1H-indol-3-yl)-maleinimide;

(±)-2-[1-(2-hydroxy-3-(4-morpholino)propyl)-5,6-dimethoxy-1H-indol-3-yl]-3-(5,6-dimethoxy-1H-indol-3-yl)-maleinimide;

(+)-2-[5-acetylamino-1-(2-hydroxy-3-(4-morpholino)propyl)-1H-indol-3-yl]-3-(5-acetylamino-1H-indol-3-yl)-maleinimide;

(+)-2-[5-amino-1-(2-hydroxy-3-(4-morpholino)propyl)-1H-indol-3-yl]-3-(5-amino-1H-indol-3-yl)-maleinimide;

(+)-2-[5-benzyloxy-1-(2-hydroxy-3-(4-morpholino)propyl)-1H-indol-3-yl]-3-(5-benzyloxy-1H-indol-3-yl)-maleinimide;

(+)-2-[5-bromo-1-(2-hydroxy-3-(4-morpholino)propyl)-1H-indol-3-yl]-3-(5-bromo-1H-indol-3-yl)-maleinimide;

(+)-2-[5-chloro-1-(2-hydroxy-3-(4-morpholino)propyl)-1H-indol-3-yl]-3-(5-chloro-1H-indol-3-yl)-maleinimide;

(+)-2-[5-fluoro-1-(2-hydroxy-3-(4-morpholino)propyl)-1H-indol-3-yl]-3-(5-fluoro-1H-indol-3-yl)-maleinimide;

(+)-2-[5-hydroxy-1-(2-hydroxy-3-(4-morpholino)propyl)-1H-indol-3-yl]-3-(5-hydroxy-1H-indol-3-yl)-maleinimide;

(+)-2-[5-trifluoromethyl-1-(2-hydroxy-3-(4-morpholino)propyl)-1H-indol-3-yl]-3-(5-trifluoromethyl-1H-indol-3-yl)-maleinimide;

(+)-2-[1-(2-hydroxy-3-(4-morpholino)propyl)-5-methoxy-1H-indol-3-yl]-3-(5-methoxy-1H-indol-3-yl)-maleinimide;

(+)-2-[1-(2-hydroxy-3-(4-morpholino)propyl)-4,5-methylendioxy-1H-indol-3-yl]-3-(4,5-methylendioxy-1H-indol-3-yl)-maleinimide;

(+)-2-[1-(2-hydroxy-3-(4-morpholino)propyl)-5,6-methylendioxy-1H-indol-3-yl]-3-(5,6-methylendioxy-1H-indol-3-yl)-maleinimide;

(+)-2-[1-(2-hydroxy-3-(4-morpholino)propyl)-5-methyl-1H-indol-3-yl]-3-(5-methyl -1H-indol-3-yl)-maleinimide;

(+)-2-[1-(2-hydroxy-3-(4-morpholino)propyl)-5-nitro-1H-indol-3-yl]-3-(5-nitro-1H-indol-3-yl)-maleinimide;

(+)-2-[1-(2-hydroxy-3-(4-morpholino)propyl)-5-methylthio-1H-indol-3-yl]-3-(5-methylthio-1H-indol-3-yl)-maleinimide;

(+)-2-[1-(2-hydroxy-3-(4-morpholino)propyl)-4,5-dimethoxy-1H-indol-3-yl]-3-(4,5-dimethoxy-1H-indol-3-yl)-maleinimide;

(+)-2-[1-(2-hydroxy-3-(4-morpholino)propyl)-5,6-dimethoxy-1H-indol-3-yl]-3-(5,6-dimethoxy-1H-indol-3-yl)-maleinimide;

(−)-2-[5-acetylamino-1-(2-hydroxy-3-(4-morpholino)propyl)-1H-indol-3-yl]-3-(5-acetylamino-1H-indol-3-yl)-maleinimide;

(−)-2-[5-amino-1-(2-hydroxy-3-(4-morpholino)propyl)-1H-indol-3-yl]-3-(5-amino-1H-indol-3-yl)-maleinimide;

(−)-2-[5-benzyloxy-1-(2-hydroxy-3-(4-morpholino)propyl)-1H-indol-3-yl]-3-(5-benzyloxy-1H-indol-3-yl)-maleinimide;

(−)-2-[5-bromo-1-(2-hydroxy-3-(4-morpholino)propyl)-1H-indol-3-yl]-3-(5-bromo-1H-indol-3-yl)-maleinimide;

(−)-2-[5-chloro-1-(2-hydroxy-3-(4-morpholino)propyl)-1H-indol-3-yl]-3-(5-chloro-1H-indol-3-yl)-maleinimide;

(−)-2-[5-fluoro-1-(2-hydroxy-3-(4-morpholino)propyl)-1H-indol-3-yl]-3-(5-fluoro-1H-indol-3-yl)-maleinimide;

(−)-2-[5-hydroxy-1-(2-hydroxy-3-(4-morpholino-propyl)-1H-indol-3-yl]-3-(5-hydroxy-1H-indol-3-yl)-maleinimide;
(−)-2-[5-trifluoromethyl-1-(2-hydroxy-3-(4-morpholino)propyl)-1H-indol-3-yl]-3-(5-trifluoromethyl-1H-indol-3-yl)-maleinimide;
(−)-2-[1-(2-hydroxy-3-(4-morpholino)propyl)-5-methoxy-1H-indol-3-yl]-3-(5-methoxy-1H-indol-3-yl)-maleinimide;
(−)-2-[1-(2-hydroxy-3-(4-morpholino)propyl)-4,5-methylendioxy-1H-indol-3-yl]-3-(4,5-methylendioxy-1H-indol-3-yl)-maleinimide;
(−)-2-[1-(2-hydroxy-3-(4-morpholino)propyl)-5,6-methylendioxy-1H-indol-3-yl]-3-(5,6-methylendioxy-1H-indol-3-yl)-maleinimide;
(−)-2-[1-(2-hydroxy-3-(4-morpholino)propyl)-5-methyl-1H-indol-3-yl]-3-(5-methyl-1H-indol-3-yl)-maleinimide;
(−)-2-[1-(2-hydroxy-3-(4-morpholino)propyl)-5-nitro-1H-indol-3-yl]-3-(5-nitro-1H-indol-3-yl)-maleinimide;
(−)-2-[1-(2-hydroxy-3-(4-morpholino)propyl)-5-methylthio-1H-indol-3-yl]-3-(5-methylthio-1H-indol-3-yl)-maleinimide;
(−)-2-[1-(2-hydroxy-3-(4-morpholinopropyl)-4,5-dimethoxy-1H-indol-3-yl]-3-(4,5-dimethoxy-1H-indol-3-yl)-maleinimide;
(−)-2-[1-(2-hydroxy-3-(4-morpholinopropyl)-5,6-dimethoxy-1H-indol-3-yl]-3-(5,6-dimethoxy-1H-indol-3-yl)-maleinimide;
(±)-2-[5-acetylamino-1-(2-hydroxy-3-(1-piperidino)propyl)-1H-indol-3-yl]-3-(5-acetylamino-1H-indol-3-yl)-maleinimide;
(±)-2-[5-amino-1-(2-hydroxy-3-(1-piperidino)propyl)-1H-indol-3-yl]-3-(5-amino-1H-indol-3-yl)-maleinimide;
(±)-2-[5-benzyloxy-1-(2-hydroxy-3-(1-piperidino)propyl)-1H-indol-3-yl]-3-(5-benzyloxy-1H-indol-3-yl)-maleinimide;
(±)-2-[5-bromo-1-(2-hydroxy-3-(1-piperidino)propyl)-1H-indol-3-yl]-3-(5-bromo-1H-indol-3-yl)-maleinimide;
(±)-2-[5-chloro-1-(2-hydroxy-3-(1-piperidino)propyl)-1H-indol-3-yl]-3-(5-chloro-1H-indol-3-yl)-maleinimide;
(±)-2-[5-fluoro-1-(2-hydroxy-3-(1-piperidino)propyl)-1H-indol-3-yl]-3-(5-fluoro-1H-indol-3-yl)-maleinimide;
(±)-2-[5-hydroxy-1-(2-hydroxy-3-(1-piperidino)propyl)-1H-indol-3-yl]-3-(5-hydroxy-1H-indol-3-yl)-maleinimide;
(±)-2-[5-trifluoromethyl-1-(2-hydroxy-3-(1-piperidino)propyl)-1H-indol-3-yl]-3-(5-trifluoromethyl-1H-indol-3-yl)-maleinimide;
(±)-2-[1-(2-hydroxy-3-(1-piperidino)propyl)-5-methoxy-1H-indol-3-yl]-3-(5-methoxy-1H-indol-3-yl)-maleinimide;
(±)-2-[1-(2-hydroxy-3-(1-piperidino)propyl)-4,5-methylendioxy-1H-indol-3-yl]-3-(4,5-methylendioxy-1H-indol-3-yl)-maleinimide;
(±)-2-[1-(2-hydroxy-3-(1-piperidino)propyl)-5,6-methylendioxy-1H-indol-3-yl]-3-(5,6-methylendioxy-1H-indol-3-yl)-maleinimide;
(±)-2-[1-(2-hydroxy-3-(1-piperidino)propyl)-5-methyl-1H-indol-3-yl]-3-(5-methyl-1H-indol-3-yl)-maleinimide;
(±)-2-[1-(2-hydroxy-3-(1-piperidino)propyl)-5-nitro-1H-indol-3-yl]-3-(5-nitro-1H-indol-3-yl)-maleinimide;
(±)-2-[1-(2-hydroxy-3-(1-piperidino)propyl)-5-methylthio-1H-indol-3-yl]-3-(5-methylthio-1H-indol-3-yl)-maleinimide;
(±)-2-[1-(2-hydroxy-3-(1-piperidino)propyl)-4,5-dimethoxy-1H-indol-3-yl]-3-(4,5-dimethoxy-1H-indol-3-yl)-maleinimide;
(±)-2-[1-(2-hydroxy-3-(1-piperidino)propyl)-5,6-dimethoxy-1H-indol-3-yl]-3-(5,6-dimethoxy-1H-indol-3-yl)-maleinimide;
(+)-2-[5-acetylamino-1-(2-hydroxy-3-(1-piperidino)propyl)-1H-indol-3-yl]-3-(5-acetylamino-1H-indol-3-yl)-maleinimide;
(+)-2-[5-amino-1-(2-hydroxy-3-(1-piperidino)propyl)-1H-indol-3-yl]-3-(5-amino-1H-indol-3-yl)-maleinimide;
(+)-2-[5-benzyloxy-1-(2-hydroxy-3-(1-piperidino)propyl)-1H-indol-3-yl]-3-(5-benzyloxy-1H-indol-3-yl)-maleinimide;
(+)-2-[5-bromo-1-(2-hydroxy-3-(1-piperidino)propyl)-1H-indol-3-yl]-3-(5-bromo-1H-indol-3-yl)-maleinimide;
(+)-2-[5-chloro-1-(2-hydroxy-3-(1-piperidino)propyl)-1H-indol-3-yl]-3-(5-chloro-1H-indol-3-yl)-maleinimide;
(+)-2-[5-fluoro-1-(2-hydroxy-3-(1-piperidino)propyl)-1H-indol-3-yl]-3-(5-fluoro-1H-indol-3-yl)-maleinimide;
(+)-2-[5-hydroxy-1-(2-hydroxy-3-(1-piperidino)propyl)-1H-indol-3-yl]-3-(5-hydroxy-1H-indol-3-yl)-maleinimide;
(+)-2-[5-trifluoromethyl-1-(2-hydroxy-3-(1-piperidino)propyl)-1H-indol-3-yl]-3-(5-trifluoromethyl-1H-indol-3-yl)-maleinimide;
(+)-2-[1-(2-hydroxy-3-(1-piperidino)propyl)-5-methoxy-1H-indol-3-yl]-3-(5-methoxy-1H-indol-3-yl)-maleinimide;
(+)-2-[1-(2-hydroxy-3-(1-piperidino)propyl)-4,5-methylendioxy-1H-indol-3-yl]-3-(4,5-methylendioxy-1H-indol-3-yl)-maleinimide;
(+)-2-[1-(2-hydroxy-3-(1-piperidino)propyl)-5,6-methylendioxy-1H-indol-3-yl]-3-(5,6-methylendioxy-1H-indol-3-yl)-maleinimide;
(+)-2-[1-(2-hydroxy-3-(1-piperidino)propyl)-5-methyl-1H-indol-3-yl]-3-(5-methyl-1H-indol-3-yl)-maleinimide;
(+)-2-[1-(2-hydroxy-3-(1-piperidino)propyl)-5-nitro-1H-indol-3-yl]-3-(5-nitro-1H-indol-3-yl)-maleinimide;
(+)-2-[1-(2-hydroxy-3-(1-piperidino)propyl)-5-methylthio-1H-indol-3-yl]-3-(5-methylthio-1H-indol-3-yl)-maleinimide;
(+)-2-[1-(2-hydroxy-3-(1-piperidino)propyl)-4,5-dimethoxy-1H-indol-3-yl]-3-(4,5-dimethoxy-1H-indol-3-yl)-maleinimide;
(+)-2-[1-(2-hydroxy-3-(1-piperidino)propyl)-5,6-dimethoxy-1H-indol-3-yl]-3-(5,6-dimethoxy-1H-indol-3-yl)-maleinimide;
(−)-2-[5-acetylamino-1-(2-hydroxy-3-(1-piperidino)propyl)-1H-indol-3-yl]-3-(5-acetylamino-1H-indol-3-yl)-maleinimide;
(−)-2-[5-amino-1-(2-hydroxy-3-(1-piperidino)propyl)-1H-indol-3-yl]-3-(5-amino-1H-indol-3-yl)-maleinimide;
(−)-2-[5-benzyloxy-1-(2-hydroxy-3-(1-piperidino)propyl)-1H-indol-3-yl]-3-(5-benzyloxy-1H-indol-3-yl)-maleinimide;
(−)-2-[5-bromo-1-(2-hydroxy-3-(1-piperidino)propyl)-1H-indol-3-yl]-3-(5-bromo-1H-indol-3-yl)-maleinimide;

(−)-2-[5-chloro-1-(2-hydroxy-3-(1-piperidino)propyl)-1H-indol-3-yl]-3-(5-chloro-1H-indol-3-yl)-maleinimide;
(−)-2-[5-fluoro-1-(2-hydroxy-3-(1-piperidino)propyl)-1H-indol-3-yl]-3-(5-fluoro-1H-indol-3-yl)-maleinimide;
(−)-2-[5-hydroxy-1-(2-hydroxy-3-(1-piperidino)propyl)-1H-indol-3-yl]-3-(5-hydroxy-1H-indol-3-yl)-maleinimide;
(−)-2-[5-trifluoromethyl-1-(2-hydroxy-3-(1-piperidino)propyl)-1H-indol-3-yl]-3-(5-trifluoromethyl-1H-indol-3-yl)-maleinimide;
(−)-2-[1-(2-hydroxy-3-(1-piperidino)propyl)-5-methoxy-1H-indol-3-yl]-3-(5-methoxy-1H-indol-3-yl)-maleinimide;
(−)-2-[1-(2-hydroxy-3-(1-piperidino)propyl)-6-methoxy-1H-indol-3-yl]-3-(1H-indol-3-yl)-maleinimide;
(−)-2-[1-(2-hydroxy-3-(1-piperidino)propyl)-4,5-methylendioxy-1H-indol-3-yl]-3-(4,5-methylendioxy-1H-indol-3-yl)-maleinimide;
(−)-2-[1-(2-hydroxy-3-(1-piperidino)propyl)-5,6-methylendioxy-1H-indol-3-yl]-3-(5,6-methylendioxy-1H-indol-3-yl)-maleinimide;
(−)-2-[1-(2-hydroxy-3-(1-piperidino)propyl)-5-methyl-1H-indol-3-yl]-3-(5-methyl-1H-indol-3-yl)-maleinimide;
(−)-2-[1-(2-hydroxy-3-(1-piperidino)propyl)-5-nitro-1H-indol-3-yl]-3-(5-nitro-1H-indol-3-yl)-maleinimide;
(−)-2-[1-(2-hydroxy-3-(1-piperidino)propyl)-5-methylthio-1H-indol-3-yl]-3-(5-methylthio-1H-indol-3-yl)-maleinimide;
(−)-2-[1-(2-hydroxy-3-(1-piperidino)propyl)-4,5-dimethoxy-1H-indol-3-yl]-3-(4,5-dimethoxy-1H-indol-3-yl)-maleinimide;
(−)-2-[1-(2-hydroxy-3-(1-piperidino)propyl)-5,6-dimethoxy-1H-indol-3-yl]-3-(5,6-dimethoxy-1H-indol-3-yl)-maleinimide;
(±)-2-[5-acetylamino-1-(2,3-dihydroxypropyl)-1H-indol-3-yl]-3-(5-acetylamino-1H-indol-3-yl)-maleinimide;
(±)-2-[5-amino-1-(2,3-dihydroxypropyl)-1H-indol-3-yl]-3-(5-amino-1H-indol-3-yl)-maleinimide;
(±)-2-[5-benzyloxy-1-(2,3-dihydroxypropyl)-1H-indol-3-yl]-3-(5-benzyloxy-1H-indol-3-yl)-maleinimide;
(±)-2-[5-bromo-1-(2,3-dihydroxypropyl)-1H-indol-3-yl]-3-(5-bromo-1H-indol-3-yl)-maleinimide;
(±)-2-[5-chloro-1-(2,3-dihydroxypropyl)-1H-indol-3-yl]-3-(5-chloro-1H-indol-3-yl)-maleinimide;
(±)-2-[5-fluoro-1-(2,3-dihydroxypropyl)-1H-indol-3-yl]-3-(5-fluoro-1H-indol-3-yl)-maleinimide;
(±)-2-[5-hydroxy-1-(2,3-dihydroxypropyl)-1H-indol-3-yl]-3-(5-hydroxy-1H-indol-3-yl)-maleinimide;
(±)-2-[5-trifluoromethyl-1-(2,3-dihydroxypropyl)-1H-indol-3-yl]-3-(5-trifluoromethyl-1H-indol-3-yl)-maleinimide;
(±)-2-[1-(2,3-dihydroxypropyl)-5-methoxy-1H-indol-3-yl]-3-(5-methoxy-1H-indol-3-yl)-maleinimide;
(±)-2-[1-(2,3-dihydroxypropyl)-4,5-methylendioxy-1H-indol-3-yl]-3-(4,5-methylendioxy-1H-indol-3-yl)-maleinimide;
(±)-2-[1-(2,3-dihydroxypropyl)-5,6-methylendioxy-1H-indol-3-yl]-3-(5,6-methylendioxy-1H-indol-3-yl)-maleinimide;
(±)-2-[1-(2,3-dihydroxypropyl)-5-methyl-1H-indol-3-yl]-3-(5-methyl-1H-indol-3-yl)-maleinimide;
(±)-2-[1-(2,3-dihydroxypropyl)-5-nitro-1H-indol-3-yl]-3-(5-nitro-1H-indol-3-yl)-maleinimide;
(±)-2-[1-(2,3-dihydroxypropyl)-5-methylthio-1H-indol-3-yl]-3-(5-methylthio-1H-indol-3-yl)-maleinimide;
(±)-2-[1-(2,3-dihydroxypropyl)-4,5-dimethoxy-1H-indol-3-yl]-3-(4,5-dimethoxy-1H-indol-3-yl)-maleinimide;
(±)-2-[1-(2,3-dihydroxypropyl)-5,6-dimethoxy-1H-indol-3-yl]-3-(5,6-dimethoxy-1H-indol-3-yl)-maleinimide;
(+)-2-[5-acetylamino-1-(2,3-dihydroxypropyl)-1H-indol-3-yl]-3-(5-acetylamino-1H-indol-3-yl)-maleinimide;
(+)-2-[5-amino-1-(2,3-dihydroxypropyl)-1H-indol-3-yl]-3-(5-amino-1H-indol-3-yl)-maleinimide;
(+)-2-[5-benzyloxy-1-(2,3-dihydroxypropyl)-1H-indol-3-yl]-3-(5-benzyloxy-1H-indol-3-yl)-maleinimide;
(+)-2-[5-bromo-1-(2,3-dihydroxypropyl)-1H-indol-3-yl]-3-(5-bromo-1H-indol-3-yl)-maleinimide;
(+)-2-[5-chloro-1-(2,3-dihydroxypropyl)-1H-indol-3-yl]-3-(5-chloro-1H-indol-3-yl)-maleinimide;
(+)-2-[5-fluoro-1-(2,3-dihydroxypropyl)-1H-indol-3-yl]-3-(5-fluoro-1H-indol-3-yl)-maleinimide;
(+)-2-[5-hydroxy-1-(2,3-dihydroxypropyl)-1H-indol-3-yl]-3-(5-hydroxy-1H-indol-3-yl)-maleinimide;
(+)-2-[5-trifluoromethyl-1-(2,3-dihydroxypropyl)-1H-indol-3-yl]-3-(5-trifluoromethyl-1H-indol-3-yl)-maleinimide;
(+)-2-[1-(2,3-dihydroxypropyl)-5-methoxy-1H-indol-3-yl]-3-(5-methoxy-1H-indol-3-yl)-maleinimide;
(+)-2-[1-(2,3-dihydroxypropyl)-4,5-methylendioxy-1H-indol-3-yl]-3-(4,5-methylendioxy-1H-indol-3-yl)-maleinimide;
(+)-2-[1-(2,3-dihydroxypropyl)-5,6-methylendioxy-1H-indol-3-yl]-3-(5,6-methylendioxy-1H-indol-3-yl)-maleinimide;
(+)-2-[1-(2,3-dihydroxypropyl)-5-methyl-1H-indol-3-yl]-3-(5-methyl-1H-indol-3-yl)-maleinimide;
(+)-2-[1-(2,3-dihydroxypropyl)-5-nitro-1H-indol-3-yl]-3-(5-nitro-1H-indol-3-yl)-maleinimide;
(+)-2-[1-(2,3-dihydroxypropyl)-5-methylthio-1H-indol-3-yl]-3-(5-methylthio-1H-indol-3-yl)-maleinimide;
(+)-2-[1-(2,3-dihydroxypropyl)-4,5-dimethoxy-1H-indol-3-yl]-3-(4,5-dimethoxy-1H-indol-3-yl)-maleinimide;
(+)-2-[1-(2,3-dihydroxypropyl)-5,6-dimethoxy-1H-indol-3-yl]-3-(5,6-dimethoxy-1H-indol-3-yl)-maleinimide;
(−)-2-[5-acetylamino-1-(2,3-dihydroxypropyl)-1H-indol-3-yl]-3-(5-acetyl amino-1H-indol-3-yl)-maleinimide;
(−)-2-[5-amino-1-(2,3-dihydroxypropyl)-1H-indol-3-yl]-3-(5-amino-1H-indol-3-yl)-maleinimide;
(−)-2-[5-benzyloxy-1-(2,3-dihydroxypropyl)-1H-indol-3-yl]-3-(5-benzyloxy-1H-indol-3-yl)-maleinimide;
(−)-2-[5-bromo-1-(2,3-dihydroxypropyl)-1H-indol-3-yl-3-(5-bromo-1H-indol-3-yl)-maleinimide;
(−)-2-[5-chloro-1-(2,3-dihydroxypropyl)-1H-indol-3-yl]-3-(5-chloro-1H-indol-3-yl)-maleinimide;
(−)-2-[5-fluoro-1-(2,3-dihydroxypropyl)-1H-indol-3-yl]-3-(5-fluoro-1H-indol-3-yl)-maleinimide;
(−)-2-[5-hydroxy-1-(2,3-dihydroxypropyl)-1H-indol-3-yl]-3-(5-hydroxy-1H-indol-3-yl)-maleinimide;
(−)-2-[5-trifluoromethyl-1-(2,3-dihydroxypropyl)-1H-indol-3-yl]-3-(5-trifluoromethyl-1H-indol-3-yl)-maleinimide;
(−)-2-[1-(2,3-dihydroxypropyl)-5-methoxy-1H-indol-3-yl]-3-(5-methoxy-1H-indol-3-yl)-maleinimide;

(−)-2-[1-(2,3-dihydroxypropyl)-4,5-methylendioxy-1H-indol-3-yl]-3-(4,5-methylendioxy-1H-indol-3-yl)-maleinimide;
(−)-2-[1-(2,3-dihydroxypropyl)-5,6-methylendioxy-1H-indol-3-yl]-3-(5,6-methylendioxy-1H-indol-3-yl)-maleinimide;
(−)-2-[1-(2,3-dihydroxypropyl)-5-methyl-1H-indol-3-yl]-3-(5-methyl-1H-indol-3-yl)-maleinimide;
(−)-2-[1-(2,3-dihydroxypropyl)-5-nitro-1H-indol-3-yl]-3-(5-nitro-1H-indol-3-yl)-maleinimide;
(−)-2-[1-(2,3-dihydroxypropyl)-5-methylthio-1H-indol-3-yl]-3-(5-methylthio-1H-indol-3-yl)-maleinimide;
(−)-2-[1-(2,3-dihydroxypropyl)-4,5-dimethoxy-1H-indol-3-yl]-3-(4,5-dimethoxy-1H-indol-3-yl)-maleinimide;
(−)-2-[1-(2,3-dihydroxypropyl)-5,6-dimethoxy-1H-indol-3-yl]-3-(5,6-dimethoxy-1H-indol-3-yl)-maleinimide;
2-[5-acetylamino-1-(3-hydroxypropyl)-1H-indol-3-yl]-3-(5-acetylamino-1H-indol-3-yl)-maleinimide;
2-[5-amino-1-(3-hydroxypropyl)-1H-indol-3-yl]-3-(5-amino-1H-indol-3-yl)-maleinimide;
2-[5-benzyloxy-1-(3-hydroxypropyl)-1H-indol-3-yl]-3-(5-benzyloxy-1H-indol-3-yl)-maleinimide;
2-[5-bromo-1-(3-hydroxypropyl)-1H-indol-3-yl]-3-(5-bromo-1H-indol-3-yl)-maleinimide;
2-[5-chloro-1-(3-hydroxypropyl)-1H-indol-3-yl]-3-(5-chloro-1H-indol-3-yl)-maleinimide;
2-[5-fluoro-1-(3-hydroxypropyl)-1H-indol-3-yl]-3-(5-fluoro-1H-indol-3-yl)-maleinimide;
2-[5-hydroxy-1-(3-hydroxypropyl)-1H-indol-3-yl]-3-(5-hydroxy-1H-indol-3-yl)-maleinimide;
2-[5-trifluoromethyl-1-(3-hydroxypropyl)-5-trifluoromethyl-1H-indol-3-yl]-3-(5-trifluoromethyl-1H-indol-3-yl)-maleinimide;
2-[1-(3-hydroxypropyl)-5-methoxy-1H-indol-3-yl]-3-(5-methoxy-1H-indol-3-yl)-maleinimide;
2-[1-(3-hydroxypropyl)-4,5-methylendioxy-1H-indol-3-yl]-3-(4,5-methylendioxy-1H-indol-3-yl)-maleinimide;
2-[1-(3-hydroxypropyl)-5,6-methylendioxy-1H-indol-3-yl]-3-(5,6-methylendioxy-1H-indol-3-yl)-maleinimide;
2-[1-(3-hydroxypropyl)-5-methyl-1H-indol-3-yl]-3-(5-methyl-1H-indol-3-yl)-maleinimide;
2-[1-(3-hydroxypropyl)-5-nitro-1H-indol-3-yl]-3-(5-nitro-1H-indol-3-yl)-maleinimide;
2-[1-(3-hydroxypropyl)-5-methylthio-1H-indol-3-yl]-3-(5-methylthio-1H-indol-3-yl)-maleinimide;
2-[1-(3-hydroxypropyl)-4,5-dimethoxy-1H-indol-3-yl]-3-(4,5-dimethoxy-1H-indol-3-yl)-maleinimide;
2-[1-(3-hydroxypropyl)-5,6-dimethoxy-1H-indol-3-yl]-3-(5,6-dimethoxy-1H-indol-3-yl)-maleinimide;
2-(5-acetylamino-1H-indol-3-yl)-3-[5-acetylamino-1-(3-isothiocyanatopropyl)-1H-indol-3-yl]-maleinimide;
2-(5-amino-1H-indol-3-yl)-3-[5-amino-1-(3-isothiocyanatopropyl)-1H-indol-3-yl]-maleinimide;
2-(5-benzyloxy-1H-indol-3-yl)-3-[5-benzyloxy-1-(3-isothiocyanatopropyl)-1H-indol-3-yl]-maleinimide;
2-(5-bromo-1H-indol-3-yl)-3-[5-bromo-1-(3-isothiocyanatopropyl)-1H-indol-3-yl]-maleinimide;
2-(5-chloro-1H-indol-3-yl)-3-[5-chloro-1-(3-isothiocyanatopropyl)-1H-indol-3-yl]-maleinimide;
2-(5-fluoro-1H-indol-3-yl)-3-[5-fluoro-1-(3-isothiocyanatopropyl)-1H-indol-3-yl]-maleinimide;
2-(5-hydroxy-1H-indol-3-yl)-3-[5-hydroxy-1-(3-isothiocyanatopropyl)-1H-indol-3-yl]-maleinimide;
2-(5-trifluoromethyl-1H-indol-3-yl)-3-[5-trifluoromethyl-1-(3-isothiocyanatopropyl)-1H-indol-3-yl]-maleinimide;
2-[1-(3-isothiocyanatopropyl)-5-methoxy-1H-indol-3-yl]-3-(5-methoxy-1H-indol-3-yl)-maleinimide;
2-[1-(3-isothiocyanatopropyl)-4,5-methylendioxy-1H-indol-3-yl]-3-(4,5-methylendioxy-1H-indol-3-yl)-maleinimide;
2-[1-(3-isothiocyanatopropyl)-5,6-methylendioxy-1H-indol-3-yl]-3-(5,6-methylendioxy-1H-indol-3-yl)-maleinimide;
2-[1-(3-isothiocyanatopropyl)-5-methyl-1H-indol-3-yl]-3-(5-methyl-1H-indol-3-yl)-maleinimide;
2-[1-(3-isothiocyanatopropyl)-5-nitro-1H-indol-3-yl]-3-(5-nitro-1H-indol-3-yl)-maleinimide;
2-[1-(3-isothiocyanatopropyl)-5-methylthio-1H-indol-3-yl]-3-(5-methylthio-1H-indol-3-yl)-maleinimide;
2-[1-(3-isothiocyanatopropyl)-4,5-dimethoxy-1H-indol-3-yl]-3-(4,5-dimethoxy-1H-indol-3-yl)-maleinimide;
2-[1-(3-isothiocyanatopropyl)-5,6-dimethoxy-1H-indol-3-yl]-3-(5,6-dimethoxy-1H-indol-3-yl)-maleinimide;
(±)-2-(5-acetylamino-1H-indol-3-yl)-3-[5-acetylamino-1-(2-methoxy-3-dimethylaminopropyl)-1H-indol-3-yl]-maleinimide;
(±)-2-(5-amino-1H-indol-3-yl)-3-[5-amino-1-(2-methoxy-3-dimethylaminopropyl)-1H-indol-3-yl]-maleinimide;
(±)-2-(5-benzyloxy-1H-indol-3-yl)-3-[5-benzyloxy-1-(2-methoxy-3-dimethylaminopropyl)-1H-indol-3-yl]-maleinimide;
(±)-2-(5-bromo-1H-indol-3-yl)-3-[5-bromo-1-(2-methoxy-3-dimethylaminopropyl)-1H-indol-3-yl]-maleinimide;
(±)-2-(5-chloro-1H-indol-3-yl)-3-[5-chloro-1-(2-methoxy-3-dimethylaminopropyl)-1H-indol-3-yl]-maleinimide;
(±)-2-(5-fluoro-1H-indol-3-yl)-3-[5-fluoro-1-(2-methoxy-3-dimethylaminopropyl)-1H-indol-3-yl]-maleinimide;
(±)-2-(5-hydroxy-1H-indol-3-yl)-3-[5-hydroxy-1-(2-methoxy-3-dimethylaminopropyl)-1H-indol-3-yl]-maleinimide;
(±)-2-(5-trifluoromethyl-1H-indol-3-yl)-3-[5-trifluoromethyl-1-(2-methoxy-3-dimethylaminopropyl)-1H-indol-3-yl]-maleinimide;
(±)-2-(5-methoxy-1H-indol-3-yl)-3-[5-methoxy-1-(2-methoxy-3-dimethylaminopropyl)-1H-indol-3-yl]-maleinimide;
(±)-2-[1-(2-methoxy-3-dimethylaminopropyl)-4,5-methylendioxy-1H-indol-3-yl]-3-(4,5-methylendioxy-1H-indol-3-yl)-maleinimide;
(±)-2-[1-(2-methoxy-3-dimethylaminopropyl)-5,6-methylendioxy-1H-indol-3-yl]-3-(5,6-methylendioxy-1H-indol-3-yl)-maleinimide;
(±)-2-[1-(2-methoxy-3-dimethylaminopropyl)-5-methyl-1H-indol-3-yl]-3-(5-methyl-1H-indol-3-yl)-maleinimide;
(±)-2-[1-(2-methoxy-3-dimethylaminopropyl)-5-nitro-1H-indol-3-yl]-3-(5-nitro-1H-indol-3-yl)-maleinimide;
(±)-2-[1-(2-methoxy-3-dimethylaminopropyl)-5-methylthio-1H-indol-3-yl]-3-(5-methylthio-1H-indol-3-yl)-maleinimide;
(±)-2-(4,5-dimethoxy-1H-indol-3-yl)-3-[4,5-dimethoxy-1-(2-methoxy-3-dimethylaminopropyl)-1H-indol-3-yl]-maleinimide;
(±)-2-(5,6-dimethoxy-1H-indol-3-yl)-3-[5,6-dimethoxy-1-(2-methoxy-3-dimethylaminopropyl)-1H-indol-3-yl]-maleinimide;

(+)-2-(5-acetylamino-1H-indol-3-yl)-3-[5-acetylamino-1-(2-methoxy-3-dimethylaminopropyl)-1H-indol-3-yl]-maleinimide;
(+)-2-(5-amino-1H-indol-3-yl)-3-[5-amino-1-(2-methoxy-3-dimethylaminopropyl)-1H-indol-3-yl]-maleinimide;
(+)-2-(5-benzyloxy-1H-indol-3-yl)-3-[5-benzyloxy-1-(2-methoxy-3-dimethylaminopropyl)-1H-indol-3-yl]-maleinimide;
(+)-2-(5-bromo-1H-indol-3-yl)-3-[5-bromo-1-(2-methoxy-3-dimethylaminopropyl)-1H-indol-3-yl]-maleinimide;
(+)-2-(5-chloro-1H-indol-3-yl)-3-[5-chloro-1-(2-methoxy-3-dimethylaminopropyl)-1H-indol-3-yl]-maleinimide;
(+)-2-(5-fluoro-1H-indol-3-yl)-3-[5-fluoro-1-(2-methoxy-3-dimethylaminopropyl)-1H-indol-3-yl]-maleinimide;
(+)-2-(5-hydroxy-1H-indol-3-yl)-3-[5-hydroxy-1-(2-methoxy-3-dimethylaminopropyl)-1H-indol-3-yl]-maleinimide;
(+)-2-(5-trifluoromethyl-1H-indol-3-yl)-3-[5-trifluoromethyl-1-(2-methoxy-3-dimethylaminopropyl)-1H-indol-3-yl]-maleinimide;
(+)-2-(5-methoxy-1H-indol-3-yl)-3-[5-methoxy-1-(2-methoxy-3-dimethylaminopropyl)-1H-indol-3-yl]-maleinimide;
(+)-2-[1-(2-methoxy-3-dimethylaminopropyl)-4,5-methylendioxy-1H-indol-3-yl]-3-(4,5-methylendioxy-1H-indol-3-yl)-maleinimide;
(+)-2-[1-(2-methoxy-3-dimethylaminopropyl)-5,6-methylendioxy-1H-indol-3-yl]-3-(5,6-methylendioxy-1H-indol-3-yl)-maleinimide;
(+)-2-[1-(2-methoxy-3-dimethylaminopropyl)-5-methyl-1H-indol-3-yl]-3-(5-methyl-1H-indol-3-yl)-maleinimide;
(+)-2-[1-(2-methoxy-3-dimethylaminopropyl)-5-nitro-1H-indol-3-yl]-3-(5-nitro-1H-indol-3-yl)-maleinimide;
(+)-2-[1-(2-methoxy-3-dimethylaminopropyl)-5-methylthio-1H-indol-3-yl]-3-(5-methylthio-1H-indol-3-yl)-maleinimide;
(+)-2-(4,5-dimethoxy-1H-indol-3-yl)-3-[4,5-dimethoxy-1-(2-methoxy-3-dimethylaminopropyl)-1H-indol-3-yl]-maleinimide;
(+)-2-(5,6-dimethoxy-1H-indol-3-yl)-3-[5,6-dimethoxy-1-(2-methoxy-3-dimethylaminopropyl)-1H-indol-3-yl]-maleinimide;
(−)-2-(5-acetylamino-1H-indol-3-yl)-3-[5-acetylamino-1-(2-methoxy-3-dimethylaminopropyl)-1H-indol-3-yl]-maleinimide;
(−)-2-(5-amino-1H-indol-3-yl)-3-[5-amino-1-(2-methoxy-3-dimethylaminopropyl)-1H-indol-3-yl]-maleinimide;
(−)-2-(5-benzyloxy-1H-indol-3-yl)-3-[5-benzyloxy-1-(2-methoxy-3-dimethylaminopropyl)-1H-indol-3-yl]-maleinimide;
(−)-2-(5-bromo-1H-indol-3-yl)-3-[5-bromo-1-(2-methoxy-3-dimethylaminopropyl)-1H-indol-3-yl]-maleinimide;
(−)-2-(5-chloro-1H-indol-3-yl)-3-[5-chloro-1-(2-methoxy-3-dimethylaminopropyl)-1H-indol-3-yl]-maleinimide;
(−)-2-(5-fluoro-1H-indol-3-yl)-3-[5-fluoro-1-(2-methoxy-3-dimethylaminopropyl)-1H-indol-3-yl]-maleinimide;
(−)-2-(5-hydroxy-1H-indol-3-yl)-3-[5-hydroxy-1-(2-methoxy-3-dimethylaminopropyl)-1H-indol-3-yl]-maleinimide;
(−)-2-(5-trifluoromethyl-1H-indol-3-yl)-3-[5-trifluoromethyl-1-(2-methoxy-3-dimethylaminopropyl)-1H-indol-3-yl]-maleinimide;
(−)-2-(5-methoxy-1H-indol-3-yl)-3-[5-methoxy-1-(2-methoxy-3-dimethylaminopropyl)-1H-indol-3-yl]-maleinimide;
(−)-2-[1-(2-methoxy-3-dimethylaminopropyl)-4,5-methylendioxy-1H-indol-3-yl]-3-(4,5-methylendioxy-1H-indol-3-yl)-maleinimide;
(−)-2-[1-(2-methoxy-3-dimethylaminopropyl)-5,6-methylendioxy-1H-indol-3-yl]-3-(5,6-methylendioxy-1H-indol-3-yl)-maleinimide;
(−)-2-[1-(2-methoxy-3-dimethylaminopropyl)-5-methyl-1H-indol-3-yl]-3-(5-methyl-1H-indol-3-yl)-maleinimide;
(−)-2-[1-(2-methoxy-3-dimethylaminopropyl)-5-nitro-1H-indol-3-yl]-3-(5-nitro-1H-indol-3-yl)-maleinimide;
(−)-2-[1-(2-methoxy-3-dimethylaminopropyl)-5-methylthio-1H-indol-3-yl]-3-(5-methylthio-1H-indol-3-yl)-maleinimide;
(−)-2-(4,5-dimethoxy-1H-indol-3-yl)-3-[4,5-dimethoxy-1-(2-methoxy-3-dimethylaminopropyl)-1H-indol-3-yl]-maleinimide;
(−)-2-(5,6-dimethoxy-1H-indol-3-yl)-3-[5,6-dimethoxy-1-(2-methoxy-3-dimethylaminopropyl)-1H-indol-3-yl]-maleinimide;
2-(5-acetylamino-1H-indol-3-yl)-3-[5-acetylamino-1-(2-dimethylaminoethyl)-1H-indol-3-yl]-maleinimide;
2-(5-amino-1H-indol-3-yl)-3-[5-amino-1-(2-dimethylaminoethyl)-1H-indol-3-yl]-maleinimide;
2-(5-benzyloxy-1H-indol-3-yl)-3-[5-benzyloxy-1-(2-dimethylaminoethyl)-1H-indol-3-yl]-maleinimide;
2-(5-bromo-1H-indol-3-yl)-3-[5-bromo-1-(2-dimethylaminoethyl)-1H-indol-3-yl]-maleinimide;
2-(5-chloro-1H-indol-3-yl)-3-[5-chloro-1-(2-dimethylaminoethyl)-1H-indol-3-yl]-maleinimide;
2-(5-fluoro-1H-indol-3-yl)-3-[5-fluoro-1-(2-dimethylaminoethyl)-1H-indol-3-yl]-maleinimide;
2-(5-hydroxy-1H-indol-3-yl)-3-[5-hydroxy-1-(2-dimethylaminoethyl)-1H-indol-3-yl]-maleinimide;
2-(5-trifluoromethyl-1H-indol-3-yl)-3-[5-trifluoromethyl-1-(2-dimethylaminoethyl)-1H-indol-3-yl]-maleinimide;
2-(5-methoxy-1H-indol-3-yl)-3-[5-methoxy-1-(2-dimethylaminoethyl)-1H-indol-3-yl]-maleinimide;
2-[1-(2-dimethylaminoethyl)-4,5-methylendioxy-1H-indol-3-yl]-3-(4,5-methylendioxy-1H-indol-3-yl)-maleinimide;
2-[1-(2-dimethylaminoethyl)-5,6-methylendioxy-1H-indol-3-yl]-3-(5,6-methylendioxy-1H-indol-3-yl)-maleinimide;
2-(5-methyl-1H-indol-3-yl)-3-[5-methyl-1-(2-dimethylaminoethyl)-1H-indol-3-yl]-maleinimide;
2-[1-(2-dimethylaminoethyl)-5-nitro-1H-indol-3-yl]-3-(5-nitro-1H-indol-3-yl)-maleinimide;
2-[1-(2-dimethylaminoethyl)-5-methylthio-1H-indol-3-yl]-3-(5-methylthio-1H-indol-3-yl)-maleinimide;
2-(4,5-dimethoxy-1H-indol-3-yl)-3-[4,5-dimethoxy-1-(2-dimethylaminoethyl)-1H-indol-3-yl]-maleinimide;
2-(5,6-dimethoxy-1H-indol-3-yl)-3-[5,6-dimethoxy-1-(2-dimethylaminoethyl)-1H-indol-3-yl]-maleinimide;
2-(5-acetylamino-1H-indol-3-yl)-3-[5-acetylamino-1-(3-dimethylaminopropyl)-1H-indol-3-yl]-maleinimide;
2-(5-amino-1H-indol-3-yl)-3-[5-amino-1-(3-dimethylaminopropyl)-1H-indol-3-yl]-maleinimide;
2-(5-benzyloxy-1H-indol-3-yl)-3-[5-benzyloxy-1-(3-dimethylaminopropyl)-1H-indol-3-yl]-maleinimide;

2-(5-bromo-1H-indol-3-yl)-3-[5-bromo-1-(3-dimethylaminopropyl)-1H-indol-3-yl]-maleinimide;
2-(5-chloro-1H-indol-3-yl)-3-[5-chloro-1-(3-dimethylaminopropyl)-1H-indol-3-yl]-maleinimide;
2-(5-fluoro-1H-indol-3-yl)-3-[5-fluoro-1-(3-dimethylaminopropyl)-1H-indol-3-yl]-maleinimide;
2-(5-hydroxy-1H-indol-3-yl)-3-[5-hydroxy-1-(3-dimethylaminopropyl)-1H-indol-3-yl]-maleinimide;
2-(5-trifluoromethyl-1H-indol-3-yl)-3-[5-trifluoromethyl-1-(3-dimethylaminopropyl)-1H-indol-3-yl]-maleinimide;
2-(5-methoxy-1H-indol-3-yl)-3-[5-methoxy-1-(3-dimethylaminopropyl)-1H-indol-3-yl]-maleinimide;
2-[1-(3-dimethylaminopropyl)-4,5-methylendioxy-1H-indol-3-yl]-3-(4,5-methylendioxy-1H-indol-3-yl)-maleinimide;
2-[1-(3-dimethylaminopropyl)-5,6-methylendioxy-1H-indol-3-yl]-3-(5,6-methylendioxy-1H-indol-3-yl)-maleinimide;
2-(5-methyl-1H-indol-3-yl)-3-[5-methyl-1-(3-dimethylaminopropyl)-1H-indol-3-yl]-maleinimide;
2-[1-(3-dimethylaminopropyl)-5-nitro-1H-indol-3-yl]-3-(5-nitro-1H-indol-3-yl)-maleinimide;
2-[1-(3-dimethylaminopropyl)-5-methylthio-1H-indol-3-yl]-3-(5-methylthio-1H-indol-3-yl)-maleinimide;
2-(4,5-dimethoxy-1H-indol-3-yl)-3-[4,5-dimethoxy-1-(3-dimethylaminopropyl)-1H-indol-3-yl]-maleinimide;
2-(5,6-dimethoxy-1H-indol-3-yl)-3-[5,6-dimethoxy-1-(3-dimethylaminopropyl)-1H-indol-3-yl]-maleinimide;
2-(5-acetylamino-1H-indol-3-yl)-3-[5-acetylamino-1-(3-methylaminopropyl)-1H-indol-3-yl]-maleinimide;
2-(5-amino-1H-indol-3-yl)-3-[5-amino-1-(3methylaminopropyl)-1H-indol-3-yl]-maleinimide;
2-(5-benzyloxy-1H-indol-3-yl)-3-[5-benzyloxy-1-(3-methylaminopropyl)-1H-indol-3-yl]-maleinimide;
2-(5-bromo-1H-indol-3-yl)-3-[5-bromo-1-(3-methylaminopropyl)-1H-indol-3-yl]-maleinimide;
2-(5-chloro-1H-indol-3-yl)-3-[5-chloro-1-(3methylaminopropyl)-1H-indol-3-yl]-maleinimide;
2-(5-fluoro-1H-indol-3-yl)-3-[5-fluoro-1-(3-methylaminopropyl)-1H-indol-3-yl]-maleinimide;
2-(5-hydroxy-1H-indol-3-yl)-3-[5-hydroxy-1-(3-methylaminopropyl)-1H-indol-3-yl]-maleinimide;
2-(5-trifluoromethyl-1H-indol-3-yl)-3-[5-trifluoromethyl-1-(3-methylaminopropyl)-1H-indol-3-yl]-maleinimide;
2-(5-methoxy-1H-indol-3-yl)-3-[5-methoxy-1-(3-methylaminopropyl)-1H-indol-3-yl]-maleinimide;
2-[1-(3-methylaminopropyl)-4,5-methylendioxy-1H-indol-3-yl]-3-(4,5-methylendioxy-1H-indol-3-yl)-maleinimide;
2-[1-(3-methylaminopropyl)-5,6-methylendioxy-1H-indol-3-yl]-3-(5,6-methylendioxy-1H-indol-3-yl)-maleinimide;
2-(5-methyl-1H-indol-3-yl)-3-[5-methyl-1-(3-methylaminopropyl)-1H-indol-3-yl]-maleinimide;
2-[1-(3-methylaminopropyl)-5-nitro-1H-indol-3-yl]-3-(5-nitro-1H-indol-3-yl)-maleinimide;
2-[1-(3-methylaminopropyl)-5-methylthio-1H-indol-3-yl]-3-(5-methylthio-1H-indol-3-yl)-maleinimide;
2-(4,5-dimethoxy-1H-indol-3-yl)-3-[5,6-dimethoxy-1-(3-methylaminopropyl)-1H-indol-3-yl]-maleinimide;
2-(5,6-dimethoxy-1H-indol-3-yl)-3-[5,6-dimethoxy-1-(3-methylaminopropyl)-1H-indol-3-yl]-maleinimide;
2-(5-acetylamino-1H-indol-3-yl)-3-[5-acetylamino-1-(3-4-morpholino)propyl)-1H-indol-3-yl]-maleinimide;
2-(5-amino-1H-indol-3-yl)-3-[5-amino-1-(3-(4-morpholino)propyl)-1H-indol-3-yl]-maleinimide;
2-(5-benzyloxy-1H-indol-3-yl)-3-[5-benzyloxy-1-(3-(4-morpholino)propyl)-1H-indol-3-yl]-maleinimide;
2-(5-bromo-1H-indol-3-yl)-3-[5-bromo-1-(3-(4-morpholino)propyl)-1H-indol-3-yl]-maleinimide;
2-(5-chloro-1H-indol-3-yl)-3-[5-chloro-1-(3-(4-morpholino)propyl)-1H-indol-3-yl]-maleinimide;
2-(5-fluoro-1H-indol-3-yl)-3-[5-fluoro-1-(3-(4-morpholino)propyl)-1H-indol-3-yl]-maleinimide;
2-(5-hydroxy-1H-indol-3-yl)-3-[5-hydroxy-1-(3-(4-morpholino)propyl)-1H-indol-3-yl]-maleinimide;
2-(5-trifluoromethyl-1H-indol-3-yl)-3-[5-trifluoromethyl-1-(3-(4-morpholino)propyl)-1H-indol-3-yl]-maleinimide;
2-(4,5-methylendioxy-1H-indol-3-yl)-3-[4,5-methylendioxy-1-(3-(4-morpholino)propyl)-1H-indol-3-yl]-maleinimide;
2-(5,6-methylendioxy-1H-indol-3-yl)-3-[5,6-methylendioxy-1-(3-(4-morpholino)propyl)-1H-indol-3-yl]-maleinimide;
2-(5-methyl-1H-indol-3-yl)-3-[5-methyl-1-(3-(4-morpholino)propyl)-1H-indol-3-yl]-maleinimide;
2-[1-(3-(4-morpholino)propyl)-5-nitro-1H-indol-3-yl]-3-(5-nitro-1H-indol-3-yl)-maleinimide;
2-(5-methylthio-1H-indol-3-yl)-3-[5-methylthio-1-(3-(4-morpholino)propyl)-1H-indol-3-yl]-maleinimide;
2-(4,5-dimethoxy-1H-indol-3-yl)-3-[4,5-dimethoxy-1-(3-(4-morpholino)propyl)-1H-indol-3-yl]-maleinimide;
2-(5,6-dimethoxy-1H-indol-3-yl)-3-[5,6-dimethoxy-1-(3-(4-morpholino)propyl)-1H-indol-3-yl]-maleinimide;
2-(5-acetylamino-1H-indol-3-yl)-3-[5-acetyl amino-1-(3-(2-nitroguanidino)propyl)-1H-indol-3-yl]-maleinimide;
2-(5-amino-1H-indol-3-yl)-3-[5-amino-1-(3-(2-nitroguanidino)propyl)-1H-indol-3-yl]-maleinimide;
2-(5-benzyloxy-1H-indol-3-yl)-3-[5-benzyloxy-1-(3-(2-nitroguanidino)propyl)-1H-indol-3-yl]-maleinimide;
2-(5-bromo-1H-indol-3-yl)-3-[5-bromo-1-(3-(2-nitroguanidino)propyl)-1H-indol-3-yl]-maleinimide;
2-(5-chloro-1H-indol-3-yl)-3-[5-chloro-1-(3-(2-nitroguanidino)propyl)-1H-indol-3-yl]-maleinimide;
2-(5-fluoro-1H-indol-3-yl)-3-[5-fluoro-1-(3-(2-nitroguanidino)propyl)-1H-indol-3-yl]-maleinimide;
2-(5-hydroxy-1H-indol-3-yl)-3-[5-hydroxy-1-(3-(2-nitroguanidino)propyl)-1H-indol-3-yl]-maleinimide;
2-(5-trifluoromethyl-1H-indol-3-yl)-3-[5-trifluoromethyl-1-(3-(2-nitroguanidino)propyl)-1H-indol-3-yl]-maleinimide;
2-(5-methoxy-1H-indol-3-yl)-3-[5-methoxy-1-(3-(2-nitroguanidino)propyl)-1H-indol-3-yl]-maleinimide;
2-(4,5-methylendioxy-1H-indol-3-yl)-3-[4,5-methylendioxy-1-(3-(2-nitroguanidino)propyl)-1H-indol-3-yl]-maleinimide;
2-(5,6-methylendioxy-1H-indol-3-yl)-3-[5,6-methylendioxy-1-(3-(2-nitroguanidino)propyl)-1H-indol-3-yl]-maleinimide;
2-(5-methyl-1H-indol-3-yl)-3-[5-methyl-1-(3-(2-nitroguanidino)propyl)-1H-indol-3-yl]-maleinimide;
2-(5-nitro-1H-indol-3-yl)-3-[5-nitro-1-(3-(2-nitroguanidino)propyl)-1H-indol-3-yl]-maleinimide;
2-(5-methylthio-1H-indol-3-yl)-3-[5-methylthio-1-(3-(2-nitroguanidino)propyl)-1H-indol-3-yl]-maleinimide;
2-(4,5-dimethoxy-1H-indol-3-yl)-3-[4,5-dimethoxy-1-(3-(2-nitroguanidino)propyl)-1H-indol-3-yl]-maleinimide;
2-(5,6-dimethoxy-1H-indol-3-yl)-3-[5,6-dimethoxy-1-(3-(2-nitroguanidino)propyl)-1H-indol-3-yl]-maleinimide;

2-(5-acetylamino-1H-indol-3-yl)-3-[5-acetylamino-1-(3-(1-piperidino)propyl)-1H-indol-3-yl]-maleinimide;
2-(5-amino-1H-indol-3-yl)-3-[5-amino-1-(3-(1-piperidino)propyl)-1H-indol-3-yl]-maleinimide;
2-(5-benzyloxy-1H-indol-3-yl)-3-[5-benzyloxy-1-(3-(1-piperidino)propyl)-1H-indol-3-yl]-maleinimide;
2-(5-bromo-1H-indol-3-yl)-3-[5-bromo-1-(3-(1-piperidino)propyl)-1H-indol-3-yl]-maleinimide;
2-(5-chloro-1H-indol-3-yl)-3-[5-chloro-1-(3-(1-piperidino)propyl)-1H-indol-3-yl]-maleinimide;
2-(5-fluoro-1H-indol-3-yl)-3-[5-fluoro-1-(3-(1-piperidino)propyl)-1H-indol-3-yl]-maleinimide;
2-(5-hydroxy-1H-indol-3-yl)-3-[5-hydroxy-1-(3-(1-piperidino)propyl)-1H-indol-3-yl]-maleinimide;
2-(5-trifluoromethyl-1H-indol-3-yl)-3-[5-trifluoromethyl-1-(3-(1-piperidino)propyl)-1H-indol-3-yl]-maleinimide;
2-(5-methoxy-1H-indol-3-yl)-3-[5-methoxy-1-(3-(1-piperidino)propyl)-1H-indol-3-yl]-maleinimide;
2-(4,5-methylendioxy-1H-indol-3-yl)-3-[4,5-methylendioxy-1-(3-(1-piperidino)propyl)-1H-indol-3-yl]-maleinimide;
2-(5,6-methylendioxy-1H-indol-3-yl)-3-[5,6-methylendioxy-1-(3-(1-piperidino)propyl)-1H-indol-3-yl]-maleinimide;
2-(5-methyl-1H-indol-3-yl)-3-[5-methyl-1-(3-(1-piperidino)propyl)-1H-indol-3-yl]-maleinimide;
2-(5-nitro-1H-indol-3-yl)-3-[5-nitro-1-(3-(1-piperidino)propyl)-1H-indol-3-yl]-maleinimide;
2-(5-methylthio-1H-indol-3-yl)-3-[5-methylthio-1-(3-(1-piperidino)propyl)-1H-indol-3-yl]-maleinimide;
2-(4,5-dimethoxy-1H-indol-3-yl)-3-[4,5-dimethoxy-1-(3-(1-piperidino)propyl)-1H-indol-3-yl]-maleinimide;
2-(5,6-dimethoxy-1H-indol-3-yl)-3-[5,6-dimethoxy-1-(3-(1-piperidino)propyl)-1H-indol-3-yl]-maleinimide;
2-[1-(3-(amidinothio)propyl)-4-dimethylamino-1H-indol-3-yl]-3-(1H-indol-3-yl)-maleinimide;
2-[1-(3-(amidinothio)propyl)-5-dimethylamino-1H-indol-3-yl]-3-(1H-indol-3-yl)-maleinimide;
2-[1-(3-(amidinothio)propyl)-6-dimethylamino-1H-indol-3-yl]-3-(1H-indol-3-yl)-maleinimide;
2-[1-(3-(amidinothio)propyl)-7-dimethylamino-1H-indol-3-yl]-3-(1H-indol-3-yl)-maleinimide;
2-[1-(2-aminoethyl)-4-dimethylamino-1H-indol-3-yl]-3-(1H-indol-3-yl)-maleinimide;
2-[1-(2-aminoethyl)-5-dimethylamino-1H-indol-3-yl]-3-(1H-indol-3-yl)-maleinimide;
2-[1-(2-aminoethyl)-6-dimethylamino-1H-indol-3-yl]-3-(1H-indol-3-yl)-maleinimide;
2-[1-(2-aminoethyl)-7-dimethylamino-1H-indol-3-yl]-3-(1H-indol-3-yl)-maleinimide;
2-[1-(3-aminopropyl)-4-dimethylamino-1H-indol-3-yl]-3-(1H-indol-3-yl)-maleinimide;
2-[1-(3-aminopropyl)-5-dimethylamino-1H-indol-3-yl]-3-(1H-indol-3-yl)-maleinimide;
2-[1-(3-aminopropyl)-6-dimethylamino-1H-indol-3-yl]-3-(1H-indol-3-yl)-maleinimide;
2-[1-(3-aminopropyl)-7-dimethylamino-1H-indol-3-yl]-3-(1H-indol-3-yl)-maleinimide;
(±)-2-[1-(3-ethoxy-2-hydroxypropyl)-4-dimethylamino-1H-indol-3-yl]-3-(1H-indol-3-yl)-maleinimide;
(±)-2-[1-(3-ethoxy-2-hydroxypropyl)-5-dimethylamino-1H-indol-3-yl]-3-(1H-indol-3-yl)-maleinimide;
(±)-2-[1-(3-ethoxy-2-hydroxypropyl)-6-dimethylamino-1H-indol-3-yl]-3-(1H-indol-3-yl)-maleinimide;
(±)-2-[1-(3-ethoxy-2-hydroxypropyl)-7-dimethylamino-1H-indol-3-yl]-3-(1H-indol-3-yl)-maleinimide;
2-[1-(2-diethylaminoethyl)-4-dimethylamino-1H-indol-3-yl]-3-(1H-indol-3-yl)-maleinimide;
2-[1-(2-diethylaminoethyl)-5-dimethylamino-1H-indol-3-yl]-3-(1H-indol-3-yl)-maleinimide;
2-[1-(2-diethylaminoethyl)-6-dimethylamino-1H-indol-3-yl]-3-(1H-indol-3-yl)-maleinimide;
2-[1-(2-diethylaminoethyl)-7-dimethylamino-1H-indol-3-yl]-3-(1H-indol-3-yl)-maleinimide;
(±)-2-[1-(3-diethylamino-2-hydroxypropyl)-4-dimethylamino-1H-indol-3-yl]-3-(1H-indol-3-yl)-maleinimide;
(±)-2-[1-(3-diethylamino-2-hydroxypropyl)-5-dimethylamino-1H-indol-3-yl]-3-(1H-indol-3-yl)-maleinimide;
(±)-2-[1-(3-diethylamino-2-hydroxypropyl)-6-dimethylamino-1H-indol-3-yl]-3-(1H-indol-3-yl)-maleinimide;
(±)-2-[1-(3-diethylamino-2-hydroxypropyl)-7-dimethylamino-1H-indol-3-yl]-3-(1H-indol-3-yl)-maleinimide;
2-[1-(3-ethylaminopropyl)-4-dimethylamino-1H-indol-3-yl]-3-(1H-indol-3-yl)-maleinimide;
2-[1-(3-ethylaminopropyl)-5-dimethylamino-1H-indol-3-yl]-3-(1H-indol-3-yl)-maleinimide;
2-[1-(3-ethyl aminopropyl)-6-dimethylamino -1H-indol-3-yl]-3-(1H-indol-3-yl)-maleinimide;
2-[1-(3-ethylaminopropyl)-7-dimethylamino-1H-indol-3-yl]-3-(1H-indol-3-yl)-maleinimide;
(±)-2-[1-(2-hydroxy-3-dimethylaminopropyl)-4-dimethylamino-1H-indol-3-yl]-3-(1H-indol-3-yl)-maleinimide;
(±)-2-[1-(2-hydroxy-3-dimethylaminopropyl)-5-dimethylamino-1H-indol-3-yl]-3-(1H-indol-3-yl)-maleinimide;
(±)-2-[1-(2-hydroxy-3-dimethylaminopropyl)-6-dimethylamino-1H-indol-3-yl]-3-(1H-indol-3-yl)-maleinimide;
(±)-2-[1-(2-hydroxy-3-dimethylaminopropyl)-7-dimethylamino-1H-indol-3-yl]-3-(1H-indol-3-yl)-maleinimide;
(±)-2-[1-(2-hydroxy-3-(4-morpholino)propyl)-4-dimethylamino-1H-indol-3-yl]-3-(1H-indol-3-yl)-maleinimide;
(±)-2-[1-(2-hydroxy-3-(4-morpholino)propyl)-5-dimethylamino-1H-indol-3-yl]-3-(1H-indol-3-yl)-maleinimide;
(±)-2-[1-(2-hydroxy-3-(4-morpholino)propyl)-6-dimethylamino-1H-indol-3-yl]-3-(1H-indol-3-yl)-maleinimide;
(±)-2-[1-(2-hydroxy-3-(4-morpholino)propyl)-7-dimethylamino-1H-indol-3-yl]-3-(1H-indol-3-yl)-maleinimide;
(±)-2-[1-(2-hydroxy-3-(1-piperidino)propyl)-4-dimethylamino-1H-indol-3-yl]-3-(1H-indol-3-yl)-maleinimide;
(±)-2-[1-(2-hydroxy-3-(1-piperidino)propyl)-5-dimethylamino-1H-indol-3-yl]-3-(1H-indol-3-yl)-maleinimide;
(±)-2-[1-(2-hydroxy-3-(1-piperidino)propyl)-6-dimethylamino-1H-indol-3-yl]-3-(1H-indol-3-yl)-maleinimide;
(±)-2-[1-(2-hydroxy-3-(1-piperidino)propyl)-7-dimethylamino-1H-indol-3-yl]-3-(1H-indol-3-yl)-maleinimide;

(±)-2-[1-(2,3-dihydroxypropyl)-4-dimethylamino-1H-indol-3-yl]-3-(1H-indol-3-yl)-maleinimide;
(±)-2-[1-(2,3-dihydroxypropyl)-5-dimethylamino-1H-indol-3-yl]-3-(1H-indol-3-yl)-maleinimide;
(±)-2-[1-(2,3-dihydroxypropyl)-6-dimethylamino-1H-indol-3-yl]-3-(1H-indol-3-yl)-maleinimide;
(±)-2-[1-(2,3-dihydroxypropyl)-7-dimethylamino-1H-indol-3-yl]-3-(1H-indol-3-yl)-maleinimide;
2-[1-(3-hydroxypropyl)-4-dimethylamino-1H-indol-3-yl]-3-(1H-indol-3-yl)-maleinimide;
2-[1-(3-hydroxypropyl)-5-dimethylamino-1H-indol-3-yl-3-(1H-indol-3-yl)-maleinimide;
2-[1-(3-hydroxypropyl)-6-dimethylamino-1H-indol-3-yl]-3-(1H-indol-3-yl)-maleinimide;
2-[1-(3-hydroxypropyl)-7-dimethylamino-1H-indol-3-yl]-3-(1H-indol-3-yl)-maleinimide;
2-(1H-indol-3-yl)-3-[1-(3-isothiocyanatopropyl)-4-dimethylamino-1H-indol-3-yl]-maleinimide;
2-(1H-indol-3-yl)-3-[1-(3-isothiocyanatopropyl)-5-dimethylamino-1H-indol-3-yl]-maleinimide;
2-(1H-indol-3-yl)-3-[1-(3-isothiocyanatopropyl)-6-dimethylamino-1H-indol-3-yl]-maleinimide;
2-(1H-indol-3-yl)-3-[1-(3-isothiocyanatopropyl)-7-dimethylamino-1H-indol-3-yl]-maleinimide;
(±)-2-(1H-indol-3-yl)-3-[1-(2-methoxy-3-dimethylaminopropyl)-4-dimethylamino-1H-indol-3-yl]-maleinimide;
(±)-2-(1H-indol-3-yl)-3-[1-(2-methoxy-3-dimethylaminopropyl)-5-dimethylamino-1H-indol-3-yl]-maleinimide;
(±)-2-(1H-indol-3-yl)-3-[1-(2-methoxy-3-dimethylaminopropyl)-6-dimethylamino-1H-indol-3-yl]-maleinimide;
(±)-2-(1H-indol-3-yl)-3-[1-(2-methoxy-3-dimethylaminopropyl)-7-dimethylamino-1H-indol-3-yl]-maleinimide;
2-(1H-indol-3-yl)-3-[4-dimethylamino-1-(2-dimethylaminoethyl)-1H-indol-3-yl]-maleinimide;
2-(1H-indol-3-yl)-3-[5-dimethylamino-1-(2-dimethylaminoethyl)-1H-indol-3-yl]-maleinimide;
2-(1H-indol-3-yl)-3-[6-dimethylamino-1-(2-dimethylaminoethyl)-1H-indol-3-yl]-maleinimide;
2-(1H-indol-3-yl)-3-[7-dimethylamino-1-(2-dimethylaminoethyl)-1H-indol-3-yl]-maleinimide;
2-(1H-indol-3-yl)-3-[4-dimethylamino-1-(3-dimethylaminopropyl)-1H-indol-3-yl]-maleinimide;
2-(1H-indol-3-yl)-3-[5-dimethylamino-1-(3-dimethylaminopropyl)-1H-indol-3-yl]-maleinimide;
2-(1H-indol-3-yl)-3-[6-dimethylamino-1-(3-dimethylaminopropyl)-1H-indol-3-yl]-maleinimide;
2-(1H-indol-3-yl)-3-[7-dimethylamino-1-(3-dimethylaminopropyl)-1H-indol-3-yl]-maleinimide;
2-(1H-indol-3-yl)-3-[4-dimethylamino-1-(3-methylaminopropyl)-1H-indol-3-yl]-maleinimide;
2-(1H-indol-3-yl)-3-[5-dimethylamino-1-(3methylaminopropyl)-1H-indol-3-yl]-maleinimide;
2-(1H-indol-3-yl)-3-[6-dimethylamino-1-(3methylaminopropyl)-1H-indol-3-yl]-maleinimide;
2-(1H-indol-3-yl)-3-[7-dimethylamino-1-(3-methylaminopropyl)-1H-indol-3-yl]-maleinimide;
2-(1H-indol-3-yl)-3-[4-dimethylamino-1-(3-(4-morpholino)propyl)-1H-indol-3-yl]-maleinimide;
2-(1H-indol-3-yl)-3-[5-dimethylamino-1-(3-(4-morpholino)propyl)-1H-indol-3-yl]-maleinimide;
2-(1H-indol-3-yl)-3-[6-dimethylamino-1-(3-(4-morpholino)propyl)-1H-indol-3-yl]-maleinimide;
2-(1H-indol-3-yl)-3-[7-dimethylamino-1-(3-(4-morpholino)propyl)-1H-indol-3-yl]-maleinimide;
2-(1H-indol-3-yl)-3-[4-dimethylamino-1-(3-(2-nitroguanidino)propyl)-1H-indol-3-yl]-maleinimide;
2-(1H-indol-3-yl)-3-[5-dimethylamino-1-(3-(2-nitroguanidino)propyl)-1H-indol-3-yl]-maleinimide;
2-(1H-indol-3-yl)-3-[6-dimethylamino-1-(3-(2-nitroguanidino)propyl)-1H-indol-3-yl]-maleinimide;
2-(1H-indol-3-yl)-3-[7-dimethylamino-1-(3-(2-nitroguanidino)propyl)-1H-indol-3-yl]-maleinimide;
2-(1H-indol-3-yl)-3-[4-dimethylamino-1-(3-(1-piperidino)propyl)-1H-indol-3-yl]-maleinimide;
2-(1H-indol-3-yl)-3-[5-dimethylamino-1-(3-(1-piperidino)propyl)-1H-indol-3-yl]-maleinimide;
2-(1H-indol-3-yl)-3-[6-dimethylamino-1-(3-(1-piperidino)propyl)-1H-indol-3-yl]-maleinimide;
2-(1H-indol-3-yl)-3-[7-dimethylamino-1-(3-(1-piperidino)propyl)-1H-indol-3-yl]-maleinimide;
2-[1-(3-(amidinothio)propyl)-5-dimethylamino-1H-indol-3-yl]-3-(5-dimethylamino-1H-indol-3-yl)-maleinimide;
2-[1-(2-aminoethyl)-5-dimethylamino-1H-indol-3-yl]-3-(5-dimethylamino-1H-indol-3-yl)-maleinimide;
2-[1-(3-aminopropyl)-5-dimethylamino-1H-indol-3-yl]-3-(5-dimethylamino-1H-indol-3-yl)-maleinimide;
(±)-2-[1-(3-ethoxy-2-hydroxypropyl)-5-dimethylamino-1H-indol-3-yl]-3-(5-dimethylamino-1H-indol-3-yl)-maleinimide;
2-[1-(2-diethylaminoethyl)-5-dimethylamino-1H-indol-3-yl]-3-(5-dimethylamino-1H-indol-3-yl)-maleinimide;
(±)-2-[1-(3-diethylamino-2-hydroxypropyl)-5-dimethylamino-1H-indol-3-yl]-3-(5-dimethylamino-1H-indol-3-yl)-maleinimide;
2-[1-(3-ethylaminopropyl)-5-dimethylamino-1H-indol-3-yl]-3-(5-dimethylamino-1H-indol-3-yl)-maleinimide;
(±)-2-[1-(2-hydroxy-3-dimethylaminopropyl)-5-dimethylamino-1H-indol-3-yl]-3-(5-dimethylamino-1H-indol-3-yl)-maleinimide;
(±)-2-[1-(2-hydroxy-3-(4-morpholino)propyl)-5-dimethylamino-1H-indol-3-yl]-3-(5-dimethylamino-1H-indol-3-yl)-maleinimide;
(±)-2-[1-(2-hydroxy-3-(1-piperidino)propyl)-5-dimethylamino-1H-indol-3-yl]-3-(5-dimethylamino-1H-indol-3-yl)-maleinimide;
(±)-2-[1-(2,3-dihydroxypropyl)-5-dimethylamino-1H-indol-3-yl]-3-(5-dimethylamino-1H-indol-3-yl)-maleinimide;
2-[1-(3-hydroxypropyl)-5-dimethylamino-1H-indol-3-yl]-3-(5-dimethylamino-1H-indol-3-yl)-maleinimide;
2-[1-(3-isothiocyanatopropyl)-5-dimethylamino-1H-indol-3-yl]-3-(5-dimethylamino-1H-indol-3-yl)-maleinimide;
(±)-2-[1-(2-Methoxy-3-dimethylaminopropyl)-5-dimethylamino-1H-indol-3-yl]-3-(5-dimethylamino-1H-indol-3-yl)-maleinimide;
2-(5-dimethylamino-1H-indol-3-yl)-3-[5-dimethylamino-1-(2-dimethylaminoethyl)-1H-indol-3-yl]-maleinimide;
2-(5-dimethylamino-1H-indol-3-yl)-3-[5-dimethylamino-1-(3-dimethylaminopropyl)-1H-indol-3-yl]-maleinimide;
2-(5-dimethylamino-1H-indol-3-yl)-3-[5-dimethylamino-1-(3-methylaminopropyl)-1H-indol-3-yl]-maleinimide;
2-(5-dimethylamino-1H-indol-3-yl)-3-[5-dimethylamino-1-(3-(4-morpholino)propyl)-1H-indol-3-yl]-maleinimide;

2-(5-dimethylamino-1H-indol-3-yl)-3-[5-dime-
thylamino-1-(3-(2-nitroguanidino)propyl)-1H-indol-
3-yl]-maleinimide;
2-(5-dimethylamino-1H-indol-3-yl)-3-[5-dime-
thylamino-1-(3-(1-piperidino)propyl)-1H-indol-3-yl]-
maleinimide.

We claim:
1. A compound of formula

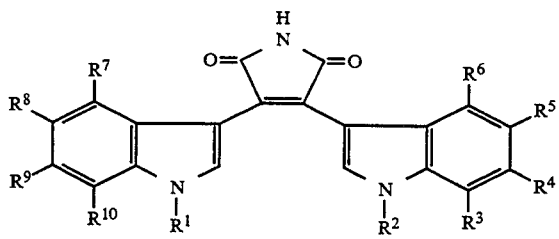

or a pharmaceutically acceptable salt thereof wherein
$R^1$ and $R^2$ are each independently hydrogen, a
straight or branched alkyl of from one to eighteen
carbon atoms, unsubstituted or substituted benzyl
wherein the substituent is alkyl of from one to three
carbon atoms, alkoxy of from one to four carbon
atoms, halogen, aminoalkyl of from one to twelve
carbon atoms which is unsubstituted, mono- or
disubstituted on the nitrogen by benzyl or alkyl of
from one to four carbon atoms alkoxycarbonylal-
kyl of from one to six carbon atoms or $CH_2$—
$CO$—$NR^{11}R^{12}$ wherein $R^{11}$ and $R^{12}$ are each inde-
pendently hydrogen, alkyl of from one to six car-
bon atoms, benzyl, haloalkyl of from one to six
carbon atoms, hydroxy alkyl of from one to six
carbon atoms wherein $R^{11}$ or $R^{12}$ can each be un-
substituted or substituted by halogen, alkoxy alkyl,
by one to three hydroxy groups, or $R^{11}$ and $R^{12}$ are
each independently acyl of from one to four carbon
atoms or glycoside;
$R^3$, $R^4$, $R^5$, $R^6$, $R^7$, $R^8$, $R^9$, and $R^{10}$ are each indepen-
dently hydrogen, halogen, alkyl of from one to
four carbon atoms, alkoxy of from one to four
carbon atoms, acyloxy of from one to four carbon
atoms, nitro, amino which is unsubstituted or
mono- or disubstituted by benzyl, alkyl of from one
to four carbon atoms, benzyloxy, hydroxy, ami-
noalkoxy of from one to twelve carbon atoms and
which nitrogen can be unsubstituted or mono- or
disubstituted by benzyl or by alkyl of from one to
four carbon atoms or the substituents form a ring
containing from three to six carbon atoms or the
alkyl is unsubstituted or substituted by alkyl of
from one to four carbon atoms, hydroxy, alkoxy of
from one to four carbon atoms, trifluoromethyl or
two neighboring substituents form methylene,
with the proviso that not all of $R^1$ to $R^{10}$ are hydro-
gen and $R^{10}$ can also be cyanoalkyl or when $R^4$ or
$R^4$ and $R^9$ are hydroxy, the others of $R^1$ to $R^{10}$ are
not hydrogen.

2. A compound according to claim 1 wherein $R^1$ and
$R^2$ are each independently hydrogen, straight or
branched alkyl of from one to four carbon atoms, ami-
noalkyl of from one to four carbon atoms which alkyl is
unsubstituted or substituted by alkoxy of from one to
four carbon atoms or by hydroxy and which nitrogen is
unsubstituted, mono- or disubstituted by alkyl of from
one to four carbon atoms;

$R^3$, $R^6$, $R^7$, and $R^{10}$ are each hydrogen and $R^4$, $R^5$,
$R^8$, and $R^9$ are each independently hydrogen, halo-
gen, alkyl of from one to four carbon atoms, alkoxy
of from one to four carbon atoms, benzyloxy, hy-
droxy, aminoalkoxy of from one to four carbon
atoms, the alkyl portion of which is unsubstituted
or substituted by alkoxy of from one to four carbon
atoms and the nitrogen portion of which is unsub-
stituted, mono- or disubstituted by alkyl of from
one to four carbon atoms or two substituents of $R^4$,
$R^5$, $R^8$, and $R^9$ form a ring containing from three to
six carbon atoms, wherein the alkyl chain is unsub-
stituted or substituted by an alkyl of from one to
four carbon atoms or two substituents from $R^4$, $R^5$,
$R^8$, and $R^9$ together form methylenedioxy.

3. A compound according to claim 1 wherein $R^1$ and
$R^2$ are each independently hydrogen, straight or
branched alkyl of from one to four carbon atoms, ami-
noalkyl of from one to four carbon atoms, the alkyl
portion of which can be unsubstituted or substituted by
alkoxy of from one to four carbon atoms and the nitro-
gen of which can be unsubstituted, mono- or disubsti-
tuted by alkyl of from one to four carbon atoms;
$R^3$, $R^6$, $R^7$, and $R^{10}$ are each hydrogen;
$R^4$, $R^5$, $R^8$, and $R^9$ are each independently hydrogen,
alkyl of from one to four carbon atoms, alkoxy of
from one to four carbon atoms, halogen, amino,
nitro, dimethylamino, trifluoromethyl, benzyloxy,
hydroxy, aminoalkoxy of from one to four carbon
atoms, which alkyl portion is unsubstituted or sub-
stituted by alkoxy of from one to four carbon atoms
and which nitrogen portion is unsubstituted or
mono- or disubstituted by alkyl of from one to four
carbon atoms or two adjacent substituents of $R^4$,
$R^5$, $R^8$, and $R^9$ are together methylenedioxy.

4. A compound named 2-(1H-indol-3-yl)-3-(1-methyl-
1H-indol-3-yl)-maleinimide.

5. A compound named 2-(1H-indol-3-yl-3-[1-(3-dime-
thylaminopropyl)-1H-indol-3-yl]maleinimide.

6. A compound according to claim 1 named 2-(5-
hydroxy-1H-indol-3-yl)-3-(1H-indol-3-yl)-maleinimide.

7. A compound according to claim 1 named 2-(5-ben-
zyloxy-1H-indol-3-yl)-3-(1H-indol-3-yl)-maleinimide.

8. A compound according to claim 1 named 2,3-bis-
(5-methoxy-1H-indol-3-yl)maleinimide.

9. A compound according to claim 1 named 2-(1H-
indol-3-yl)-3-(5,6-methylenedioxy-1H-indol-3-yl)-
maleinimide.

10. A compound according to claim 1 named 2-(1H-
indol-3-yl)-3-(5,6-dimethoxy-1H-indol-3-yl)-maleini-
mide.

11. A compound according to claim 1 named 2,3-bis-
(5,6-methylenedioxy-1H-indol-3-yl)-maleinimide.

12. A compound according to claim 1 named 2,3-
bis(1-methyl-1H-indol-3-yl)-maleinimide.

13. A compound according to claim 1 selected from
the group consisting of:
2-[1-(3-diethylaminopropyl)-6-methoxy-1H-indol-3-
yl]-3-(5-methoxy-1H-indol-3-yl)-maleinimide,
2-[1-(3-diethylaminopropyl)-5-methoxy-1H-indol-3-
yl]-3-(5,6-dimethoxy-1-methyl-1H-indol-3-yl)-
maleinimide,
2-[1-(3-diethylaminopropyl)-5-methoxy-1H-indol-3-
yl]-3-(6-methoxy-1H-indol-3-yl)-maleinimide, and
2-[1-(3-diethylaminopropyl)-6-methoxy-1H-indol-3-
yl]-3-(5-methoxy-1H-indol-3-yl)-maleinimide.

14. A compound according to claim 1 selected from
the group consisting of:

2-(1H-indol-3-yl)-3-(5-methoxy-1H-indol-3-yl)maleinimide,
2,3-bis-(5-fluoro-1H-indol-3-yl)-maleinimide,
2,3-bis-(5-benzyloxy-1H-indol-3-yl)maleinimide,
2,3-bis-(5-chloro-1H-indol-3-yl)maleinimide,
2,3-bis-(5-methyl-1H-indol-3-yl)maleinimide, and,
2,3-bis-(5-bromo-1H-indol-3-yl)maleinimide.

15. A compound according to claim 1 named 2-(5-bromo-1H-indol-3-yl)-3-(1H-indol-3-yl)-maleinamide.

16. A compound according to claim 1 named 2-(5-fluoro-1H-indol-3-yl)-3-(1H-indol-3-yl)-maleinimide.

17. A compound according to claim 1 named 2-[1-(3-diethylaminopropyl)-5-fluoro-1H-indol-3-yl]-3-(1H-indol-3-yl)maleinimide.

18. A compound according to claim 1 named (±)-2-[1-(2,3-dihydroxypropyl)-5-methoxy-1H-indol-3-yl]-3-(1H-indol-3-yl)maleinimide.

19. A compound according to claim 1 named (±)-2-[1-(3-ethoxy-2-hydroxypropyl)-5-methoxy-1H-indol-3-yl]-3-(1H-indol-3-yl)maleinimide.

20. A compound according to claim 1 named 2-[1-(2-cyanoethyl)-5-methoxy-1H-indol-3-yl]-3-(1-methyl-1H-indol-3-yl)maleinimide.

21. A compound according to claim 1 named 2-[1-(2-cyanoethyl)-1H-indol-3-yl]-3-(1-methyl-1H-indol-3-yl)maleinimide.

22. A compound according to claim 1 named 2-[1-(2-cyanoethyl)-1H-indol-3-yl]-3-(5-methoxy-1-methyl-1H-indol-3-yl)maleinimide.

23. A compound according to claim 1 named 2-(1H-indol-3-yl)-3-[1-(3-diisopropylaminopropyl)-1H-indol-3-yl]maleinimide.

24. A pharmaceutical composition for the treatment of heart and blood vessel diseases comprising an effective amount of a compound according to claim 1, including those compounds wherein $R^1$ to $R^{10}$ are hydrogen and those wherein $R^4$ or $R^4$ and $R^9$ are hydroxyl and the remaining substituents of $R^1$ to $R^{10}$ are hydrogen, together with a pharmaceutically acceptable carrier.

25. A method of treating heart and blood vessel diseases in mammals which comprises administering to said mammal a pharmaceutical composition according to claim 24 in unit dosage form.

26. A compound according to claim 1 wherein $R^1$ and $R^2$ are each independently hydrogen, methyl, ethyl, n-propyl, isopropyl, n-butyl, benzyl, acetyl, methoxycarbonylmethyl, 2-methoxyethyl, 2-aminoethyl, 3-aminopropyl, 1-amino-2-propyl, 2-dimethylaminoethyl, 3-dimethylamino-1-propyl, 3-dimethlylamino-2-propyl, 2-diethylaminoethyl, 2-(N-benzyl -N-methylamino)-ethyl, 3-(N-benzyl-N-methylamino)-propyl, 3-dimethylamino-2-hydroxy-1-propyl, glucosyl, rhamnosyl, ribosyl, deoxyribosyl, aminoglycosyl, 3-hydroxypropyl, 2-carboxyethyl, 2-dimethylaminoethylcarbonyl, dimethylaminomethylcarbonyl, 2-hydroxyethoxymethyl, (2-hydroxy -1-hydroxymethyl)-ethoxymethyl or (3-hydroxy-1-hydroxymethyl)-propoxymethyl radicals and $R^5$ and $R^8$ are each independently hydrogen, chlorine, bromine, fluorine, trifluoromethyl, methyl, ethyl, hydroxyl, benzyloxy, methoxy, amino, dimethylamino, 2-aminoethoxy, 3-aminopropoxy, 1-amino-2-propoxy, 2-dimethylaminoethoxy, 3-dimethylamino-1-propoxy, 3-dimethylamino-2-propoxy, 2-diethylaminoethoxy, 2-[N-benzyl-N-methylamino]-ethoxy, 3-[N-benzyl-N methylamino]-propoxy, 3-dimethylamino-2-hydroxy-1-propoxy, or $R^4$ and $R^5$ together and $R^8$ and $R^9$ together are each independently methylenedioxy.

27. A compound selected from the group consisting of:
2-(5-benzyloxy-1H-indol-3-yl)-3-[1-(3-dimethylaminopropyl)-1H-indol-3-yl]maleinimide,
2-[5-benzyloxy-1-(3-dimethylaminopropyl)-1H-indol-3-yl]-3-(1H-indol-3-yl)maleinimide,
2-(5-methoxy-1H-indol-3-yl)-3-[5-methoxy-1-(3-dimethylaminopropyl)-1H-indol-3-yl]maleinimide,
(±)-2-(1H-indol-3-yl)-3-[1-(3-dimethylamino-2-methoxypropyl)-1H-indol-3-yl]maleinimide,
2-(1H-indol-3-yl)-3-[5-(3-dimethylaminopropyloxy)-1H-indol-3-yl]maleinimide.
2-(5-fluoro-1H-indol-3-yl)-3-[5-fluoro-1-(3-dimethylaminopropyl)-1H-indol-3-yl]maleinimide,
2-(5-benzyloxy-1H-indol-3-yl)-3-[5-benzyloxy -1-(3-dimethylaminopropyl-1H-indol-3-yl]maleinimide,
2-[5-benzyloxy-1-(3-dimethylaminopropyl)-1H-indol-indol-3-yl]-3-(1-methyl-1H-indol-3-yl)maleinimide,
2-(5-chloro-1H-indol-3-yl)-3-[5-chloro-1-(3-dimethylaminopropyl)-1H-indol-3-yl]maleinimide,
2-(5-methyl-1H-indol-3-yl)-3-[5-methyl-1-(3-dimethylaminopropyl)-1H-indol-3-yl]maleinimide,
2-(5-bromo-1H-indol-3-yl)-3-[5-bromo-1-(3-dimethylaminopropyl)-1H-indol-3-yl]maleinimide,
2-(1H-indol-3-yl)-3-[1-(2-dimethylaminoethyl)-1H-indol-3-yl]maleinimide,
2-[1-(3-diethylaminopropyl)-1H-indol-3-yl]-3-(1H-indol-3-yl)maleinimide,
2-(5-methoxy-1-indol-3-yl)-3-[1-(3-dimethylaminopropyl)-1H-indol-3-yl]maleinimide,
2-(1H-indol-3-yl)-3-[5-methoxy-1-(3-dimethylaminopropyl)-1H-indol-3-yl]maleinimide,
2-(5-fluoro-1H-indol-3-yl)-3-[1-(3-dimethylaminopropyl)-1H-indol-3-yl]maleinimide,
2-[1-(3-diethylaminopropyl)-5-methoxy-1H-indol-3-yl[-3-(1H-indol-3-yl)maleinimide,
2-[1-(3-diethylaminopropyl)-1H-indol-3-yl)-3-(5-methoxy-1H-indol-3-yl)maleinimide,
2-[5-fluoro-1-(3-dimethylaminopropyl)-1H-indol-3-yl)maleinimide, and
2-(5-fluoro-1H-indol-3-yl)-3-[1-(3-dimethylaminopropyl)-1H-indol-3-yl]maleinimide.

28. A compound selected from the group consisting of:
(±)-2-[1-(3-diethylamino-2-hydroxypropyl)-1H-indol-3-yl]-3-(1H-indol-3-yl)maleinimide,
(+)-2-[1-(3-diethylamino-2-hydroxypropyl)-1H-indol-3-yl]-3-(1H-indol-3-yl)maleinimide,
(−)-2-[1-(3-diethylamino-2-hydroxypropyl)-1H-indol-3-yl]-3-(1H-indol-3-yl)maleinimide,
(±)-2-[1-(2,3-dihydroxypropyl)-1H-indol-3-yl]-3-(1H-indol-3-yl)maleinimide,
(+)-2-[1-(2,3-dihydroxypropyl)-1H-indol-3-yl]-3-(1H-indol-3-yl)maleinimide,
(−)-2-[1-(2,3-dihydroxypropyl)-1H-indol-3-yl]-3-(1H-indol-3-yl)maleinimide,
(±)-2-[1-(3-ethoxy-2-hydroxypropyl)-1H-indol-3-yl]-3-(1H-indol-3-yl)maleinimide,
(+)-2-[1-(3-ethoxy-2-hydroxypropyl)-1H-indol-3-yl]-3-(1H-indol-3-yl)maleinimide,
(−)-2-[1-(3-ethoxy-2-hydroxypropyl)-1H-indol-3-yl]-3-(1H-indol-3-yl)maleinimide,
(±)-2-[1-(3-diethylamino-2-hydroxypropyl)-5-methoxy-1H-indol-3-yl]-3-(1H-indol-3-yl)maleinimide,
(+)-2-[1-(3-diethylamino-2-hydroxypropyl)-5-methoxy-1H-indol-3-yl]-3-(1H-indol-3-yl)maleinimide, (−)-2-[1-(3-diethylamino-2-hydroxypropyl)-5-methoxy-1H-indol-3-yl]-3-(1H-indol-3-yl)maleinimide,
(±)-2-[1-(3-diethylamino-2-hydroxypropyl)-1H-indol-3-yl]-3-(5-methoxy-1H-indol-3-yl)maleinimide,
(+)-2-[1-(3-diethylamino-2-hydroxypropyl)-1H-indol-3-yl]-3-(5-methoxy-1H-indol-3-yl)maleinimide, and
(−)-2-[1-(3-diethylamino-2-hydroxypropyl)-1H-indol-3-yl]-3-(5-methoxy-1H-indol-3-yl)maleinimide.

* * * * *

UNITED STATES PATENT AND TRADEMARK OFFICE
CERTIFICATE OF CORRECTION

PATENT NO. : 5,380,746
DATED : January 10, 1995
INVENTOR(S) : Barth, et al.

It is certified that error appears in the above-indentified patent and that said Letters Patent is hereby corrected as shown below:

Column 109, line 56, delete [ methylene ] and insert instead -- methylenedioxy -- .

Column 112, line 29, insert -- H -- after the first "1" to read "-1H-indol-".

Signed and Sealed this

Twenty-first Day of March, 1995

Attest:

BRUCE LEHMAN

Attesting Officer    Commissioner of Patents and Trademarks